(12) United States Patent
Roth et al.

(10) Patent No.: US 9,006,450 B2
(45) Date of Patent: Apr. 14, 2015

(54) COMPOUNDS, PHARMACEUTICAL COMPOSITIONS AND USES THEREOF

(75) Inventors: Gerald Juergen Roth, Biberach an der Riss (DE); Martin Fleck, Warthausen (DE); Thorsten Lehmann-Lintz, Ochsenhausen (DE); Heike Neubauer, Eberhardzell (DE); Bernd Nosse, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 422 days.

(21) Appl. No.: 13/165,159

(22) Filed: Jun. 21, 2011

(65) Prior Publication Data

US 2012/0157425 A1 Jun. 21, 2012

(30) Foreign Application Priority Data

Jul. 1, 2010 (EP) .................................... 10168113

(51) Int. Cl.
| | |
|---|---|
| *A61K 31/445* | (2006.01) |
| *C07D 211/72* | (2006.01) |
| *C07D 211/34* | (2006.01) |
| *A61K 45/06* | (2006.01) |
| *C07D 401/04* | (2006.01) |
| *C07D 401/12* | (2006.01) |
| *C07D 401/14* | (2006.01) |
| *C07D 405/04* | (2006.01) |
| *C07D 405/14* | (2006.01) |
| *C07D 409/04* | (2006.01) |
| *C07D 411/04* | (2006.01) |
| *C07D 411/14* | (2006.01) |
| *C07D 413/04* | (2006.01) |
| *C07D 413/14* | (2006.01) |
| *C07D 417/04* | (2006.01) |
| *C07D 487/04* | (2006.01) |
| *C07D 495/04* | (2006.01) |
| *C07D 498/04* | (2006.01) |

(52) U.S. Cl.
CPC .............. *C07D 211/34* (2013.01); *A61K 45/06* (2013.01); *C07D 401/04* (2013.01); *C07D 401/12* (2013.01); *C07D 401/14* (2013.01); *C07D 405/04* (2013.01); *C07D 405/14* (2013.01); *C07D 409/04* (2013.01); *C07D 411/04* (2013.01); *C07D 411/14* (2013.01); *C07D 413/04* (2013.01); *C07D 413/14* (2013.01); *C07D 417/04* (2013.01); *C07D 487/04* (2013.01); *C07D 495/04* (2013.01); *C07D 498/04* (2013.01)

(58) Field of Classification Search
None
See application file for complete search history.

(56) References Cited

FOREIGN PATENT DOCUMENTS

| | | |
|---|---|---|
| OA | 13029 A | 11/2006 |
| WO | 2004037809 A1 | 5/2004 |
| WO | 2008110611 A1 | 9/2008 |
| WO | 2009081197 A1 | 7/2009 |
| WO | 2009144555 A1 | 12/2009 |
| WO | 2012003414 A1 | 1/2012 |

OTHER PUBLICATIONS

Gu et al., J. of Medicinal Chemistry, N-{3[2-(4-Alkoxyphenoxy)thiazol-5-yl]-1-methylprop-2-ynyl} carboxy Derivatives as Acetyl-CoA Carboxylase Inhibitors-Improvements of Cardiovasecular and Neurological Liabilities via Structural Modifications, 2007, vol. 50, No. 5, pp. 1078-1082.

Haque et al., Bioorganic & Medicinal Chemistry Letters, Potent biphenyl- and 3-phenyl-CoA carboxylase, 2009, vol. 19, No. 20, pp. 5872-5876.

International Search Report, form PCT/ISA/210, and Written Opinion, form PCT/ISA?237, for corresponding application PCT/EP2011/061012, date of mailing Oct. 28, 2011.

*Primary Examiner* — Heidi Reese

(74) *Attorney, Agent, or Firm* — Michael P. Morris; Alan R. Stempel

(57) ABSTRACT

The invention relates to new piperidine derivatives of the formula I

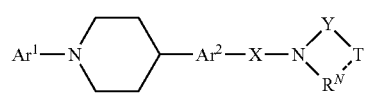

to their use as medicaments, to methods for their therapeutic use and to pharmaceutical compositions containing them.

9 Claims, No Drawings

COMPOUNDS, PHARMACEUTICAL COMPOSITIONS AND USES THEREOF

FIELD OF THE INVENTION

This invention relates to new compounds, in particular piperidine derivatives, to processes for preparing such compounds, to their use as inhibitors of acetyl-CoA carboxylases, to methods for their therapeutic use, in particular in diseases and conditions mediated by the inhibition of acetyl-CoA carboxylase enzyme(s), and to pharmaceutical compositions comprising them.

BACKGROUND OF THE INVENTION

Obesity is major public health issues not only for the EU, USA, Japan but also for the world in general. It is associated with a number of serious diseases including diabetes, dyslipidemia, hypertension, cardiovascular and cerebrovascular diseases. Although the underlying mechanisms are not yet fully understood, the impairement of insulin action in target tissues by accumulation of excess lipids is generally regarded as a key mechanism linking obesity to secondary pathologies (G. Wolf, Nutrition Reviews Vol. 66(10):597-600; D B Savage, K F Petersen, G I Shulman, Physiol Rev. 2007; 87:507-520). Therefore, understanding of cellular lipid metabolism in insulin target tissues is crucial in order to elucidate the development of diseases associated with obesity.

A central event in lipid metabolism is the generation of malonyl-CoA via carboxylation of acetyl-CoA by the two mammalian ACC isoforms ACC1 (ACC-alpha, also termed ACCA) and ACC2 (ACC-beta, also designated ACCB) (D Saggerson, Annu Rev Nutr. 2008; 28:253-72). The malonyl-CoA generated is used for de novo fatty acid synthesis and acts as inhibitor of CPT-1, thereby regulating mitochondrial fatty acid oxidation. Furthermore, malonyl-CoA is also described to act centrally to control food intake, and may play an important role in controlling insulin secretion from the pancreas (G D Lopaschuk, J R Ussher, J S Jaswal. Pharmacol Rev. 2010; 62:237-64; D Saggerson Annu Rev Nutr. 2008; 28:253-72), further coordinating the regulation of intermediary metabolism.

Therefore ACC1 and ACC2 have been shown to be major regulators of fatty acid metabolism and are presently considered as an attractive target to regulate the human diseases of obesity, diabetes and cardiovascular complications (S J Wakil and L A Abu-Elheiga, J. Lipid Res. 2009. 50: S138-S143; L. Tong, H J Harwood Jr. Journal of Cellular Biochemistry 99:1476-1488, 2006).

As a result of its unique position in intermediary metabolism, inhibition of ACC offers the ability to inhibit de novo fatty acid production in lipogenic tissues (liver and adipose) while at the same time stimulating fatty acid oxidation in oxidative tissues (liver, heart, and skeletal muscle) and therefore offers an attractive modality for favorably affecting, in a concerted manner, a multitude of cardiovascular risk factors associated with obesity, diabetes, insulin resistance, nonalcoholic steatohepatitis (NASH) and the metabolic syndrome (L. Tong, H J Harwood Jr. Journal of Cellular Biochemistry 99:1476-1488, 2006; J W Corbett, J H Jr. Harwood, Recent Pat Cardiovasc Drug Discov. 2007 November; 2(3):162-80).

Furthermore recent data show that cellular toxicity mediated by lipids (lipotoxicity) is implicated in the susceptibitlity to diabetes associated nephropathy (for review see M Murea, B I Freedmann, J S Parks, P A Antinozzi, S C Elbein, L M Ma; Clin J Am Soc Nephrol. 2010; 5:2373-9). A large-scale genome-wide association study in japanese patients identified single nucleotide polymorphism in the ACC2 gene (ACACB) associated with diabetic nephropathy risk which was replicated in nine independent cohorts. In the kidney, dysregulation of fatty acid metabolism leading to increased fatty acid levels is believed to lead to glomerular and tubular dysfunction (M Murea, B I Freedmann, J S Parks, P A Antinozzi, S C Elbein, L M Ma; Clin J Am Soc Nephrol. 2010; 5:2373-9). Therefore inhibitors targeting ACC as key molecule involved in lipid oxidation have the potential to be beneficial for favorably affecting diabetic nephropathy.

Additionally, insulin resistance, deregulated lipid metabolism, lipotoxicity and increased intramuscular lipids have also been described to play a role in type 1 diabetes (I E Schauer, J K Snell-Bergeon, B C Bergman, D M Maahs, A Kretowski, R H Eckel, M Rewers Diabetes 2011; 60:306-14; P Ebeling, B Essen-Gustaysson, J A Tuominen and V A Koivisto Diabetologia 41: 111-115; K J Nadeau, J G Regensteiner, T A Bauer, M S Brown, J L Dorosz, A Hull, P Zeitler, B Draznin, J E B. Reusch J Clin Endocrinol Metab, 2010, 95:513-521). Therefore ACC inhibitors are also considered as interesting drugs for the treatment of type 1 diabetes.

In addition ACC inhibitors also have the potential to intervene in the progression of diseases that result from the rapid growth of malignant cells or invading organisms that are dependent on endogenous lipid synthesis to sustain their rapid proliferation. De novo lipogenesis is known to be required for growth of many tumor cells and ACC up-regulation has been recognized in multiple human cancers, promoting lipogenesis to meet the need of cancer cells for rapid growth and proliferation (C Wang, S Rajput, K Watabe, D F Liao, D Cao Front Biosci 2010; 2:515-26). This is further demonstrated in studies using ACC inhibitors which induced growth arrest and selective cytotoxicity in cancer cells and by RNA interference-mediated knock-down of ACC which inhibited growth and induced apoptosis in different types of cancer cells. Furthermore, ACC1 associates with and is regulated by the breast cancer susceptibility gene 1 (BRCA1). Commonly occurring BRCA1 mutations lead to ACC1 activation and breast cancer susceptibility (C Wang, S Rajput, K Watabe, D F Liao, D Cao Front Biosci 2010; 2:515-26)

Furthermore in central nervous system disorders including but not limited to Alzheimer's disease, Parkinson disease and epilepsy, impairements in neuronal energy metabolism have been described (Ogawa M, Fukuyama H, Ouchi Y, Yamauchi H, Kimura J, J Neurol Sci. 1996; 139(1):78-82). Interventions targeting this metabolic defect may prove beneficial to the patients. One promising intervention is therefore to provide the glucose-compromised neuronscerebral brain neurons with ketone bodies as an alternative substrate (S T Henderson Neurotherapeutics, 2008, 5:470-480; L C Costantini, L J Barr, J L Vogel, S T Henderson BMC Neurosci. 2008, 9 Suppl 2:S16; KW Barañano, A L Hartman. Curr Treat Options Neurol. 2008; 10:410-9). ACC inhibition leading to increased fatty acid oxidation may thereby result in increases in the blood levels of ketone bodies thereby providing an alternative energy substrate for the brain.

Preclinical and clinical evidence indicates that ketone bodies can provide neuroprotective effects in models of Parkinson's disease, AD, hypoxia, ischemia, amyotrophic lateral sclerosis and glioma (L C Costantini, L J Barr, J L Vogel, S T Henderson BMC Neurosci. 2008, 9 Suppl 2:S16) and improved cognitive scores in Alzheimers Diseases patients (M A Reger, S T Henderson, C Hale, B Cholerton, L D Baker, G S Watson, K Hydea, D Chapmana, S Craft Neurobiology of Aging 25 (2004) 311-314). The end result of increased ketone levels is an improvement in mitochondrial efficiency and reduction in the generation of reactive oxygen species (for reviews see L C Costantini, L J Barr, J L Vogel, S T Henderson BMC Neurosci. 2008, 9 Suppl 2:S16; K W Barañano, A L Hartman. Curr Treat Options Neurol. 2008; 10:410-9).

Furthermore, the potential of ACC inhibitors as antifungal agents and as antibacterial agents is well documented (L. Tong, H J Harwood Jr. Journal of Cellular Biochemistry 99:1476-1488, 2006). In addition, ACC inhibitors can be used to combat viral infections. It was discovered recently that viruses rely on the metabolic network of their cellular hosts to provide energy and building blocks for viral replication (Munger J, B D Bennett, A Parikh, X J Feng, J McArdle, H A Rabitz, T Shenk, J D Rabinowitz. Nat. Biotechnol. 2008; 26:1179-86). A flux measurement approach to quantify changes in metabolic activity induced by human cytomegalovirus (HCMV) elucidated that infection with HCMV markedly changed fluxes through much of the central carbon metabolism, including glycolysis, tricarboxylic acid cycle and fatty acid biosynthesis. Pharmacological inhibition of fatty acid biosynthesis suppressed the replication of two divergent enveloped viruses (HCMV and influenza A) indicating that fatty acid synthesis is essential for the replication. These examples show that acetyl-CoA fluxes and de novo fatty acid biosynthesis are critical to viral survival and propagation as the newly synthesized fatty acids and phospholipids are important for formation of viral envelopes. Changing the metabolic flux influences the absolute quantity of phospholipid available, the chemical composition and physical properties of the envelope negatively affect viral growth and replication. Hence, ACC inhibitors acting on key enzymes in the fatty acid metabolism, have the potential to be antiviral drugs.

Aim of the Present Invention

The aim of the present invention is to provide new compounds, in particular new piperidine derivatives, which are active with regard to acetyl-CoA carboxylase enzyme(s).

Another aim of the present invention is to provide new compounds, in particular new piperidine derivatives, which are active with regard to ACC2

A further aim of the present invention is to provide new compounds, in particular new piperidine derivatives, which have an inhibitory effect on the enzyme acetyl-CoA carboxylase enzyme(s) in vitro and/or in vivo and possess suitable pharmacological and pharmacokinetic properties to use them as medicaments.

A further aim of the present invention is to provide new compounds, in particular new piperidine derivatives, which have an inhibitory effect on the enzyme ACC2 in vitro and/or in vivo and possess suitable pharmacological and pharmacokinetic properties to use them as medicaments.

A further aim of the present invention is to provide effective ACC inhibitors, in particular for the treatment of metabolic disorders, for example of obesity and/or diabetes.

A further aim of the present invention is to provide methods for treating a disease or condition mediated by the inhibition of acetyl-CoA carboxylase enzyme(s) in a patient.

A further aim of the present invention is to provide a pharmaceutical composition comprising at least one compound according to the invention.

A further aim of the present invention is to provide a combination of at least one compound according to the invention with one or more additional therapeutic agents.

A further aim of the present invention is to provide methods for the synthesis of the new compounds, in particular piperidine derivatives.

A further aim of the present invention is to provide starting and/or intermediate compounds suitable in methods for the synthesis of the new compounds.

Further aims of the present invention become apparent to the one skilled in the art by the description hereinbefore and in the following and by the examples.

Object of the Invention

Within the scope of the present invention it has now surprisingly been found that the new compounds of general formula (I) as described hereinafter exhibit an inhibiting activity with regard to enzyme(s) of acetyl-CoA carboxylases.

According to another aspect of the present invention it has been found that the new compounds of general formula (I) as described hereinafter exhibit an inhibiting activity with regard to ACC2.

Therefore, in a first aspect the present invention provides a compound of general formula (I)

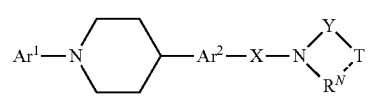

wherein
$Ar^1$ is selected from the group $Ar^1$-G1 consisting of aryl and heteroaryl all of which may be optionally substituted with one or more substituents $R^A$, wherein two substituents $R^A$ linked to adjacent C-atoms of $Ar^1$ may be connected with each other and together form a $C_{3-5}$-alkylene bridging group in which 1, 2 or 3 $CH_2$-groups may be replaced by O, C(=O), S, S(=O), S(=O)$_2$, NH or N($C_{1-4}$-alkyl)-, wherein the alkylene bridge may optionally be substituted by one or two $C_{1-3}$-alkyl groups; and
$R^A$ is selected from the group $R^A$-G1 consisting of H, F, Cl, Br, I, CN, OH, —NO$_2$, $C_{1-6}$-alkyl, $C_{2-6}$-alkenyl, $C_{2-6}$-alkynyl, $C_{3-10}$-carbocyclyl, $C_{3-10}$-carbocyclyl-$C_{1-3}$-alkyl, $C_{1-6}$-alkyl-O—, $C_{3-6}$-alkenyl-O—, $C_{3-6}$-alkynyl-O—, $C_{3-10}$-carbocyclyl-O—, $C_{3-10}$-carbocyclyl-$C_{1-3}$-alkyl-O—, $C_{1-6}$-alkyl-S—, $C_{1-6}$-alkyl-S(=O)—, $C_{1-6}$-alkyl-S(=O)$_2$—, $C_{3-10}$-carbocyclyl-S—, $C_{3-10}$-carbocyclyl-$C_{1-3}$-alkyl-S—, $C_{1-4}$-alkyl-C(=O)—, $C_{3-10}$-carbocyclyl-C(=O)—, $R^{N1}R^{N2}N$—, $R^{N1}R^{N2}N$—$C_{2-3}$-alkyl-O—, $R^{N1}R^{N2}N$—C(=O)—, $R^{N1}R^{N2}N$—S(=O)$_2$—, $C_{1-6}$-alkyl-C(=O)—$NR^{N1}$—, $C_{1-6}$-alkyl-S(=O)$_2$—$NR^{N1}$—, $C_{1-6}$-alkyl-C(=O)—$NR^{N1}$—$C_{1-3}$-alkyl-, HO—C(=O)—, $C_{1-6}$-alkyl-O—C(=O)—, heterocyclyl, heterocyclyl-O—, heterocyclyl-$C_{1-3}$-alkyl, heterocyclyl-$C_{1-3}$-alkyl-O—, heterocyclyl-C(=O)—, aryl, aryl-$C_{1-3}$-alkyl, aryl-O—, aryl-$C_{1-3}$-alkyl-O—, heteroaryl, heteroaryl-$C_{1-3}$-alkyl, heteroaryl-O—, heteroaryl-$C_{1-3}$-alkyl-O— and heteroaryl-C(=O)—,
wherein in each carbocyclyl and heterocyclyl, a $CH_2$-group may optionally be replaced by —C(=O)— or —C(=$CR^{Alk}_2$)—, and
wherein each carbocyclyl and heterocyclyl may be optionally substituted with one or more $C_{1-4}$-alkyl, which may be optionally substituted with one or more substituents $R^C$, and
wherein each alkyl, carbocyclyl and heterocyclyl may be optionally substituted with one or more substituents $R^C$, and wherein each heterocyclyl may be optionally substituted with aryl or heteroaryl, and wherein each aryl and heteroaryl group may be optionally substituted with one or more substituents L, $R^C$ is selected from the group $R^C$-G1 consisting of F, Cl, Br, CN, OH, $C_{1-4}$-alkyl-O—, $C_{3-7}$-cycloalkyl-O—, $C_{3-7}$-cycloalkyl-$C_{1-3}$-alkyl-O—, $H_2N$—, $(C_{1-4}$-alkyl)NH—, $(C_{1-4}$-alkyl)$_2$N—, $H_2N$—C(=O)—, $(C_{1-4}$-alkyl)NH—C(=O)—, $(C_{1-4}$-alkyl)$_2$N—C(=O)—, $C_{1-4}$-alkyl-C(=O)—, $C_{1-4}$-alkyl-S(=O)$_2$—, HO—C(=O)— and $C_{1-4}$-alkyl-O—C(=O)—, wherein each alkyl or cycloalkyl may be optionally substituted with one or more substituents selected from F and OH, and $R^{N1}$ is selected from the group $R^{N1}$-G1 consisting of H, $C_{1-6}$-alkyl, $C_{3-10}$-carbocyclyl, $C_{3-10}$-carbocyclyl-$C_{1-3}$-alkyl, $C_{3-6}$-alkenyl, $C_{3-6}$-alkynyl, heterocyclyl, heterocyclyl-$C_{1-3}$-alkyl, aryl, aryl-$C_{1-3}$-alkyl, heteroaryl and heteroaryl-$C_{1-3}$-alkyl, wherein each carbocyclyl and heterocyclyl may be optionally substituted with one or more $C_{1-4}$-alkyl, aryl or aryl-$C_{1-3}$-alkyl-, and wherein in each carbocyclyl and heterocyclyl a $CH_2$-group may optionally be replaced by —C(=O)—, and wherein each alkyl, carbocyclyl and heterocyclyl may be optionally substituted with one or more substituents $R^C$, and wherein each aryl and heteroaryl group may be optionally substituted with one or more substituents L, $R^{N2}$ is selected from the group $R^{N2}$-G1 consisting of H and $C_{1-6}$-alkyl, and $R^{Alk}$ is selected from the group $R^{Alk}$-G1 consisting of H and $C_{1-6}$-alkyl which may be substituted with one or more F atoms, and $Ar^2$ is selected from the group $Ar^2$-G1 consisting of phenyl and a 5- or 6-membered monocyclic aromatic carbocyclic ring system containing 1, 2 or 3 heteroatoms selected from N, O, or S, wherein all of the before mentioned groups may be optionally substituted with one or more substituents L, and L is selected from the group L-G1 consisting of F, Cl, Br, CN, OH, $C_{1-4}$-alkyl-, $C_{1-4}$-alkyl-O—, $C_{1-4}$-alkyl-S—, $C_{1-4}$-alkyl-S(=O)$_2$—, $C_{1-4}$-alkyl-$NR^{N2}$—S(=O)$_2$—, $H_2N$—, $(C_{1-4}$-alkyl)NH—, $(C_{1-4}$-alkyl)$_2$N—, $H_2N$—$C_{1-4}$-alkyl-, $(C_{1-4}$-alkyl)NH—$C_{1-4}$-alkyl-, $(C_{1-4}$-alkyl)$_2$N—$C_{1-4}$-alkyl-, $C_{3-7}$-cycloalkyl-, $C_{3-7}$-cycloalkyl-$C_{1-3}$-alkyl-O— and heterocyclyl, wherein each alkyl may be optionally substituted with one or more F-atoms and/or with a substituent selected from OH, $C_{1-3}$-alkyl-O— and CN; and wherein two substituents L attached to an aryl or heteroaryl group may be linked to each other and form a $C_{2-5}$-alkylene bridging group in which 1 or 2 —$CH_2$-groups may be replaced by a group independently of each other selected from O, S, NH and N($C_{1-4}$-alkyl)-, wherein the $C_{2-5}$-alkylene bridging group is optionally be substituted by 1 or 2 $C_{1-3}$-alkyl groups;

X is selected from the group X-G1 consisting of a straight chain $C_{1-3}$-alkylene group which may be optionally substituted with one or more $C_{1-3}$-alkyl and $C_{1-3}$-alkyl-O—$C_{1-3}$-alkyl, and wherein two alkyl substituents may be connected with each other and together form a $C_{1-5}$-alkylene bridging group in which 1 or 2 —$CH_2$-groups may be replaced by a group independently of each other selected from O, S, NH or N($C_{1-4}$-alkyl)-, wherein the $C_{1-5}$-alkylene bridging group is optionally be substituted by 1 or 2 $C_{1-3}$-alkyl groups; and Y is selected from the group Y-G1 consisting of —C(=O)—, —C(=S)— and —S(=O)$_2$—;

$R^N$ is selected from the group $R^N$-G1 consisting of H and $C_{1-3}$-alkyl,

T is selected from the group T-G1 consisting of $C_{1-6}$-alkyl, $C_{2-6}$-alkenyl, $C_{2-6}$-alkynyl, $C_{3-10}$-carbocyclyl, $C_{3-10}$-carbocyclyl-$C_{1-3}$-alkyl-, $C_{1-6}$-alkyl-O—, $C_{3-10}$-carbocyclyl-O—, $C_{3-10}$-carbocyclyl-$C_{1-3}$-alkyl-O—, $C_{1-6}$-alkyl-S—, $C_{3-10}$-carbocyclyl-S—, $C_{3-10}$-carbocyclyl-$C_{1-3}$-alkyl-S—, $C_{1-4}$-alkyl-C(=O)—, $C_{1-4}$-alkyl-S(=O)$_2$—, $R^{N1}R^{N2}$—N—, $R^{N1}R^{N2}$—N—$C_{1-3}$-alkyl-, $R^{N1}R^{N2}$—N—CO—, $C_{1-4}$-alkyl-C(=O)—$R^{N2}$N—$C_{1-3}$-alkyl-, $C_{1-3}$-alkyl-O—N=CH—, $C_{1-4}$-alkyl-O—C(=O)—$R^{N2}$N—$C_{1-3}$-alkyl-, heterocyclyl, aryl, heteroaryl and heteroaryl-$C_{1-3}$-alkyl-, wherein in each carbocyclyl and heterocyclyl a $CH_2$-group may optionally be replaced by —C(=O)—, and wherein each carbocyclyl and heterocyclyl may be optionally substituted with one or more $C_{1-4}$-alkyl, which may be optionally substituted with one or more substituents $R^C$, and wherein each alkyl, carbocyclyl and heterocyclyl may be optionally substituted with one or more substituents $R^C$, and wherein each aryl and heteroaryl group may be optionally substituted with one or more substituents L, or the groups T and $R^N$ may be connected with each other and together form a group which is selected from the group (T-$R^N$)-G1 consisting of $C_{2-5}$-alkylene which may be optionally substituted with one or more substituents selected from F, Cl, Br, OH, CN, $C_{1-4}$-alkyl, $C_{3-10}$-carbocyclyl, $C_{3-10}$-carbocyclyl-$C_{1-3}$-alkyl, $C_{1-4}$-alkyl-O—, $C_{3-7}$-cycloalkyl-O—, $C_{3-10}$-carbocyclyl-$C_{1-3}$-alkyl-O—, $H_2N$—, $(C_{1-4}$-alkyl)NH—, $(C_{1-4}$-alkyl)$_2$N—, $C_{1-4}$-alkyl-C(=O)—, $C_{1-4}$-alkyl-S(=O)$_2$—, HO—C(=O)—, $Cl\_4$-alkyl-O—C(=O)—, wherein each alkyl or carbocyclyl may be optionally substituted with one or more substituents selected from $R^C$, including any tautomers and stereoisomers thereof, or a salt thereof or a solvate or hydrate thereof.

In a further aspect the present invention relates to processes for preparing a compound of general formula (I) and to new intermediate compounds in these processes.

A further aspect of the invention relates to a salt of the compounds of general formula (I) according to this invention, in particular to a pharmaceutically acceptable salt thereof.

In a further aspect this invention relates to a pharmaceutical composition, comprising one or more compounds of general formula (I) or one or more pharmaceutically acceptable salts thereof according to the invention, optionally together with one or more inert carriers and/or diluents.

In a further aspect this invention relates to a method for treating diseases or conditions which are mediated by inhibiting the activity of acetyl-CoA carboxylase enzyme(s) in a patient in need thereof characterized in that a compound of general formula (I) or a pharmaceutically acceptable salt thereof is administered to the patient.

According to another aspect of the invention, there is provided a method for treating a metabolic disease or disorder in a patient in need thereof characterized in that a compound of general formula (I) or a pharmaceutically acceptable salt thereof is administered to the patient.

According to another aspect of the invention, there is provided a method for treating a cardiovascular disease or disorder in a patient in need thereof characterized in that a compound of general formula (I) or a pharmaceutically acceptable salt thereof is administered to the patient.

According to another aspect of the invention, there is provided a method for treating a neurodegenerative disease or disorder or for treating a disease or disorder of the central nervous system in a patient in need thereof characterized in that a compound of general formula (I) or a pharmaceutically acceptable salt thereof is administered to the patient.

According to another aspect of the invention, there is provided a method for treating a cancer, a malignant disorder or a neoplasia in a patient in need thereof characterized in that a compound of general formula (I) or a pharmaceutically acceptable salt thereof is administered to the patient.

According to another aspect of the invention, there is provided the use of a compound of the general formula (I) or a physiologically acceptable salt thereof for the manufacture of a medicament for a therapeutic method as described hereinbefore and hereinafter.

According to another aspect of the invention, there is provided a compound of the general formula (I) or a physiologically acceptable salt thereof for a therapeutic method as described hereinbefore and hereinafter.

In a further aspect this invention relates to a method for treating a disease or condition mediated by the inhibition of acetyl-CoA carboxylase enzyme(s) in a patient that includes the step of administering to the patient in need of such treatment a therapeutically effective amount of a compound of the general formula (I) in combination with a therapeutically effective amount of one or more additional therapeutic agents.

In a further aspect this invention relates to a use of a compound of the general formula (I) in combination with one or more additional therapeutic agents for the treatment or prevention of diseases or conditions which are mediated by the inhibition of the enzyme(s) acetyl-CoA carboxylase.

In a further aspect this invention relates to a pharmaceutical composition which comprises a compound according to general formula (I) or a pharmaceutically acceptable salt thereof and one or more additional therapeutic agents, optionally together with one or more inert carriers and/or diluents.

Other aspects of the invention become apparent to the one skilled in the art from the specification and the experimental part as described hereinbefore and hereinafter.

DETAILED DESCRIPTION

Unless otherwise stated, the groups, residues, and substituents, particularly $Ar^1$, $Ar^2$, X, Y, $R^N$, T, $R^A$, $R^C$, $R^{N1}$, $R^{N2}$, $R^{Alk}$, L, T, are defined as above and hereinafter. If residues, substituents, or groups occur several times in a compound, as for example $R^C$, $R^{N1}$, $R^{N2}$ or L, they may have the same or different meanings. Some preferred meanings of individual groups and substituents of the compounds according to the invention will be given hereinafter. Any and each of these definitions may be combined with each other.

$Ar^1$:

$Ar^1$-G1:

The group $Ar^1$ is preferably selected from the group $Ar^1$-G1 as defined hereinbefore and hereinafter.

$Ar^1$-G2:

In one embodiment the group $Ar^1$ is selected from the group $Ar^1$-G2 consisting of phenyl, dihydronaphthyl, tetrahydronaphthyl, naphthyl and a 5- or 6-membered monocyclic or 9- or 10-membered bicyclic-ring system containing 1, 2 or 3 heteroatoms selected from N, O, S, or $S(O)_r$, with r=1 or 2 wherein at least one of the heteroatoms is part of an aromatic ring, and wherein all of the before mentioned groups may be optionally substituted with one or more substituents $R^A$, particularly wherein all of the before mentioned groups may be optionally substituted with a substituent $R^A$ and optionally one or more substituents L, and wherein two substituents $R^A$ linked to adjacent C-atoms of $Ar^1$ may be connected with each other and together form a $C_{3-5}$-alkylene bridging group in which 1, 2 or 3 $CH_2$-groups may be replaced by O, C(=O), S, S(=O), $S(=O)_2$, NH or $N(C_{1-4}$-alkyl)-, wherein the alkylene bridging group may optionally be substituted by one or two $C_{1-3}$-alkyl groups.

$Ar^1$-G3:

In another embodiment the group $Ar^1$ is selected from the group $Ar^1$-G3 consisting of phenyl, naphthyl, pyridyl, 2H-pyridin-2-onyl, pyrimidinyl, pyridazinyl, pyrazinyl, furanyl, thienyl, pyrrolyl, imidazolyl, triazolyl, oxazolyl, isoxazolyl, pyrazolyl, thiazolyl, quinolinyl, isoquinolinyl, indolyl, benzofuranyl, benzoimidazolyl, benzooxazolyl, benzotriazolyl, 2,3-dihydrobenzofuranyl, benzo[1,3]dioxolyl and 2,3-dihydro-benzo[1,4]dioxinyl, wherein the before mentioned bicyclic groups preferably are linked to the piperidine ring of the core structure of the formula (I) via an aromatic or heteroaromatic ring of the bicyclic group, and wherein all of the before mentioned mono- and bicyclic groups may be optionally substituted with one or more substituents $R^A$, particularly wherein all of the before mentioned mono- or bicyclic groups may be optionally substituted with a substituent $R^A$ and optionally one or more substituents L.

$Ar^1$-G4:

In another embodiment the group $Ar^1$ is selected from the group $Ar^1$-G4 consisting of phenyl, naphthyl, pyridyl, 2H-pyridin-2-onyl, pyrimidinyl, pyridazinyl, pyrazinyl, furanyl, oxazolyl, isoxazolyl, pyrazolyl, thiazolyl, quinolinyl, indolyl, benzofuranyl, 2,3-dihydrobenzofuranyl, benzo[1,3]dioxolyl, 2,3-dihydro-benzo[1,4]dioxinyl and 3,4-dihydro-2H-benzo[b][1,4]dioxepinyl, wherein the before mentioned bicyclic groups preferably are linked to the piperidine ring of the core structure of the formula (I) via an aromatic or heteroaromatic ring of the bicyclic group, and wherein all of the before mentioned mono- and bicyclic groups may be optionally substituted with one or more substituents $R^A$, particularly wherein all of the before mentioned mono- or bicyclic groups may be optionally substituted with a substituent $R^A$ and optionally one or more substituents L.

$Ar^1$-G5:

In another embodiment the group $Ar^1$ is selected from the group $Ar^1$-G5 consisting of:

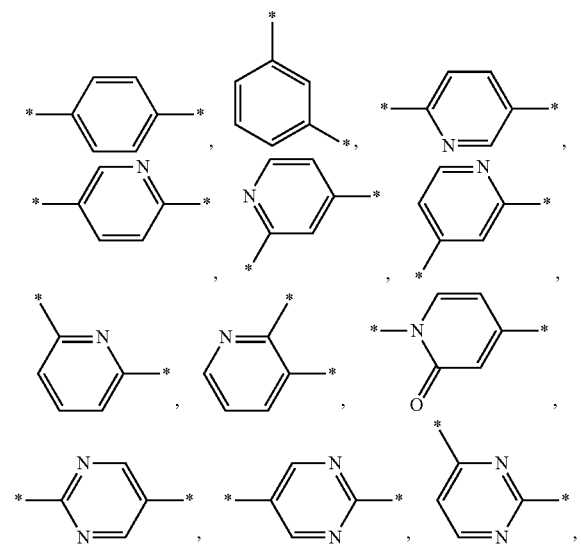

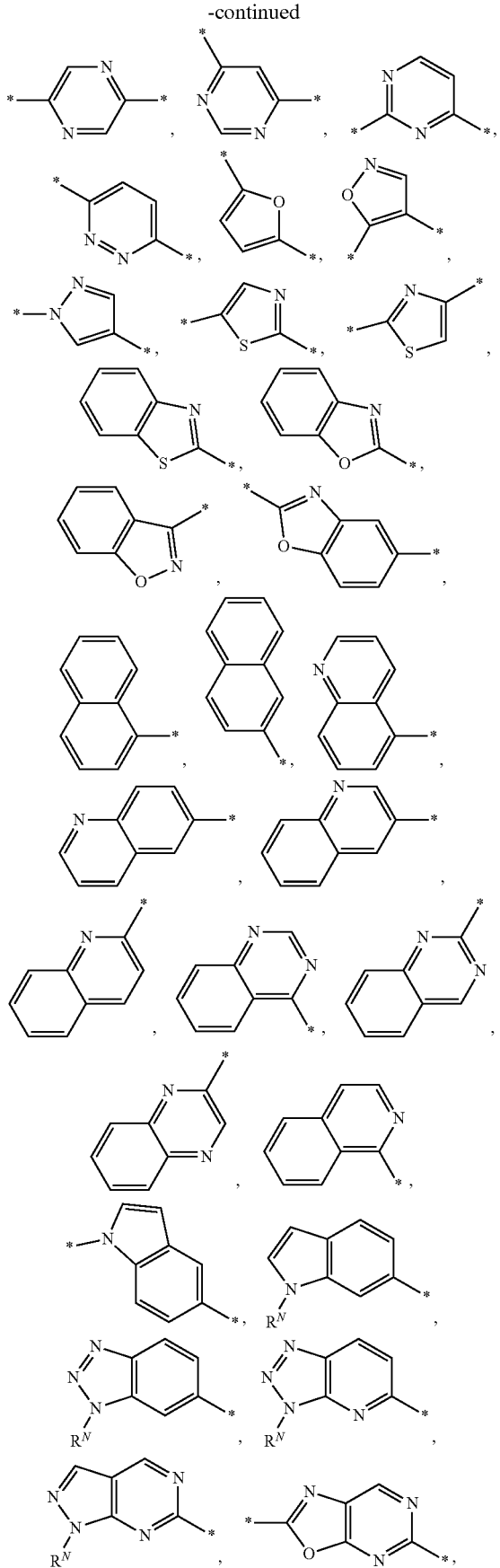

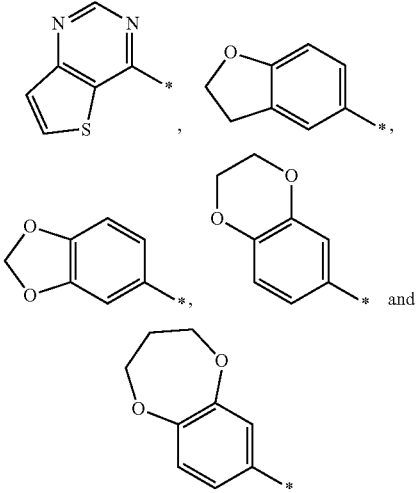

wherein the asterisk to the right side of each cyclic group indicates the bond which is connected to the piperidine ring of the core structure of the formula (I), and if existing the asterisk to the left side of each cyclic group indicates the bond which is connected to a substituent $R^A$ or H, and in addition each of the before mentioned cyclic groups is optionally substituted with one or more further substituents $R^A$, in particular one or more substituents L, and the substituent $R^N$ is defined as hereinbefore and hereinafter.

$Ar^1$-G6:

In another embodiment the group $Ar^1$ is selected from the group $Ar^1$-G6 consisting of:

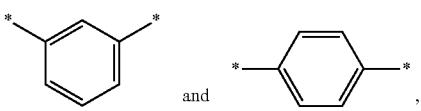 [SMILES: *c1cccc(*)c1 ; *c1ccc(*)cc1]

wherein the asterisk to the right side of the cyclic group indicates the bond which is connected to the piperidine ring of the core structure of the formula (I), and the asterisk to the left side of the cyclic group indicates the bond which is connected to a substituent $R^A$ or H, and in addition the before mentioned cyclic group is optionally substituted with one or more further substituents $R^A$, in particular one or more substituents L.

Examples of members of the group $Ar^1$-G6 are without being limited to it:

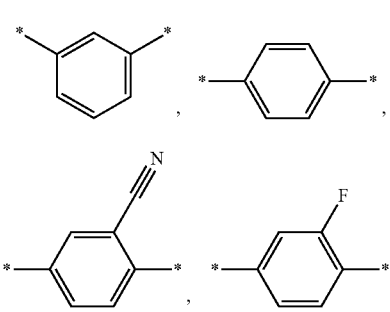

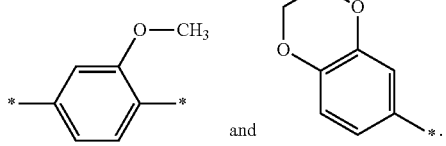

Ar¹-G7:

In another embodiment the group Ar¹ is selected from the group Ar¹-G7 consisting of 6-membered aromatic rings containing 1 or 2 N-atoms, wherein said rings may be optionally substituted with one or more substituents $R^A$, particularly wherein said rings may be optionally substituted with a substituent $R^A$ and optionally one or more substituents L. Examples of members of the group Ar¹-G7 are:

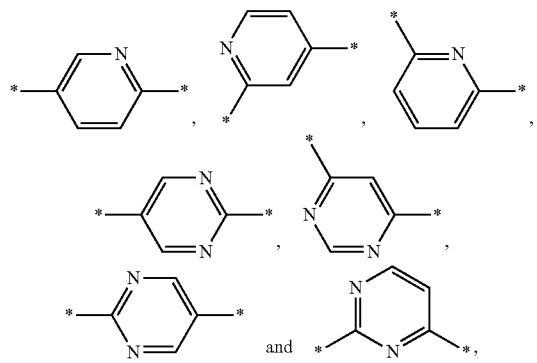

wherein the asterisk to the right side of each cyclic group indicates the bond which is connected to the piperidine ring of the core structure of the formula (I), and the asterisk to the left side of each cyclic group indicates the bond which is connected to a substituent $R^A$, and in addition each of the before mentioned cyclic groups is optionally substituted with one or more further substituents $R^A$, in particular one or more substituents L.

Preferred examples of members of the group Ar¹-G7 are without being limited to it:

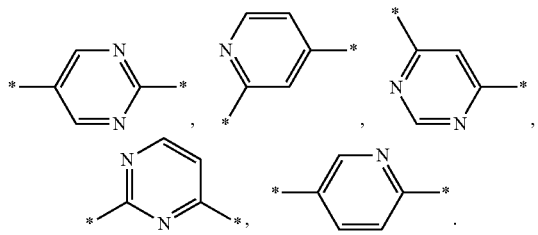

$R^A$:
$R^A$-G1:

The group $R^A$ is preferably selected from the group $R^A$-G1 as defined hereinbefore and hereinafter,
$R^A$-G2:

In another embodiment the group $R^A$ is selected from the group $R^A$-G2 consisting of H, F, Cl, Br, I, CN, OH, $NO_2$, $C_{1-6}$-alkyl, $C_{3-10}$-carbocyclyl, $C_{3-10}$-carbocyclyl-$C_{1-3}$-alkyl, $C_{1-6}$-alkyl-O—, $C_{3-6}$-alkenyl-O—, $C_{3-6}$-alkynyl-O—, $C_{3-10}$-carbocyclyl-O—, $C_{3-10}$-carbocyclyl-$C_{1-3}$-alkyl-O—, $C_{1-6}$-alkyl-S—, $C_{3-10}$-carbocyclyl-S—, $C_{3-10}$-carbocyclyl-$C_{1-3}$-alkyl-S—, $C_{1-4}$-alkyl-C(=O)—, $R^{N1}R^{N2}N$—, $R^{N1}R^{N2}N$—$C_{2-3}$-alkyl-O—, $R^{N1}R^{N2}N$—C(=O)—, HO—C(=O)—, $C_{1-6}$-alkyl-O—C(=O)—, heterocyclyl, heterocyclyl-O—, heterocyclyl-$C_{1-3}$-alkyl, heterocyclyl-$C_{1-3}$-alkyl-O—, heterocyclyl-C(=O)—, aryl, aryl-$C_{1-3}$-alkyl, aryl-O—, aryl-$C_{1-3}$-alkyl-O—, heteroaryl, heteroaryl-$C_{1-3}$-alkyl, heteroaryl-O— and heteroaryl-$C_{1-3}$-alkyl-O—;

wherein heterocyclyl is defined as hereinbefore and hereinafter, or alternatively each heterocyclyl is selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroquinolinyl, dihydroisoquinolinyl, dihydroindolyl, dihydroisoindolyl, oxetanyl, tetrahydrofuranyl and tetrahydropyranyl, or from the group consisting of

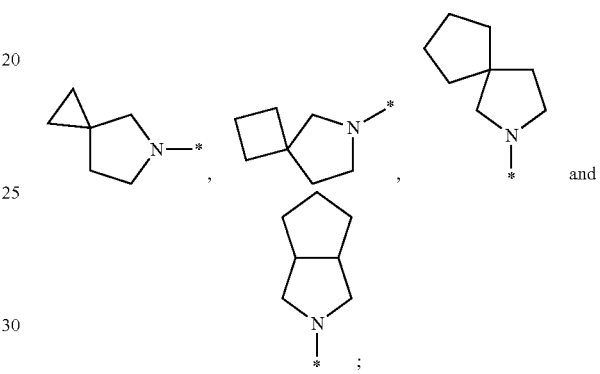

and wherein carbocyclyl is defined as hereinbefore and hereinafter, or each carbocyclyl is preferably selected from $C_{3-7}$-cycloalkyl, indanyl and tetrahydronaphthyl; and wherein heteroaryl is defined as hereinbefore and hereinafter, or each heteroaryl is preferably selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, benzofuranyl, indolyl, quinolinyl and indazolyl; and wherein in each heterocyclyl and carbocyclyl a —$CH_2$-group may optionally be replaced by —C(=O)— or —C(=$CR^{Alk}_2$)—; and wherein each carbocyclyl and heterocyclyl may be optionally substituted with one or more $C_{1-3}$-alkyl, which may be substituted as defined hereinafter, and wherein each alkyl, carbocyclyl and heterocyclyl may be optionally substituted with one or more substituents selected from F; and wherein each alkyl, carbocyclyl and heterocyclyl may be optionally substituted with 1, 2 or 3 substituents $R^C$, which are selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH— and ($C_{1-3}$-alkyl)$_2$N—, HO—C(=O)— and $C_{1-4}$-alkyl-O—C(=O)—; and wherein each $R^{N1}$ is selected from the group $R^{N1}$-G1, $R^{N1}$-G2 or $R^{N1}$-G3 as defined hereinbefore and hereinafter; and each $R^{N2}$ is selected from the group $R^{N2}$-G1 or $R^{N2}$-G2 as defined hereinbefore and hereinafter; and wherein each carbocyclyl or heterocyclyl may be optionally substituted with an aryl or heteroaryl group, in particular with phenyl or pyridyl, and wherein each aryl and heteroaryl group may be optionally substituted with one or more substituents L, wherein L is selected from the groups L-G1, L-G2 or L-G3 as defined hereinbefore and hereinafter.

$R^A$-G2a:

In another embodiment the group $R^A$ is selected from the group $R^A$-G2a consisting of $C_{1-6}$-alkyl-O—, $C_{3-6}$-alkenyl-O—, $C_{3-6}$-alkynyl-O—, $C_{3-10}$-carbocyclyl-O—, $C_{3-10}$-carbocyclyl-$C_{1-3}$-alkyl-O—, $C_{1-6}$-alkyl-S—, $C_{3-10}$-carbocyclyl-S—, $C_{3-10}$-carbocyclyl-$C_{1-3}$-alkyl-S—, heterocyclyl-O— and heterocyclyl-$C_{1-3}$-alkyl-O—;

wherein heterocyclyl is defined as hereinbefore and hereinafter, or each heterocyclyl is preferably selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroquinolinyl, dihydroisoquinolinyl, dihydroindolyl, dihydroisoindolyl, oxetanyl, tetrahydrofuranyl and tetrahydropyranyl, or from the group consisting of

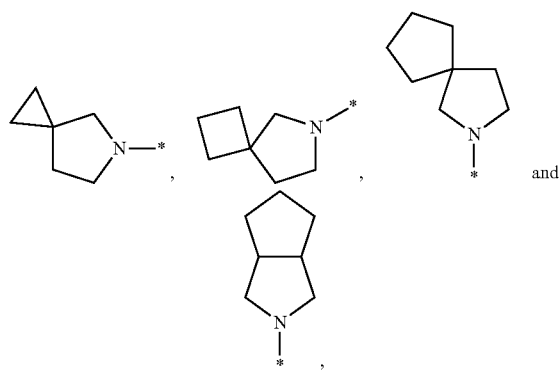

and wherein carbocyclyl is defined as hereinbefore and hereinafter, or each carbocyclyl is preferably selected from $C_{3-7}$-cycloalkyl, indanyl and tetrahydronaphthyl; and wherein in each heterocyclyl and carbocyclyl a $CH_2$-group may optionally be replaced by —C(=O)— or —C(=$CR^{Alk}_2$)—; and wherein each carbocyclyl and heterocyclyl may be optionally substituted with one or more $C_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with 1, 2 or 3 substituents $R^C$, which are selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2N$—, $(C_{1-3}$-alkyl)NH— and $(C_{1-3}$-alkyl)$_2$N—, HO—C(=O)— and $C_{1-4}$-alkyl-O—C(=O)—.

$R^A$-G2b:

In another embodiment the group $R^A$ is selected from the group $R^A$-G2b consisting of $C_{1-6}$-alkyl, $C_{3-10}$-carbocyclyl, $C_{3-10}$-carbocyclyl-$C_{1-3}$-alkyl, heterocyclyl, heterocyclyl-$C_{1-3}$-alkyl, aryl, aryl-$C_{1-3}$-alkyl, heteroaryl and heteroaryl-$C_{1-3}$-alkyl;

wherein heterocyclyl is defined as hereinbefore and hereinafter, or each heterocyclyl is preferably selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroquinolinyl, dihydroisoquinolinyl, dihydroindolyl, dihydroisoindolyl, oxetanyl, tetrahydrofuranyl and tetrahydropyranyl, or from the group consisting of

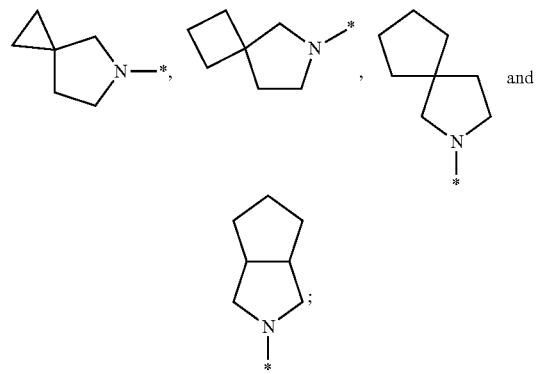

and wherein carbocyclyl is defined as hereinbefore and hereinafter, or each carbocyclyl is preferably selected from $C_{3-7}$-cycloalkyl, indanyl and tetrahydronaphthyl; and wherein heteroaryl is defined as hereinbefore and hereinafter, or each heteroaryl is preferably selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, benzofuranyl, indolyl, quinolinyl and indazolyl; and wherein in each heterocyclyl and carbocyclyl a $CH_2$-group may optionally be replaced by —C(=O)— or —C(=$CR^{Alk}_2$)—; and wherein each carbocyclyl and heterocyclyl may be optionally substituted with one or more $C_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with 1, 2 or 3 substituents $R^C$, which are selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2N$—, $(C_{1-3}$-alkyl)NH— and $(C_{1-3}$-alkyl)$_2$N—, HO—C(=O)— and $C_{1-4}$-alkyl-O—C(=O)—; and wherein each carbocyclyl or heterocyclyl may be optionally substituted with an aryl or heteroaryl group, in particular with phenyl or pyridyl; and wherein each aryl and heteroaryl group may be optionally substituted with one or more substituents L, wherein L is selected from the groups L-G1, L-G2 or L-G3 as defined hereinbefore and hereinafter.

$R^A$-G3:

In another embodiment the group $R^A$ is selected from the group $R^A$-G3 consisting of F, Cl, Br, I, CN, $NO_2$, $C_{1-6}$-alkyl, $C_{3-10}$-carbocyclyl-, $C_{3-10}$-carbocyclyl-$C_{1-3}$-alkyl, $C_{1-6}$-alkyl-O—, $C_{3-6}$-alkenyl-O—, $C_{3-6}$-alkynyl-O—, $C_{1-4}$-alkyl-S—, $C_{3-10}$-carbocyclyl-O—, $C_{3-10}$-carbocyclyl-$C_{1-3}$-alkyl-O—, $C_{1-4}$-alkyl-C(=O)—, $R^{N1}R^{N2}N$—, $R^{N1}R^{N2}N$—$C_{2-3}$-alkyl-O—, $R^{N1}R^{N2}N$—C(=O)—, HO—C(=O)—, $C_{1-4}$-alkyl-O—C(=O)—, heterocyclyl, heterocyclyl-$C_{1-3}$-alkyl, heterocyclyl-O—, heterocyclyl-$C_{1-3}$-alkyl-O—, heterocyclyl-C (=O)—, phenyl, phenyl-O—, phenyl-$C_{1-3}$-alkyl-, phenyl-$C_{1-3}$-alkyl-O—, heteroaryl, heteroaryl-$C_{1-3}$-alkyl, heteroaryl-O— and heteroaryl-$C_{1-3}$-alkyl-O—;

wherein each heterocyclyl is selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroisoindolyl, oxetanyl, tetrahydrofuranyl and tetrahydropyranyl, or from the group consisting of

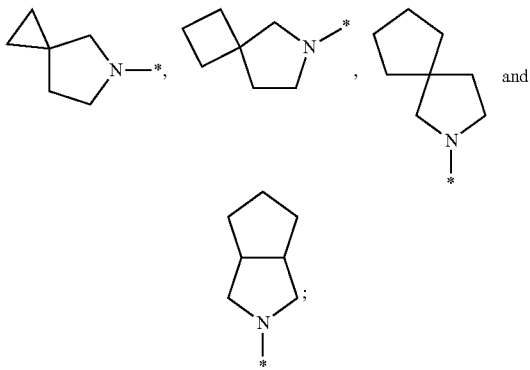

and wherein carbocyclyl is defined as hereinbefore and hereinafter, or each carbocyclyl is preferably selected from $C_{3-6}$-cycloalkyl, indanyl and tetrahydronaphthyl; most preferably carbocyclyl denotes $C_{3-6}$-cycloalkyl; and wherein in each carbocyclyl, pyrrolidinyl and piperidinyl a $CH_2$-group may optionally be replaced by —C(=O)— or —C(=$CR^{Alk}_2$)-; and wherein each heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, indazolyl, benzofuranyl, indolyl and quinolinyl; and wherein each carbocyclyl or heterocyclyl may be optionally substituted with one or more $C_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with one or two substituents $R^C$, which are selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-4}$-alkyl-O—C(=O)—; and wherein each $R^{N1}$ is selected from the group $R^{N1}$-G1, $R^{N1}$-G2 or $R^{N1}$-G3; and each $R^{N2}$ is selected from the group $R^{N2}$-G1 or $R^{N2}$-G2 as defined hereinbefore and hereinafter; and wherein each carbocyclyl and heterocyclyl may be optionally substituted with an aryl or heteroaryl group, in particular with phenyl or pyridyl; and wherein each phenyl and heteroaryl group may be optionally substituted with one or more substituents L, wherein L is selected from the groups L-G1, L-G2 or L-G3 as defined hereinbefore and hereinafter.

$R^A$-G4:

In another embodiment the group $R^A$ is selected from the group $R^A$-G4 consisting of F, Cl, Br, I, CN, $NO_2$, $C_{1-6}$-alkyl, $C_{3-10}$-carbocyclyl-, $C_{3-10}$-carbocyclyl-$C_{1-3}$-alkyl, $C_{1-5}$-alkyl-O—, $C_{3-5}$-alkenyl-O—, $C_{3-5}$-alkynyl-O—, $C_{3-10}$-carbocyclyl-O—, $C_{3-10}$-carbocyclyl-$C_{1-3}$-alkyl-O—, $R^{N1}R^{N2}N$—, $R^{N1}R^{N2}N$—C(=O)—, heterocyclyl, heterocyclyl-$C_{1-3}$-alkyl, heterocyclyl-O—, heterocyclyl-$C_{1-3}$-alkyl-O—, heterocyclyl-C(=O)—, phenyl, phenyl-O—, phenyl-$C_{1-3}$-alkyl-, phenyl-$C_{1-3}$-alkyl-O—, heteroaryl, heteroaryl-$C_{1-3}$-alkyl, heteroaryl-O— and heteroaryl-$C_{1-3}$-alkyl-O—;

wherein carbocyclyl is defined as hereinbefore and hereinafter, or each carbocyclyl is preferably selected from $C_{3-6}$-cycloalkyl, indanyl and tetrahydronaphthyl; most preferably carbocyclyl denotes $C_{3-6}$-cycloalkyl; and wherein each heterocyclyl is selected from the group consisting of azetidinyl, pyrrolidinyl, piperidinyl, piperazinyl, N—$C_{1-4}$-alkyl-piperazin-1-yl, N—$C_{1-4}$-alkylsulfonyl-piperazin-1-yl, morpholinyl, dihydroisoindolyl, oxetanyl, tetrahydrofuranyl and tetrahydropyranyl, or from the group consisting of

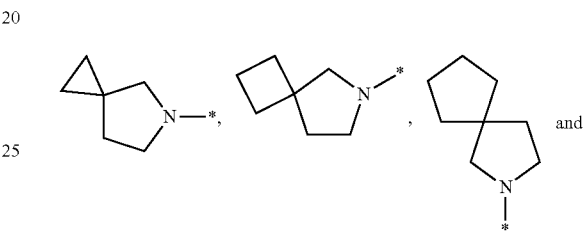

and wherein in each carbocyclyl and heterocyclyl a $CH_2$-group may optionally be replaced by —C(=O)— or —C(=$CR^{Alk}_2$)—; and wherein each heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, triazolyl, tetrazolyl, indazolyl, benzofuranyl, indolyl, and quinolinyl; and wherein each carbocyclyl and heterocyclyl may be optionally substituted with one or more $C_{1-3}$-alkyl, which may be substituted as defined hereinafter; and wherein each alkyl, carbocyclyl and heterocyclyl may be optionally substituted with one or more substituents selected from F; and wherein each alkyl, carbocyclyl and heterocyclyl may be optionally substituted with one or two substituents $R^C$, which are selected from the group $R^C$-G1, $R^C$-G2 or $R^C$-G3 as defined hereinbefore and hereinafter; even more preferably $R^C$ is selected from Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-4}$-alkyl-O—C(=O)—; and wherein each $R^{N1}$ is selected from the group $R^{N1}$-G1, $R^{N1}$-G2 or $R^{N1}$-G3; and each $R^{N2}$ is selected from the group $R^{N2}$-G1 or $R^{N2}$-G2 as defined hereinbefore and hereinafter; and wherein each carbocyclyl and heterocyclyl may be optionally substituted with an aryl or heteroaryl group, in particular with phenyl or pyridyl; and wherein each phenyl and heteroaryl group may be optionally substituted with one or more substituents L, wherein L is selected from the groups L-G1, L-G2 or L-G3 as defined hereinbefore and hereinafter.

$R^A$-G5:

In another embodiment the group $R^A$ is selected from the group $R^A$-G5 consisting of F, Cl, Br, I, CN, $C_{1-5}$-alkyl, $C_{3-6}$-cycloalkyl, $C_{1-5}$-alkyl-O—, $C_{3-5}$-alkenyl-O—, $C_{3-5}$-alkynyl-O—, $C_{3-6}$-cycloalkyl-O—, $C_{3-6}$-cycloalkyl-$C_{1-3}$-alkyl-O—, $R^{N1}R^{N2}N$—, phenyl, phenyl-O—, phenyl-$C_{1-3}$-alkyl-O—, heteroaryl, heteroaryl-O— and heteroaryl-$C_{1-3}$-alkyl-O—; and wherein each cycloalkyl may be optionally substituted with one or more $C_{1-3}$-alkyl, which may be substituted as defined hereinafter; and wherein each alkyl and cycloalkyl may be optionally substituted with one or more substituents selected from F; and wherein in each cycloalkyl group a $CH_2$-group may optionally be replaced by —O—; and wherein each alkyl and cycloalkyl may be optionally substituted with one or two substituents $R^C$, wherein $R^C$ is defined as hereinbefore and hereinafter; preferably $R^C$ is selected from the group consisting of Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-3}$-alkyl-O—C(=O)—; and wherein each $R^{N1}$ is selected from the group $R^{N1}$-G1, $R^{N1}$-G2 or $R^{N1}$-G3 as defined hereinbefore and hereinafter; preferably $R^{N1}$ is selected from the group consisting of H, $C_{1-6}$-alkyl, $C_{3-6}$-cycloalkyl, $C_{3-6}$-cycloalkyl-$CH_2$—, wherein each cycloalkyl may be optionally substituted with one or more $C_{1-4}$-alkyl, and wherein each alkyl and cycloalkyl may be optionally substituted with one or more substituents selected from F, and wherein each alkyl and cycloalkyl may be optionally substituted with a substituent selected from OH, $C_{1-3}$-alkyl-O— and $H_2N$—; and wherein each $R^{N2}$ is selected from the group $R^{N2}$-G1 or $R^{N2}$-G2 as defined hereinbefore and hereinafter; and wherein heteroaryl is defined as hereinbefore and hereinafter; preferably heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, benzofuranyl, indolyl and quinolinyl; and wherein each phenyl and heteroaryl group may be optionally substituted with one or more substituents L, wherein L is selected from the groups L-G1, L-G2 or L-G3 as defined hereinbefore and hereinafter.

$R^A$-G5a:

In another embodiment the group $R^A$ is selected from the group $R^A$-G5a consisting of $C_{1-5}$-alkyl-O—, $C_{3-5}$-alkenyl-O—, $C_{3-5}$-alkynyl-O—, $C_{3-6}$-cycloalkyl-O— and $C_{3-6}$-cycloalkyl-$C_{1-3}$-alkyl-O—;

wherein each cycloalkyl may be optionally substituted with one or more $C_{1-3}$-alkyl, which may be substituted as defined hereinafter; and wherein each alkyl and cycloalkyl may be optionally substituted with one or more substituents selected from F; and wherein in each cycloalkyl group a $CH_2$-group may optionally be replaced by —O—; and wherein each alkyl and cycloalkyl may be optionally substituted with one or two substituents $R^C$, wherein $R^C$ is defined as hereinbefore and hereinafter; preferably $R^C$ is selected from the group consisting of Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-3}$-alkyl-O—C(=O)—.

$R^A$-G5b:

In another embodiment the group $R^A$ is selected from the group $R^A$-G5b consisting of $C_{1-5}$-alkyl, $C_{3-6}$-cycloalkyl, phenyl and heteroaryl;

wherein each cycloalkyl may be optionally substituted with one or more $C_{1-3}$-alkyl, which may be substituted as defined hereinafter; and wherein each alkyl and cycloalkyl may be optionally substituted with one or more substituents selected from F; and wherein in each cycloalkyl group a $CH_2$-group may optionally be replaced by —O—; and wherein each alkyl and cycloalkyl may be optionally substituted with one or two substituents $R^C$, wherein $R^C$ is defined as hereinbefore and hereinafter; preferably $R^C$ is selected from the group consisting of Cl, Br, CN, OH, $C_{1-3}$-alkyl-O—, $C_{3-6}$-cycloalkyl-O—, HO—$C_{1-3}$-alkyl-O—, $H_2N$—, ($C_{1-3}$-alkyl)NH—, ($C_{1-3}$-alkyl)$_2$N—, HO—C(=O)— and $C_{1-3}$-alkyl-O—C(=O)—; and wherein heteroaryl is defined as hereinbefore and hereinafter; preferably heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, benzofuranyl, indolyl and quinolinyl; and wherein each phenyl and heteroaryl group may be optionally substituted with one or more substituents L, wherein L is selected from the groups L-G1, L-G2 or L-G3 as defined hereinbefore and hereinafter.

In the embodiments with regard to $R^A$ as described hereinbefore and hereinafter it is to be understood that the double or triple bond in the groups $C_{3-n}$-alkenyl-O— and $C_{3-n}$-alkynyl-O— (with n being an integer) is preferably not conjugated with the O-atom of that group.

$R^A$-G6:

In another embodiment the group $R^A$ is selected from the group $R^A$-G6 consisting of F, Cl, Br, I, CN, methyl, ethyl, n-propyl, isopropyl, n-butyl, sec-butyl, tert-butyl, $F_3C$—, HO—$CH_2CH_2$—, cyclopropyl,

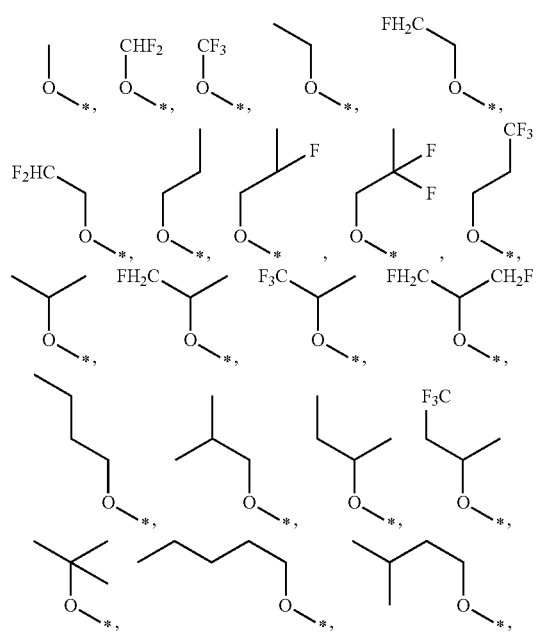

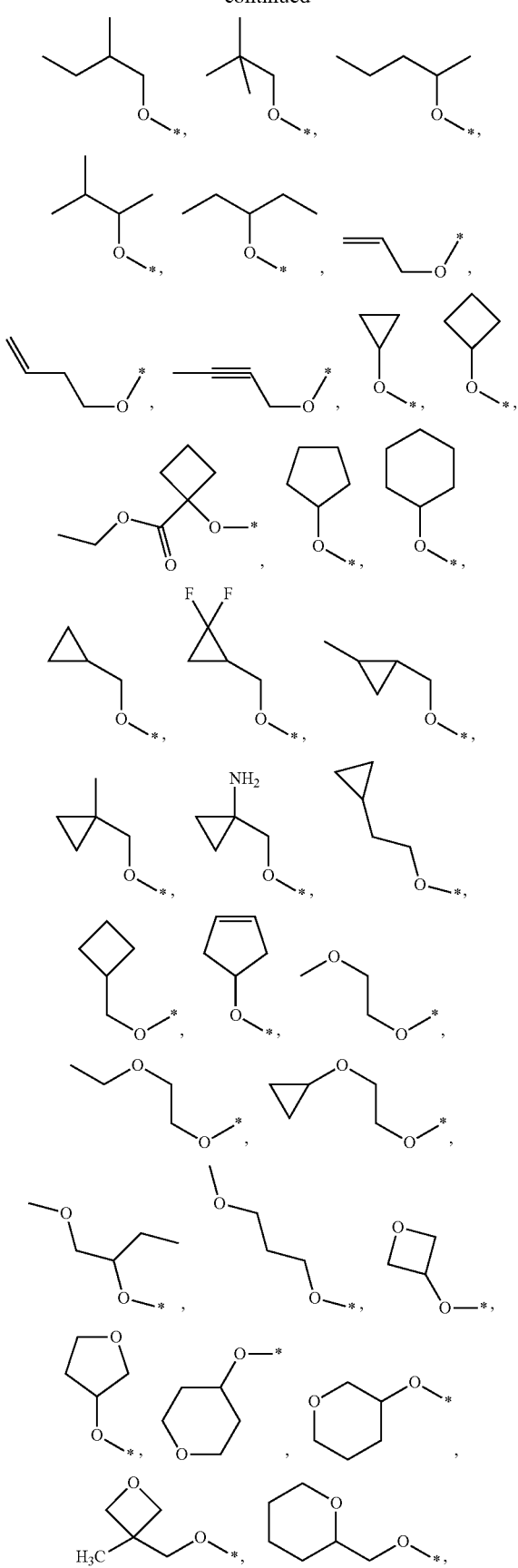
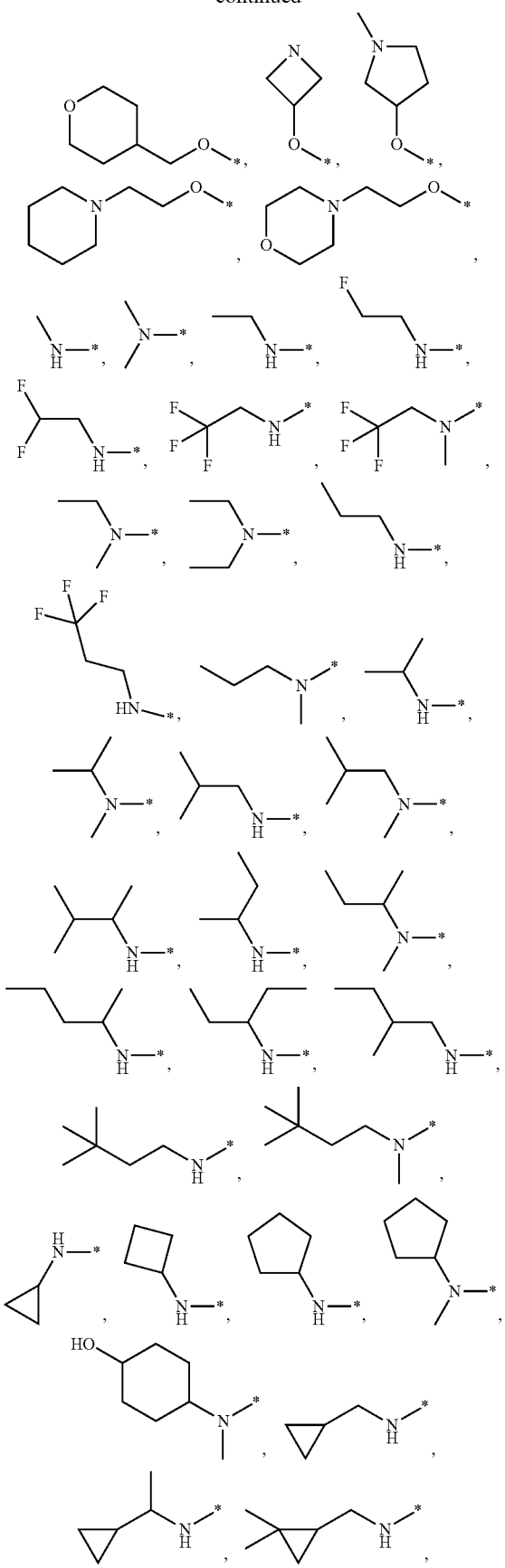

-continued
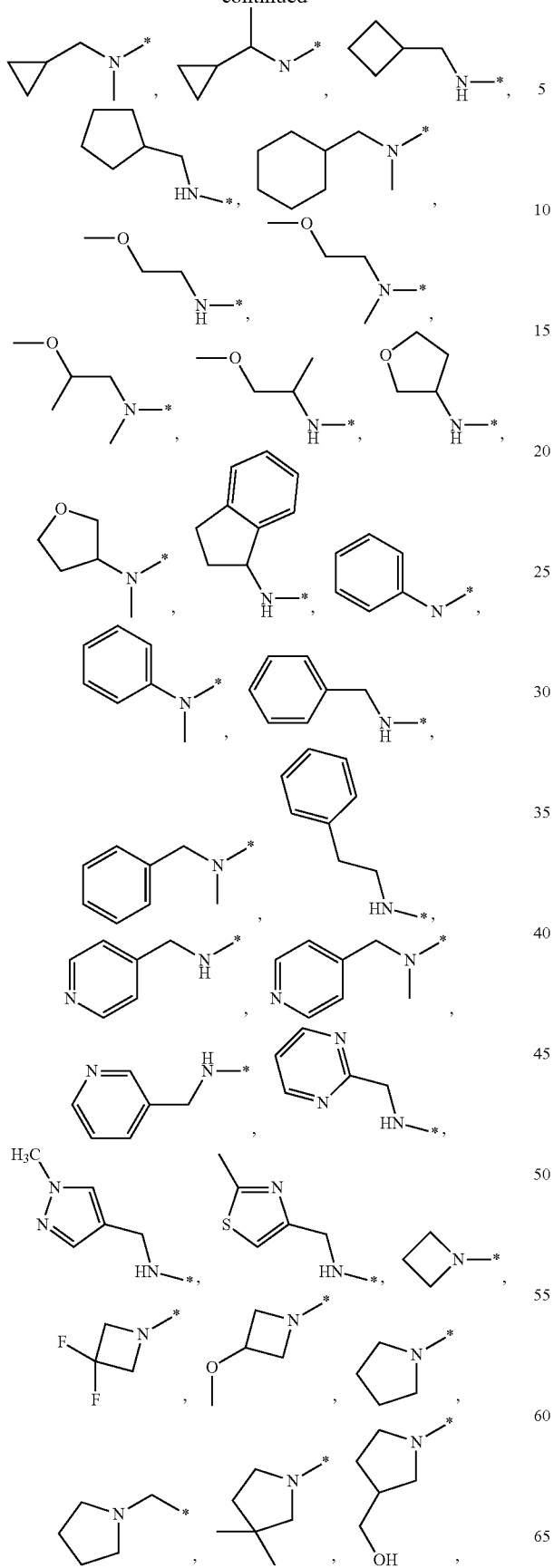
,
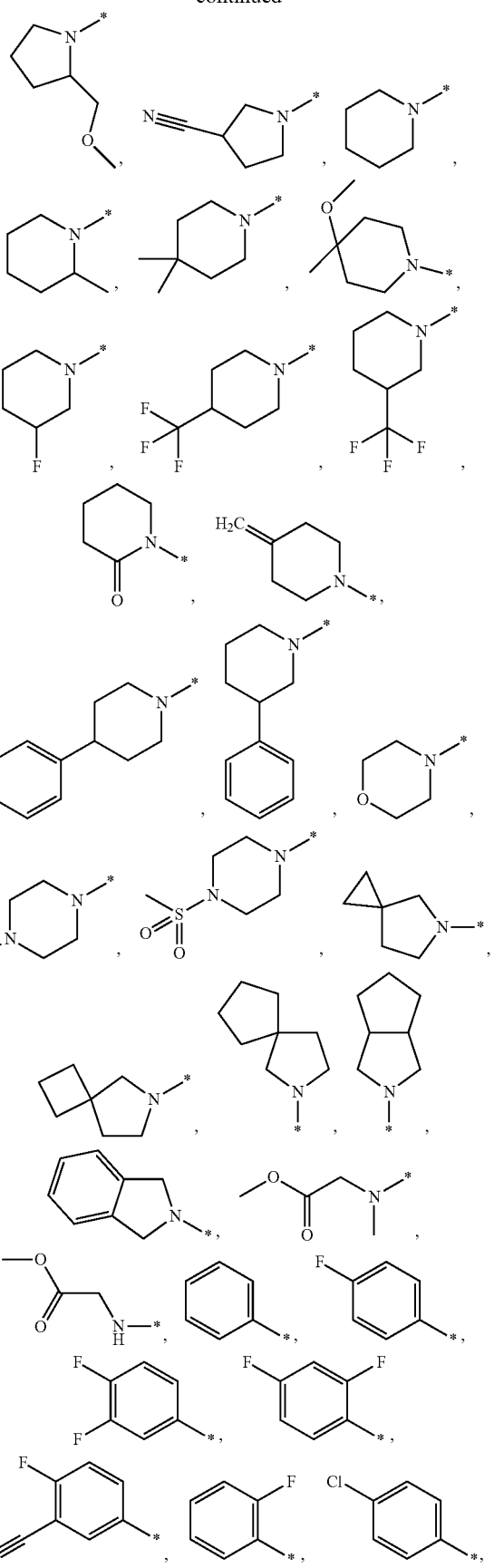

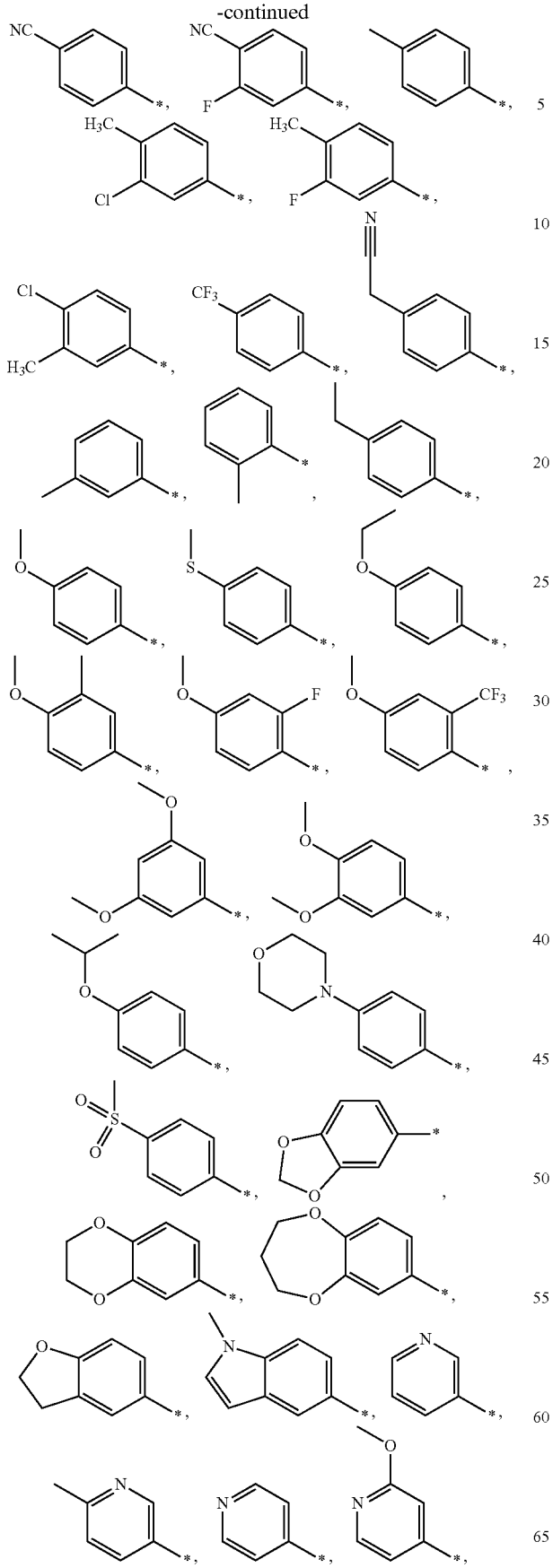
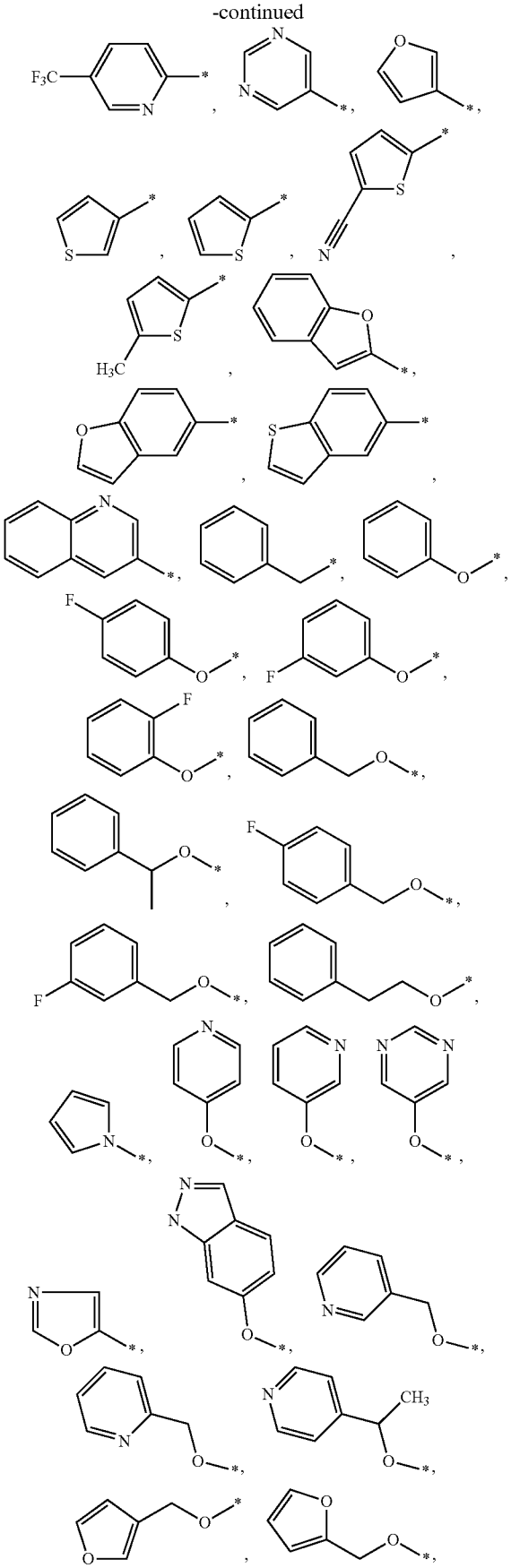

-continued

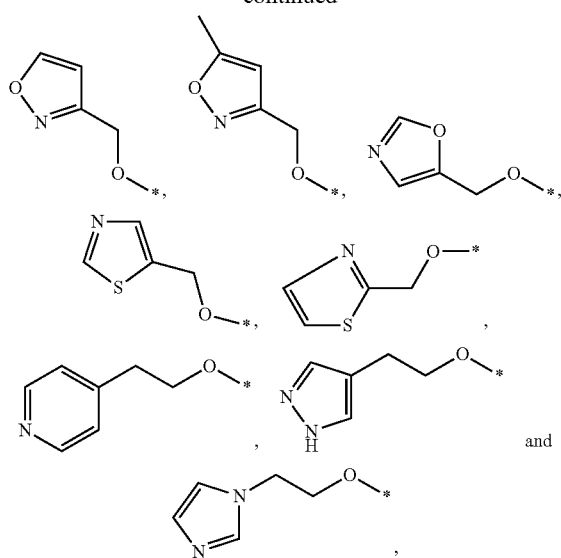

wherein each alkyl group and each cycloalkyl and heterocyclyl ring may be optionally substituted with one or more F atoms; and wherein each phenyl and heteroaryl ring may be optionally substituted with one or more substituents L.

$R^A$-G7:

In another embodiment the group $R^A$ is selected from the group $R^A$-G7 consisting of F, Cl, Br, CN, $F_3C$—,

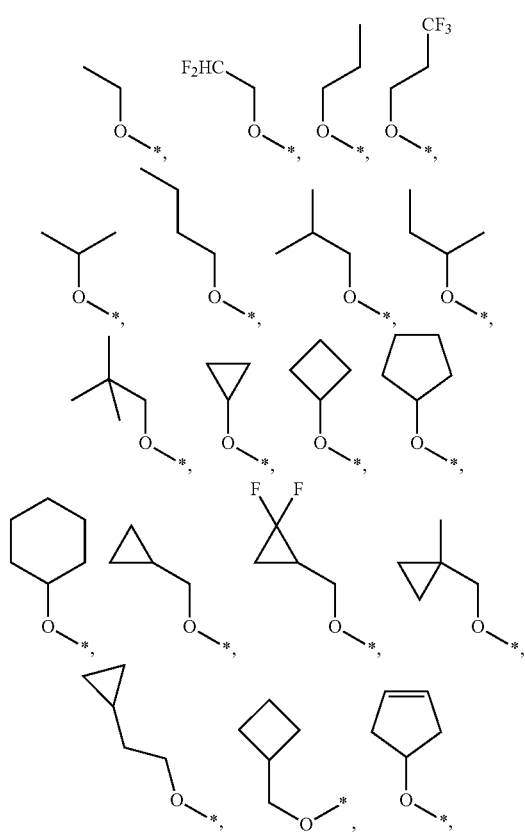

-continued

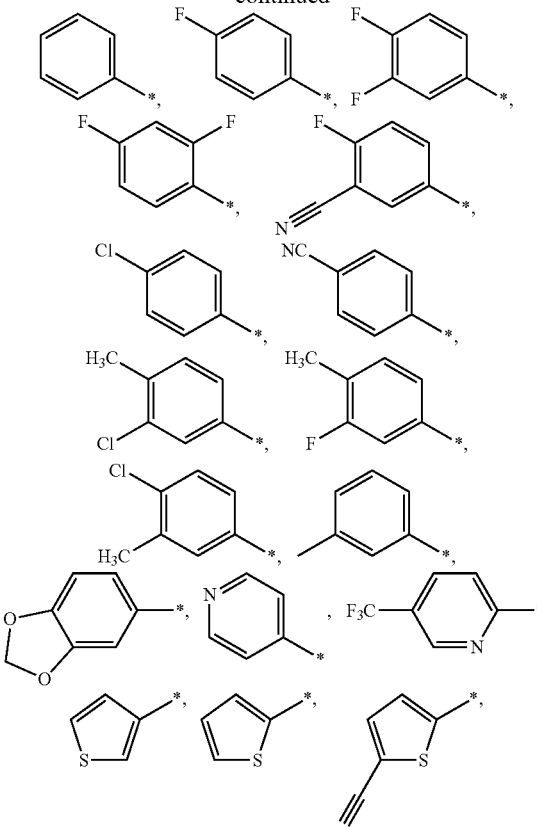

$R^C$ $R^C$-G1:

The group $R^C$ is preferably selected from the group $R^C$-G1 as defined hereinbefore and hereinafter.

$R^C$-G2:

In another embodiment the group $R^C$ is selected from the group $R^C$-G2 consisting of F, Cl, Br, CN, OH, $C_{1-4}$-alkyl-O—, $C_{3-6}$-cycloalkyl-O—, $C_{3-6}$-cycloalkyl-$CH_2$—O—, $H_2N$—, $(C_{1-3}$-alkyl)NH—, $(C_{1-3}$-alkyl$)_2$N—, $C_{1-3}$-alkyl-C(=O)—, $C_{1-3}$-alkyl-S(=O)$_2$—, HO—C(=O)— and $C_{1-4}$-alkyl-O—C(=O)—, wherein each alkyl or cycloalkyl may be optionally substituted with one or more substituents selected from F and OH.

$R^C$-G3:

In another embodiment the group $R^C$ is selected from the group $R^C$-G3 consisting of F, Cl, Br, CN, OH, $C_{1-3}$-alkyl-O—, $C_{3-6}$-cycloalkyl-O—, $H_2N$—, $(C_{1-3}$-alkyl)NH—, $(C_{1-3}$-alkyl$)_2$N—, $C_{1-3}$-alkyl-C(=O)—, $C_{1-3}$-alkyl-S(=O)$_2$—, HO—C(=O)— and $C_{1-3}$-alkyl-O—C(=O)—, wherein each alkyl may be optionally substituted with one or more F-atoms and/or may be substituted with OH.

$R^{N1}$ $R^{N1}$-G1:

The group $R^{N1}$ is preferably selected from the group $R^{N1}$-G1 as defined hereinbefore and hereinafter.

$R^{N1}$-G2:

In another embodiment the group $R^{N1}$ is selected from the group $R^{N1}$-G2 consisting of H, $C_{1-6}$-alkyl, $C_{3-10}$-carbocyclyl, $C_{3-10}$-carbocyclyl-$C_{1-3}$-alkyl, $C_{3-6}$-alkynyl, heterocyclyl, heterocyclyl-$C_{1-3}$-alkyl, phenyl, phenyl-$C_{1-3}$-alkyl, pyridyl, pyridyl-$C_{1-3}$-alkyl and oxazolyl-$C_{1-3}$-alkyl;

wherein carbocyclyl is defined as hereinbefore and hereinafter, or each carbocyclyl is preferably selected from $C_{3-7}$-cycloalkyl, indanyl and tetrahydrofuranyl; and wherein heterocyclyl is defined as hereinbefore and hereinafter, or each heterocyclyl is preferably selected from tetrahydrofuranyl, tetrahydropyranyl, pyrrolidinyl, piperidinyl, piperazinyl and morpholinyl; and wherein heteroaryl is defined as hereinbefore and hereinafter, or heteroaryl preferably denotes pyridyl, pyrazolyl and oxazolyl; and wherein each carbocyclyl and heterocyclyl, may be optionally substituted with one or more $C_{1-4}$-alkyl; and wherein each alkyl, carbocyclyl, heterocyclyl, including piperazinyl and morpholinyl, may be optionally substituted with one or more substituents selected from F; and wherein each alkyl, carbocyclyl, heterocyclyl, including piperazinyl and morpholinyl, may be optionally substituted with a substituent selected from OH, $C_{1-3}$-alkyl-O—, $H_2N$—, HO—C(=O)— and $C_{1-4}$-alkyl-O—C(=O)—; and wherein each phenyl and heteroaryl may be optionally substituted with one or more substituents L.

With regard to an alkenyl or alkynyl group, for example $R^{N1}$, attached to the N-atom of an amino-group it is to be understood that the double or triple bond is preferably not conjugated with the N-atom.

$R^{N1}$-G3:

In another embodiment the group $R^{N1}$ is selected from the group $R^{N1}$-G3 consisting of H, $C_{1-6}$-alkyl, $C_{3-6}$-cycloalkyl, $C_{3-6}$-cycloalkyl-$CH_2$—, heterocyclyl, heterocyclyl-$CH_2$—, phenyl, phenyl-$CH_2$—, pyridyl, pyridyl-$CH_2$—, pyrazolyl-$CH_2$— and oxazolyl-$C_{1-3}$-alkyl;

wherein heterocyclyl is defined as hereinbefore and hereinafter, or each heterocyclyl is preferably selected from tetrahydrofuranyl, tetrahydropyranyl, pyrrolidinyl and piperidinyl; and wherein each cycloalkyl and heterocyclyl may be optionally substituted with one or more $C_{1-4}$-alkyl; and wherein each alkyl, cycloalkyl and heterocyclyl may be optionally substituted with one or more substituents selected from F; and wherein each alkyl, cycloalkyl and heterocyclyl may be optionally substituted with a substituent selected from OH, $C_{1-3}$-alkyl-O—, $H_2N$—, HO—C(=O)— and $C_{1-4}$-alkyl-O—C(=O)—; and wherein each phenyl and heteroaryl, including pyridyl, pyrazolyl and oxazolyl, may be optionally substituted with one or more substituents L.

With regard to an alkenyl or alkynyl group, for example $R^{N1}$, attached to the N-atom of an amino-group it is to be understood that the double or triple bond is preferably not conjugated with the N-atom.

$R^{N2}$ $R^{N2}$-G1:

The group $R^{N2}$ is preferably selected from the group $R^{N2}$-G1 as defined hereinbefore and hereinafter.

$R^{N2}$-G2:

In another embodiment the group $R^{N2}$ is selected from the group $R^{N2}$-G2 consisting of H and $C_{1-4}$-alkyl.

$R^{Alk}$:

$R^{Alk}$-G1:

The group $R^{Alk}$ is preferably selected from the group $R^{Alk}$-G1 as defined hereinbefore and hereinafter.

$R^{Alk}$-G2:

In another embodiment the group $R^{Alk}$ is selected from the group $R^{Alk}$-G2 consisting of H and $C_{1-3}$-alkyl which may be substituted with one or more F atoms.

$Ar^2$:

$Ar^2$-G1:

The group $Ar^2$ is preferably selected from the group $Ar^2$-G1 as defined hereinbefore and hereinafter.

$Ar^2$-G2:

In another embodiment the group $Ar^2$ is selected from the group $Ar^2$-G2 consisting of phenyl, pyridyl, pyrimidinyl, pyridazinyl, pyrazinyl, furanyl, thienyl, pyrrolyl, imidazolyl, triazolyl, oxazolyl, isoxazolyl, pyrazolyl and thiazolyl, wherein all of the before mentioned groups may be optionally substituted with one or more substituents L.

$Ar^2$-G3:

In another embodiment the group $Ar^2$ is selected from the group $Ar^2$-G3 consisting of phenyl and pyridyl, wherein all of the before mentioned groups may be optionally substituted with one or more substituents L.

$Ar^2$-G4:

In another embodiment the group $Ar^2$ is selected from the group $Ar^2$-G4 consisting of:

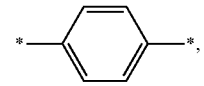

wherein the before mentioned group may be optionally substituted with one or more substituents L.

L:

L-G1:

The group L is preferably selected from the group L-G1 as defined hereinbefore and hereinafter.

L-G2:

In another embodiment the group L is selected from the group L-G2 consisting of F, Cl, Br, CN, OH, $C_{1-3}$-alkyl-, $C_{1-3}$-alkyl-O—, $C_{1-3}$-alkyl-S—, $H_2N$—, ($C_{1-3}$-alkyl)NH—, ($C_{1-3}$-alkyl)$_2$N— and heterocyclyl;

wherein each alkyl may be optionally substituted with one or more F-atoms and/or a substituent selected from OH, $C_{1-3}$-alkyl-O— and CN; and wherein heterocyclyl is defined as hereinbefore and hereinafter, or heterocyclyl preferably denotes a $C_{3-6}$-cycloalkyl ring wherein one or two —$CH_2$-groups are replaced by a group selected from —O—, —NH—, —N($C_{1-3}$-alkyl)-; and wherein two substituents L attached to an aryl or heteroaryl group may be linked to each other and form a $C_{2-5}$-alkylene bridging group in which 1 or 2-$CH_2$-groups may be replaced by a group independently of each other selected from O, NH and N($C_{1-4}$-alkyl)-, wherein the $C_{2-5}$-alkylene bridging group is optionally be substituted by 1 or 2 $C_{1-3}$-alkyl groups.

L-G3:

In another embodiment the group L is selected from the group L-G3 consisting of F, Cl, CN, OH, $C_{1-3}$-alkyl-, $C_{1-3}$-alkyl-O—, $C_{1-3}$-alkyl-S—, $H_2N$—, ($C_{1-3}$-alkyl)NH—, ($C_{1-3}$-alkyl)$_2$N— and heterocyclyl;

wherein each alkyl may be optionally substituted with one or more F-atoms and/or a substituent selected from OH, $CH_3$—O— and CN; and wherein heterocyclyl is defined as hereinbefore and hereinafter or heterocyclyl preferably denotes a $C_{3-6}$-cycloalkyl ring wherein one or two —$CH_2$-groups are replaced by a group selected from —O—, —NH—, —N($C_{1-3}$-alkyl)-; and wherein two substituents L attached to adjacent C-atoms of an aryl or heteroaryl group may be linked to each other and form a —$CH_2$—$CH_2$—O—, —O—$CH_2$—$CH_2$—O— or —O—$CH_2$—O— bridging group which is optionally substituted by 1 or 2 $CH_3$— groups.

X:

X-G1:

The group X is preferably selected from the group X-G1 as defined hereinbefore and hereinafter, in particular from a group consisting of a straight chain $C_{1-3}$-alkylene group which may be optionally substituted with 1, 2 or 3 groups selected from $C_{1-3}$-alkyl and $C_{1-3}$-alkyl-O—$C_{1-3}$-alkyl; even more preferably optionally substituted with 1 or 2 groups independently selected from methyl, ethyl or methoxymethyl; and wherein two alkyl substituents may be connected with each other and together form a $C_{1-5}$-alkylene bridging group in which 1 or 2 $CH_2$-groups may be replaced by O, S, NH or N($C_{1-4}$-alkyl)-, wherein the $C_{1-5}$-alkylene bridging group may optionally be substituted by one or two $C_{1-3}$-alkyl groups.

X-G2:

In another embodiment the group X is selected from the group X-G2 consisting of:

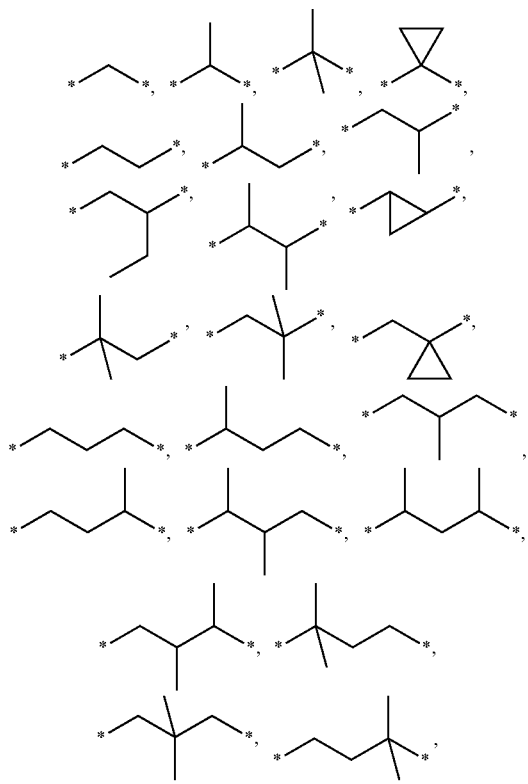

even more preferably selected from the group X-G3 consisting of:

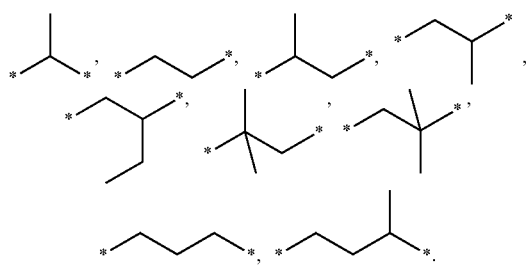

X-GC1:

According an embodiment X-GC1 the group X is —$CH_2$— which may be optionally substituted with one or two $C_{1-3}$-alkyl groups, preferably with one or two groups independently selected from methyl and ethyl, and wherein two alkyl substituents may be connected with each other and together form a $C_{2-5}$-alkylene bridging group in which 1 or 2 $CH_2$-groups may be replaced by O, S, NH or N($C_{1-4}$-alkyl)-, wherein the $C_{1-5}$-alkylene bridging group may optionally be substituted by one or two $C_{1-3}$-alkyl groups.

Examples of this embodiment are:

X-GC1a:

According an embodiment X-GC1a the group X is

embracing

and

A preferred example of the group X-GC1 is

wherein the asterisk to the right hand side indicates the bond which is connected to the N atom of the core structure of the formula (I) and the asterisk to the left hand side indicates the bond which is connected to $Ar^2$.

X-GC2:

According to another embodiment X-GC2 the group X is —$CH_2$—$CH_2$— which may be optionally substituted with one or more $C_{1-3}$-alkyl groups, preferably with one or two groups independently selected from methyl and ethyl, and wherein two alkyl substituents may be connected with each other and together form a $C_{1-5}$-alkylene bridging group in which 1 or 2 $CH_2$-groups may be replaced by O, S, NH or $N(C_{1-4}$-alkyl)-, wherein the $C_{1-5}$-alkylene bridging group may optionally be substituted by one or two $C_{1-3}$-alkyl groups.

Examples of this embodiment are:

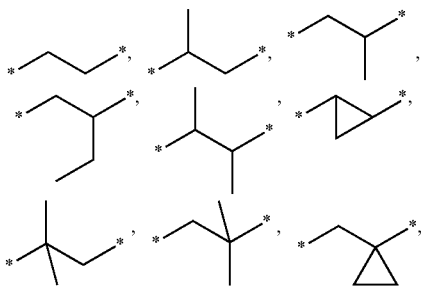

X-GC3:
According another embodiment X-GC3 the group X is $-CH_2-CH_2-CH_2-$ which may be optionally substituted with one or more $C_{1-3}$-alkyl groups, preferably with one or two groups independently selected from methyl and ethyl, and wherein two alkyl substituents may be connected with each other and together form a $C_{1-5}$-alkylene bridging group in which 1 or 2 $CH_2$-groups may be replaced by O, S, NH or $N(C_{1-4}$-alkyl)-, wherein the $C_{1-5}$-alkylene bridging group may optionally be substituted by one or two $C_{1-3}$-alkyl groups.

Examples of this embodiment are:

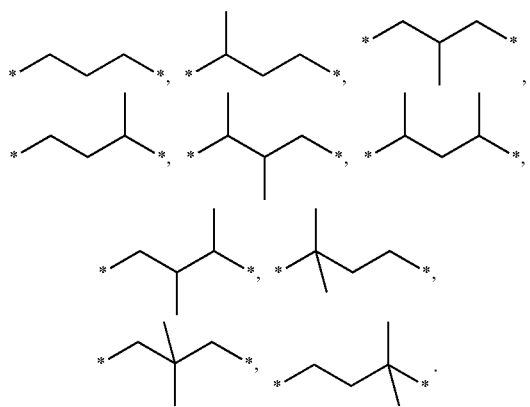

Y:
Y-G1:
The group Y is preferably selected from the group Y-G1 as defined hereinbefore and hereinafter.
Y-G2:
In another embodiment the group Y is selected from the group Y-G2 consisting of $-C(=O)-$ and $-S(=O)_2-$.
Y-G3:
In another embodiment the group Y is selected from the group Y-G3 consisting of $-S(=O)_2-$.
Y-G4:
In another embodiment the group Y is selected from the group Y-G4 consisting of $-C(=O)-$.

$R^N$:
$R^N$-G1:
The group $R^N$ is preferably selected from the group $R^N$-G1 as defined hereinbefore and hereinafter.
$R^N$-G2:
In another embodiment the group $R^N$ is selected from the group $R^N$-G2 consisting of H and methyl.
$R^N$-G3:
In another embodiment the group $R^N$ is selected from the group $R^N$-G3 consisting of H.

T:
T-G1:
The group T is preferably selected from the group T-G1 as defined hereinbefore and hereinafter.
T-G2:
In another embodiment the group T is selected from the group T-G2 consisting of $C_{1-6}$-alkyl, $C_{2-6}$-alkenyl, $C_{2-6}$-alkynyl, $C_{3-7}$-cycloalkyl, $C_{3-7}$-cycloalkyl-$C_{1-3}$-alkyl, $C_{1-6}$-alkyl-O—, $C_{3-7}$-cycloalkyl-O—, $C_{3-7}$-cycloalkyl-$C_{1-3}$-alkyl-O—, $C_{1-6}$-alkyl-S—, $C_{3-7}$-cycloalkyl-S—, $C_{3-7}$-cycloalkyl-$C_{1-3}$-alkyl-S—, $C_{1-4}$-alkyl-C(=O)—, $C_{1-4}$-alkyl-S(=O)$_2$—, $R^{T1}R^{T2}$—N—, $R^{T1}R^{T2}$—N—$C_{1-3}$-alkyl-, $R^{T1}R^{T2}$—N—CO—, $C_{1-4}$-alkyl-C(=O)—$R^{T2}$N—$C_{1-3}$-alkyl, heterocyclyl, phenyl and heteroaryl;
wherein in each cycloalkyl and heterocyclyl a $CH_2$-group may optionally be replaced by —C(=O)—; and
wherein each cycloalkyl and heterocyclyl may be optionally substituted with one or more $C_{1-4}$-alkyl, which may be optionally substituted with one or more substituents $R^C$; and
wherein each alkyl, cycloalkyl and heterocyclyl may be optionally substituted with one or more substituents $R^C$; and
wherein $R^C$ is selected from the group consisting of $R^C$-G1, $R^C$-G2 or $R^C$-G3 as defined hereinbefore and hereinafter,
wherein $R^{T1}$ is selected from the group $R^{T1}$-G1 or $R^{T1}$-G2 as defined as hereinbefore and hereinafter; and
wherein $R^{T2}$ is selected from the group $R^{T2}$-G1 or $R^{T2}$-G2 as defined as hereinbefore and hereinafter; and
wherein heterocyclyl is defined as hereinbefore and hereinafter; preferably heterocyclyl is azetidinyl, pyrrolidinyl, piperidinyl, oxetanyl, tetrahydrofuranyl or tetrahydropyranyl; and
wherein heteroaryl is selected from the group consisting of phenyl, pyridyl, pyrimidinyl, pyridazinyl, pyrazinyl, furanyl, thienyl, pyrrolyl, imidazolyl, pyrazolyl, triazolyl, oxazolyl, isoxazolyl, thiazolyl and isothiazolyl; and
wherein each aryl and heteroaryl group may be optionally substituted with one or more substituents L.
T-G3:
In another embodiment the group T is selected from the group T-G3 consisting of $C_{1-4}$-alkyl, $C_{3-6}$-cycloalkyl, $C_{1-4}$-alkyl-O—, $R^{T1}R^{T2}$—N—, heterocyclyl, phenyl and heteroaryl,
wherein in each cycloalkyl and heterocyclyl a $CH_2$-group may optionally be replaced by —C(=O)—; and
wherein each cycloalkyl and heterocyclyl may be optionally substituted with one or more $C_{1-4}$-alkyl, which may be optionally substituted with one or more substituents $R^C$; and
wherein each alkyl, cycloalkyl and heterocyclyl may be optionally substituted with one or more substituents $R^C$; and
wherein $R^C$ is selected from the group consisting of $R^C$-G1, $R^C$-G2 or $R^C$-G3 as defined hereinbefore and hereinafter; and wherein $R^{T1}$ is selected from the group $R^{T1}$-G1 or $R^{T1}$-G2 as defined as hereinbefore and hereinafter; preferably $R^{T1}$ denotes H, $C_{1-4}$-alkyl, $C_{3-6}$-cycloalkyl or $C_{3-6}$-cycloalkyl-$C_{1-3}$-alkyl; and wherein $R^{T2}$ is selected from the group $R^{T2}$-G1 or $R^{T2}$-G2 as defined as hereinbefore and hereinafter; preferably $R^{T2}$ denotes H or $C_{1-4}$-alkyl; and wherein heterocyclyl is defined as hereinbefore and hereinafter, preferably heterocyclyl is selected from the group consisting of

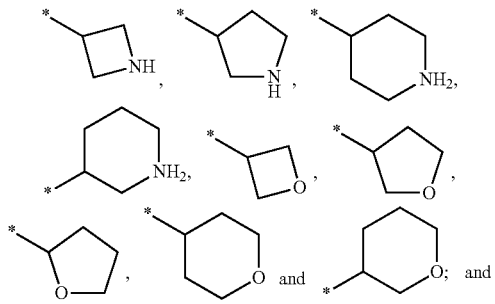

wherein heteroaryl is selected from the group consisting of phenyl, pyridyl, pyrimidinyl, pyridazinyl, pyrazinyl, furanyl, thienyl, pyrrolyl, imidazolyl, pyrazolyl, triazolyl, oxazolyl, isoxazolyl and thiazolyl; and wherein each heteroaryl group may be optionally substituted with one or more substituents L.

T-G4:

In another embodiment the group T is selected from the group T-G4 consisting of $C_{1-3}$-alkyl, $C_{3-5}$-cycloalkyl, $C_{1-3}$-alkyl-O— and $R^{T1}R^{T2}$—N—;

wherein each cycloalkyl may be optionally substituted with one or more $C_{1-3}$-alkyl; and wherein $R^{T1}$ and $R^{T2}$ are independently of each other selected from H and $C_{1-3}$-alkyl.

Preferred examples of the group T-G4 are $H_3C$—, $H_3C$—O—, $(H_3C)_2N$—,

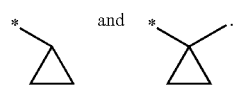

T-G5:

In another embodiment the group T is selected from the group T-G5 consisting of $H_3C$—, $H_2FC$—, $HF_2C$—, $F_3C$—, NC—$CH_2$—, $F_3C$—$CH_2$—, $(H_3C)_2CF$—, $H_5C_2$—, n-propyl, i-propyl, n-butyl, i-butyl, $H_3C$—$(H_3CO)CH$—, $H_3C$—$(HO)CH$—, NC—$CH_2$—, NC—$CH_2$—$CH_2$—, cyclopropyl, cyclobutyl, cyclopropyl-$CH_2$—,

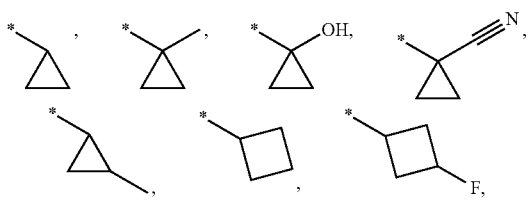

-continued

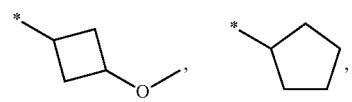

HO—$CH_2$—, HO—$CH_2$—$CH_2$—, $(CH_3)_2CH$—(HO)CH—, $H_3C$—(HO)CH—, $H_3C$—O—$CH_2$—, $H_3C$—O—$CH_2$—$CH_2$—, $H_3C$—O—,

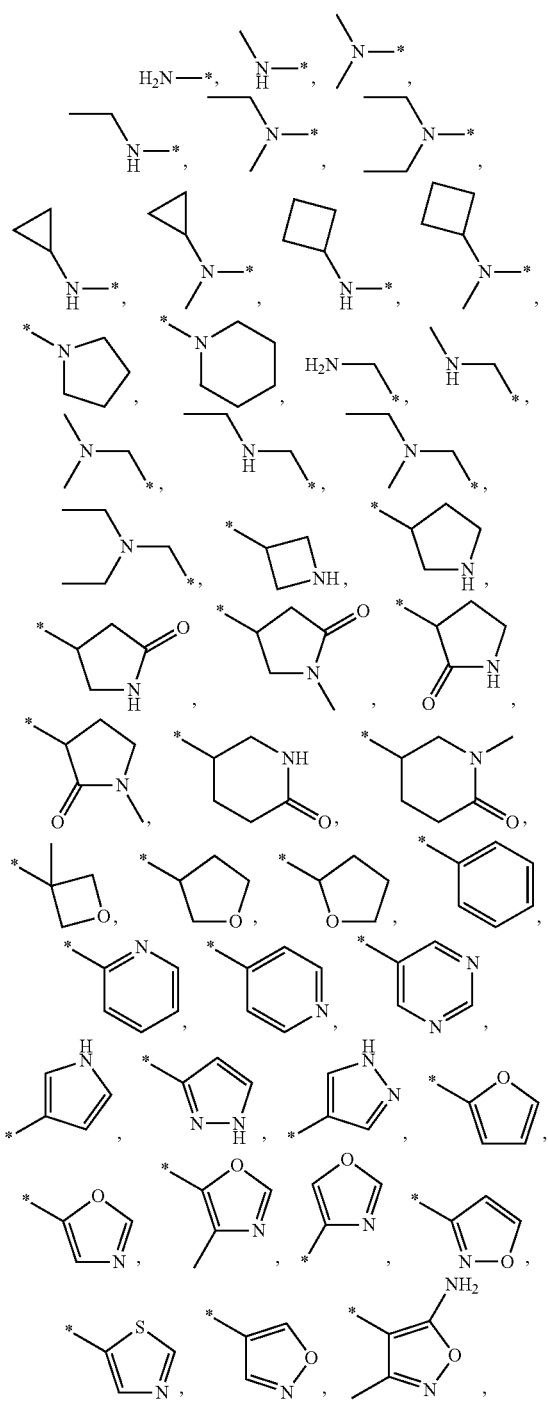

-continued

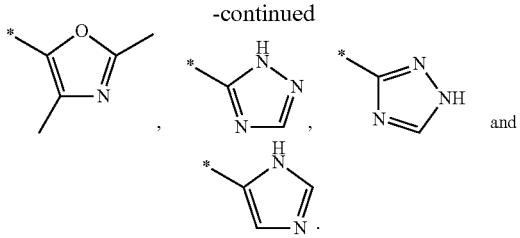

T-G6:

In another embodiment the group T is selected from the group T-G6 consisting of H$_3$C—, F$_3$C—, H$_3$C—CH$_2$—, H$_3$C—O—, (H$_3$C)$_2$N—,

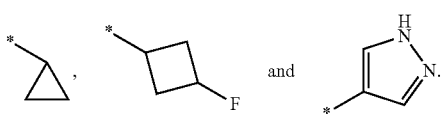

T-G7:

In another embodiment the group T is selected from the group T-G7 consisting of H$_3$C—, (H$_3$C)$_2$N— and cyclopropyl.

(T-R$^N$):

(T-R$^N$)-G1:

In an embodiment the groups T and R$^N$ are connected with each other and together form a group which is preferably selected from the group (T-R$^N$)-G1 as defined hereinbefore and hereinafter.

(T-R$^N$)-G2:

In another embodiment the groups T and R$^N$ are connected with each other such that the group

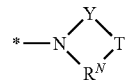

is selected from the group (T-R$^N$)-G2 consisting of:

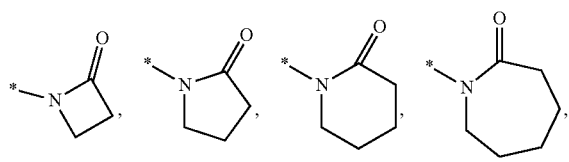

all of which may be optionally substituted with one or more substituents selected from F, Cl, Br, OH, CN, C$_{1-4}$-alkyl, C$_{3-6}$-cycloalkyl, C$_{3-6}$-cycloalkyl-C$_{1-3}$-alkyl, C$_{1-4}$-alkyl-O—, C$_{3-6}$-cycloalkyl-O—, C$_{3-6}$-cycloalkyl-C$_{1-3}$-alkyl-O—, H$_2$N—, (C$_{1-4}$-alkyl)NH—, (C$_{1-4}$-alkyl)$_2$N—, C$_{1-4}$-alkyl-C(=O)—, C$_{1-4}$-alkyl-S(=O)$_2$—, HO—C(=O)— and C$_{1-4}$-alkyl-O—C(=O)—, wherein each alkyl or cycloalkyl may be optionally substituted with one or more substituents selected from F, and wherein each alkyl or cycloalkyl may be optionally substituted with a substituent selected from Cl, Br, OH, CN, C$_{1-3}$-alkyl-O—, C$_{3-6}$-cycloalkyl-O—, C$_{3-6}$-cycloalkyl-C$_{1-3}$-alkyl-O—, H$_2$N—, (C$_{1-3}$-alkyl)NH—, (C$_{1-3}$-alkyl)$_2$N—, C$_{1-4}$-alkyl-C(=O)—, C$_{1-4}$-alkyl-S(=O)$_2$—, HO—C(=O)— and C$_{1-4}$-alkyl-O—C(=O)—.

(T-R$^N$)-G3:

In another embodiment the groups T and R$^N$ are connected with each other such that the group is selected from the group (T-R$^N$)-G3 consisting of:

all of which may be substituted with one or more F atoms and/or C$_{1-3}$-alkyl.

R$^{T1}$

R$^{T1}$-G1:

The group R$^{T1}$ is preferably selected from the group R$^{T1}$-G1 consisting of H, C$_{1-6}$-alkyl, C$_{3-6}$-cycloalkyl, C$_{3-6}$-cycloalkyl-C$_{1-3}$-alkyl, phenyl and pyridyl, wherein each cycloalkyl may be optionally substituted with one or more C$_{1-4}$-alkyl, and wherein each alkyl and cycloalkyl may be optionally substituted with one or more substituents selected from F, and wherein each alkyl and cycloalkyl may be optionally substituted with a substituent selected from OH, C$_{1-3}$-alkyl-O—, C$_{1-3}$-alkyl-C(=O)—, HO—C(=O)— and C$_{1-4}$-alkyl-O—C(=O)—; and wherein each phenyl and pyridyl group may be optionally substituted with one or more substituents L.

R$^{T1}$-G2:

In another embodiment the group R$^{T1}$ is selected from the group R$^{T1}$-G2 consisting of methyl, ethyl, n-propyl, isopropyl, HOOC—CH$_2$—, H$_3$C—CO—, phenyl, pyridinyl, wherein the groups phenyl and pyridyl may be substituted with one or more substituents L.

R$^{T2}$

R$^{T2}$-G1:

The group R$^{T2}$ is preferably selected from the group R$^{T2}$-G1 consisting of H and C$_{1-4}$-alkyl.

R$^{T2}$-G2:

In another embodiment the group R$^{T2}$ is selected from the group R$^{T2}$-G2 consisting of H, methyl, ethyl, n-propyl and isopropyl.

Examples of preferred subgeneric embodiments according to the present invention are set forth in the following table, wherein each substituent group of each embodiment is defined according to the definitions as set forth hereinbefore and wherein all other substituents of the formula (I) are defined according to the definitions as set forth hereinbefore:

| Embodiment | Ar$^1$ | R$^4$ | Ar$^2$ | X | Y | R$^N$ and T |
|---|---|---|---|---|---|---|
| E-1 | Ar$^1$-G1 | R$^4$-G1 | Ar$^2$-G1 | X-G1 | Y-G1 | R$^N$-G1, T-G1 or (T-R$^N$)-G1 |
| E-2 | Ar$^1$-G2 | R$^4$-G2 | Ar$^2$-G2 | X-G1 | Y-G1 | R$^N$-G1, T-G2 or (T-R$^N$)-G2 |

| Embodiment | Ar¹ | R⁴ | Ar² | X | Y | R^N and T |
|---|---|---|---|---|---|---|
| E-3 | Ar¹-G3 | R⁴-G3 | Ar²-G2 | X-G1 | Y-G1 | R^N-G1, T-G2 or (T-R^N)-G2 |
| E-4 | Ar¹-G4 | R⁴-G5 | Ar²-G3 | X-G1 | Y-G1 | R^N-G1, T-G2 |
| E-5 | Ar¹-G4 | R⁴-G5 | Ar²-G3 | X-G1 | Y-G1 | (T-R^N)-G2 |
| E-6 | Ar¹-G6 | R⁴-G4 | Ar²-G3 | X-G1 | Y-G1 | R^N-G1, T-G3 or (T-R^N)-G2 |
| E-7 | Ar¹-G7 | R⁴-G4 | Ar²-G3 | X-G1 | Y-G1 | R^N-G1, T-G3 or (T-R^N)-G2 |
| E-8 | Ar¹-G6 | R⁴-G5 | Ar²-G4 | X-G1 | Y-G1 | R^N-G1, T-G3 or (T-R^N)-G2 |
| E-9 | Ar¹-G7 | R⁴-G5 | Ar²-G4 | X-G1 | Y-G1 | R^N-G1, T-G3 or (T-R^N)-G2 |
| E-10 | Ar¹-G5 | R⁴-G6 | Ar²-G3 | X-G2 | Y-G1 | R^N-G1, T-G4 or (T-R^N)-G3 |
| E-11 | Ar¹-G1 | R⁴-G1 | Ar²-G1 | X-GC1 | —C(=O)— | R^N-G1, T-G1 or (T-R^N)-G1 |
| E-12 | Ar¹-G1 | R⁴-G1 | Ar²-G1 | X-GC2 | —C(=O)— | R^N-G1, T-G1 or (T-R^N)-G1 |
| E-13 | Ar¹-G1 | R⁴-G1 | Ar²-G1 | X-GC3 | —C(=O)— | R^N-G1, T-G1 or (T-R^N)-G1 |
| E-14 | Ar¹-G6 | R⁴-G4 | Ar²-G3 | X-GC1 | —C(=O)— | R^N-G1, T-G3 or (T-R^N)-G2 |
| E-15 | Ar¹-G6 | R⁴-G4 | Ar²-G3 | X-GC2 | —C(=O)— | R^N-G1, T-G3 or (T-R^N)-G2 |
| E-16 | Ar¹-G6 | R⁴-G4 | Ar²-G3 | X-GC3 | —C(=O)— | R^N-G1, T-G3 or (T-R^N)-G2 |
| E-17 | Ar¹-G7 | R⁴-G4 | Ar²-G3 | X-GC1 | —C(=O)— | R^N-G1, T-G3 or (T-R^N)-G2 |
| E-18 | Ar¹-G7 | R⁴-G4 | Ar²-G3 | X-GC2 | —C(=O)— | R^N-G1, T-G3 or (T-R^N)-G2 |
| E-19 | Ar¹-G7 | R⁴-G4 | Ar²-G3 | X-GC3 | —C(=O)— | R^N-G1, T-G3 or (T-R^N)-G2 |

The following preferred embodiments of compounds of the formula (I) are described using generic formulas (I.1) to (I.7a), wherein any tautomers and stereoisomers, solvates, hydrates and salts thereof, in particular the pharmaceutically acceptable salts thereof, are encompassed.

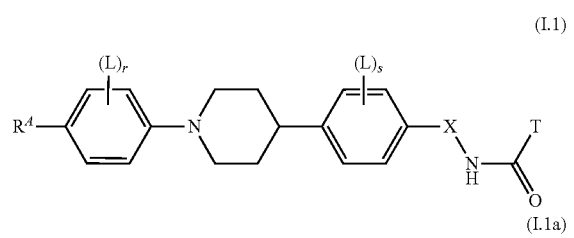

(I.1)

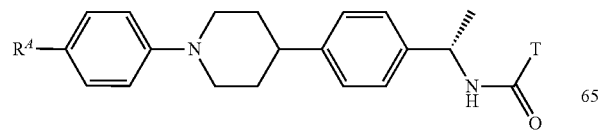

(I.1a)


(I.1b)

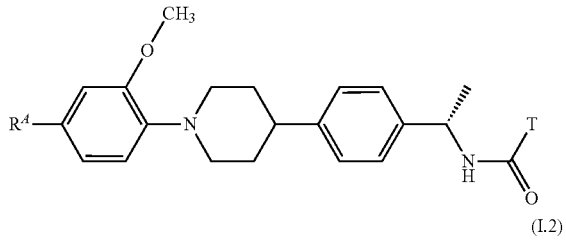

(I.1c)

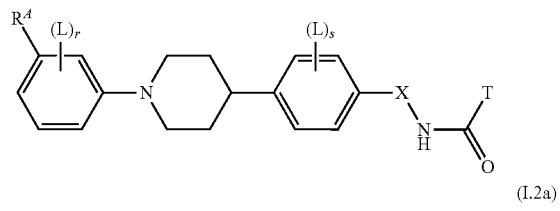

(I.2)

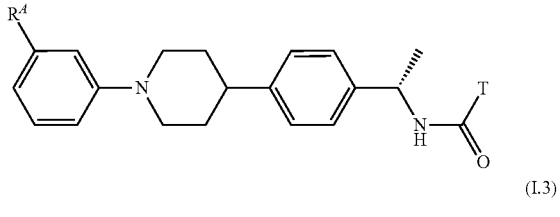

(I.2a)

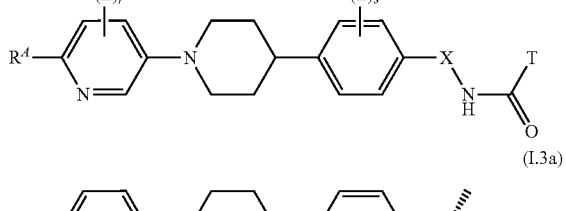

(I.3)

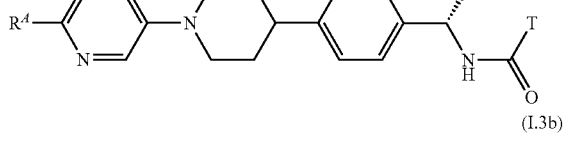

(I.3a)

(I.3b)

(I.4)

-continued

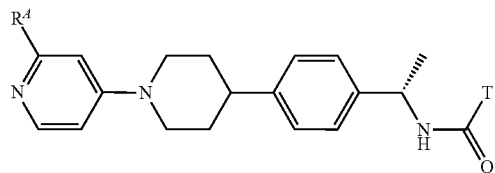
(I.4a)

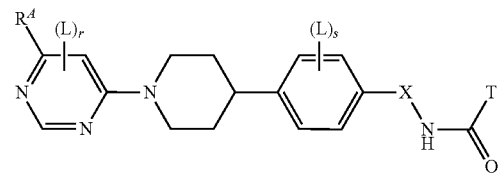
(I.5)

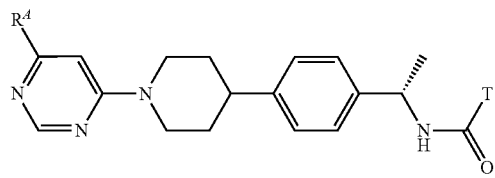
(I.5a)

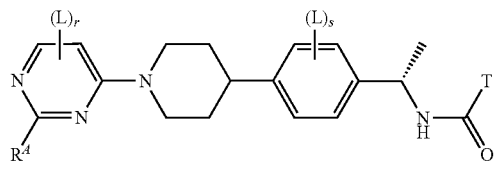
(I.5b)

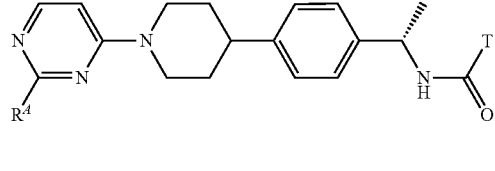
(I.5c)

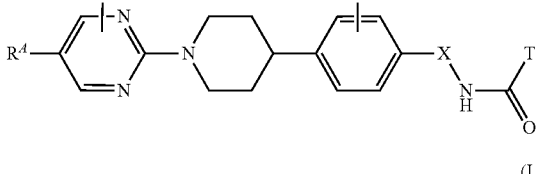
(I.6)

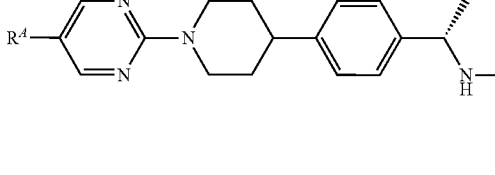
(I.6a)

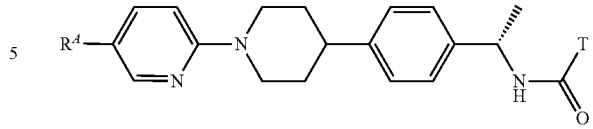
(I.7)

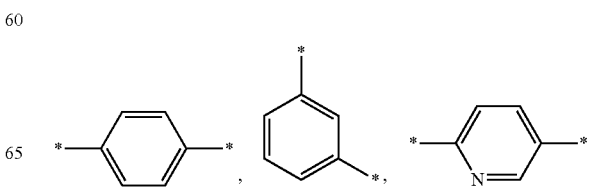
(I.7a)

wherein in each of the above formulas (I.1) to (I.7a) the groups $R^A$, L, X and T are defined as hereinbefore and hereinafter; and r is 0, 1 or 2; and s is 0, 1 or 2.

Preferred embodiments of the above formulas (I.1) to (I.7a) according to the present invention are set forth in the following table, wherein each group $R^A$, X, T, L of each embodiment is defined according to the definitions set forth hereinbefore and wherein all other substituents of the formula (I) are defined according to the definitions set forth hereinbefore and r is 0, 1 or 2 and s is 0, 1 or 2:

| Embodiment | Formula | $R^A$ | X | T | L |
|---|---|---|---|---|---|
| E-A | (I.1) | $R^A$-G2 | X-G1 | T-G2 | L-G2 |
| E-B | (I.1) | $R^A$-G2a | X-GC1 | T-G3 | L-G3 |
| E-C | (I.1) | $R^A$-G5a | X-GC1 | T-G4 | L-G3 |
| E-D | (I.1a) | $R^A$-G5a | — | T-G4 | — |
| E-E | (I.1b) | $R^A$-G5a | — | T-G4 | — |
| E-Ea | (I-1c) | $R^A$-G5a | — | T-G4 | — |
| E-F | (I.2) | $R^A$-G2 | X-G1 | T-G2 | L-G2 |
| E-G | (I.2) | $R^A$-G2a | X-GC1 | T-G3 | L-G3 |
| E-H | (I.2) | $R^A$-G5a | X-GC1 | T-G4 | L-G3 |
| E-I | (I.2a) | $R^A$-G5a | — | T-G4 | — |
| E-J | (I.3) | $R^A$-G2 | X-G1 | T-G2 | L-G2 |
| E-K | (I.3) | $R^A$-G2a | X-GC1 | T-G3 | L-G3 |
| E-L | (I.3) | $R^A$-G5a | X-GC1 | T-G4 | L-G3 |
| E-M | (I.3a) | $R^A$-G5a | — | T-G4 | — |
| E-Ma | (I.3b) | $R^A$-G5a | — | T-G4 | — |
| E-N | (I.4) | $R^A$-G2 | X-G1 | T-G2 | L-G2 |
| E-O | (I.4) | $R^A$-G2a | X-GC1 | T-G3 | L-G3 |
| E-P | (I.4) | $R^A$-G5a | X-GC1 | T-G4 | L-G3 |
| E-Q | (I.4a) | $R^A$-G5a | — | T-G4 | — |
| E-R | (I.5) | $R^A$-G2 | X-G1 | T-G2 | L-G2 |
| E-S | (I.5) | $R^A$-G2a | X-GC1 | T-G3 | L-G3 |
| E-T | (I.5) | $R^A$-G5a | X-GC1 | T-G4 | L-G3 |
| E-U | (I.5a) | $R^A$-G5a | — | T-G4 | — |
| E-Ua | (I.15b) | $R^A$-G5a | — | T-G4 | L-G3 |
| E-Ub | (I-5c) | $R^A$-G5a | — | T-G4 | — |
| E-V | (I.6) | $R^A$-G2 | X-G1 | T-G2 | L-G2 |
| E-W | (I.6) | $R^A$-G2b | X-GC1 | T-G3 | L-G3 |
| E-X | (I.6) | $R^A$-G5b | X-GC1 | T-G4 | L-G3 |
| E-Y | (I.6a) | $R^A$-G5b | — | T-G4 | — |
| E-Za | (I.7) | $R^A$-G2a | X-GC1 | T-G3 | L-G3 |
| E-Zb | (I.7) | $R^A$-G5a | X-GC1 | T-G4 | L-G3 |
| E-Zc | (I.7a) | $R^A$-G5a | — | T-G4 | — | including any tautomers and stereoisomers, solvates, hydrates and salts thereof, in particular the pharmaceutically acceptable salts thereof.

One preferred embodiment concerns compounds of formula (I), wherein $Ar^1$ is selected from the group consisting of

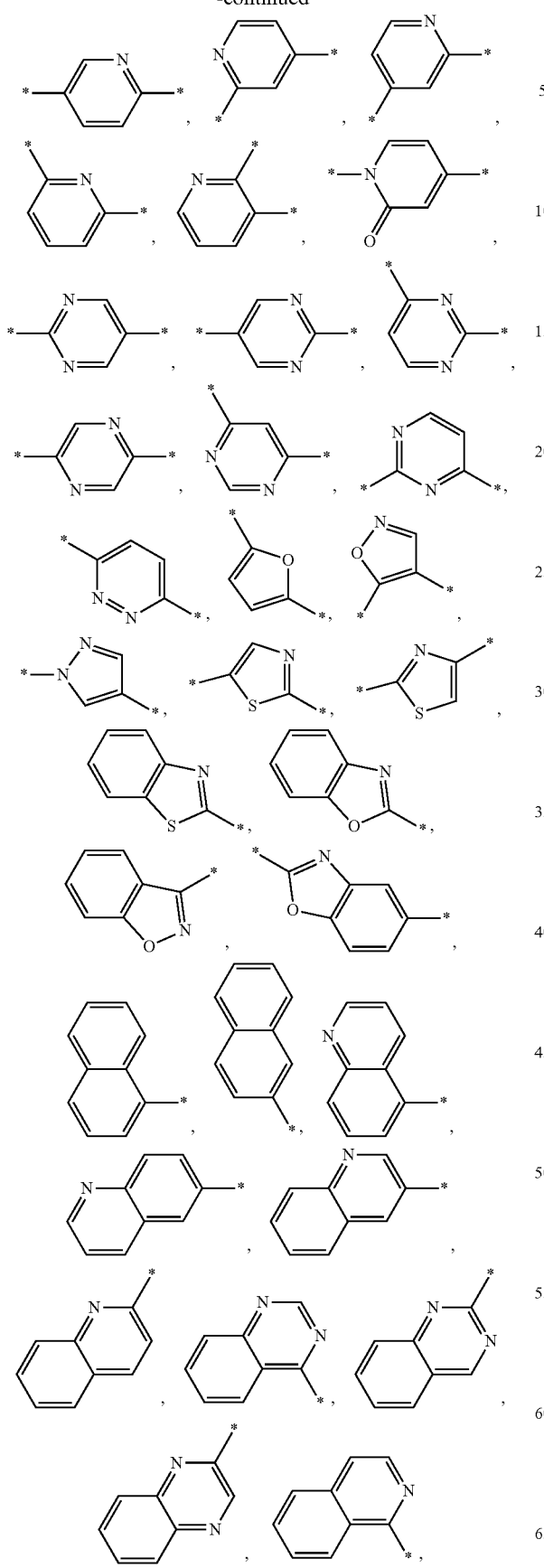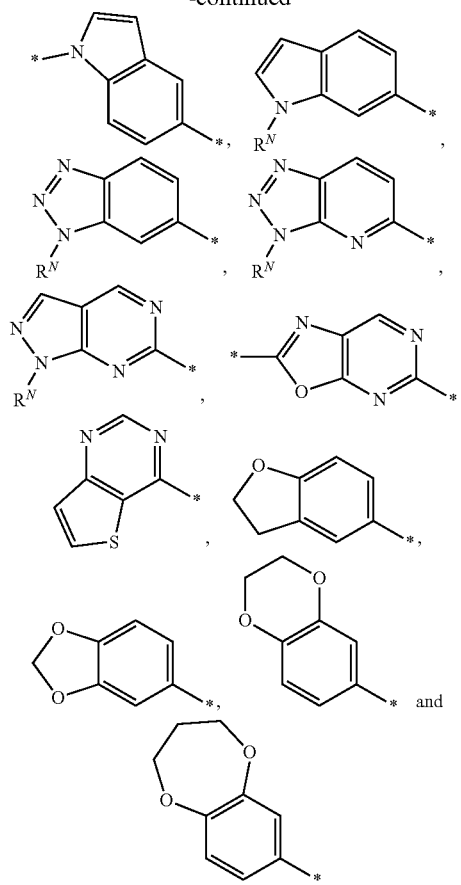

wherein the asterisk to the right side of each cyclic group indicates the bond which is connected to the piperidine ring of the core structure of the formula (I), and if existing the asterisk to the left side of each cyclic group indicates the bond which is connected to a substituent $R^A$ or H, and in addition each of the before mentioned cyclic groups is optionally substituted with one or more further substituents $R^A$, $R^A$ is selected from the group $R^A$-G7 consisting of F, Cl, Br, CN, $F_3C-$,

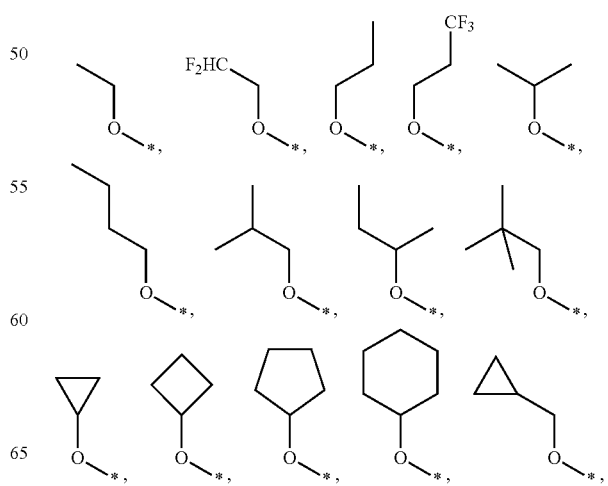

-continued
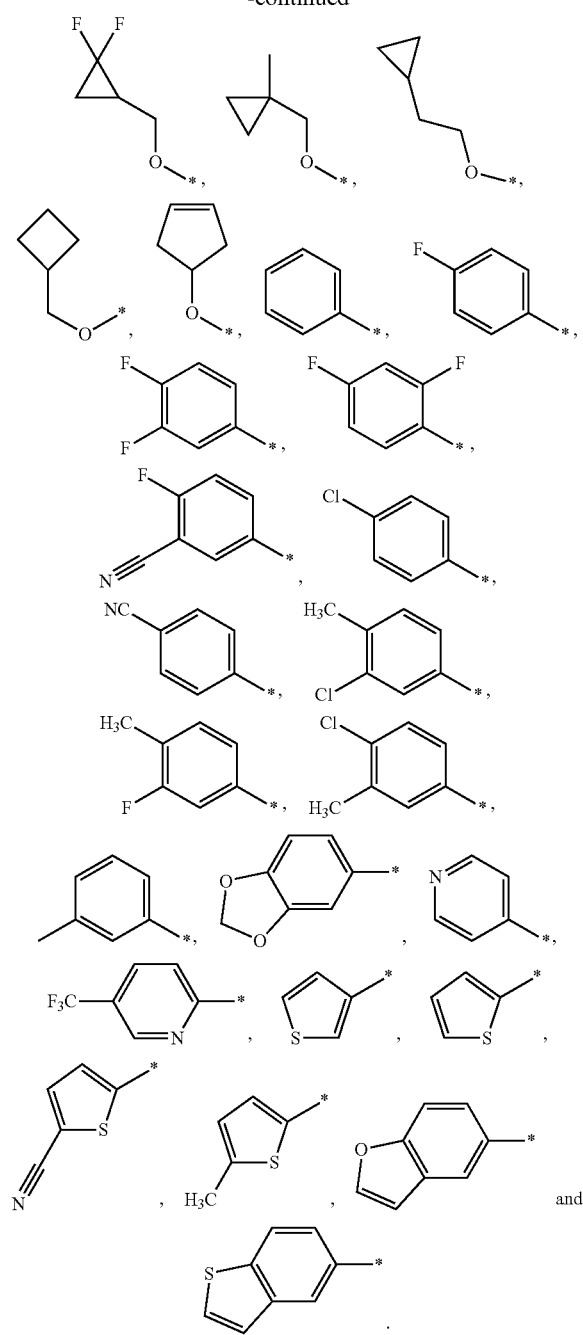
Ar² is
X is —CH(CH₃)—
Rᴺ is H or CH₃,
Y is —C(═O)— and
T is selected from the group consisting of H₃C—, F₃C—, H₃C—CH₂—, H₃C—O—, (H₃C)₂N—,
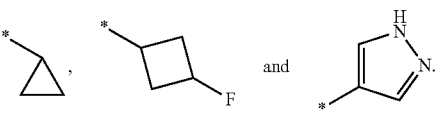
or a salt thereof.
Particularly preferred compounds are:
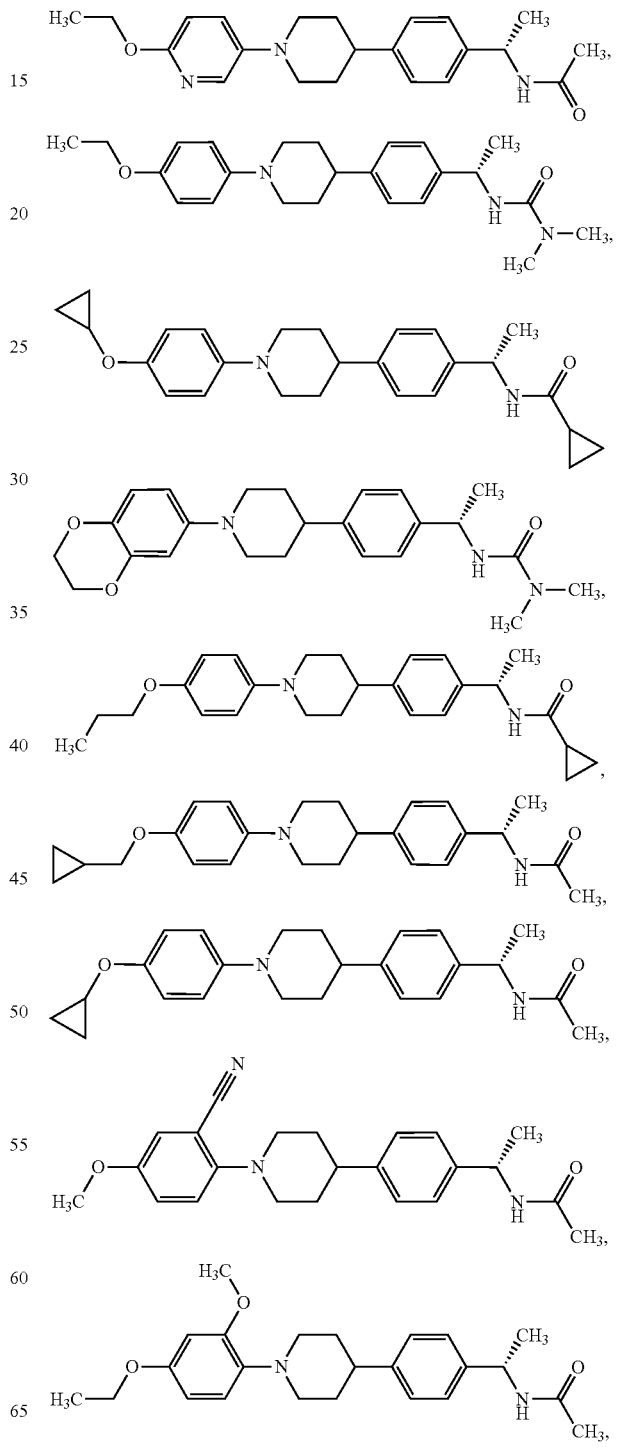

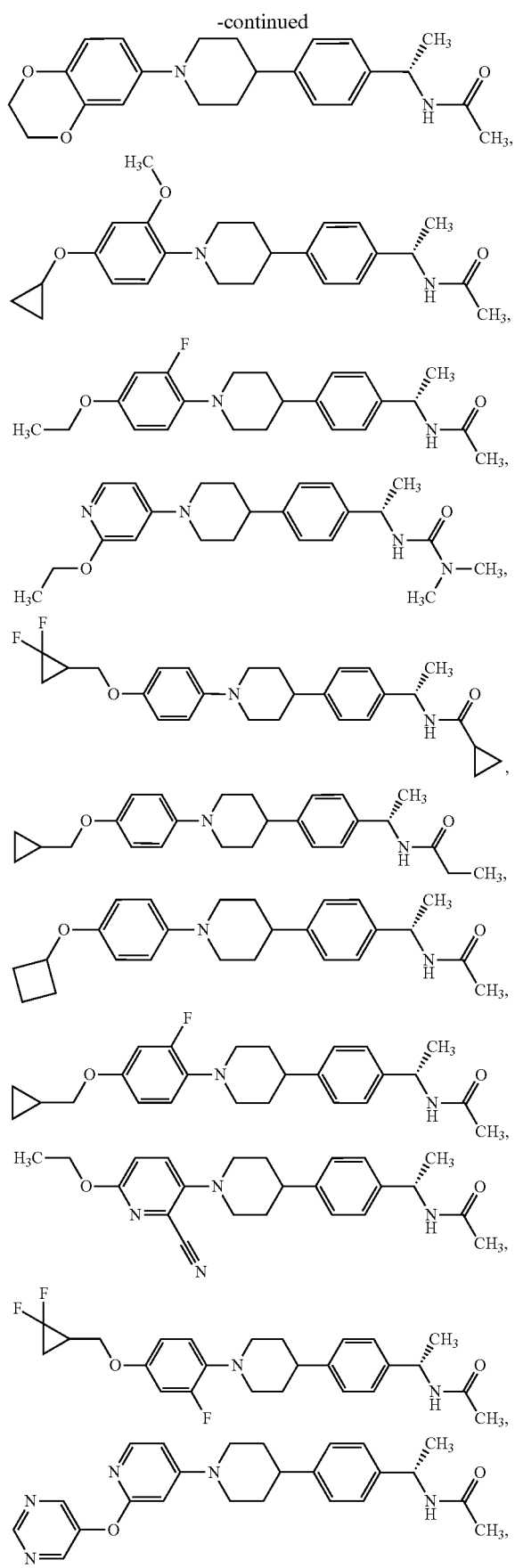

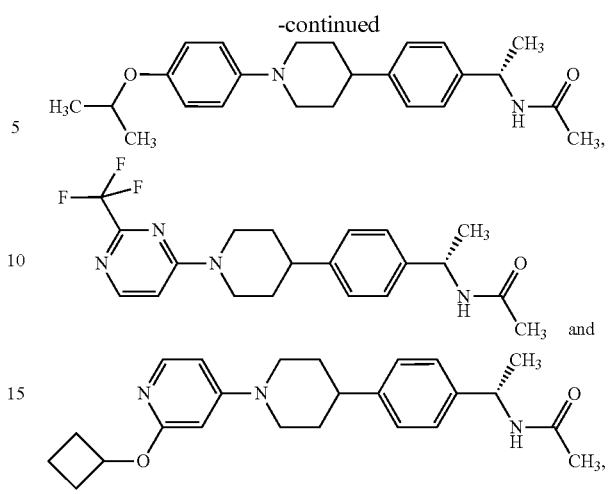

or a pharmaceutically acceptable salt thereof.

Particularly preferred compounds, including their tautomers and stereoisomers, the salts thereof, or any solvates or hydrates thereof, are also described in the experimental section hereinafter.

The compounds according to the invention may be obtained using methods of synthesis which are known to the one skilled in the art and described in the literature of organic synthesis. Preferably the compounds are obtained analogously to the methods of preparation explained more fully hereinafter, in particular as described in the experimental section.

Compounds of the general formula (I) can be prepared by the following methods:

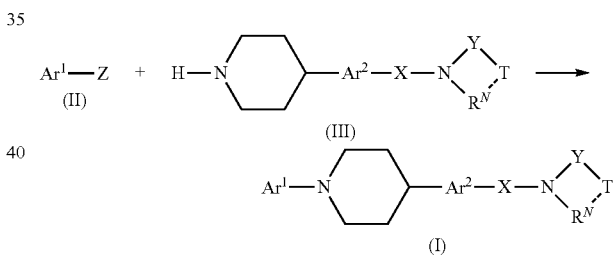

Compounds of general formula (I) may be prepared by palladium-mediated Buchwald reactions or copper-mediated Ullmann reactions of aryl halogenides or aryl triflates (II) with piperidines (III) wherein Z is a leaving group which for example denotes Cl, Br, I or OTf (triflate).

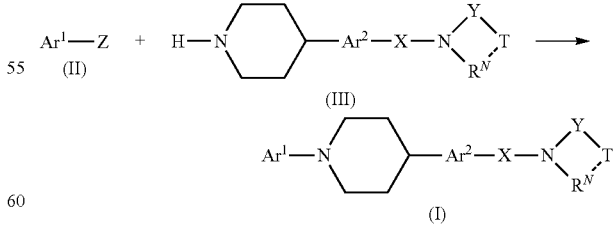

Compounds of general formula (I) may alternatively be prepared by nucleophilic aromatic substitution reactions ($S_NAr$) of aryl/heteroaryl halogenides or aryl/heteroaryl triflates (II) with piperidines (III), wherein Z is a leaving group which for example denotes Cl, Br, I, S(=O)CH$_3$ or triflate.

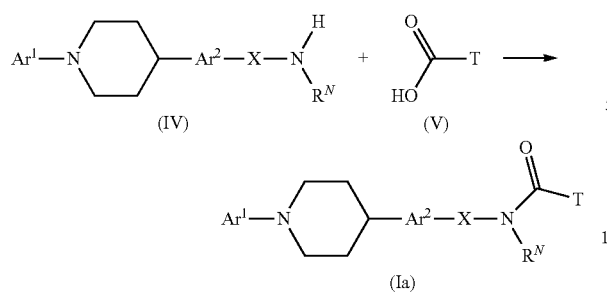

Compounds of general formula (Ia) may be prepared by amide coupling reactions of amines (IV) with carboxylic acids (V) mediated by coupling reagents such as eg TBTU, HOBt or HATU. Alternatively, ketenes such as diketene can be used as carboxylic acid equivalent.

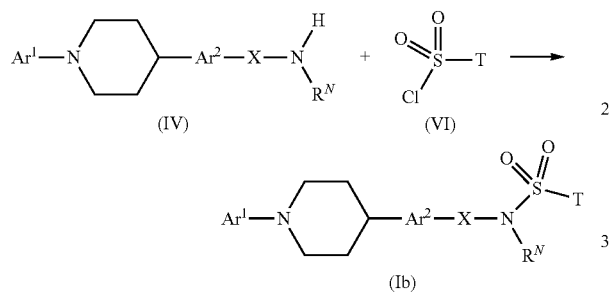

Compounds of general formula (Ib) may be prepared by sulfonylation of amines (IV) with sulfonyl chlorides (VI).

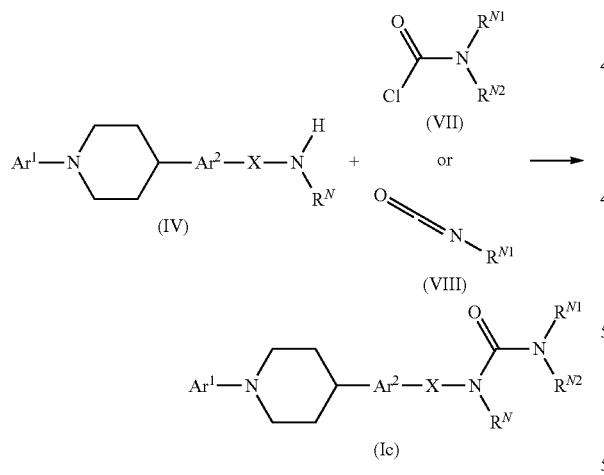

Compounds of general formula (Ic) may be prepared by urea forming reactions such as reaction of amines (IV) with carbamoyl chlorides (VII) or isocyanates (VIII).

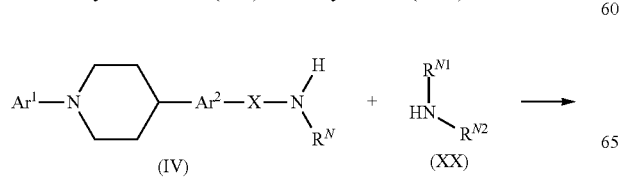

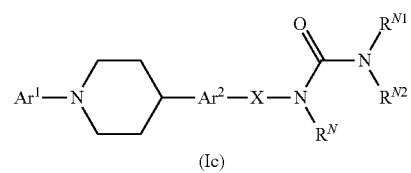

Alternatively, compounds of general formula (Ic) may be prepared by reaction of amines (IV) with amines (XX) after reaction with reagents such as CDI or CDT.

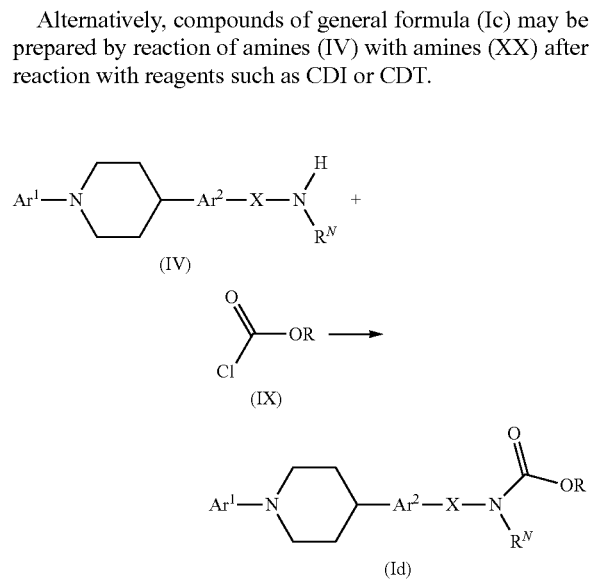

Compounds of general formula (Id) may be prepared by urethane forming reactions such as reaction of amines (IV) with chloro formates (IX).

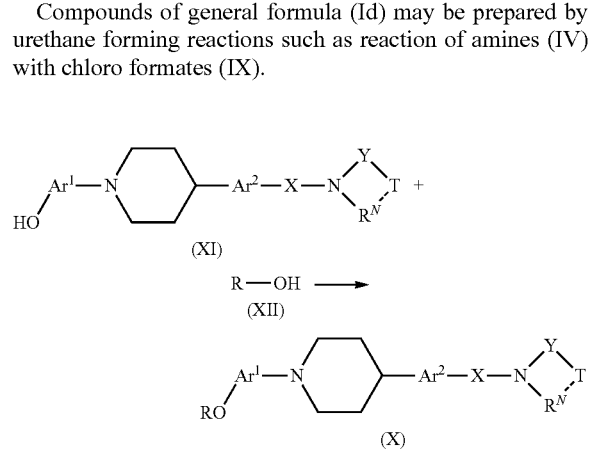

Compounds of general formula (X) may be prepared by Mitsunobu reactions of aromatic alcohols (XI) with alcohols (XII) mediated by coupling reagents such as azodicarboxylates (e.g. DEAD, DIAT etc.) and phosphines (e.g. triphenylphosphine).

-continued

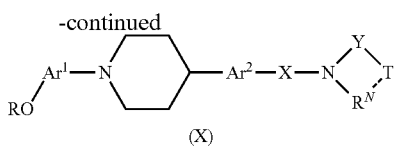
(X)

Compounds of general formula (X) may be alternatively prepared by alkylation reactions of aromatic alcohols (XI) with electrophiles (XIII) wherein Z is a leaving group which for example denotes Cl, Br, I, S(=O)CH₃ or triflate.

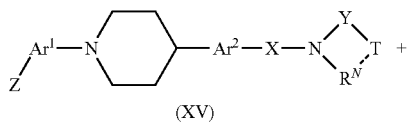
(XV)

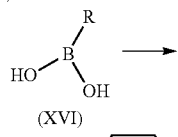
(XVI)

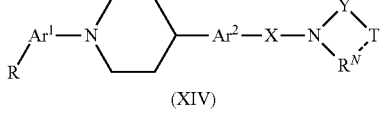
(XIV)

Compounds of general formula (XIV) may be prepared by palladium-catalyzed Suzuki coupling reactions of aryl/heteroaryl halogenides or aryl/heteroaryl triflates (XV) with boronic acids (XVI) or trimethylboroxine wherein Z is a leaving group which for example denotes Cl, Br, I or triflate.

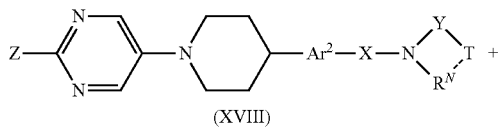
(XVIII)
R →
(XIX)

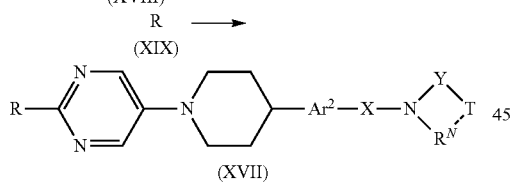
(XVII)

Compounds of general formula (XVII) may be prepared by nucleophilic aromatic substitution reactions (S_NAr) of pyrimidines (XVIII) with nucleophiles R (XIX), wherein Z is a leaving group which for example denotes Cl, Br, I, S(=O)CH₃ or triflate and wherein R is a nucleophile, such as for example an alcohol or an amine and wherein the reaction may be performed with other regioisomers of pyrimidine or other heteroaryls also. Alcohols may be deprotonated by an appropriate base before used as nucleophiles.

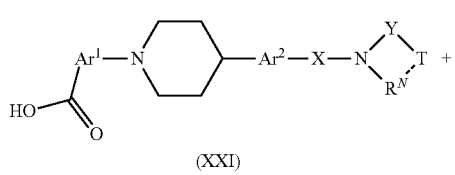
(XXI)

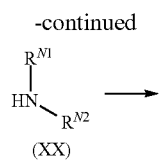
(XX)

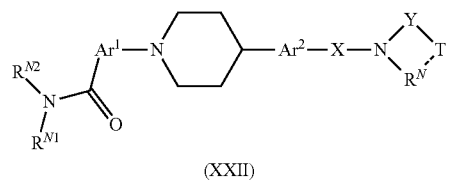
(XXII)

Compounds of general formula (XXII) may be prepared by amide coupling reactions of amines (XX) with carboxylic acids (XXI) mediated by coupling reagents such as eg TBTU, HOBt or HATU.

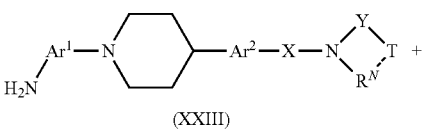
(XXIII)

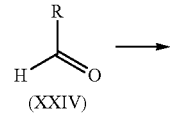
(XXIV)

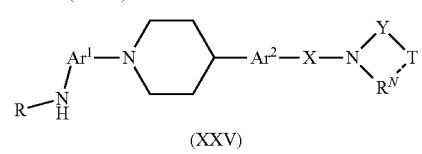
(XXV)

Compounds of general formula (XXV) may be prepared by reductive amination of aromatic amines (XXIII) with aldehydes (XXIV) using reducing agents such as sodium borohydride, NaB(OAc)₃H or NaBH₃(CN).

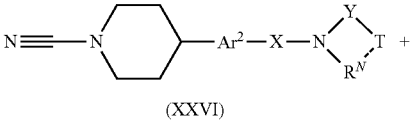
(XXVI)

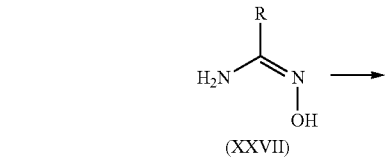
(XXVII)

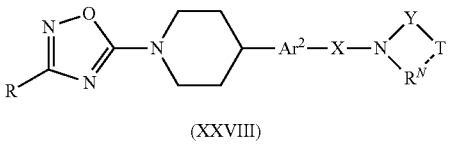
(XXVIII)

Compounds of general formula (XXVIII) may be prepared by condensation reactions of nitriles (XXVI) with hydroxyamidines (XXVII) using a catalyst such as zinc(II)chloride.

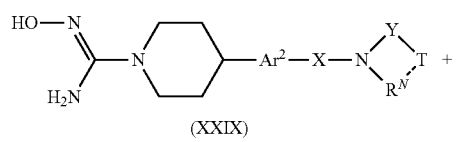

(XXIX)

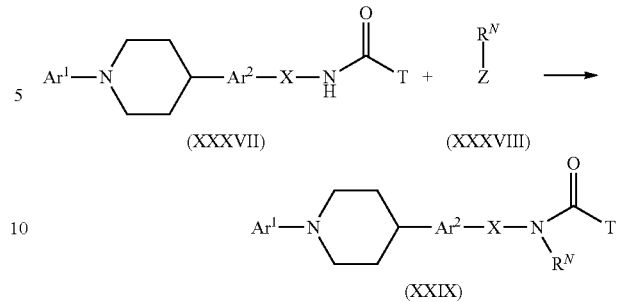

(XXXVII)  (XXXVIII)

↓

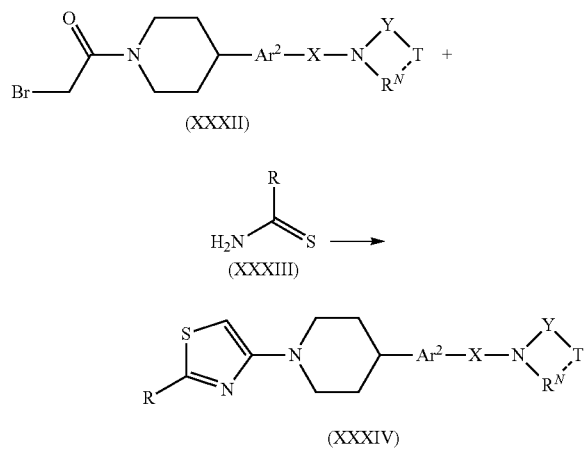

Compounds of general formula (XXXIX) may be prepared by reaction of amides (XXXVII) with alkylating reagents $R^N Z$ after deprotonation with bases such as sodium hydride wherein Z is a leaving group which for example denotes Cl, Br, I, $S(=O)CH_3$ or triflate.

Terms nd Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of the formula (I) according to the present invention including their tautomers, stereoisomers and mixtures thereof and the salts thereof, in particular the pharmaceutically acceptable salts thereof, and the solvates and hydrates of such compounds, including the solvates and hydrates of such tautomers, stereoisomers and salts thereof.

Compounds of general formula (XXIX) may be prepared by condensation reactions of hydroxyamidines (XXIX) with carbonyl chlorides (XXX).

Compounds of general formula (XXXIV) may be prepared by condensation reactions of acetyl bromides (XXXII) with thioamides (XXXIII).

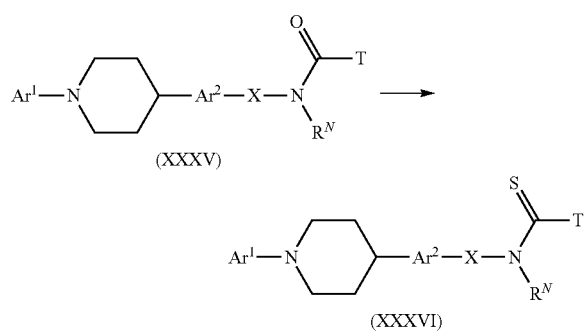

Compounds of general formula (XXXVI) may be prepared by reaction of amides (XXXV) with reagents such as Lawesson's reagent or $P_2S_5$.

The terms "treatment" and "treating" embraces both preventative, i.e. prophylactic, or therapeutic, i.e. curative and/or palliative, treatment. Thus the terms "treatment" and "treating" comprise therapeutic treatment of patients having already developed said condition, in particular in manifest form. Therapeutic treatment may be symptomatic treatment in order to relieve the symptoms of the specific indication or causal treatment in order to reverse or partially reverse the conditions of the indication or to stop or slow down progression of the disease. Thus the compositions and methods of the present invention may be used for instance as therapeutic treatment over a period of time as well as for chronic therapy. In addition the terms "treatment" and "treating" comprise prophylactic treatment, i.e. a treatment of patients at risk to develop a condition mentioned hereinbefore, thus reducing said risk.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

The terms "modulated" or "modulating", or "modulate(s)", as used herein, unless otherwise indicated, refers to the inhibition of the Acetyl-CoA carboxylases (ACC) enzyme(s) with one or more compounds of the present invention.

The terms "mediated" or "mediating" or "mediate", as used herein, unless otherwise indicated, refers to the (i) treatment, including prevention the particular disease or condition, (ii) attenuation, amelioration, or elimination of one or more symptoms of the particular disease or condition, or (iii) prevention or delay of the onset of one or more symptoms of the particular disease or condition described herein.

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In the groups, radicals, or moieties defined below, the number of carbon atoms is often specified preceding the group, for example, $C_{1-6}$-alkyl means an alkyl group or radical having 1 to 6 carbon atoms. In general, for groups comprising two or more subgroups, the last named subgroup is the radical attachment point, for example, the substituent "aryl-$C_{1-3}$-alkyl-" means an aryl group which is bound to a $C_{1-3}$-alkyl-group, the latter of which is bound to the core or to the group to which the substituent is attached.

In case a compound of the present invention is depicted in form of a chemical name and as a formula in case of any discrepancy the formula shall prevail.

An asterisk is may be used in sub-formulas to indicate the bond which is connected to the core molecule as defined.

The numeration of the atoms of a substituent starts with the atom which is closest to the core or to the group to which the substituent is attached. For example, the term "3-carboxypropyl-group" represents the following substituent:

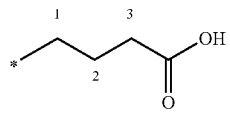

wherein the carboxy group is attached to the third carbon atom of the propyl group. The terms "1-methylpropyl-", "2,2-dimethylpropyl-" or "cyclopropylmethyl-" group represent the following groups:

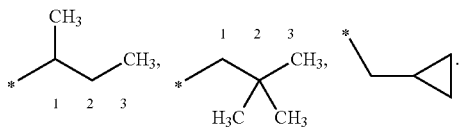

The asterisk may be used in sub-formulas to indicate the bond which is connected to the core molecule as defined.

In a definition of a group the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

In the following the term bicyclic includes spirocyclic.

Unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof and solvates thereof such as for instance hydrates including solvates of the free compounds or solvates of a salt of the compound.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like. For example, such salts include acetates, ascorbates, benzenesulfonates, benzoates, besylates, bicarbonates, bitartrates, bromides/hydrobromides, Ca-edetates/edetates, camsylates, carbonates, chlorides/hydrochlorides, citrates, edisylates, ethane disulfonates, estolates esylates, fumarates, gluceptates, gluconates, glutamates, glycolates, glycollylarsnilates, hexylresorcinates, hydrabamines, hydroxymaleates, hydroxynaphthoates, iodides, isothionates, lactates, lactobionates, malates, maleates, mandelates, methanesulfonates, mesylates, methylbromides, methylnitrates, methylsulfates, mucates, napsylates, nitrates, oxalates, pamoates, pantothenates, phenylacetates, phosphates/diphosphates, polygalacturonates, propionates, salicylates, stearates subacetates, succinates, sulfamides, sulfates, tannates, tartrates, teoclates, toluenesulfonates, triethiodides, ammonium, benzathines, chloroprocaines, cholines, diethanolamines, ethylenediamines, meglumines and procaines. Further pharmaceutically acceptable salts can be formed with cations from metals like aluminum, calcium, lithium, magnesium, potassium, sodium, zinc and the like. (also see Pharmaceutical salts, Birge, S. M. et al., J. Pharm. Sci., (1977), 66, 1-19).

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, ethyl acetate, ethanol, isopropanol, or acetonitrile, or a mixture thereof.

Salts of other acids than those mentioned above which for example are useful for purifying or isolating the compounds of the present invention (e.g. trifluoro acetate salts) also comprise a part of the invention.

The term halogen generally denotes fluorine, chlorine, bromine and iodine.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C—$, $H_3C—CH_2—$, $H_3C—CH_2—CH_2—$, $H_3C—CH_2—CH(CH_3)—$, $H_3C—CH_2—CH_2—CH_2—$, $H_3C—CH_2—CH(CH_3)—$, $H_3C—CH(CH_3)—CH_2—$, $H_3C—C(CH_3)_2—$, $H_3C—CH_2—CH_2—CH_2—CH_2—$, $H_3C—CH_2—CH_2—CH(CH_3)—$, $H_3C—CH_2—CH(CH_3)—$ CH$_2$—, H$_3$C—CH(CH$_3$)—CH$_2$—CH$_2$—, H$_3$C—CH$_2$—C(CH$_3$)$_2$—, H$_3$C—C(CH$_3$)$_2$—CH$_2$—, H$_3$C—CH(CH$_3$)—CH(CH$_3$)— and H$_3$C—CH$_2$—CH(CH$_2$CH$_3$)—.

The term "C$_{1-n}$-alkylene" wherein n is an integer 1 to n, either alone or in combination with another radical, denotes an acyclic, straight or branched chain divalent alkyl radical containing from 1 to n carbon atoms. For example the term C$_{1-4}$-alkylene includes —(CH$_2$)—, —(CH$_2$—CH$_2$)—, —(CH(CH$_3$))—, —(CH$_2$—CH$_2$—CH$_2$)—, —(C(CH$_3$)$_2$)—, —(CH(CH$_2$CH$_3$))—, —(CH(CH$_3$)—CH$_2$)—, —(CH$_2$—CH(CH$_3$))—, —(CH$_2$—CH$_2$—CH$_2$—CH$_2$)—, —(CH$_2$—CH$_2$—CH(CH$_3$))—, —(CH(CH$_3$)—CH$_2$—CH$_2$)—, —(CH$_2$—CH(CH$_3$)—CH$_2$)—, —(CH$_2$—C(CH$_3$)$_2$)—, —(C(CH$_3$)$_2$—CH$_2$)—, —(CH(CH$_3$)—CH(CH$_3$))—, —(CH$_2$—CH(CH$_2$CH$_3$))—, —(CH(CH$_2$CH$_3$)—CH$_2$)—, —(CH(CH$_2$CH$_2$CH$_3$))—, —(CHCH(CH$_3$)$_2$)— and —C(CH$_3$)(CH$_2$CH$_3$)—.

The term "C$_{2-n}$-alkenyl", is used for a group as defined in the definition for "C$_{1-n}$-alkyl" with at least two carbon atoms, if at least two of those carbon atoms of said group are bonded to each other by a double bond. For example the term C$_{2-3}$-alkenyl includes —CH═CH$_2$, —CH═CH—CH$_3$, —CH$_2$—CH═CH$_2$.

The term "C$_{2-n}$-alkenylene" is used for a group as defined in the definition for "C$_{1-n}$-alkylene" with at least two carbon atoms, if at least two of those carbon atoms of said group are bonded to each other by a double bond. For example the term C$_{2-3}$-alkenylene includes —CH═CH—, —CH═CH—CH$_2$—, —CH$_2$—CH═CH—.

The term "C$_{2-n}$-alkynyl", is used for a group as defined in the definition for "C$_{1-n}$-alkyl" with at least two carbon atoms, if at least two of those carbon atoms of said group are bonded to each other by a triple bond. For example the term C$_{2-3}$-alkynyl includes —C≡CH, —C≡C—CH$_3$, —CH$_2$—C≡CH.

The term "C$_{2-n}$-alkynylene" is used for a group as defined in the definition for "C$_{1-n}$-alkylene" with at least two carbon atoms, if at least two of those carbon atoms of said group are bonded to each other by a triple bond. For example the term C$_{2-3}$-alkynylene includes —C≡C—, —C≡C—CH$_2$—, —CH$_2$—C≡C—.

The term "C$_{3-n}$-carbocyclyl" as used either alone or in combination with another radical, denotes a monocyclic, bicyclic or tricyclic, saturated or unsaturated hydrocarbon radical with 3 to n C atoms. The hydrocarbon radical is preferably nonaromatic. Preferably the 3 to n C atoms form one or two rings. In case of a bicyclic or tricyclic ring system the rings may be attached to each other via a single bond or may be fused or may form a spirocyclic or bridged ring system. For example the term C$_{3-10}$-carbocyclyl includes C$_{3-10}$-cylcoalkyl, C$_{3-10}$-cycloalkenyl, octahydropentalenyl, octahydroindenyl, decahydronaphthyl, indanyl, tetrahydronaphthyl. Most preferably the term C$_{3-n}$-carbocyclyl denotes C$_{3-n}$-cylcoalkyl, in particular C$_{3-7}$-cycloalkyl.

The term "C$_{3-n}$-cycloalkyl", wherein n is an integer 4 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclopentyl, cyclohexyl, cycloheptyl, cyclooctyl, cyclononyl, cyclododecyl, bicyclo[3.2.1]octyl, spiro[4.5]decyl, norpinyl, norbonyl, norcaryl, adamantyl, etc.

The term "C$_{3-n}$-cycloalkenyl", wherein n is an integer 3 to n, either alone or in combination with another radical, denotes a cyclic, unsaturated but nonaromatic, unbranched hydrocarbon radical with 3 to n C atoms, at least two of which are bonded to each other by a double bond. For example the term C$_{3-7}$-cycloalkenyl includes cyclopropenyl, cyclobutenyl, cyclopentenyl, cyclopentadienyl, cyclohexenyl, cyclohexadienyl, cycloheptenyl, cycloheptadienyl and cycloheptatrienyl.

The term "aryl" as used herein, either alone or in combination with another radical, denotes a carbocyclic aromatic monocyclic group containing 6 carbon atoms which may be further fused to a second 5- or 6-membered carbocyclic group which may be aromatic, saturated or unsaturated. Aryl includes, but is not limited to, phenyl, indanyl, indenyl, naphthyl, anthracenyl, phenanthrenyl, tetrahydronaphthyl and dihydronaphthyl. More preferably the term "aryl" as used herein, either alone or in combination with another radical, denotes phenyl or naphthyl, most preferably phenyl.

The term "heterocyclyl" means a saturated or unsaturated mono-, bi-, tri- or spirocarbocyclic, perferably mono- or bicyclic-ring system. containing one or more heteroatoms selected from N, O or S(O)$_r$ with r=0, 1 or 2, which in addition may have a carbonyl group. More preferably the term "heterocyclyl" as used herein, either alone or in combination with another radical, means a saturated or unsaturated, even more preferably a saturated mono- or bicyclic-ring system containing 1, 2, 3 or 4 heteroatoms selected from N, O or S(O)$_r$ with r=0, 1 or 2 which in addition may have a carbonyl group. The term "heterocyclyl is intended to include all the possible isomeric forms. Examples of such groups include aziridinyl, oxiranyl, azetidinyl, oxetanyl, pyrrolidinyl, tetrahydrofuranyl, piperidinyl, tetrahydropyranyl, azepanyl, piperazinyl, morpholinyl, tetrahydrofuranonyl, tetrahydropyranonyl, pyrrolidinonyl, piperidinonyl, piperazinonyl, morpholinonyl.

Thus, the term "heterocyclyl" includes the following exemplary structures which are not depicted as radicals as each form may be attached through a covalent bond to any atom so long as appropriate valences are maintained:

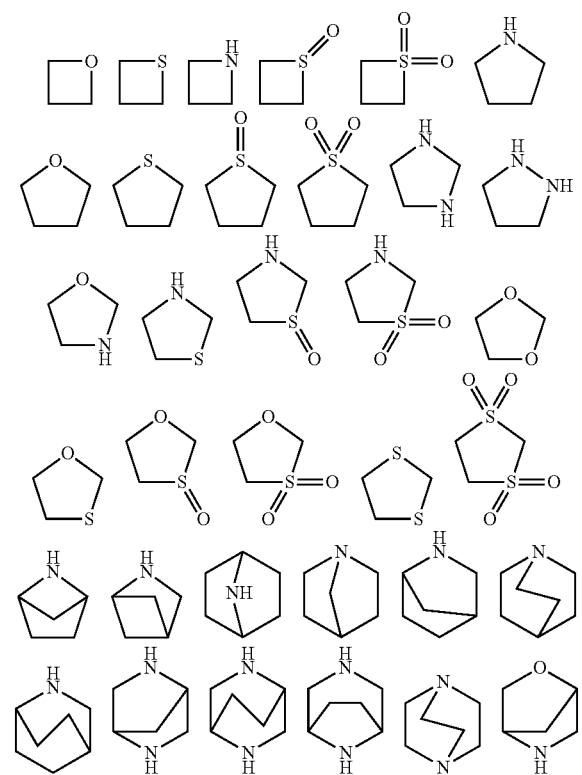

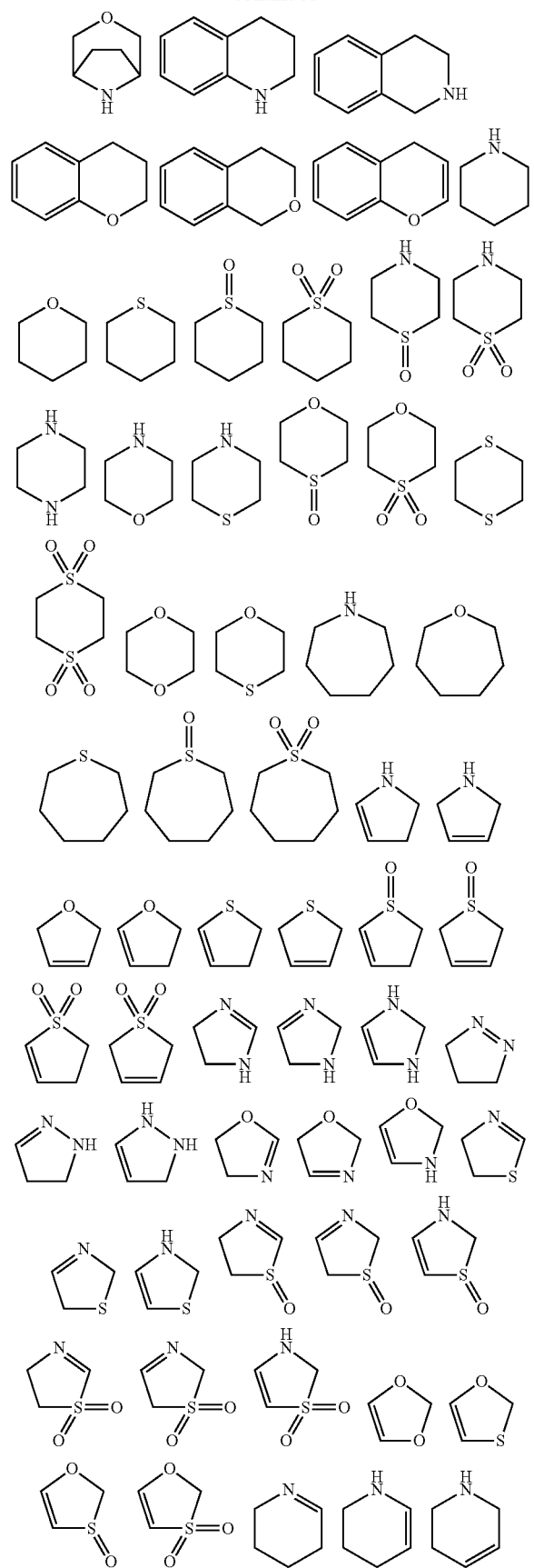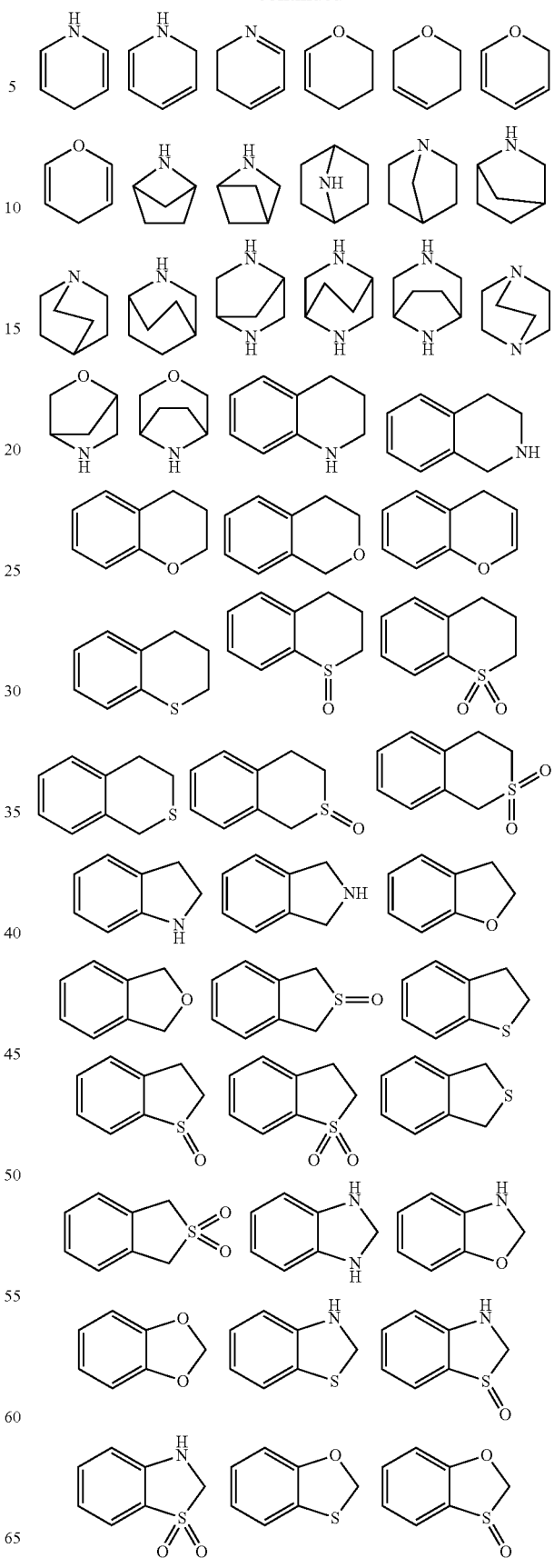

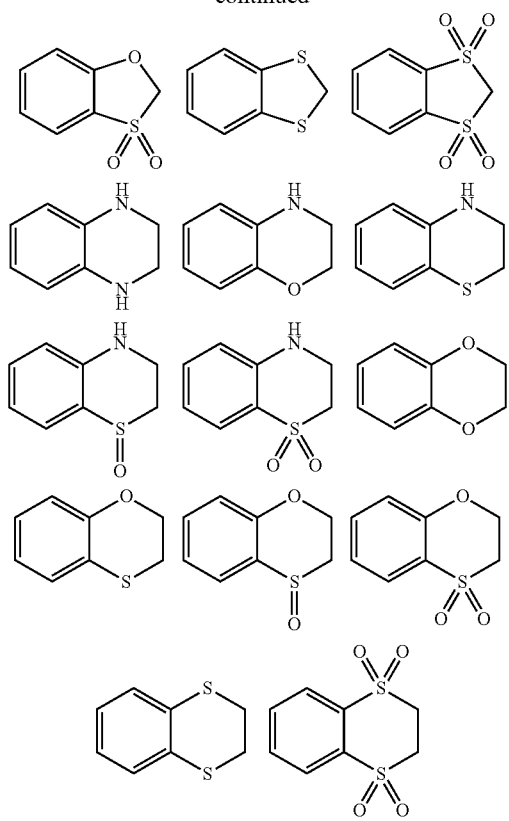

The term "heteroaryl" means a mono- or polycyclic, preferably mono- or bicyclic-ring system containing one or more heteroatoms selected from N, O or S(O)$_r$ with r=0, 1 or 2 wherein at least one of the heteroatoms is part of an aromatic ring, and wherein said ring system may have a carbonyl group. More preferably the term "heteroaryl" as used herein, either alone or in combination with another radical, means a mono- or bicyclic-ring system containing 1, 2, 3 or 4 heteroatoms selected from N, O or S(O)$_r$ with r=0, 1 or 2 wherein at least one of the heteroatoms is part of an aromatic ring, and wherein said ring system may have a carbonyl group. The term "heteroaryl" is intended to include all the possible isomeric forms.

Thus, the term "heteroaryl" includes the following exemplary structures which are not depicted as radicals as each form may be attached through a covalent bond to any atom so long as appropriate valences are maintained:

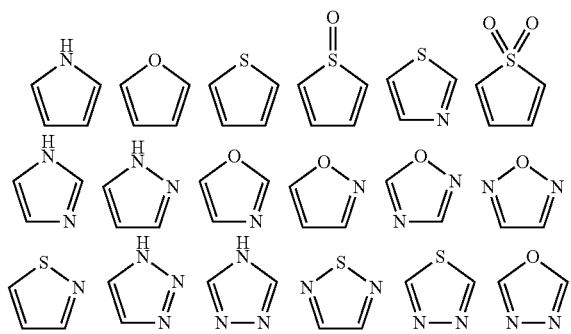

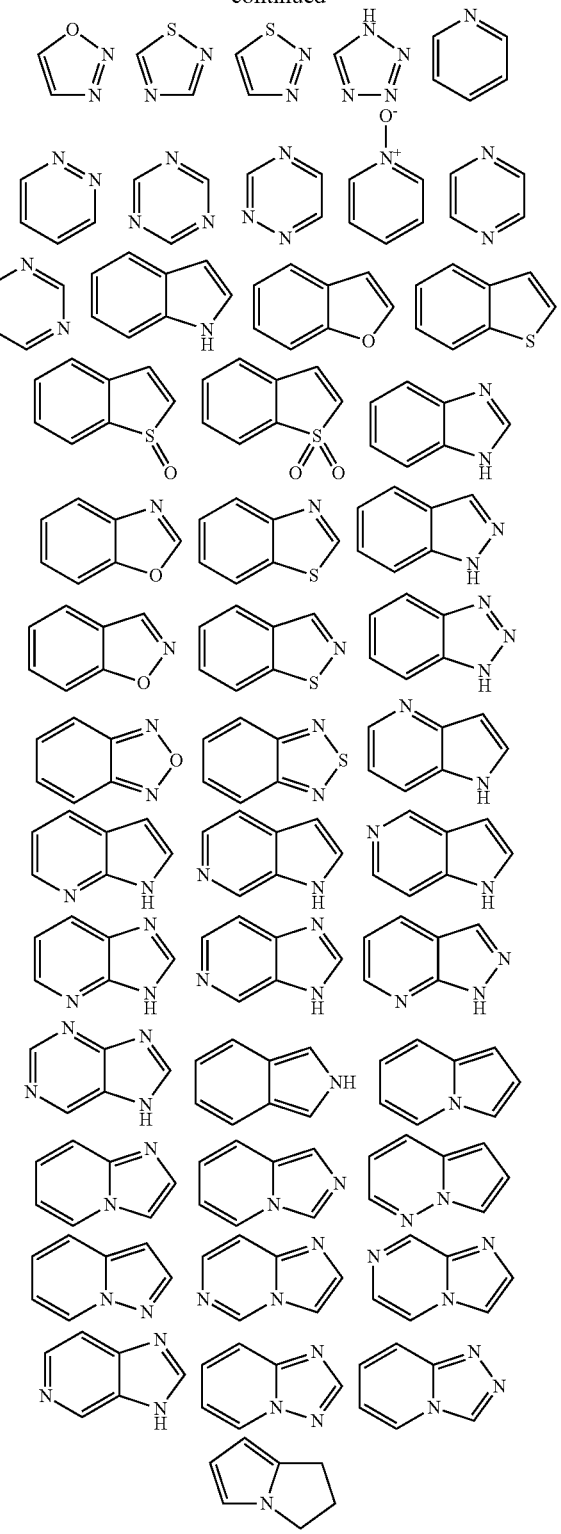

Many of the terms given above may be used repeatedly in the definition of a formula or group and in each case have one of the meanings given above, independently of one another.

Pharmacological Activity

The activity of the compounds of the invention may be demonstrated using the following ACC2 assay:

Spectrophotometric 384 Well Assay

Malonyl CoA formation by acetyl CoA carboxylases is stoichometrically linked to the consumption of ATP. ACC2 activity is measured in a NADH-linked kinetic method measuring ADP generated during the ACC reaction using a coupled lactate dehydrogenase/pyruvate kinase reaction.

For biological testing, a human ACC2 construct which lacks the 128 amino acids at the N-terminus for increased solubility (nt 385-6966 in Genbank entry AJ575592) is cloned. The protein is then expressed in insect cells using a baculoviral expression system. Protein purification is performed by anion exchange.

All compounds are dissolved in dimethyl sulfoxide (DMSO) to a concentration of 10 mM.

Assay reactions are then carried out in 384-well plates, with hACC2 in an appropriate dilution and at final assay concentrations (f.c.) of 100 mM Tris (pH 7.5), 10 mM trisodium citrate, 25 mM $KHCO_3$, 10 mM $MgCl_2$, 0.5 mg/mL BSA, 3.75 mM reduced L-glutathione, 15 U/mL lactate dehydrogenase, 0.5 mM phosphoenolpyruvate, 15 U/mL pyruvate kinase, compounds at different concentrations at final DMSO concentrations of 1%.

The enzymatic reaction is then started by addition of a mixture of NADH, acetyl Coenzyme A (both 200 μM f.c.) and ATP (500 uM f.c.). The decrease of the optical density (slope S) is then determined at 25° C. at a wavelength of 340 nm over 15 minutes in a spectrophotometric reader.

Each assay microtiter plate contains wells with vehicle instead of compound as controls for the non-inhibited enzyme (100% CTL; 'HIGH') and wells without acetyl-CoA as controls for non-specific NADH degradation (0% CTL; 'LOW').

The slope S is used for calculation of % CTL=(S(compound)−S('LOW'))/(S('HIGH')−S('LOW'))*100. Compounds will give values between 100% CTL (no inhibition) and 0% CTL (complete inhibition).

For IC50 value determination, the sample slope in the presence of the test compound after subtraction of the low controls (S(compound)−S('LOW')) are used.

An IC50 value is derived from the compound slopes at different dosages after subtraction of the low controls (S(compound)−S('LOW')) by non-linear regression curve fitting (equation y=(A+((B−A)/(1+((C/x)^D))))).

The compounds of general formula (I) according to the invention for example have $IC_{50}$ values below 30000 nM, particularly below 1000 nM, preferably below 300 nM.

In the following table the activity expressed as IC50 (μM) of compounds according to the invention is presented wherein the IC50 values are determined in the ACC2 assay as described hereinbefore. The term "Ex." refers to the example numbers according to the following experimental section.

| Ex. | IC50 [μM] |
|---|---|
| 1.1 | 0.13 |
| 1.2 | 0.05 |
| 1.3 | 0.09 |
| 1.4 | 0.32 |
| 1.5 | 0.35 |
| 1.6 | 0.14 |
| 1.7 | 0.14 |
| 1.8 | 0.12 |
| 1.9 | 0.05 |
| 1.10 | 0.22 |
| 1.11 | 0.30 |
| 1.12 | 0.08 |
| 1.13 | 0.10 |
| 1.14 | 0.10 |
| 1.15 | 0.24 |
| 1.16 | 0.09 |
| 1.17 | 0.45 |
| 1.18 | 0.35 |
| 1.19 | 0.26 |
| 1.20 | 0.29 |
| 1.21 | 0.08 |
| 1.22 | 0.14 |
| 1.23 | 0.05 |
| 1.24 | 0.21 |
| 1.25 | 0.15 |
| 1.26 | 0.09 |
| 1.27 | 5.8 |
| 1.28 | 0.05 |
| 1.29 | 0.08 |
| 1.30 | 0.23 |
| 1.31 | 0.18 |
| 1.32 | 0.09 |
| 1.33 | 0.12 |
| 1.34 | 0.26 |
| 1.35 | 0.32 |
| 1.36 | 0.41 |
| 1.37 | 0.11 |
| 1.38 | 0.35 |
| 1.39 | 0.13 |
| 1.40 | 0.14 |
| 1.41 | 0.32 |
| 1.42 | 0.63 |
| 1.43 | 4.1 |
| 1.44 | 0.18 |
| 1.45 | 0.37 |
| 1.46 | 0.70 |
| 1.47 | 2.9 |
| 1.48 | 11.3 |
| 1.49 |  |
| 1.50 | 0.12 |
| 1.51 | 0.09 |
| 1.52 | 0.11 |
| 1.53 | 0.82 |
| 1.54 | 0.13 |
| 1.55 | 0.24 |
| 1.56 | 0.72 |
| 1.57 | 0.10 |
| 1.58 | 0.12 |
| 1.59 | 0.14 |
| 1.60 | 0.18 |
| 1.61 | 0.21 |
| 1.62 | 0.20 |
| 1.63 | 1.3 |
| 1.64 | 0.07 |
| 1.65 | 20.0 |
| 1.66 | 0.42 |
| 1.67 | 0.36 |
| 1.68 | 23.9 |
| 1.69 | 4.0 |
| 1.70 | 7.4 |
| 1.71 | 0.08 |
| 1.72 | 23.7 |
| 1.73 | 3.4 |
| 1.74 | 0.10 |
| 1.75 | 2.2 |
| 1.76 | 1.9 |
| 1.77 | 0.90 |
| 1.78 | 3.4 |
| 1.79 | 0.18 |
| 1.80 | 0.53 |
| 1.81 | 0.28 |
| 1.82 | 0.16 |
| 1.83 | 0.10 |
| 1.84 | 0.18 |
| 1.85 | 0.14 |
| 1.86 | 0.21 |
| 1.87 | 1.2 |
| 1.88 | 0.54 |
| 1.89 | 0.39 |
| 1.90 | 0.23 |
| 1.91 | 0.60 |

| Ex. | IC50 [μM] |
|---|---|
| 1.92 | 0.12 |
| 1.93 | 0.58 |
| 1.94 | 0.21 |
| 1.95 | 1.2 |
| 1.96 | 0.36 |
| 1.97 | 0.53 |
| 1.98 | 0.47 |
| 1.99 | 0.33 |
| 1.100 | 0.52 |
| 1.101 | 0.05 |
| 1.102 | 0.16 |
| 1.103 | 0.09 |
| 1.104 | 0.20 |
| 1.105 | 0.24 |
| 1.106 | 0.17 |
| 1.107 | 0.52 |
| 1.108 | 0.93 |
| 1.109 | 3.1 |
| 1.110 | 4.5 |
| 1.111 | 0.17 |
| 1.112 | 0.21 |
| 1.113 | 0.14 |
| 1.114 | 0.13 |
| 1.115 | 0.11 |
| 1.116 | 0.77 |
| 1.117 | 0.06 |
| 1.118 | 0.12 |
| 1.119 | 0.26 |
| 1.120 | 0.25 |
| 1.121 | 8.1 |
| 1.122 | 0.12 |
| 1.123 | 0.07 |
| 1.124 | 0.18 |
| 1.125 | 0.10 |
| 1.126 | 0.23 |
| 1.127 | 0.33 |
| 1.128 | 0.12 |
| 1.129 | 3.5 |
| 1.130 | 0.08 |
| 1.131 | 0.19 |
| 1.132 | 0.84 |
| 1.133 | 0.13 |
| 1.134 | 0.28 |
| 1.135 | 0.34 |
| 1.136 | 0.50 |
| 1.137 | 16.0 |
| 1.138 | 0.16 |
| 1.139 | 0.07 |
| 1.140 | 0.09 |
| 1.141 | 0.32 |
| 1.142 | 0.06 |
| 1.143 | 0.12 |
| 1.144 | 0.06 |
| 1.145 | 0.14 |
| 1.146 | 1.1 |
| 1.147 | 0.49 |
| 1.148 | 0.70 |
| 1.149 | 0.14 |
| 1.150 | 0.13 |
| 1.151 | 0.11 |
| 1.152 | 0.08 |
| 1.153 | 0.52 |
| 1.154 | 0.30 |
| 1.155 | 0.41 |
| 1.156 | 0.60 |
| 1.157 | 0.58 |
| 1.158 | 1.3 |
| 1.159 | 2.7 |
| 1.160 | 2.1 |
| 1.161 | 0.64 |
| 1.162 | 3.1 |
| 1.163 | 0.67 |
| 1.164 | 0.77 |
| 1.165 | 0.10 |
| 1.166 | 4.0 |
| 1.167 | 0.91 |
| 1.168 | 0.50 |
| 1.169 | 1.7 |
| 1.170 | 0.40 |
| 1.171 | 16.3 |
| 1.172 | 0.25 |
| 1.173 | 0.82 |
| 1.174 | 7.5 |
| 1.175 | 1.1 |
| 1.176 | 0.03 |
| 1.177 | 0.04 |
| 1.178 | 0.17 |
| 1.179 | 0.31 |
| 1.180 | 0.53 |
| 1.181 | 0.09 |
| 1.182 | 0.21 |
| 1.183 | 0.15 |
| 1.184 | 1.2 |
| 1.185 | 22.1 |
| 1.186 | 0.17 |
| 1.187 | 0.03 |
| 1.188 | 0.08 |
| 1.189 | 0.06 |
| 1.190 | 1.4 |
| 1.191 | 0.39 |
| 1.192 | 0.12 |
| 1.200 | 0.45 |
| 1.201 | 4.6 |
| 1.202 | 1.9 |
| 1.203 | 0.62 |
| 1.204 | 0.45 |
| 1.205 | 0.66 |
| 1.206 | 4.7 |
| 1.207 | 5.1 |
| 1.300 | 23.3 |
| 2.1 | 2.1 |
| 2.3 | 0.99 |
| 2.4 | 1.8 |
| 2.5 | 0.83 |
| 2.6 | 0.92 |
| 2.7 | 1.6 |
| 2.8 | 0.96 |
| 2.9 | 0.46 |
| 2.10 | 1.6 |
| 2.11 | 1.3 |
| 2.12 | 0.53 |
| 2.13 | 1.9 |
| 3.1 | 0.36 |
| 3.2 | 0.33 |
| 3.3 | 0.11 |
| 3.4 | 0.11 |
| 3.5 | 0.59 |
| 3.6 | 0.24 |
| 3.7 | 0.74 |
| 3.8 | 0.34 |
| 3.9 | 13.3 |
| 3.10 | 1.6 |
| 3.11 | 3.0 |
| 3.12 | 0.06 |
| 3.13 | 0.47 |
| 3.14 | 0.42 |
| 3.20 | 7.4 |
| 4.1 | 2.5 |
| 4.2 | 1.3 |
| 4.3 | 0.45 |
| 4.4 | 1.8 |
| 4.5 | 2.6 |
| 4.6 | 1.6 |
| 4.7 | 0.95 |
| 4.8 | 0.97 |
| 4.9 | 1.9 |
| 4.10 | 0.67 |
| 4.11 | 0.85 |
| 4.12 | 11.6 |
| 4.13 | 3.2 |
| 4.14 | 2.4 |
| 4.15 | 0.22 |
| 4.16 | 1.1 |
| 4.17 | 0.44 |

| Ex. | IC50 [μM] |
|---|---|
| 4.18 | 0.32 |
| 4.19 | 0.10 |
| 4.20 | 1.3 |
| 4.21 | 0.52 |
| 4.22 | 1.1 |
| 4.23 | 0.72 |
| 4.24 | 2.1 |
| 4.25 | 0.23 |
| 4.26 | 0.29 |
| 4.27 | 0.33 |
| 4.28 | 0.06 |
| 4.29 | 1.7 |
| 4.30 | 1.1 |
| 4.31 | 2.0 |
| 4.32 | 2.3 |
| 4.33 | 0.51 |
| 4.34 | 9.5 |
| 4.35 | 0.51 |
| 4.36 | 1.2 |
| 4.37 | 0.30 |
| 4.38 | 0.44 |
| 4.39 | 1.9 |
| 4.40 | 0.93 |
| 4.41 | 0.10 |
| 4.42 | 0.53 |
| 4.43 | 0.41 |
| 4.44 | 0.65 |
| 4.45 | 1.5 |
| 4.46 | 0.21 |
| 4.47 | 0.08 |
| 4.48 | 0.13 |
| 4.49 | 0.21 |
| 4.50 | 0.46 |
| 4.51 | 0.31 |
| 4.52 | 0.53 |
| 4.53 | 0.16 |
| 4.54 | 1.8 |
| 4.101 | 2.7 |
| 4.102 | 0.47 |
| 4.201 | 0.06 |
| 4.202 | 0.15 |
| 4.301 | 0.39 |
| 4.302 | 0.20 |
| 4.303 | 15.6 |
| 4.304 | 0.24 |
| 4.305 | 1.4 |
| 4.306 | 0.12 |
| 5.1 | 0.20 |
| 5.2 | 0.33 |
| 5.3 | 0.13 |
| 5.4 | 0.09 |
| 5.5 | 0.02 |
| 5.6 | 0.06 |
| 5.7 | 0.05 |
| 5.8 | 19.2 |
| 5.9 | 25.4 |
| 5.10 | 0.10 |
| 5.11 | 0.15 |
| 5.12 | 0.22 |
| 5.13 | 3.0 |
| 5.14 | |
| 5.15 | 4.9 |
| 5.16 | 0.26 |
| 5.17 | 1.2 |
| 5.18 | |
| 5.19 | 1.0 |
| 5.20 | 1.2 |
| 5.21 | 0.86 |
| 5.22 | 2.3 |
| 5.23 | 0.42 |
| 5.24 | 0.99 |
| 5.25 | 2.4 |
| 5.26 | 9.0 |
| 5.27 | 5.2 |
| 5.28 | 8.0 |
| 5.29 | 0.17 |
| 5.30 | 0.18 |
| 5.31 | 1.0 |
| 5.32 | 3.8 |
| 5.33 | 0.33 |
| 5.34 | 3.2 |
| 5.35 | 2.8 |
| 5.36 | 3.1 |
| 5.37 | 2.9 |
| 5.38 | 0.57 |
| 5.39 | 0.34 |
| 5.40 | 0.41 |
| 5.41 | 5.0 |
| 5.42 | 0.21 |
| 5.43 | 0.63 |
| 5.44 | 0.07 |
| 5.45 | |
| 5.46 | 1.6 |
| 5.47 | 0.80 |
| 5.48 | 0.42 |
| 5.49 | 2.6 |
| 5.50 | 0.09 |
| 5.51 | 4.8 |
| 5.52 | 19.6 |
| 5.53 | 7.7 |
| 5.54 | 9.3 |
| 5.55 | 7.6 |
| 5.56 | 1.2 |
| 5.57 | 0.23 |
| 5.58 | 0.86 |
| 5.200 | 7.5 |
| 5.201 | 0.79 |
| 6.1 | 0.46 |
| 6.2 | 2.8 |
| 6.3 | 2.6 |
| 6.4 | 2.1 |
| 6.5 | 0.38 |
| 6.6 | 0.99 |
| 6.7 | 0.77 |
| 6.8 | 0.19 |
| 6.9 | 0.15 |
| 6.10 | 0.25 |
| 6.11 | 0.34 |
| 6.12 | 1.3 |
| 6.13 | 1.1 |
| 6.14 | 0.19 |
| 6.15 | 1.0 |
| 6.16 | 0.57 |
| 6.17 | 1.9 |
| 6.18 | 1.1 |
| 6.19 | 1.5 |
| 6.20 | 0.67 |
| 6.21 | 1.6 |
| 6.22 | 0.67 |
| 6.23 | 0.42 |
| 6.24 | 3.9 |
| 6.25 | 0.34 |
| 6.26 | 0.28 |
| 6.27 | 4.8 |
| 6.28 | 1.3 |
| 6.29 | 3.6 |
| 6.30 | 1.1 |
| 6.31 | 2.8 |
| 6.32 | 0.86 |
| 6.33 | 3.1 |
| 6.34 | 0.25 |
| 6.35 | 7.1 |
| 6.36 | 9.1 |
| 6.37 | 0.76 |
| 6.38 | 0.09 |
| 6.39 | 1.3 |
| 6.40 | 1.2 |
| 6.41 | 4.1 |
| 6.42 | 2.8 |
| 6.43 | 1.1 |
| 6.44 | 25.0 |
| 6.45 | 2.6 |
| 6.46 | 10.4 |
| 6.47 | 0.73 |

| Ex. | IC50 [μM] |
|---|---|
| 6.48 | 3.7 |
| 6.49 | 8.3 |
| 7.1 | 0.58 |
| 7.2 | 0.19 |
| 8.1 | 0.44 |
| 8.2 | 0.30 |
| 8.3 | 0.20 |
| 8.4 | 0.40 |
| 8.5 | 0.22 |
| 8.6 | 0.33 |
| 8.7 | 0.16 |
| 8.8 | 0.29 |
| 8.9 | 0.60 |
| 8.10 | 0.10 |
| 8.11 | 1.8 |
| 8.12 | 2.3 |
| 8.13 | 0.11 |
| 8.14 | 0.13 |
| 8.15 | 0.83 |
| 8.16 | 5.6 |
| 8.17 | 0.29 |
| 8.18 | 2.7 |
| 8.19 | 6.0 |
| 8.20 | 12.0 |
| 8.21 | 1.5 |
| 8.22 | 14.6 |
| 8.23 | 0.57 |
| 8.24 | 12.4 |
| 8.25 | 0.71 |
| 8.26 | 0.84 |
| 8.27 | 2.6 |
| 8.28 | 0.15 |
| 8.29 | 0.89 |
| 8.30 | 0.16 |
| 8.31 | 1.2 |
| 8.32 | 3.2 |
| 8.33 | 3.5 |
| 8.34 | 0.26 |
| 8.35 | 0.49 |
| 8.36 | 2.2 |
| 8.37 | 0.66 |
| 8.38 | 1.2 |
| 8.39 | 0.11 |
| 8.40 | 1.4 |
| 8.41 | 4.2 |
| 8.42 | 0.09 |
| 8.43 | 2.1 |
| 8.44 | 0.29 |
| 8.45 | 7.0 |
| 8.46 | 1.0 |
| 8.47 | 2.6 |
| 8.48 | 1.6 |
| 8.49 | 26.6 |
| 8.50 | 1.1 |
| 8.51 | 0.76 |
| 8.52 | 3.0 |
| 8.53 | 0.30 |
| 8.54 | 1.5 |
| 8.55 | 0.30 |
| 8.56 | 1.0 |
| 8.57 | 3.2 |
| 8.58 | 0.37 |
| 8.59 | 0.84 |
| 8.60 | 0.18 |
| 8.61 | 0.30 |
| 8.62 | 0.20 |
| 8.63 | 0.10 |
| 8.64 | 0.12 |
| 8.65 | 0.22 |
| 8.66 | 0.06 |
| 8.67 | 27.7 |
| 9.1 | 0.37 |
| 9.2 | 0.30 |
| 9.3 | 1.4 |
| 9.4 | 0.04 |
| 9.5 | 0.26 |
| 9.6 | 0.13 |
| 9.7 | 0.56 |
| 9.8 | 0.20 |
| 9.9 | 0.21 |
| 9.10 | 0.53 |
| 9.11 | 0.17 |
| 9.12 | 0.25 |
| 9.13 | 0.57 |
| 9.14 | 0.27 |
| 9.15 | 0.37 |
| 9.16 | 0.69 |
| 9.17 | 0.55 |
| 9.18 | 0.15 |
| 9.19 | 0.14 |
| 9.20 | 0.09 |
| 9.21 | 0.10 |
| 9.22 | 0.16 |
| 9.23 | 0.20 |
| 9.24 | 0.47 |
| 9.25 | 1.1 |
| 9.26 | 0.22 |
| 9.27 | 0.07 |
| 9.28 | 0.78 |
| 9.29 | 0.06 |
| 9.30 | 2.3 |
| 9.31 | 4.8 |
| 9.32 | 0.99 |
| 9.33 | 0.12 |
| 9.34 | 0.15 |
| 9.35 | 0.21 |
| 9.36 | 3.3 |
| 9.37 | 0.69 |
| 9.38 | 0.41 |
| 9.40 | 2.9 |
| 9.41 | 0.22 |
| 9.42 | 0.16 |
| 9.43 | 0.43 |
| 9.44 | 0.48 |
| 9.45 | 0.38 |
| 9.46 | 0.56 |
| 10.1 | 0.05 |
| 10.2 | 0.20 |
| 10.3 | 0.13 |
| 10.4 | 2.0 |
| 10.5 | 0.54 |
| 10.6 | 0.10 |
| 10.7 | 0.04 |
| 10.8 | 0.20 |
| 10.9 | 0.02 |
| 10.10 | 0.07 |
| 10.11 | 5.8 |
| 10.12 | 0.36 |
| 10.13 | 0.09 |
| 10.14 | 0.10 |
| 10.15 | 0.55 |
| 10.16 | 0.71 |
| 10.17 | 0.02 |
| 10.18 | 0.18 |
| 10.19 | |
| 10.20 | 2.7 |
| 10.21 | 0.07 |
| 10.22 | 1.1 |
| 10.23 | 0.29 |
| 10.24 | 0.07 |
| 10.25 | 0.32 |
| 10.26 | 0.41 |
| 10.27 | 0.97 |
| 10.28 | |
| 10.29 | 0.13 |
| 10.30 | 0.13 |
| 10.31 | 0.18 |
| 10.32 | 0.41 |
| 10.33 | 0.64 |
| 10.34 | 0.21 |
| 10.35 | 1.1 |
| 10.36 | 0.21 |
| 10.37 | 0.19 |
| 10.38 | 3.0 |

| Ex. | IC50 [μM] | Ex. | IC50 [μM] |
|---|---|---|---|
| 10.39 | | 10.116 | 0.46 |
| 10.40 | 6.9 | 10.117 | 0.68 |
| 10.41 | 1.9 | 10.118 | 0.15 |
| 10.42 | | 10.119 | 0.31 |
| 10.43 | 0.03 | 10.120 | 0.74 |
| 10.44 | 0.10 | 10.121 | 0.11 |
| 10.45 | 1.1 | 10.122 | 0.15 |
| 10.46 | 0.14 | 10.123 | 0.42 |
| 10.47 | 0.27 | 10.124 | 0.09 |
| 10.48 | 1.2 | 10.125 | 0.64 |
| 10.49 | 0.26 | 10.126 | 1.3 |
| 10.50 | 0.05 | 10.127 | 1.6 |
| 10.51 | 1.5 | 10.128 | 0.14 |
| 10.52 | 0.07 | 10.129 | 0.34 |
| 10.53 | 0.08 | 10.130 | 0.04 |
| 10.54 | 0.42 | 10.201 | 0.34 |
| 10.55 | 0.64 | 10.202 | 0.57 |
| 10.56 | 0.32 | 10.203 | 0.16 |
| 10.57 | 0.24 | 10.204 | 0.35 |
| 10.58 | 0.76 | 10.301 | 0.32 |
| 10.59 | | 10.302 | 0.43 |
| 10.60 | 0.39 | 10.303 | 0.16 |
| 10.61 | 0.53 | 10.304 | 0.75 |
| 10.62 | 0.05 | 10.305 | 0.46 |
| 10.63 | 0.03 | 10.306 | 0.31 |
| 10.64 | 7.0 | 10.307 | 0.31 |
| 10.65 | 0.33 | 10.308 | 0.08 |
| 10.66 | 0.16 | 10.309 | 0.08 |
| 10.67 | 0.09 | 10.310 | 0.04 |
| 10.68 | 0.32 | 10.311 | 0.18 |
| 10.69 | 0.27 | 10.312 | 0.16 |
| 10.70 | 0.23 | 10.313 | 0.12 |
| 10.71 | 0.15 | 10.314 | 0.28 |
| 10.72 | 1.2 | 10.315 | 0.12 |
| 10.73 | 0.18 | 11.1 | 0.18 |
| 10.74 | 1.2 | 11.2 | 0.08 |
| 10.75 | 0.05 | 11.3 | 0.25 |
| 10.76 | 0.11 | 11.4 | 0.45 |
| 10.77 | 1.6 | 11.5 | 0.20 |
| 10.78 | 0.20 | 11.6 | 0.18 |
| 10.79 | 1.1 | 11.7 | 0.17 |
| 10.80 | 0.14 | 11.8 | 0.49 |
| 10.81 | 10.4 | 11.9 | 0.38 |
| 10.82 | 0.15 | 11.10 | 0.27 |
| 10.83 | 1.9 | 11.11 | 0.82 |
| 10.84 | 1.3 | 11.12 | 0.30 |
| 10.85 | 2.6 | 11.13 | 4.6 |
| 10.86 | 5.9 | 11.14 | 3.5 |
| 10.87 | 0.07 | 11.15 | 0.23 |
| 10.88 | 0.03 | 11.16 | 0.43 |
| 1.089 | 0.79 | 11.17 | 1.2 |
| 10.90 | 0.35 | 11.18 | 6.2 |
| 10.91 | 0.17 | 11.19 | 0.88 |
| 10.92 | 0.37 | 11.20 | 1.3 |
| 10.93 | 4.3 | 11.21 | 0.89 |
| 10.94 | 2.3 | 11.22 | 0.82 |
| 10.95 | 2.0 | 11.23 | 1.5 |
| 10.96 | 0.60 | 11.24 | 0.37 |
| 10.97 | 8.2 | 11.25 | 0.24 |
| 10.98 | 0.90 | 11.26 | 0.38 |
| 10.99 | 0.38 | 11.27 | 0.30 |
| 10.100 | 0.09 | 11.28 | 0.35 |
| 10.101 | 0.08 | 11.29 | 3.8 |
| 10.102 | 0.24 | 11.30 | 8.4 |
| 10.103 | 0.56 | 11.31 | 0.69 |
| 10.104 | 0.17 | 11.32 | 1.1 |
| 10.105 | 0.10 | 11.33 | 0.59 |
| 1.0106 | 0.38 | 11.34 | 23.2 |
| 10.107 | 0.11 | 11.35 | 0.71 |
| 10.108 | 0.09 | 11.36 | 0.58 |
| 10.109 | 0.09 | 11.37 | 0.93 |
| 10.110 | 0.43 | 11.38 | 0.56 |
| 10.111 | 0.17 | 11.39 | 6.6 |
| 10.112 | 0.12 | 11.40 | 8.1 |
| 10.113 | 0.53 | 11.41 | 3.1 |
| 10.114 | 0.41 | 11.42 | 7.1 |
| 10.115 | 0.41 | 11.43 | 3.3 |

-continued

| Ex. | IC50 [μM] |
|---|---|
| 11.44 | 5.0 |
| 11.45 | 1.5 |
| 11.46 | 2.8 |
| 11.47 | 0.54 |
| 11.48 | 0.58 |
| 11.49 | 0.35 |
| 11.50 | 4.2 |
| 11.51 | 7.8 |
| 11.52 | 18.5 |
| 11.53 | 6.0 |
| 11.54 | 3.7 |
| 11.55 | 3.7 |
| 11.56 | 2.3 |
| 11.57 | 0.42 |
| 11.58 | 0.26 |
| 11.59 | 6.1 |
| 11.60 | 5.3 |
| 11.61 | 1.3 |
| 11.62 | 3.3 |
| 11.63 | 2.0 |
| 11.64 | 17.9 |
| 11.65 | 4.7 |
| 11.66 | 2.2 |
| 11.67 | 26.4 |
| 11.68 | 0.61 |
| 11.69 | 0.20 |
| 11.70 | 4.5 |
| 11.71 | 2.3 |
| 11.72 | 10.5 |
| 11.73 | 15.6 |
| 11.74 | 8.3 |
| 11.75 | 3.8 |
| 11.76 | 6.0 |
| 11.77 | 0.28 |
| 11.78 | 0.61 |
| 11.79 | 4.0 |
| 11.80 | 2.3 |
| 11.81 | 2.3 |
| 11.82 | 0.87 |
| 11.83 | 0.41 |
| 11.84 | 6.5 |
| 11.85 | 13.9 |
| 11.86 | 0.77 |
| 11.87 | 0.79 |
| 11.88 | 1.6 |
| 11.89 | 0.76 |
| 11.90 | 0.23 |
| 11.91 | 0.44 |
| 11.92 | 0.32 |
| 11.93 | 0.55 |
| 11.94 | 1.7 |
| 11.95 | 2.0 |
| 11.96 | 0.35 |
| 11.97 | 0.33 |
| 11.98 | 0.66 |
| 11.99 | 2.5 |
| 11.100 | 5.2 |
| 11.101 | 4.0 |
| 11.102 | 3.2 |
| 11.103 | 2.6 |
| 11.104 | 0.60 |
| 11.105 | 1.7 |
| 11.106 | 1.6 |
| 11.107 | 2.4 |
| 11.108 | 0.11 |
| 11.109 | 0.08 |
| 11.110 | 0.23 |
| 11.111 | 0.64 |
| 11.112 | 1.1 |
| 11.113 | 0.20 |
| 11.114 | 0.18 |
| 11.115 | 1.5 |
| 11.116 | 14.5 |
| 11.117 | 4.3 |
| 11.118 | 0.29 |
| 11.119 | 0.24 |
| 11.120 | 0.28 |

-continued

| Ex. | IC50 [μM] |
|---|---|
| 11.121 | 0.47 |
| 11.122 | 1.4 |
| 11.123 | 0.20 |
| 11.124 | 0.88 |
| 11.125 | 0.34 |
| 11.126 | 0.81 |
| 11.127 | 3.5 |
| 11.128 | 0.41 |
| 11.129 | 1.3 |
| 11.130 | 0.37 |
| 11.131 | 1.1 |
| 11.132 | 3.0 |
| 12.1 | 0.61 |
| 13.1 | 0.09 |
| 13.2 | 0.13 |
| 13.3 | 0.17 |
| 14.1 | 0.47 |
| 14.2 | 2.7 |
| 14.3 | 1.4 |
| 14.4 | |
| 14.5 | 1.7 |
| 14.50 | 3.8 |
| 14.51 | 0.61 |
| 14.52 | |
| 14.53 | 4.9 |
| 14.54 | 1.1 |
| 14.55 | 1.7 |
| 14.56 | 14.7 |
| 14.57 | 14.2 |
| 14.58 | 7.1 |
| 14.59 | 1.5 |
| 14.60 | 2.1 |
| 14.61 | 0.53 |
| 14.62 | 13.3 |
| 14.63 | 1.6 |
| 14.64 | 3.8 |
| 14.65 | 3.7 |
| 14.66 | 2.2 |
| 14.67 | 1.9 |
| 14.68 | 7.8 |
| 14.69 | 12.1 |
| 14.70 | 0.79 |
| 15.1 | 2.8 |
| 15.2 | 0.35 |
| 15.3 | 0.20 |
| 15.4 | |
| 15.5 | 17.7 |
| 15.6 | 0.26 |
| 15.7 | 1.5 |
| 15.8 | 8.4 |
| 15.9 | 19.9 |
| 15.10 | 3.2 |
| 15.11 | 0.16 |
| 15.12 | 2.2 |
| 15.13 | 0.97 |
| 15.14 | 0.88 |
| 15.15 | 0.99 |
| 15.16 | |
| 15.17 | 0.30 |
| 15.18 | 0.33 |
| 15.19 | 3.9 |
| 15.20 | 3.9 |
| 15.21 | 1.2 |
| 15.22 | 13.2 |
| 15.23 | 6.4 |
| 16.1 | 1.4 |
| 16.2 | 4.8 |
| 16.3 | |
| 16.4 | 0.62 |
| 16.5 | 2.5 |
| 16.6 | 0.45 |
| 16.7 | 1.4 |
| 16.8 | 3.9 |
| 16.9 | 6.7 |
| 16.10 | 0.93 |
| 16.11 | 1.3 |
| 17.1 | 2.9 |

-continued

| Ex. | IC50 [μM] |
|---|---|
| 17.2 | 4.2 |
| 17.3 | 7.5 |
| 17.4 | 11.3 |
| 18.1 | 9.8 |
| 18.2 | 1.4 |
| 18.3 | 0.18 |
| 18.4 | 1.8 |
| 18.5 | 1.9 |
| 18.6 | 0.26 |
| 18.7 | 3.6 |
| 18.8 | 0.26 |
| 18.9 | 1.6 |
| 18.10 | 11.5 |
| 18.11 | 0.74 |
| 18.12 | 0.42 |
| 18.13 | 6.1 |
| 18.14 | 10.2 |
| 18.15 | 7.2 |
| 18.16 | 5.1 |
| 18.17 | 7.9 |
| 18.18 | 1.1 |
| 18.19 | 20.5 |
| 18.20 | 0.53 |
| 18.21 | 2.6 |
| 18.22 | 11.4 |
| 18.23 | 3.1 |
| 18.24 | 5.2 |
| 18.25 | 7.1 |
| 18.26 | 2.5 |
| 18.27 | 10.4 |
| 18.28 | 16.9 |
| 18.29 | 6.5 |
| 18.30 | 5.2 |
| 18.31 | 9.3 |
| 18.32 | 5.3 |
| 18.33 | 1.5 |
| 18.34 | 3.5 |
| 18.35 | 7.3 |
| 18.36 | 13.2 |
| 18.37 | 6.4 |
| 18.38 | 3.1 |
| 18.39 | 15.2 |
| 18.40 | 6.6 |
| 18.41 | 21.4 |
| 18.42 | 14.0 |
| 18.43 | 16.8 |
| 18.44 | 18.3 |
| 18.45 | 17.2 |
| 18.46 | 6.0 |
| 18.47 | 29.1 |
| 18.48 | 3.6 |
| 18.49 | 1.3 |
| 18.50 | 13.3 |
| 18.51 | 13.8 |
| 18.52 | 13.6 |
| 18.53 | 15.1 |
| 18.54 | 2.1 |
| 18.55 | 8.8 |
| 18.56 | 14.9 |
| 18.57 | 22.4 |
| 18.58 | 18.1 |
| 18.59 | 18.5 |
| 18.60 | 15.5 |
| 18.61 | 18.9 |
| 18.62 | 11.8 |
| 18.63 | 23.1 |
| 18.64 | 25.4 |
| 18.65 | 10.2 |
| 18.66 | 15.8 |
| 18.67 | 23.7 |
| 18.68 | 19.0 |
| 18.69 | 20.8 |
| 18.70 | 17.4 |
| 18.71 | 14.8 |
| 18.72 | 8.9 |
| 18.73 | 17.9 |
| 18.74 | 24.5 |

-continued

| Ex. | IC50 [μM] |
|---|---|
| 18.75 | 17.8 |
| 18.76 | 4.0 |
| 18.77 | 1.7 |
| 18.78 | 12.7 |
| 18.79 | 16.7 |
| 18.80 | 27.2 |
| 18.81 | 16.5 |
| 18.82 | 6.2 |
| 18.83 | 8.7 |
| 18.84 | 18.1 |
| 18.85 | |
| 18.86 | 11.3 |
| 18.87 | |
| 18.88 | 16.6 |
| 18.89 | 1.2 |
| 18.90 | 1.2 |
| 18.91 | 0.91 |
| 18.92 | 2.2 |
| 18.93 | 0.80 |
| 18.94 | 2.2 |
| 18.95 | 0.19 |
| 19.1 | 0.11 |
| 19.2 | 0.04 |
| 19.3 | 0.70 |
| 19.4 | 0.07 |
| 19.5 | 0.08 |
| 19.6 | 0.08 |
| 19.7 | 0.59 |
| 19.8 | 1.5 |
| 19.9 | 1.3 |
| 19.10 | 0.10 |
| 19.11 | 0.14 |
| 19.12 | 0.18 |
| 19.13 | 0.09 |
| 19.14 | 0.40 |
| 19.15 | 0.08 |
| 19.16 | 0.27 |
| 19.17 | 0.33 |
| 19.18 | 0.34 |
| 19.19 | 0.11 |
| 19.20 | 0.13 |
| 19.21 | 0.22 |
| 19.22 | |
| 19.23 | 0.12 |
| 19.24 | 0.24 |
| 19.25 | 0.07 |
| 19.26 | 0.15 |
| 19.27 | 0.41 |
| 19.28 | 0.23 |
| 19.29 | 0.92 |
| 19.30 | 0.54 |
| 19.31 | 0.75 |
| 19.32 | 0.27 |
| 19.33 | 0.40 |
| 19.34 | 0.52 |
| 19.35 | 27.4 |
| 19.36 | |
| 19.37 | 1.2 |
| 19.38 | 1.2 |
| 20.1 | 0.60 |
| 20.2 | 0.22 |
| 20.3 | 0.18 |
| 20.4 | 0.19 |
| 21.1 | 0.26 |
| 21.2 | 0.15 |
| 21.3 | 0.32 |
| 22.1 | 1.1 |
| 22.2 | 2.5 |
| 22.3 | 1.0 |
| 22.4 | 0.39 |
| 22.5 | 0.94 |
| 22.6 | 1.2 |
| 22.7 | 4.1 |
| 22.8 | 2.9 |
| 22.9 | 3.1 |
| 22.10 | 0.24 |
| 22.11 | 0.39 |

-continued

| Ex. | IC50 [µM] |
|---|---|
| 22.12 | 3.3 |
| 22.13 | 0.44 |
| 23.1 | 0.29 |
| 24.1 | 1.0 |
| 24.2 | 1.9 |
| 24.3 | 1.1 |
| 24.4 | 1.3 |
| 25.1 | 2.7 |
| 25.2 | 10.3 |
| 25.3 | 0.95 |
| 26.1 | 1.9 |
| 26.2 | 4.1 |
| 26.3 | 0.71 |
| 26.4 | 9.1 |
| 27.1 | 0.15 |
| 27.2 | 2.7 |
| 27.3 | 0.86 |
| 28.1 | 9.3 |
| 29.1 | 1.6 |
| 29.2 | 1.7 |
| 29.3 | 6.7 |
| 29.4 | |
| 30.1 | 2.7 |
| 31.1 | 1.6 |
| 32.1 | 7.2 |
| 33.1 | 1.7 |
| 33.2 | 8.9 |
| 34.1 | 0.42 |
| 34.2 | 0.04 |
| 35.1 | 5.4 |
| 36.1 | 1.6 |
| 37.1 | 23.1 |
| 38.1 | 0.43 |
| 38.2 | 0.29 |
| 39.1 | 12.0 |
| 39.2 | 1.5 |
| 40.1 | 0.29 |
| 40.2 | 0.08 |

In view of their ability to inhibit the enzyme(s) acetyl-CoA carboxylase, the compounds of general formula (I) according to the invention and the corresponding salts thereof are theoretically suitable for the treatment, including preventative treatment of all those diseases or conditions which may be affected or which are mediated by the inhibition of the enzyme(s) acetyl-CoA carboxylase, in particular ACC2, activity.

Accordingly, the present invention relates to a compound of general formula (I) as a medicament.

Furthermore, the present invention relates to the use of a compound of general formula (I) for the treatment and/or prevention of diseases or conditions which are mediated by the inhibition of acetyl-CoA carboxylase enzyme(s), in particular ACC2, in a patient, preferably in a human.

In yet another aspect the present invention relates a method for treating, including preventing a disease or condition mediated by the inhibition of acetyl-CoA carboxylase enzyme(s) in a mammal that includes the step of administering to a patient, preferably a human, in need of such treatment a therapeutically effective amount of a compound of the present invention, or a pharmaceutical composition thereof.

Diseases and conditions mediated by inhibitors of acetyl-CoA carboxylases embrace metabolic and/or cardiovascular and/or neurodegenerative diseases or conditions.

According to one aspect the compounds of the present invention are particularly suitable for treating diabetes mellitus, in particular Type 2 diabetes, Type 1 diabetes, and diabetes-related diseases, such as ishyperglycemia, metabolic syndrome, impaired glucose tolerance, diabetic neuropathy, diabetic nephropathy, diabetic retinopathy, dyslipidemia, hypertension, hyperinsulinemia, and insulin resistance syndrome, hepatic insulin resistance, including complications such as macro- and microvascular disorders, including thromboses, hypercoagulable and prothrombotic states (arterial and venous), high blood pressure, coronary artery disease and heart failure, increased abdominal girth, hypercoagulability, hyperuricemia, micro-albuminemia.

According to another aspect the compounds of the present invention are particularly suitable for treating overweight, obesity, including visceral (abdominal) obesity, nonalcoholic fatty liver disease (NAFLD) and obesity related disorders, such as for example weight gain or weight maintenance Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25-29.9 $kg/m^2$, and obesity is typically defined as a BMI of 30 $kg/m^2$ or greater.

According to another aspect the compounds of the present invention are particularly suitable for treating, including preventing, or delaying the progression or onset of diabetes or diabetes-related disorders including Type 1 (insulin-dependent diabetes mellitus, also referred to as "IDDM") and Type 2 (noninsulin-dependent diabetes mellitus, also referred to as "NIDDM") diabetes, impaired glucose tolerance, insulin resistance, hyperglycemia, pancreatic beta cell degeneration and diabetic complications (such as macro- and microvascular disorders, atherosclerosis, coronary heart disease, stroke, peripheral vascular disease, nephropathy, hypertension, neuropathy, and retinopathy).

In addition the compounds of the present invention are suitable for treating dyslipidemias in general and more specifically elevated lipid concentrations in the blood and in tissues, dysregulation of LDL, HDL and VLDL, in particular high plasma triglyceride concentrations, high postprandial plasma triglyceride concentrations, low HDL cholesterol concentration, low apoA lipoprotein concentrations, high LDL cholesterol concentrations, high apoB lipoprotein concentrations, including atherosclerosis, coronary heart disease, cerebrovascular disorders, diabetes mellitus, metabolic syndrome, obesity, insulin resistance and/or cardiovascular disorders.

ACC inhibition may lead to a centrally stimulating effect on food intake. Therefore compounds of the present invention may be suitable for treating eating disorders such as anorexia nervosa.

In addition the compounds of the present invention may provide neuroprotective effects in patients with Parkinson's disease, Alzheimer's disease, hypoxia, ischemia, amyotrophic lateral sclerosis or glioma and may improve cognitive scores in Alzheimer's diseases patients.

Further diseases and conditions mediated by inhibitors of acetyl-CoA carboxylases embrace but are not limited to:
A. disorders of fatty acid metabolism and glucose utilization disorders; disorders in which insulin resistance is involved;
B. hepatic disorders and conditions related thereto, including:
   fatty liver, hepatic steatosis, non-alcoholic hepatitis, non-alcoholic steatohepatitis (NASH), alcoholic hepatitis, acute fatty liver, fatty liver of pregnancy, drug-induced hepatitis, iron storage diseases, hepatic fibrosis, hepatic cirrhosis, hepatoma, viral hepatitis;
C. skin disorders and conditions and those associated with polyunsaturated fatty acids, such as
   eczema, acne, sebaceous gland diseases, psoriasis, keloid scar formation or prevention, other diseases related to mucous membrane fatty acid composition;

D. primary hypertriglyceridemia or secondary hypertriglyceridemias following familial histiocytic reticulosis, lipoprotein lipase deficiency, hyperlipo-proteinemias, apolipoprotein deficiency (e.g. apoCII or apoE deficiency);
E. diseases or conditions related to neoplastic cellular proliferation, for example benign or malignant tumors, cancer, neoplasias, metastases, carcinogenesis;
F. diseases or conditions related to neurological, psychiatric or immune disorders or conditions;
G. other diseases or conditions in which inflammatory reactions, cell differentiation and/or other ACC-mediated aspects may for example be involved are:
  atherosclerosis such as, for example (but not restricted thereto), coronary sclerosis including angina pectoris or myocardial infarction, stroke, ischemic, stroke and transient ischemic attack (TIA),
  peripheral occlusive disease,
  vascular restenosis or reocclusion,
  chronic inflammatory bowel diseases such as, for example, Crohn's disease and ulcerative colitis,
  pancreatitis,
  sinusitis,
  retinopathy, ischemic retinopathy,
  adipose cell tumors,
  lipomatous carcinomas such as, for example, liposarcomas,
  solid tumors and neoplasms such as, for example (but not restricted thereto), carcinomas of the gastrointestinal tract, of the liver, of the biliary tract and of the pancreas, endocrine tumors, carcinomas of the lungs, of the kidneys and the urinary tract, of the genital tract, prostate carcinomas, breast cancer (in particular breast cancer with BRCA1 mutations), etc.,
  tumors in which ACC is up regulated,
  acute and chronic myeloproliferative disorders and lymphomas, angiogenesis
  neurodegenerative disorders including Alzheimer's disease, multiple sclerosis, Parkinson's disease, epilepsy,
  erythemato-squamous dermatoses such as, for example, psoriasis,
  acne vulgaris,
  other skin disorders and dermatological conditions which are modulated by PPAR,
  eczemas and neurodermatitis,
  dermatitis such as, for example, seborrheic dermatitis or photodermatitis,
  keratitis and keratoses such as, for example, seborrheic keratoses, senile keratoses, actinic keratoses, photo-induced keratoses or keratosis follicularis,
  keloids and keloid prophylaxis,
  bacterial infections,
  fungal infections,
  warts, including condylomata or condylomata acuminata
  viral infections such as, for example, human hepatitis B virus (HBV), hepatitis C virus (HCV), West Nile virus (WNV) or Dengue virus, human Immunodeficiency virus (HIV), poxvirus and Vaccinia virus (VV), HCMV, influenza A, human papilloma viral (HPV), venereal papillomata, viral warts such as, for example, molluscum contagiosum, leukoplakia,
  papular dermatoses such as, for example, lichen planus,
  skin cancer such as, for example, basal-cell carcinomas, melanomas or cutaneous T-cell lymphomas,
  localized benign epidermal tumors such as, for example, keratoderma, epidermal naevi,
  chilblains;
  high blood pressure,
  polycystic ovary syndrome (PCOS),
  asthma,
  cystic fibrosis,
  osteoarthritis,
  lupus erythematosus (LE) or inflammatory rheumatic disorders such as, for example rheumatoid arthritis,
  vasculitis,
  wasting (cachexia),
  gout,
  ischemia/reperfusion syndrome,
  acute respiratory distress syndrome (ARDS)
  viral diseases and infections
  lipodystrophy and lipodystrophic conditions, also for treating adverse drug effect;
  myophathies and lipid myopathis (such as carnitine palmitoyltransferase I or II deficiency);
H. formation of muscles and a lean body or muscle mass formation.

The dose range of the compounds of general formula (I) applicable per day is usually from 0.001 to 10 mg, for example from 0.01 to 8 mg per kg body weight of the patient. Each dosage unit may conveniently contain from 0.1 to 1000 mg, for example 0.5 to 500 mg.

The actual therapeutically effective amount or therapeutic dosage will of course depend on factors known by those skilled in the art such as age and weight of the patient, route of administration and severity of disease. In any case the combination will be administered at dosages and in a manner which allows a therapeutically effective amount to be delivered based upon patient's unique condition.

Pharmaceutical Compositions

Suitable preparations for administering the compounds of formula (I) will be apparent to those with ordinary skill in the art and include for example tablets, pills, capsules, suppositories, lozenges, troches, solutions, syrups, elixirs, sachets, injectables, inhalatives and powders etc. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers.

Combination Therapy

The compounds of the invention may further be combined with one or more, preferably one additional therapeutic agent. According to one embodiment the additional therapeutic agent is selected from the group of therapeutic agents useful in the treatment of diseases or conditions associated with metabolic diseases or conditions such as for example diabetes mellitus, obesity, diabetic complications, hypertension, hyperlipidemia.

Therefore a compound of the invention may be combined with one or more additional therapeutic agents selected from the group consisting of anti-obesity agents (including appetite suppressants), agents which lower blood glucose, anti-diabetic agents, agents for treating dyslipidemias, such as lipid lowering agents, anti-hypertensive agents, antiatherosclerotic agents, anti-inflammatory active ingredients, agents for the treatment of malignant tumors, antithrombotic agents, agents for the treatment of heart failure and agents for the treatment of complications caused by diabetes or associated with diabetes.

Suitable anti-obesity agents include 11beta-hydroxy steroid dehydrogenase-1 (11beta-HSD type 1) inhibitors, stearoyl-CoA desaturase-1 (SCD-1) inhibitor, MCR-4 agonists, cholecystokinin-A (CCK-A) agonists, monoamine reuptake inhibitors, sympathomimetic agents, beta3 adrenergic agonists, dopamine agonists, melanocyte-stimulating hormone analogs, 5HT2c agonists, melanin concentrating hormone antagonists, leptin (the OB protein), leptin analogs, leptin agonists, galanin antagonists, lipase inhibitors, anorectic agents, neuropeptide-γ antagonists (e.g., NPY Y5 antagonists), $PY_{y3-36}$ (including analogs thereof), thyromimetic agents, dehydroepiandrosterone or an analog thereof, glucocorticoid agonists or antagonists, orexin antagonists, glucagon-like peptide-1 agonists, ciliary neurotrophic factors, human agouti-related protein (AGRP) inhibitors, ghrelin antagonists, GOAT (Ghrelin O-Acyltransferase) inhibitor, histamine 3 antagonists or inverse agonists, neuromedin U agonists, MTP/ApoB inhibitors (e.g., gut-selective MTP inhibitors), opioid antagonist, orexin antagonist, and the like.

Preferred anti-obesity agents for use in the combination aspects of the present invention include gut-selective MTP inhibitors CCKa agonists, 5HT2c agonists, MCR4 agonist, lipase inhibitor, opioid antagonists, oleoyl-estrone, obinepitide, pramlintide (Symlin®), tesofensine (NS2330), leptin, liraglutide, bromocriptine, orlistat, exenatide (Byetta®), and AOD-9604 (CAS No. 221231-10-3).

Suitable anti-diabetic agents include a sodium-glucose co-transporter (SGLT) inhibitor, a phosphodiesterase (PDE) 10 inhibitor, a diacylglycerol acyltransferase (DGAT) 1 or 2 inhibitor, a sulfonylurea (e.g., acetohexamide, chlorpropamide, diabinese, glibenclamide, glipizide, glyburide, glimepiride, gliclazide, glipentide, gliquidone, glisolamide, tolazamide, and tolbutamide), a meglitinide, an alpha-amylase inhibitor (e.g., tendamistat, trestatin and AL-3688), an alpha-glucoside hydrolase inhibitor (e.g., acarbose), an alpha-glucosidase inhibitor (e.g., adiposine, camiglibose, emiglitate, miglitol, voglibose, pradimicin-Q, and salbostatin), a PPARy agonist (e.g., balaglitazone, ciglitazone, darglitazone, englitazone, isaglitazone, pioglitazone, rosiglitazone and troglitazone), a PPAR alpha/gamma agonist (e.g., CLX-0940, GW-1536, GW-20 1929, GW-2433, KRP-297, L-796449, LR-90, MK-0767 and SB-219994), a biguanide (e.g., metformin), a GLP-1 derivative, a glucagon-like peptide 1 (GLP-1) agonist (e.g., Byetta™, exendin-3 and exendin-4), a protein tyrosine phosphatase-1 B (PTP-1B) inhibitor (e.g., trodusquemine, hyrtiosal extract), SIRT-1 activator (e.g. reservatrol), a dipeptidyl peptidease IV (DPP-IV) inhibitor (e.g., sitagliptin, vildagliptin, alogliptin, linagliptin and saxagliptin), an insulin secreatagogue, GPR119 agonist, GPR40 agonist, TGR5 agonist, MNK2 inhibitor, an A2 antagonist, a c-jun amino-terminal kinase (JNK) inhibitor, an insulin, an insulin derivative, fast acting insulins, inhalable insulins, oral insulins, an insulin mimetic, a glycogen phosphorylase inhibitor, a VPAC2 receptor agonist and a glucokinase activator. Preferred anti-diabetic agents are metformin, a glucagon-like peptide 1 (GLP-1) agonist (e.g., Byetta™).

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment or prevention of diseases or conditions which may be affected or which are mediated by the inhibition of the enzyme(s) acetyl-CoA carboxylase, in particular ACC2, in particular diseases or conditions as described hereinbefore and hereinafter.

In yet another aspect the present invention relates a method for treating, including preventing a disease or condition mediated by the inhibition of acetyl-CoA carboxylase enzyme(s) in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter, The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Further aspects of the invention include the use of a compound according to the invention or a salt thereof as a crop protection agent to combat and/or prevent fungal infestations, or to control other pests such as weeds, insects, or acarids that are harmful to crops. Another aspect of the invention relates to the use of a compound according to the invention or a salt thereof for controlling and/or preventing plant pathogenic microorganisms, for example plant pathogenic fungi. Therefore one aspect of the invention is a compound according to the formula (I) or a salt thereof for use as a fungicide, insecticide, acaricide and/or herbicide. Another aspect of the invention relates to an agricultural composition comprising a compound of the present invention together with one or more suitable carriers. Another aspect of the invention relates to an agricultural composition comprising a compound of the present invention in combination with at least one additional fungicide and/or systemically acquired resistance inducer together with one or more suitable carriers.

EXAMPLES

The Examples that follow are intended to illustrate the present invention without restricting it. The terms "ambient temperature" and "room temperature" are used interchangeably and designate a temperature of about 20° C.

Preliminary Remarks:

As a rule, 1H-NMR and/or mass spectra have been obtained for the compounds prepared. The $R_f$ values are determined using Merck silica gel 60 $F_{254}$ plates and UV light at 254 nm.

Experimental Part

The following abbreviations are used above and hereinafter:

| | |
|---|---|
| ACN | acetonitrile |
| aq. | aqueous |
| BINAP | 2,2'-bis(diphenylphosphino)-1,1'-binaphthalene |
| Boc | tert-butoxycarbonyl |
| CDI | 1,1'-carbonyldiimidazole |
| CDT | 1,1'-carbonylditriazole |
| CyH | cyclohexane |
| DCM | dichloromethane |
| DIPEA | N,N-diisopropylethylamine |

-continued

| DMA | N,N-dimethylacetamide |
| --- | --- |
| DMF | N,N-dimethylformamide |
| dppf | 1,1'-bis(diphenylphosphino)ferrocene |
| EI-MS | electron induced mass spectrometry |
| ESI | electrospray ionisation |
| EtOAc | ethyl acetate |
| FA | formic acid |
| HATU | 2-(7-aza-1H-benzotriazole-1-yl)-1,1,3,3-tetramethyluronium hexafluorophosphate |
| HCl | hydrochloric acid |
| HPLC | high performance liquid chromatography |
| KOH | potassium hydroxide |
| mCPBA | meta-chloroperoxobenzoic acid |
| MeOH | methanol |
| MS | mass spectrum |
| NaOH | soda lye |
| n.d. | not determined |
| NMP | N-methyl-2-pyrrolidone |
| PE | petroleum ether |
| $R_f$ | retention factor |
| $R_t$ | retention time |
| rt | room temperature (about 20° C.) |
| sat. | saturated |
| TBME | tert-butyl methyl ether |
| TBTU | 2-(1H-benzotriazol-1-yl)-1,1,3,3-tetramethyluronium tetrafluoroborat |
| TEA | triethylamine |
| TFA | trifluoroacetic acid |
| THF | tetrahydrofuran |
| TLC | thin layer chromatography |
| X-Phos | 2-dicyclohexylphosphino-2',4',6'-triisopropylbiphenyl |

Analytic Methods
HPLC
Method A

| time (min) | Vol % water (incl. 0.2% NH$_4$OH) | Vol % methanol (incl. 3% water) |
| --- | --- | --- |
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters) 2.5 µm; 3.0×30 mm; column temperature: 40° C.; flow: 1.3 mL/min.
Method B

| time (min) | Vol % water (incl. 0.1% TFA) | Vol % methanol |
| --- | --- | --- |
| 0.0 | 80 | 20 |
| 1.7 | 0 | 100 |
| 2.5 | 0 | 100 |
| 2.6 | 80 | 20 |

Analytical column: Sunfire C18 (Waters) 3.5 µm; 4.6×50 mm; column temperature: 60° C.; flow: 2 mL/min; detection 210-500 nm.
Method C

| time (min) | Vol % water (incl. 0.1% FA) | Vol % acetonitrile (incl. 0.1% FA) |
| --- | --- | --- |
| 0.0 | 95 | 5 |
| 0.1 | 95 | 5 |
| 3.1 | 2 | 98 |
| 4.5 | 2 | 98 |
| 5.0 | 95 | 5 |

Analytical column: X-terra MS C18 (Waters) 2.5 µm; 4.6×30 mm; column temperature: rt; flow: 1.0 mL/min; detection 210-420 nm.
Method D

| time (min) | Vol % water (incl. 0.2% FA) | Vol % methanol (incl. 3% water) |
| --- | --- | --- |
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: Zorbax StableBond C18 (Agilent) 1.8 µm; 3.0×30 mm; column temperature: 40° C.; flow: 1.3 mL/min.
Method E

| time (min) | Vol % water (incl. 0.1% TFA) | Vol % ACN (incl. 0.08% TFA) |
| --- | --- | --- |
| 0.0 | 95 | 5 |
| 2.0 | 0 | 100 |
| 2.5 | 0 | 100 |
| 2.6 | 95 | 5 |

Analytical column: Sunfire C18 (Waters) 3.5 µm; 4.6×50 mm; column temperature: 60° C.; flow: 1.5 mL/min; detection 210-500 nm.
Method F

| time (min) | Vol % water (incl. 0.2% NH$_4$OH) | Vol % methanol (incl. 3% water) |
| --- | --- | --- |
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters) 2.5 µm; 3.0×30 mm; column temperature: 60° C.; flow: 1.3 mL/min.
Method G

| Analytical Column: | XBridge C18, 3 × 30 mm, 2.5 µm (Waters) | | | |
| --- | --- | --- | --- | --- |
| time [min] | Vol % [H$_2$O, 0.2% NH$_4$OH] | Vol % [methanol] | Flow [mL/min] | Temperature [° C.] |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

Method H

| Analytical Column: | XBridge C18, 3 × 30 mm, 2.5 μm (Waters) | | | |
|---|---|---|---|---|
| time [min] | Vol % [H$_2$O, 0.2% TFA] | Vol % [methanol] | Flow [mL/min] | Temperature [° C.] |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

Method I

| time (min) | Vol % water (incl. 0.1% TFA) | Vol % ACN (incl. 0.1% TFA) |
|---|---|---|
| 0.0 | 95 | 5 |
| 2.0 | 0 | 100 |
| 2.49 | 0 | 100 |
| 2.50 | 95 | 5 |

Analytical column: Sunfire C18 (Waters) 3.5 μm; 4.6×50 mm; column temperature: 40° C.; flow: 1.5 mL/min.

Method J

| time (min) | Vol % water (incl. 0.01M NH$_4$OAc) | Vol % ACN |
|---|---|---|
| 0.0 | 50 | 50 |
| 6 | 10 | 90 |
| 15 | 10 | 90 |
| 15.1 | 40 | 60 |

Analytical column: Eclipse-XDB-C18 (Agilent), 5.0 μm; 4.6×150 mm; column temperature: rt; flow: 1.0 mL/min.

Method K

| time (min) | Vol % water (incl. 0.01M NH$_4$OAc) | Vol % ACN |
|---|---|---|
| 0.0 | 70 | 30 |
| 8 | 10 | 90 |
| 15 | 10 | 90 |
| 15.1 | 70 | 30 |

Analytical column: XBridge-C8 (Waters), 5.0 μm; 4.6×150 mm; column temperature: rt; flow: 1.0 mL/min.

Method L

| Analytical Column: | XBridge C18, 3 × 30 mm, 2.5 μm (Waters) | | | |
|---|---|---|---|---|
| time [min] | Vol % [H$_2$O, 0.1% NH$_4$OH] | Vol % [methanol] | Flow [mL/min] | Temperature [° C.] |
| 0.0 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.70 | 0 | 100 | 2.9 | 60 |

Method M

| Analytical Column: | Sunfire C18, 3 × 30 mm, 2.5 μm (Waters) | | | |
|---|---|---|---|---|
| time [min] | Vol % [H$_2$O, 0.1% TFA] | Vol % [methanol] | Flow [mL/min] | Temperature [° C.] |
| 0.0 | 95 | 5 | 2.2 | 60 |
| 0.30 | 95 | 5 | 2.2 | 60 |
| 1.50 | 0 | 100 | 2.2 | 60 |
| 1.55 | 0 | 100 | 2.9 | 60 |
| 1.65 | 0 | 100 | 2.9 | 60 |

Method N

| Analytical Column: | Sunfire C18, 4.6 × 30 mm, 3.5 μm (Waters) | | | |
|---|---|---|---|---|
| time [min] | Vol % [H$_2$O, 0.1% TFA] | Vol % [methanol, 0.1% TFA] | Flow [mL/min] | Temperature [° C.] |
| 0.0 | 95 | 5 | 4 | 60 |
| 0.15 | 95 | 5 | 4 | 60 |
| 1.7 | 0 | 100 | 4 | 60 |
| 2.25 | 0 | 100 | 4 | 60 |

Method O

| Analytical Column: | XBridge C18, 4.6 × 30 mm, 3.5 μm (Waters) | | | |
|---|---|---|---|---|
| time [min] | Vol % [H$_2$O, 0.1% TFA] | Vol % [methanol, 0.1% TFA] | Flow [mL/min] | Temperature [° C.] |
| 0.0 | 95 | 5 | 4 | 60 |
| 0.15 | 95 | 5 | 4 | 60 |
| 1.7 | 0 | 100 | 4 | 60 |
| 2.25 | 0 | 100 | 4 | 60 |

Method P

| Analytical Column: | Sunfire C18, 4.6 × 50 mm, 3.5 μm (Waters) | | | |
|---|---|---|---|---|
| time [min] | Vol % [H$_2$O, 0.1% TFA] | Vol % [methanol] | Flow [mL/min] | Temperature [° C.] |
| 0.0 | 80.0 | 20.0 | 2.0 | 60 |
| 1.7 | 0.0 | 100.0 | 2.0 | 60 |
| 2.5 | 0.0 | 100.0 | 2.0 | 60 |
| 2.6 | 80.0 | 20.0 | 2.0 | 60 |

Method Q

| Analytical Column: | StableBond C18, 3.0 × 30 mm, 1.8 μm (Agilent) | | | |
|---|---|---|---|---|
| time [min] | Vol % [H$_2$O, 0.1% HCOOH] | Vol % [acetonitrile, 0.1% HCOOH] | Flow [mL/min] | Temperature [° C.] |
| 0.0 | 95.0 | 5.0 | 1.6 | −1.0 |
| 0.1 | 95.0 | 5.0 | 1.6 | −1.0 |
| 1.75 | 5.0 | 95.0 | 1.6 | −1.0 |

-continued

| Analytical Column: | | StableBond C18_3.0 × 30 mm, 1.8 μm (Agilent) | | |
|---|---|---|---|---|
| time [min] | Vol % [$H_2O$, 0.1% HCOOH] | Vol % [acetonitrile, 0.1% HCOOH] | Flow [mL/min] | Temperature [° C.] |
| 1.9 | 5.0 | 95.0 | 1.6 | −1.0 |
| 1.95 | 95.0 | 5.0 | 1.6 | −1.0 |
| 2.0 | 95.0 | 0.0 | 1.6 | −1.0 |

Method R

| Analytical Column: | | XBridge C18_4.6 × 50 mm, 3.5 μm (Waters) | | |
|---|---|---|---|---|
| time [min] | Vol % [$H_2O$, 0.032% $NH_4OH$] | Vol % [methanol] | Flow [mL/min] | Temperature [° C.] |
| 0.0 | 95.0 | 5.0 | 1.5 | 40 |
| 2.0 | 0.0 | 100.0 | 1.5 | 40 |

Method S

| Analytical Column: | | XBridge C18_4.6 × 50 mm, 3.5 μm (Waters) | | |
|---|---|---|---|---|
| time [min] | Vol % [$H_2O$, 0.1% $NH_4OH$] | Vol % [methanol] | Flow [mL/min] | Temperature [° C.] |
| 0.0 | 95.0 | 5.0 | 1.5 | 40 |
| 2.0 | 0.0 | 100.0 | 1.5 | 40 |

Method T

| Analytical Column: | | Sunfire C18_4.6 × 30 mm, 2.5 μm (Waters) | | |
|---|---|---|---|---|
| time [min] | Vol % [$H_2O$, 0.1% TFA] | Vol % [methanol] | Flow [mL/min] | Temperature [° C.] |
| 0.0 | 95.0 | 5.0 | 4 | 60 |
| 0.05 | 95.0 | 5.0 | 3 | 60 |
| 2.05 | 0 | 100 | 3 | 60 |
| 2.10 | 0 | 100 | 4.5 | 60 |
| 2.40 | 0 | 100 | 4.5 | 60 |

Method U

| Analytical Column: | | Sunfire C18_4.6 × 30 mm, 2.5 μm (Waters) | | |
|---|---|---|---|---|
| time [min] | Vol % [$H_2O$, 0.1% TFA] | Vol % [methanol, 0.1% TFA] | Flow [mL/min] | Temperature [° C.] |
| 0.0 | 95.0 | 5.0 | 4.0 | 60 |
| 0.05 | 95.0 | 5.0 | 3.0 | 60 |
| 2.05 | 0.0 | 100.0 | 3.0 | 60 |
| 2.1 | 0.0 | 100.0 | 4.0 | 60 |
| 2.35 | 0.0 | 100.0 | 4.0 | 60 |

Method V

| Analytical Column: | | Ascentis Express C18_2.1 × 50 mm, 2.7 μm (Supelco) | | |
|---|---|---|---|---|
| time [min] | [$H_2O$, 0.1% TFA] | Vol % [acetonitrile, 0.08% TFA] | Flow [mL/min] | Temperature [° C.] |
| 0.0 | 95.0 | 5.0 | 1.5 | 60.0 |
| 0.7 | 1.0 | 99.0 | 1.5 | 60.0 |
| 0.8 | 1.0 | 99.0 | 1.5 | 60.0 |
| 0.81 | 95.0 | 5.0 | 1.5 | 60.0 |

Method W

| Analytical Column: | | XBridge C18_4.6 × 50 mm, 3.5 μm (Waters) | | |
|---|---|---|---|---|
| time [min] | Vol % [$H_2O$, 0.1% $NH_4OH$] | Vol % [methanol] | Flow [mL/min] | Temperature [° C.] |
| 0.0 | 80.0 | 20.0 | 2.0 | 60 |
| 1.7 | 0.0 | 100.0 | 2.0 | 60 |
| 2.5 | 0.0 | 100.0 | 2.0 | 60 |
| 2.6 | 80.0 | 20.0 | 2.0 | 60 |

Method X

| Analytical Column: | | XBridge C18_4.6 × 50 mm, 3.5 μm (Waters) | | |
|---|---|---|---|---|
| time [min] | Vol % [$H_2O$, 0.1% $NH_4OH$] | Vol % [methanol] | Flow [mL/min] | Temperature [° C.] |
| 0.0 | 80.0 | 20.0 | 2.0 | 60 |
| 1.7 | 0.0 | 100.0 | 2.0 | 60 |
| 2.5 | 0.0 | 100.0 | 2.0 | 60 |

Method Y

| Analytical Column: | XBridge C18_2.1 × 50 mm, 1.7 μm (Waters) | | |
|---|---|---|---|
| time [min] | Vol % [$H_2O$, 0.1% $NH_4OH$] | Flow [mL/min] | Temperature [° C.] |
| 0.0 | 95.0 | 1.5 | 60 |
| 0.7 | 0.0 | 1.5 | 60 |
| 0.8 | 0.0 | 1.5 | 60 |
| 0.81 | 95.0 | 1.5 | 60 |
| 1.9 | 95.0 | 0.2 | 60 |
| 2.0 | 0.0 | 0.2 | 60 |
| 3.0 | 0.0 | 0.2 | 60 |

Method Z

| Analytical Column: | Sunfire C18_4.6 × 50 mm, 3.5 µm (Waters) | | | |
|---|---|---|---|---|
| time [min] | Vol % [H₂O, 0.1% TFA] | Vol % [methanol] | Flow [mL/min] | Temp [° C.] |
| 0.0 | 95.0 | 5.0 | 1.5 | 40 |
| 1.3 | 0.0 | 100.0 | 1.5 | 40 |
| 2.5 | 0.0 | 100.0 | 1.5 | 40 |
| 2.6 | 95.0 | 5.0 | 1.5 | 40 |

Method AA

| Analytical Column: | XBridge C18, 4.6 × 30 mm, 3.5 µm (Waters) | | | |
|---|---|---|---|---|
| time [min] | Vol % [H₂O, 0.1% NH₄OH] | Vol % [ACN] | Flow [mL/min] | Temperature [° C.] |
| 0.0 | 95 | 5 | 4 | 60 |
| 0.15 | 95 | 5 | 4 | 60 |
| 1.7 | 0 | 100 | 4 | 60 |
| 2.1 | 0 | 100 | 4 | 60 |

Method AB

| Analytical Column: | Sunfire C18, 3 × 30 mm, 2.5 µm (Waters) | | | |
|---|---|---|---|---|
| time [min] | Vol % [H₂O, 0.1% TFA] | Vol % [methanol] | Flow [mL/min] | Temperature [° C.] |
| 0.0 | 95 | 5 | 1.8 | 60 |
| 0.05 | 95 | 5 | 1.8 | 60 |
| 2.05 | 0 | 100 | 1.8 | 60 |
| 2.1 | 0 | 100 | 2.5 | 60 |
| 2.35 | 0 | 100 | 2.5 | 60 |

Method AC

| Analytical Column: | Viridis Ethylpyridin 5 µm 3 × 100 mm | | | |
|---|---|---|---|---|
| Rate | Vol % [CO₂] | Vol % [methanol] | Flow [mL/min] | Temperature [° C.] |
| 0 | 95 | 5 | 4 | 40 |
| 14 | 65 | 35 | 4 | 40 |
| 99 | 95 | 5 | 4 | 40 |

Method AD

| Analytical Column | Sunfire C18, 3 × 30 mm, 2.5 µm | | | |
|---|---|---|---|---|
| time [min] | Vol % [H₂O, 0.2% TFA] | Vol % [methanol] | Flow [mL/min] | Temperature [° C.] |
| 0.0 | 95 | 5 | 2.2 | 60 |
| 0.05 | 95 | 5 | 2.2 | 60 |
| 1.40 | 0 | 100 | 2.2 | 60 |
| 1.80 | 0 | 100 | 2.2 | 60 |

Method AE

| time (min) | Vol % water (incl. 0.1% FA) | Vol % methanol (incl. 3% water) |
|---|---|---|
| 0.0 | 95 | 5 |
| 0.2 | 95 | 5 |
| 2.2 | 5 | 95 |
| 2.3 | 5 | 95 |
| 2.4 | 0 | 100 |
| 2.6 | 0 | 100 |

Analytical column: XBridge C18 (Waters) 2.5 µm; 3.0×30 mm; column temperature: 40° C.; flow: 1.3 mL/min.

Method AF

| time (min) | Vol % water (incl. 0.05% TFA) | Vol % ACN |
|---|---|---|
| 0.0 | 40 | 60 |
| 6 | 10 | 90 |
| 15 | 10 | 90 |
| 15.1 | 40 | 60 |

Analytical column: XBridge C18 (Waters) 3.5 µm; 4.6×50 mm; column temperature: rt;

Preparation of Starting Compounds

Example I

Example I.1

(S)—N-[1-(4-Bromo-phenyl)ethyl]-acetamide

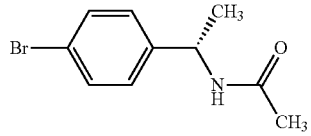

23.6 mL (250 mmol) acetic anhydride are added to 50.0 g (250 mmol) (S)-1-(4-bromophenyl)-ethylamine in 200 mL dichloromethane while keeping the reaction temperature below 30° C. Stirring is continued for 12 h at rt. After that time, saturated NaHCO₃-solution is added. The organic layer is separated, washed with water, dried over magnesium sulphate and the solvent is removed by evaporation.

$C_{10}H_{12}BrNO$ (M=242.1 g/mol), ESI-MS: 240/242 [M+H]⁺

$R_t$ (HPLC): 1.03 min (method L)

The following compounds are prepared analogously to Example I.1:

Example I.2

N-[2-(4-Bromo-phenyl)-1-methyl-ethyl]-acetamide

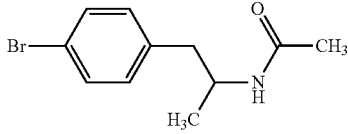

Educt: 2-(4-Bromo-phenyl)-1-methyl-ethylamine (J. Org. Chem. 1985, 50, 133).
$C_{11}H_{14}BrNO$ (M=256.1 g/mol), ESI-MS: 256 $[M+H]^+$
$R_t$ (HPLC): 2.60 min (method C)

Example I.3

(S)-Cyclopropanecarboxylic acid [1-(4-bromo-phenyl)-ethyl]-amide

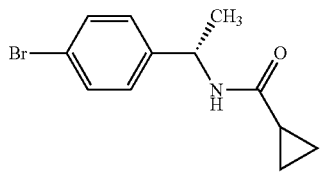

$C_{12}H_{14}BrNO$ (M=268.2 g/mol), ESI-MS: 268 $[M+H]^+$
$R_t$ (HPLC): 2.76 min (method C)

Example I.4

(S)—N-[1-(4-Bromo-phenyl)-ethyl]-propionamide

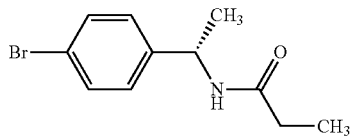

$C_{11}H_{14}BrNO$ (M=256.1 g/mol), EI-MS: 256 $[M]^+$
$R_t$ (HPLC): 1.05 min (method G)

Example I.5

N-[1-(4-Bromo-phenyl)-propyl]-acetamide

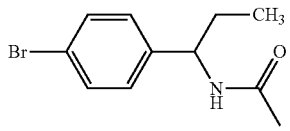

$C_{11}H_{14}BrNO$ (M=256.1 g/mol), ESI-MS: 256 $[M+H]^+$
$R_t$ (HPLC): 1.08 min (method G)

Example I.6

(R)—N-[1-(4-Bromo-phenyl)ethyl]-acetamide

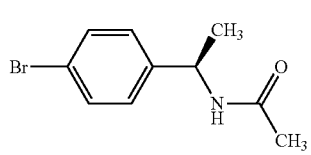

Educt: (R)-1-(4-bromophenyl)-ethylamine
$C_{10}H_{12}BrNO$ (M=242.1 g/mol), ESI-MS: 242 $[M+H]^+$
$R_t$ (HPLC): 1.63 min (method A)

Example I.7

N-[1-(4-Bromo-phenyl)-cyclopropyl]-acetamide

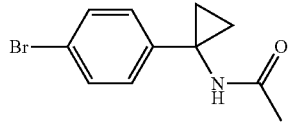

$C_{11}H_{12}BrNO$ (M=254.1 g/mol), ESI-MS: 255 $[M+H]^+$
$R_t$ (HPLC): 1.58 min (method A)

Example II

Example II.1

(S)-[1-(4-Bromo-phenyl)-ethyl]-carbamic acid methyl ester

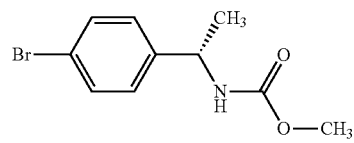

17.2 g (105 mmol) CDT are added to a mixture of 20.0 g (100 mmol) (S)-1-(4-bromophenyl)-ethylamine and 17.6 mL (125 mmol) TEA in 300 mL dichloromethane at 0° C. Stirring is continued for 15 min at 5° C. After that time, the solvent is removed in vacuo and taken up in 50 mL methanol. 33.4 mL (180 mmol) sodium methoxide in methanol (30%) are added and stirring is continued for 48 h at rt. After that time, the solvent is removed in vacuo, the residue is taken up in ethyl acetate and washed with sat. $KHSO_4$-solution (2×) and water. The organic layer is dried over magnesium sulphate and the solvent is removed by evaporation.

$C_{10}H_{12}BrNO_2$ (M=258.1 g/mol), ESI-MS: 258 $[M+H]^+$
$R_t$ (HPLC): 2.60 min (method A)

The following compounds are prepared analogously to Example II.1:

Example II.2

(S)-3-[1-(4-Bromo-phenyl)-ethyl]-1,1-dimethyl-urea

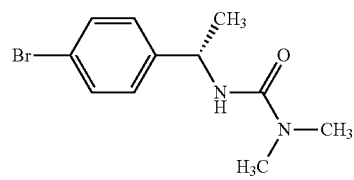

Educt: dimethylamine
$C_{11}H_{15}BrN_2O$ (M=271.2 g/mol), ESI-MS: 271 $[M+H]^+$
$R_t$ (HPLC): 1.68 min (method A)

Example III

Example III.1

(S)—N-[1-(4-Iodo-phenyl)-ethyl]-acetamide

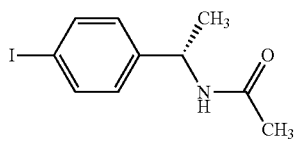

9.01 g (47.3 mmol) Copper(I) iodide are added to a mixture of 114.6 g (473.3 mmol) (S)-N-[1-(4-bromo-phenyl)-ethyl]-acetamide (1.1), 283.8 g (1.893 mmol) sodium iodide and 10.43 g (118.3 mmol) N,N'-dimethylethylendiamine in 1.3 L 1,4-dioxane. The mixture is stirred for 60 h at 120° C. After that time, the solvent is evaporated, the residue is suspended in 2 L dichloromethane and poured into a mixture of ice (1 kg), ammonia (1 L) and water (2 L). The organic layer is separated, the aq. layer is washed with dichloromethane (2×) and the combined organic layers are washed with water (2×) and dried over sodium sulphate. The solvent is evaporated and the residue is washed with diethyl ether.

$C_{10}H_{12}INO$ (M=289.1 g/mol), ESI-MS: 290 [M+H]$^+$
$R_f$ (TLC): 0.57 (silica gel, dichloromethane:methanol 9:1)

The following compounds are prepared analogously to Example III.1:

Example III.2

N-[2-(4-Iodo-phenyl)-1-methyl-ethyl]-acetamide

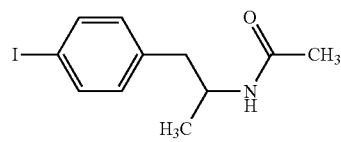

$C_{11}H_{14}INO$ (M=303.1 g/mol), ESI-MS: 304 [M+H]$^+$
$R_t$ (HPLC): 2.85 min (method C)

Example IV

Example IV.1

(S)—N-[1-(4-Pyridin-4-yl-phenyl)ethyl]-acetamide

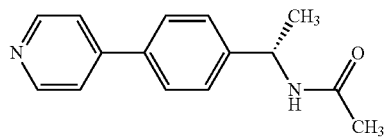

Under inert gas atmosphere 181 mg (0.248 mmol) PdCl$_2$(dppf)xCH$_2$Cl$_2$ are added to a mixture of 30.0 g (124 mmol) (S)—N-[1-(4-bromo-phenyl)-ethyl]-acetamide (1.1), 139 mL (279 mmol) 2N sodium carbonate solution and 16.8 g (136 mmol) pyridine-4-boronic acid in 300 mL 1,4-dioxane and 100 mL methanol. The mixture is stirred for 5 d at reflux. After that time, the residue is poured into water (3 L) and extracted with dichloromethane (3×). The combined organic layers are washed with water and dried over magnesium sulphate. The solvent is evaporated and the residue is triturated with acetone and tert-butyl methyl ether.

$C_{15}H_{16}N_{20}$ (M=240.3 g/mol), ESI-MS: 241 [M+H]$^+$
$R_t$ (HPLC): 1.44 min (method A)

The following compounds are prepared analogously to Example IV.1:

Example IV.2

(S)-[1-(4-Pyridin-4-yl-phenyl)-ethyl]-carbamic acid methyl ester

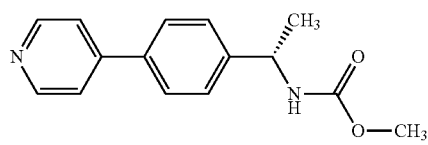

$C_{15}H_{16}N_2O_2$ (M=256.3 g/mol), ESI-MS: 257 [M+H]$^+$
$R_t$ (HPLC): 1.60 min (method A)

Example IV.3

(S)-1,1-Dimethyl-3-[1-(4-pyridin-4-yl-phenyl)ethyl]-urea

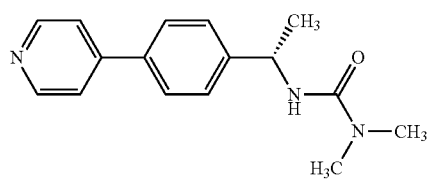 [SMILES: C[C@H](NC(=O)N(C)C)c1ccc(-c2ccncc2)cc1]

$C_{16}H_{19}N_3O$ (M=269.3 g/mol), ESI-MS: 270 [M+H]$^+$
$R_t$ (HPLC): 1.49 min (method A)

Example IV.4

(S)-Cyclopropanecarboxylic acid [1-(4-pyridin-4-yl-phenyl)ethyl]-amide

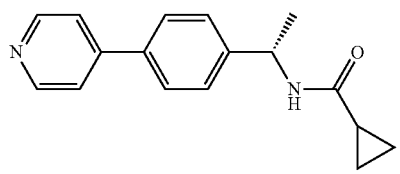 [SMILES: C[C@H](NC(=O)C1CC1)c1ccc(-c2ccncc2)cc1]

$C_{17}H_{18}N_2O$ (M=266.3 g/mol), ESI-MS: 267 [M+H]$^+$
$R_t$ (HPLC): 1.56 min (method A)

Example IV.5

(S)-[1-(4-Pyridin-4-yl-phenyl)-ethyl]-carbamic acid tert-butyl ester

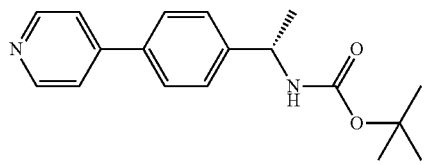 [SMILES: C[C@H](NC(=O)OC(C)(C)C)c1ccc(-c2ccncc2)cc1]

Educt: (S)-[1-(4-Bromo-phenyl)-ethyl]-carbamic acid tert-butyl ester
$C_{18}H_{22}N_2O_2$ (M=298.4 g/mol), ESI-MS: 299 [M+H]$^+$
$R_t$ (HPLC): 1.92 min (method A)

Example IV.6

(S)—N-[1-(4-Pyridin-4-yl-phenyl)-ethyl]-propionamide

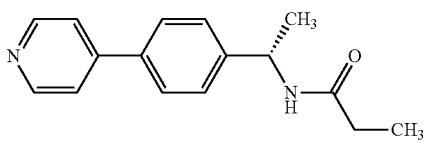

$C_{16}H_{18}N_2O$ (M=254.3 g/mol), ESI-MS: 255 [M+H]$^+$
$R_t$ (HPLC): 0.94 min (method G)

Example IV.7

N-[1-(4-Pyridin-4-yl-phenyl)-propyl]-acetamide

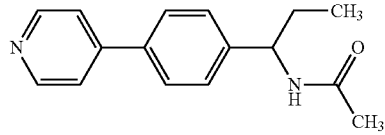

$C_{16}H_{18}N_2O$ (M=254.3 g/mol), ESI-MS: 255 [M+H]$^+$
$R_t$ (HPLC): 0.84 min (method G)

Example IV.9

(R)—N-[1-(4-Pyridin-4-yl-phenyl)ethyl]-acetamide

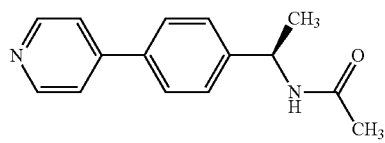 [SMILES: CC(=O)N[C@H](C)c1ccc(-c2ccncc2)cc1]

$C_{15}H_{16}N_2O$ (M=240.3 g/mol), ESI-MS: 241 [M+H]$^+$
$R_t$ (HPLC): 1.40 min (method A)

Example IV.10

N-[1-(4-Pyridin-4-yl-phenyl)-cyclopropyl]-acetamide

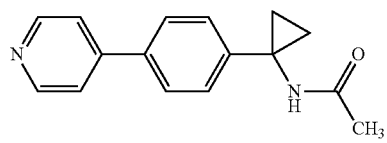 [SMILES: CC(=O)NC1(c2ccc(-c3ccncc3)cc2)CC1]

$C_{16}H_{16}N_2O$ (M=252.3 g/mol), ESI-MS: 253 [M+H]$^+$
$R_t$ (HPLC): 1.41 min (method A)

Example V

Example V.1

(S)—N[1-(Piperidin-4-yl-phenyl)-ethyl]-acetamide

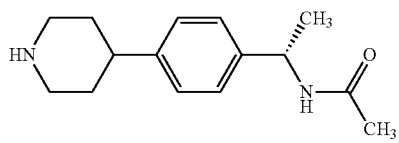 [SMILES: CC(=O)N[C@@H](C)c1ccc(C2CCNCC2)cc1]

195 mL 1N HCl are added to 21.9 g (91.1 mmol) (S)—N-[1-(4-pyridin-4-yl-phenyl)-ethyl]-acetamide (IV.1) in 500 mL ethanol. The mixture is hydrogenated (3 bar) for 6.5 h at rt using 2.00 g platinum(IV) oxide. After that time, the catalyst is filtered off and the solvent is evaporated. The residue is taken up in water, neutralized with 1N NaOH and extracted with ethyl acetate/methanol. The organic layer is dried over magnesium sulphate and the solvent is evaporated. The aq. layer is saturated with sodium chloride and extracted with THF. The organic layer is washed with saturated NaCl-solution and the solvent is evaporated. The combined residues are purified by column chromatography (silica gel; eluent A: THF, eluent B: THF/methanol/ammonia 2:1:0.1) to yield the desired product.

$C_{15}H_{22}N_2O$ (M=246.3 g/mol), ESI-MS: 247 [M+H]$^+$
$R_t$ (HPLC): 1.42 min (method A)

The following compounds are prepared analogously to Example V.1:

Example V.2

(S)-[1-(4-Piperidin-4-yl-phenyl)-ethyl]-carbamic acid methyl ester

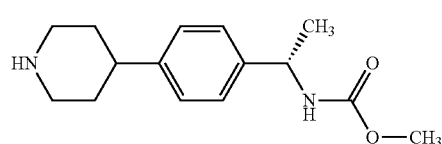

$C_{15}H_{22}N_2O_2$ (M=262.3 g/mol), ESI-MS: 263 [M+H]$^+$
$R_t$ (HPLC): 1.60 min (method A)

Example V.3

(S)-1,1-Dimethyl-3-[1-(4-piperidin-4-yl-phenyl)-ethyl]-urea

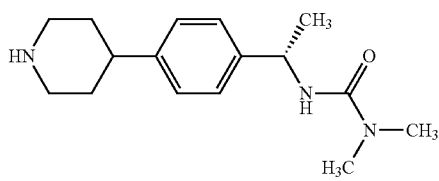 [SMILES: C[C@H](NC(=O)N(C)C)c1ccc(C2CCNCC2)cc1]

$C_{16}H_{25}N_3O$ (M=275.4 g/mol), ESI-MS: 276 [M+H]$^+$
$R_t$ (HPLC): 1.48 min (method A)

Example V.4

(S)-Cyclopropanecarboxylic acid [1-(4-piperidin-4-yl-phenyl)ethyl]-amide

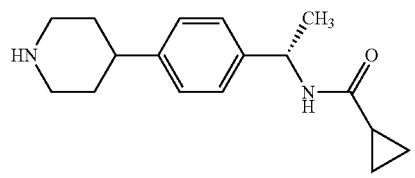 [SMILES: C[C@H](NC(=O)C1CC1)c1ccc(C2CCNCC2)cc1]

$C_{17}H_{24}N_2O$ (M=272.4 g/mol), ESI-MS: 273 [M+H]$^+$
$R_t$ (HPLC): 1.12 min (method A)

Example V.5

(S)-[1-(4-Piperidin-4-yl-phenyl)-ethyl]-carbamic acid tert-butyl ester

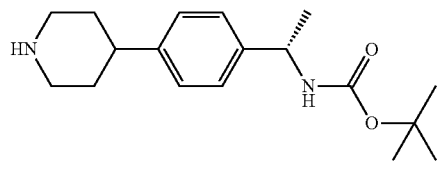 [SMILES: C[C@H](NC(=O)OC(C)(C)C)c1ccc(C2CCNCC2)cc1]

$C_{18}H_{28}N_2O_2$ (M=304.4 g/mol), ESI-MS: 305 [M+H]$^+$
$R_t$ (HPLC): 1.12 min (method A)

Example V.6

(R)—N-[1-(Piperidin-4-yl-phenyl)ethyl]-acetamide

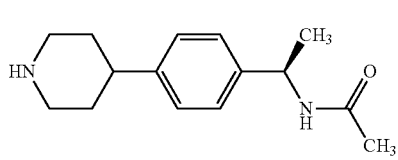 [SMILES: CC(=O)N[C@H](C)c1ccc(C2CCNCC2)cc1]

$C_{15}H_{22}N_2O$ (M=246.3 g/mol), ESI-MS: 247 [M+H]$^+$
$R_t$ (HPLC): 1.10 min (method A)

Example V.7

N-(1-(4-(Piperidin-4-yl)phenyl)cyclopropyl)acetamide

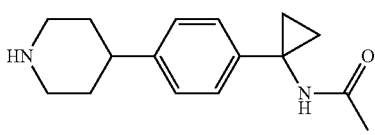 [SMILES: CC(=O)NC1(c2ccc(C3CCNCC3)cc2)CC1]

$C_{16}H_{22}N_2O$ (M=258.4 g/mol), ESI-MS: 259 [M+H]$^+$
$R_t$ (HPLC): 1.40 min (method A)

Example VI

Example VI.1

4-[4-(2-Acetylamino-propyl)-phenyl]-3,6-dihydro-2H-pyridine-1-carboxylic acid tert-butyl ester

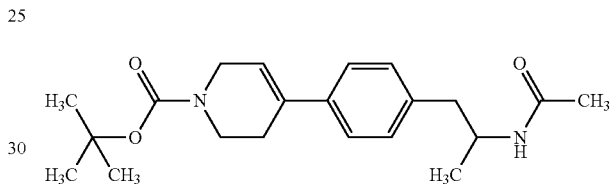

Under inert gas atmosphere 303 mg (1.00 mmol) N-[2-(4-iodo-phenyl)-1-methyl-ethyl]-acetamide (III.2) are added to a mixture of 309 mg (1.00 mmol) 4-(4,4,5,5-tetramethyl-[1,3,2]dioxaborolan-2-yl)-3,6-dihydro-2H-pyridine-1-carboxylic acid tert-butyl ester, 49 mg (0.060 mmol) PdCl$_2$(dppf)xCH$_2$Cl$_2$ and 415 mg (3.00 mol) K$_2$CO$_3$ in 5 mL DMF. The mixture is stirred for 48 h at rt. After that time, the solvent is evaporated, the residue taken up in ethyl acetate and washed with water. After drying over sodium sulphate, the solvent is removed in vacuo and the residue is purified by column chromatography (silica gel; ethyl acetate) to yield the desired product.

$C_{21}H_{30}N_2O_3$ (M=358.5 g/mol), ESI-MS: 376 [M+NH$_4$]$^+$
$R_f$ (TLC): 0.20 (silica gel, DCM/ethyl acetate 1:1)

Example VII

Example VII.1

4-[4-(2-Acetylamino-propyl)-phenyl]-piperidine-1-carboxylic acid tert-butyl ester

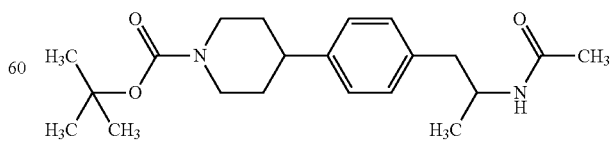

2.20 g (6.14 mmol) 4-[4-(2-Acetylamino-propyl)-phenyl]-3,6-dihydro-2H-pyridine-1-carboxylic acid tert-butyl ester (VI.1) in 100 mL methanol are hydrogenated (50 psi) for 7.0 h at rt using 250 mg palladium on charcoal(10%). After that time, the catalyst is filtered off and the solvent is evaporated to yield the desired product.

$C_{21}H_{32}N_2O_3$ (M=360.5 g/mol), ESI-MS: 361 [M+H]$^+$ $R_f$ (TLC): 0.40 (silica gel, DCM/methanol 9:1)

Example VIII

Example VIII.1

N-[1-Methyl-2-(4-piperidin-4-yl-phenyl)-ethyl]-acetamide

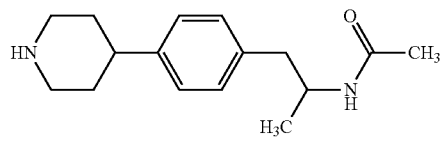

To 2.10 g (5.83 mmol) 4-[4-(2-acetylamino-propyl)-phenyl]-piperidine-1-carboxylic acid tert-butyl ester (VII.1) in 50 mL dichloromethane are added 4.4 mL (58.3 mmol) trifluoroacetic acid. The mixture is stirred for 3 h at rt. After that time, the solvent is evaporated, the residue taken up in ethyl acetate and washed with sat. NaHCO$_3$-solution. After drying over sodium sulphate, the solvent is removed in vacuo and the residue is recrystallized from diethyl ether.

$C_{16}H_{24}N_2O$ (M=260.4 g/mol), ESI-MS: 261 [M+H]$^+$ $R_f$ (TLC): 0.20 (silica gel, DCM/methanol/NH$_4$OH 5:1:0.02)

Example IX

Example IX.1

5-(4-Iodo-pyridin-2-yloxy)-pyrimidine

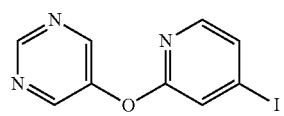 [SMILES: Ic1ccnc(Oc2cncnc2)c1]

To 259 mg (26.9 mmol) pyrimidin-5-ol (J. Chem. Soc. 1956, 2033) in 200 mL DMF are added 108 mg (26.9 mmol) sodium hydride (60% dispersion in mineral oil). The mixture is stirred for 20 min at rt. After that time, 500 mg (22.4 mmol) 2-fluoro-4-iodopyridine are added and the mixture is stirred for 12 h at 80° C. Subsequently the mixture is poured into water and extracted with ethyl acetate (3×). The combined organic layers are washed with brine. After drying over sodium sulphate, the solvent is removed in vacuo and the residue is purified by column chromatography (silica gel; heptane/ethyl acetate, gradient 0-60%) to yield the desired product.

$C_9H_{61}N_3O$ (M=299.1 g/mol), ESI-MS: 300 [M+H]$^+$

The following compounds are prepared analogously to Example IX.1:

Example IX.2

4-Iodo-2-phenoxy-pyridine

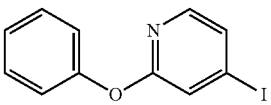 [SMILES: Ic1ccnc(Oc2ccccc2)c1]

$C_{11}H_{81}NO$ (M=297.1 g/mol), ESI-MS: 298 [M+H]$^+$

Example IX.3

5-Bromo-2-cyclopropylmethoxy-pyrimidine

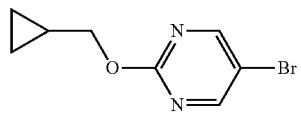 [SMILES: Brc1cnc(OCC2CC2)nc1]

Educts: 5-bromo-2-chloro-pyrimidine/cyclopropylmethanol $C_8H_9BrN_2O$ (M=229.1 g/mol), ESI-MS: 229 [M+H]$^+$ $R_t$ (HPLC): 0.98 min (method H)

Example IX.4

5-Bromo-2-ethoxy-4-methoxy-pyrimidine

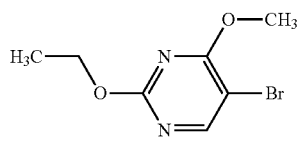

Educts: 5-bromo-2-chloro-4-methoxy-pyrimidine/ethanol $C_7H_9BrN_2O_2$ (M=233.1 g/mol), EI-MS: 232 [M]$^+$ $R_t$ (HPLC): 0.97 min (method F)

Example IX.5

5-Bromo-2-cyclopropylmethoxy-4-methoxy-pyrimidine

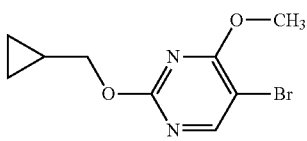

Educts: 5-bromo-2-chloro-4-methoxy-pyrimidine/cyclopropylmethanol $C_9H_{11}BrN_2O_2$ (M=259.1 g/mol), EI-MS: 258 [M]$^+$ $R_t$ (HPLC): 1.09 min (method F)

Example IX.6

5-(5-Bromo-pyridin-2-yloxy)-pyrimidine

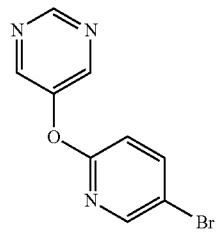 [SMILES: Brc1ccc(Oc2cncnc2)nc1]

Educts: 2,5-dibromo-pyridine/5-hydroxypyrimidine using cesium carbonate as base and DMA as solvent
$C_9H_6BrN_3O$ (M=252.1 g/mol), EI-MS: 252 $[M]^+$
$R_t$ (HPLC): 1.16 min (method M)

Example IX.7

4-Bromo-2-phenoxy-pyridine

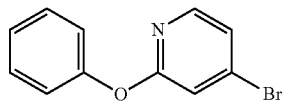 [SMILES: Brc1ccnc(Oc2ccccc2)c1]

Educts: 4-bromo-2-fluoro-pyridine/phenol
$C_{11}H_8BrNO$ (M=250.1 g/mol), ESI-MS: 250 $[M+H]^+$
$R_t$ (HPLC): 1.12 min (method G)

Example X

Example X.1

4-Iodo-1-propyl-1H-pyridin-2-one

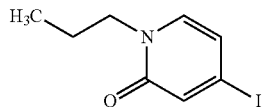

To a mixture of 2.0 g (9.05 mmol) 4-iodo-1H-pyridin-2-one and 3.13 g (22.6 mmol) potassium carbonate in 10 mL DMF are added 1.05 mL (10.9 mmol) 1-iodopropane. The mixture is stirred for 2 h at rt. Subsequently the mixture is poured into water and extracted with ethyl acetate (2×). The combined organic layers are washed with sat. $NaHCO_3$-solution. After drying over sodium sulphate, the solvent is removed in vacuo and the residue is purified by HPLC (column: Agilent Stablebond C18, 7 μM; eluent A: water+0.15% HCOOH, eluent B: MeOH) to yield the desired product.

$C_8H_{10}INO$ (M=263.1 g/mol), ESI-MS: 264 $[M+H]^+$
$R_t$ (HPLC): 1.51 min (method A)

The following compounds are prepared analogously to Example X.1:

Example X.2

1-Bromo-2-methoxy-4-propoxy-benzene

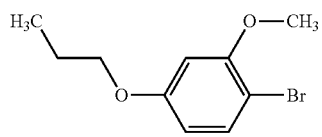

Educts: 4-bromo-3-methoxy-phenol/1-bromopropane
$C_{10}H_{13}BrO_2$ (M=245.1 g/mol), ESI-MS: 245 $[M+H]^+$
$R_t$ (HPLC): 2.12 min (method A)

Example X.3

1-Bromo-2-methyl-4-propoxy-benzene

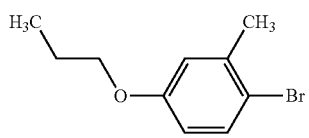

Educts: 4-bromo-3-methyl-phenol/1-bromopropane
$C_{10}H_{13}BrO$ (M=229.1 g/mol)
$R_t$ (HPLC): 2.31 min (method A)
$R_f$ (TLC): 0.79 (silica gel, cyclohexane/ethyl acetate 9:1)

Example X.4

1-Bromo-2-chloro-4-propoxy-benzene

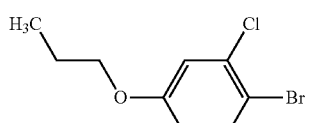

Educt: 4-bromo-3-chloro-phenol/1-bromopropane
$C_9H_{10}BrClO$ (M=249.5 g/mol)
$R_t$ (HPLC): 2.37 min (method A)
$R_f$ (TLC): 0.78 (silica gel, cyclohexane/ethyl acetate 9:1)

Example X.5

1-Bromo-4-cyclopropylmethoxy-2-methoxy-benzene

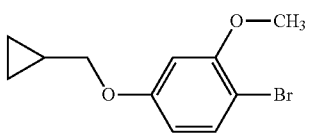

Educts: 4-bromo-3-methoxy-phenol/chloromethylcyclopropane
$C_{11}H_{13}BrO_2$ (M=257.1 g/mol), ESI-MS: 257 [M+H]$^+$
$R_t$ (HPLC): 2.11 min (method A)

Example X.6

1-Bromo-4-cyclobutoxy-2-methoxy-benzene

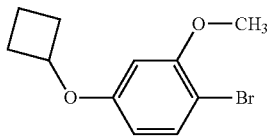

Educts: 4-bromo-3-methoxy-phenol/cyclobutylbromide
$C_{11}H_{13}BrO_2$ (M=257.1 g/mol)
ESI-MS: 257 [M+H]$^+$
$R_t$ (HPLC): 2.18 min (method A)

Example X.7

1-Bromo-4-ethoxy-2-methoxy-benzene

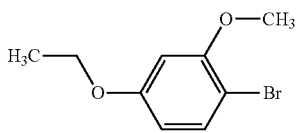

Educts: 4-bromo-3-methoxy-phenol/bromoethane
$C_9H_{11}BrO_2$ (M=231.1 g/mol)
ESI-MS: 231 [M+H]$^+$
$R_t$ (HPLC): 2.00 min (method A)

Example X.8

1-Bromo-4-sec-butyloxy-2-methoxy-benzene

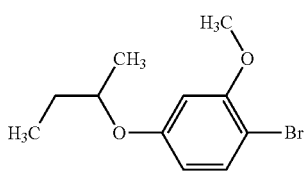

Educts: 4-bromo-3-methoxy-phenol/2-bromobutane
$C_{11}H_{15}BrO_2$ (M=259.1 g/mol)
ESI-MS: 259 [M+H]$^+$
$R_t$ (HPLC): 2.21 min (method A)

Example X.9

2-Bromo-5-isopropoxy-benzonitrile

Educts: 2-bromo-5-hydroxy-benzonitrile/2-bromopropane
$C_{10}H_{10}BrNO$ (M=240.1 g/mol)
EI-MS: 239 [M]$^+$
$R_t$ (HPLC): 1.98 min (method A)

Example X.10

2-Bromo-5-cyclobutoxy-benzonitrile

Educts: 2-bromo-5-hydroxy-benzonitrile/cyclobutyl bromide
$C_{11}H_{10}BrNO$ (M=252.1 g/mol)
EI-MS: 251 [M]$^+$
$R_t$ (HPLC): 2.07 min (method A)

Example X.11

2-Bromo-5-propoxy-benzonitrile

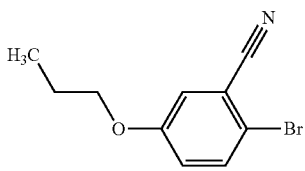

Educts: 2-bromo-5-hydroxy-benzonitrile/1-bromopropane
$C_{10}H_{10}BrNO$ (M=240.1 g/mol)
ESI-MS: 257 [M+NH$_4$]$^+$
$R_t$ (HPLC): 2.27 min (method A)

Example X.12

2-Bromo-5-cyclopropylmethoxy-benzonitrile

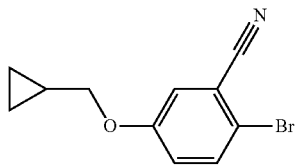 [SMILES: N#Cc1cc(OCC2CC2)ccc1Br]

Educts: 2-bromo-5-hydroxy-benzonitrile/chloromethyl-cyclopropane
$C_{11}H_{10}BrNO$ (M=252.1 g/mol)
ESI-MS: 252 [M+H]$^+$
$R_t$ (HPLC): 2.00 min (method A)

Example X.13

2-Bromo-5-ethoxy-benzonitrile

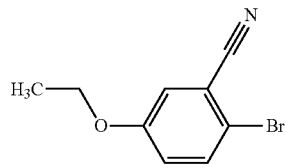

Educts: 2-bromo-5-hydroxy-benzonitrile/bromoethane
$C_9H_8BrNO$ (M=226.1 g/mol)
ESI-MS: 226 [M+H]$^+$
$R_t$ (HPLC): 1.82 min (method A)

Example X.14

5-Butoxy-2-fluoro-benzonitrile

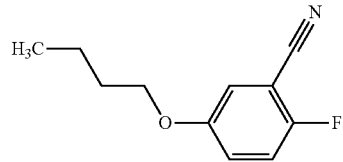

Educts: 2-fluoro-5-hydroxy-benzonitrile/1-bromobutane
$C_{11}H_{12}FNO$ (M=193.2 g/mol)
$R_t$ (HPLC): 2.02 min (method A)
$R_f$ (TLC): 0.64 (silica; cyclohexane/ethyl acetate 8:2)

Example X.15

1-Bromo-2-fluoro-4-propoxy-benzene

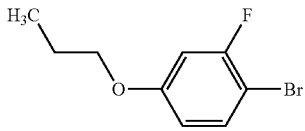

Educt: 4-bromo-3-fluoro-phenol/1-bromopropane
$C_9H_{10}BrFO$ (M=233.1 g/mol)
EI-MS: 232 [M]$^+$
$R_t$ (HPLC): 2.12 min (method F)

Example X.16

5-sec-Butoxy-2-fluoro-benzonitrile

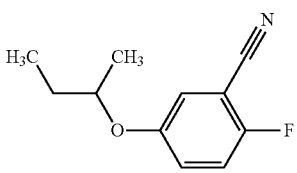

Educts: 2-fluoro-5-hydroxy-benzonitrile/2-bromobutane
$C_{11}H_{12}FNO$ (M=193.2 g/mol)
$R_t$ (HPLC): 1.86 min (method F)
$R_f$ (TLC): 0.60 (silica; cyclohexane/ethyl acetate 8:2)

Example X.17

1-Bromo-2-fluoro-4-isopropoxy-benzene

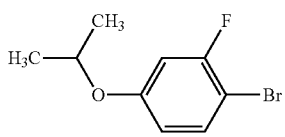

Educt: 4-bromo-3-fluoro-phenol/2-bromopropane
$C_9H_{10}BrFO$ (M=233.1 g/mol)
$R_t$ (HPLC): 2.25 min (method F)
$R_f$ (TLC): 0.27 (silica; cyclohexane)

Example X.18

1-Bromo-4-cyclopropylmethoxy-2-fluoro-benzene

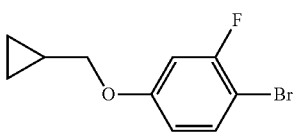 [SMILES: Fc1cc(OCC2CC2)ccc1Br]

Educt: 4-bromo-3-fluoro-phenol/chloromethylcyclopropane
$C_{10}H_{10}BrFO$ (M=245.1 g/mol)
EI-MS: 244 [M]$^+$
$R_t$ (HPLC): 2.08 min (method F)

Example X.19

1-Bromo-4-ethoxy-2-fluoro-benzene

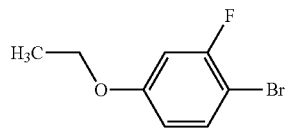

Educt: 4-bromo-3-fluoro-phenol/ethylbromide
$C_8H_8BrFO$ (M=219.1 g/mol)
$R_f$ (TLC): 0.57 min (silica gel, CyH)
$R_t$ (HPLC): 2.16 min (method F)

Example X.20

1-Bromo-3-cyclobutoxy-benzene

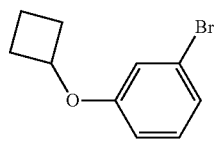 [SMILES: Brc1cccc(OC2CCC2)c1]

Educt: 3-bromo-phenol/chloro-cyclobutane
$C_{10}H_{11}BrO$ (M=227.1 g/mol)
$R_f$ (TLC): 0.58 (silica gel, CyH)
$R_t$ (HPLC): 1.40 min (method L)

Example X.21

1-Bromo-2-fluoro-4-(3-methoxy-propoxy)-benzene

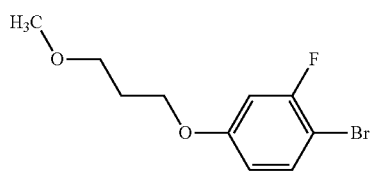

Educt: 4-bromo-3-fluoro-phenol/1-bromo-3-methoxypropane
$C_{10}H_{12}BrFO_2$ (M=263.1 g/mol),
$R_f$ (TLC): 0.49 (silica gel, CyH/EtOAc 9/1)
$R_t$ (HPLC): 0.72 min (method H)

Example X.22

2-Chloro-5-ethoxy-3-fluoro-pyridine

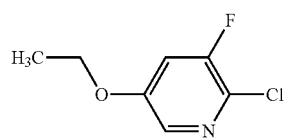

Educts: 2-chloro-3-fluoro-5-hydroxy-pyridine/ethyl bromide
$C_7H_7ClFNO$ (M=175.6 g/mol), ESI-MS: 176 [M+H]$^+$
$R_t$ (HPLC): 1.07 min (method L)

Example X.23

1-Bromo-4-(2-cyclopropyl-ethoxy)-2-fluoro-benzene

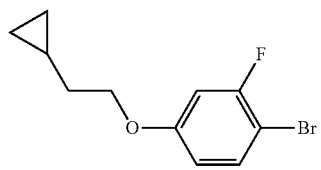 [SMILES: Fc1cc(OCCC2CC2)ccc1Br]

Educt: 4-bromo-3-fluoro-phenol/(2-iodo-ethyl)-cyclopropane
$C_{11}H_{12}BrFO$ (M=259.1 g/mol),
$R_f$ (TLC): 0.71 (silica gel, CyH/EtOAc 9/1) $R_t$ (HPLC): 1.43 min (method L)

Example X.24

2-Chloro-5-cyclopropylmethoxy-3-fluoro-pyridine

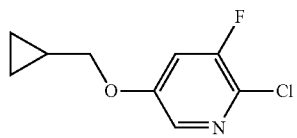 [SMILES: Fc1cc(OCC2CC2)cnc1Cl]

Educts: 2-chloro-3-fluoro-5-hydroxy-pyridine/(bromomethyl)cyclopropane
$C_9H_9ClFNO$ (M=201.6 g/mol), ESI-MS: 202 [M+H]$^+$
$R_t$ (HPLC): 1.20 min (method L)

Example X.25

2-Chloro-3-fluoro-5-propoxy-pyridine

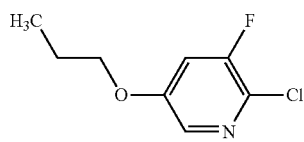

Educts: 2-chloro-3-fluoro-5-hydroxy-pyridine/1-bromopropane
$C_8H_9ClFNO$ (M=189.6 g/mol), ESI-MS: 190 [M+H]$^+$
$R_t$ (HPLC): 1.19 min (method L)

Example X.26

2-Chloro-5-propoxy-pyrimidine

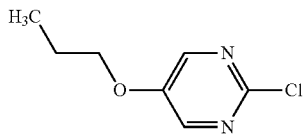

Educts: 2-chloro-5-hydroxy-pyrimidine/1-bromopropane
$C_7H_9ClN_2O$ (M=172.6 g/mol), ESI-MS: 173 [M+H]$^+$
$R_t$ (HPLC): 1.53 min (method A)

Example X.27

1-Bromo-4-(2,2-difluoro-cyclopropylmethoxy)-benzene

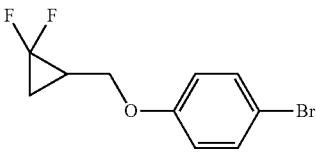 [SMILES: FC1(F)CC1COc1ccc(Br)cc1]

Educt: 4-bromo-3-phenol/2-bromomethyl-1,1-difluoro-cyclopropane
$C_{10}H_9BrF_2O$ (M=263.1 g/mol), EI-MS: 262 [M]$^+$
$R_t$ (HPLC): 1.15 min (method G)

Example X.28

1-Bromo-4-(2-cyclopropyl-ethoxy)-benzene

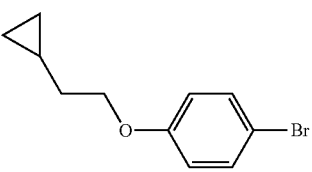

Educt: 4-bromo-phenol/(2-iodo-ethyl)-cyclopropane
$C_{11}H_{13}BrO$ (M=241.1 g/mol), EI-MS: 240 [M]$^+$
$R_t$ (HPLC): 1.30 min (method G)

Example X.29

2-Chloro-5-cyclopropylmethoxy-pyrimidine

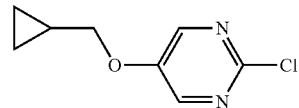 [SMILES: Clc1ncc(OCC2CC2)cn1]

Educts: 2-chloro-5-hydroxy-pyrimidine/(bromomethyl)cyclopropane
$C_8H_9ClN_2O$ (M=184.6 g/mol), ESI-MS: 185 [M+H]$^+$
$R_t$ (HPLC): 1.23 min (method N)

Example X.30

2-Chloro-5-(2,2-difluorcyclopropylmethoxy)-pyrimidine

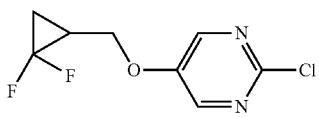 [SMILES: FC1(F)CC1COc1cnc(Cl)nc1]

Educts: 2-chloro-5-hydroxy-pyrimidine/2-bromomethyl-1,1-difluoro-cyclopropane
$C_8H_7ClF_2N_2O$ (M=220.6 g/mol), ESI-MS: 221 [M+H]$^+$
$R_t$ (HPLC): 1.21 min (method N)

Example X.31

1-Bromo-4-(2,2-difluoro-cyclopropylmethoxy)-2-fluoro-benzene

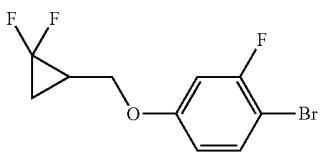 [SMILES: Fc1cc(OCC2CC2(F)F)ccc1Br]

Educt: 4-bromo-3-fluoro-phenol/2-bromomethyl-1,1-difluoro-cyclopropane
$C_{10}H_8BrF_3O$ (M=281.1 g/mol), EI-MS: 282 [M+H]$^+$
$R_t$ (HPLC): 1.31 min (method L)

Example X.32

4-Bromo-2-ethoxy-5-fluoro-pyridine

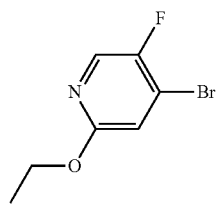

Educt: 4-bromo-5-fluoro-pyridin-2-ol/ethyl iodide using silver carbonate in methylene chloride as a base
$C_7H_7BrFNO$ (M=220.0 g/mol), EI-MS: 220 [M+H]$^+$
$R_t$ (HPLC): 1.27 min (method M)

Example XI

Example XI.1

N-(2-Chloro-pyrimidin-5-yl)-acetamide

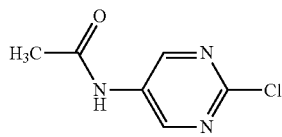

78 µL (0.83 mmol) acetic anhydride are added to 100 mg (0.77 mmol) 2-chloro-pyrimidin-5-ylamine in 20 mL dichloromethane at 0° C. Subsequently 115 µL TEA are added and stirring is continued for 12 h at rt. After that time, the solvent is removed by evaporation and the residue is washed with water.

$C_6H_6ClN_3O$ (M=171.6 g/mol)

ESI-MS: 172 [M+H]$^+$ $R_t$ (HPLC): 0.86 min (method A)

Example XII

Example XII.1

(S)-(1-{4-[1-(4-Ethoxy-phenyl)-piperidin-4-yl]-phenyl}-ethyl)-carbamic acid tert-butyl ester

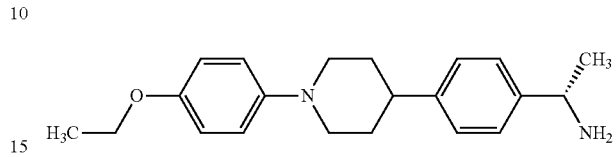

6.21 g (19.1 mmol) cesium carbonate are added to a mixture of 5.80 mg (19.1 mmol) (S)-[1-(4-piperidin-4-yl-phenyl)-ethyl]-carbamic acid tert-butyl ester (V.5), 4.21 g (21.0 mmol) 1-bromo-4-ethoxy-benzene, 454 mg (0.953 mmol) X-Phos and 214 mg (0.953 mmol) palladium(II) acetate in 50 mL toluene/10 mL tert-butanol. The mixture is stirred for 3 h at 120° C. under inert gas atmosphere. After that time, the mixture is poured into water and extracted with ethyl acetate. The organic layer is washed with water and dried over magnesium sulphate. The solvent is removed in vacuo and the residue is recrystallized from acetonitrile.

$C_{26}H_{36}N_2O_3$ (M=424.6 g/mol)

ESI-MS: 425 [M+H]$^+$ $R_t$ (HPLC): 2.10 min (method A)

Example XIII

Example XIII.1

(S)-1-{4-[1-(4-Ethoxy-phenyl)-piperidin-4-yl]-phenyl}-ethylamine dihydrochloride

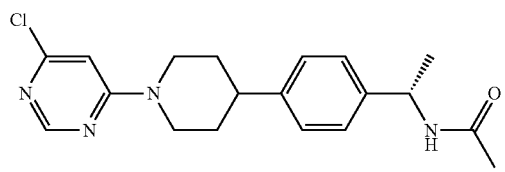

11.3 mL (14.1 mmol) 1.25 N HCl in methanol are added to 900 mg (2.12 mmol) (S)-(1-{4-[1-(4-ethoxy-phenyl)-piperidin-4-yl]-phenyl}-ethyl)-carbamic acid tert-butyl ester (XII.1) in 25 mL dichloromethane. The mixture is stirred for 14 h at rt and for 1 h at 50° C. After that time, the solvent is removed in vacuo to yield the desired product.

$C_{21}H_{28}N_2O_2$·HCl (M=397.4 g/mol)

ESI-MS: 325 [M+H]$^+$ $R_t$ (HPLC): 1.11 min (method D)

The corresponding free base is synthesized by addition of NaOH (10% in water) and immediate extraction with dichloromethane. The organic layer is washed with water (2×), dried over magnesium sulphate and the solvent is evaporated to yield the desired product.

Example XIV

Example XIV.1

(S)—N-(1-{4-[1-(6-Chloro-pyrimidin-4-yl)-piperidin-4-yl]-phenyl}-ethyl)-acetamide 0.34 mL (2.43 mmol) TEA are added to a mixture of 181 mg (1.22 mmol) 4,6-dichloropyrimidine and 300 mg (1.22 mmol) (S)-N-[1-(4-piperidin-4-yl-phenyl)-ethyl]-acetamide (V.1) in 3 mL THF. The mixture is stirred for 5 min at 80° C. and for 2 h at rt. After that time, water is added and the mixture is extracted with dichloromethane (2×). The combined organic layers are dried over sodium sulphate. The solvent is evaporated and the residue is purified by column chromatography (silica gel; dichloromethane/methanol, gradient 98:2-95:5) to yield the desired product.

$C_{19}H_{23}ClN_4O$ (M=358.9 g/mol)

ESI-MS: 359 [M+H]$^+$ $R_t$ (HPLC): 2.00 min (method B)

The following compounds are prepared analogously to Example XIV.1:

Example XIV.2

N-(2-{4-[1-(2-Chloro-pyrimidin-4-yl)-piperidin-4-yl]-phenyl}-1-methyl-ethyl)-acetamide

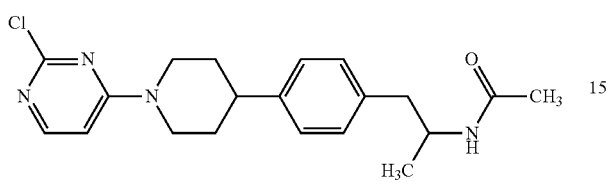

Educts: VIII.1/2,4-dichloropyrimidine
(using $K_2CO_3$ as base and acetone as solvent)
$C_{20}H_{25}ClN_4O$ (M=372.9 g/mol)
ESI-MS: 373 [M+H]$^+$

Example XIV.3

(S)—N-(1-{4-[1-(2-Chloro-pyrimidin-4-yl)-piperidin-4-yl]-phenyl}-ethyl)-acetamide

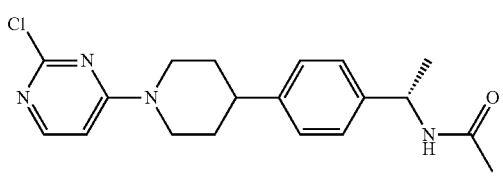 [SMILES: CC(=O)N[C@@H](C)c1ccc(C2CCN(c3cc(Cl)ncn3)CC2)cc1]

Educts: V.1/4,6-dichloropyrimidine
$C_{19}H_{23}ClN_4O$ (M=358.9 g/mol); ESI-MS: 359 [M+H]$^+$
$R_t$ (HPLC): 2.00 min (method P)

Example XIV.4

(S)-Cyclopropanecarboxylic acid (1-{4-[1-(2-chloro-5-cyano-pyrimidin-4-yl)-piperidin-4-yl]-phenyl}-ethyl)-amide

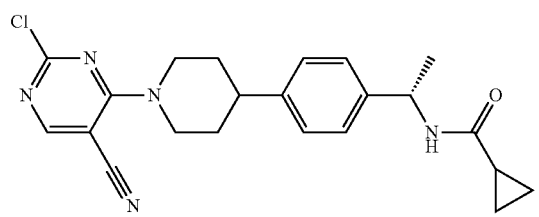 [SMILES: C[C@H](NC(=O)C1CC1)c1ccc(C2CCN(c3nc(Cl)ncc3C#N)CC2)cc1]

Educts: V.4/2,4-dichloro-5-cyanopyrimidine
(using $K_2CO_3$ as base and acetone as solvent)
$C_{22}H_{24}ClN_5O$ (M=409.9 g/mol); ESI-MS: 410 [M+H]$^+$
$R_t$ (HPLC): 1.97 min (method T)

Example XIV.5

(S)-Cyclopropanecarboxylic acid (1-{4-[1-(4-chloro-5-cyano-pyrimidin-2-yl)-piperidin-4-yl]-phenyl}-ethyl)-amide

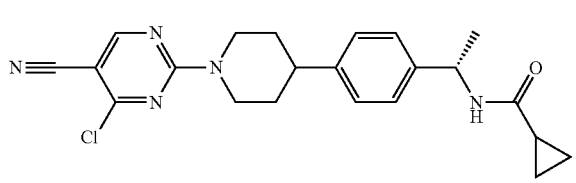 [SMILES: C[C@H](NC(=O)C1CC1)c1ccc(C2CCN(c3ncc(C#N)c(Cl)n3)CC2)cc1]

Educts: V.4/2,4-dichloro-5-cyanopyrimidine
(using $K_2CO_3$ as base and acetone as solvent)
$C_{22}H_{24}ClN_5O$ (M=409.9 g/mol); ESI-MS: 410 [M+H]$^+$
$R_t$ (HPLC): 2.07 min (method T)

Example XIV.6

(S)-Cyclopropanecarboxylic acid (1-{4-[1-(6-chloro-pyrimidin-4-yl)-piperidin-4-yl]-phenyl}-ethyl)-amide

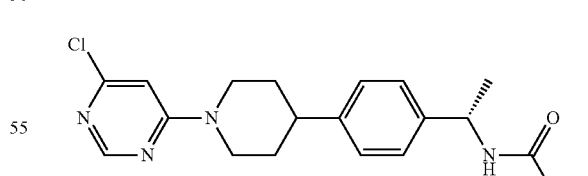

Educts: V.4/4,6-dichloropyrimidine
$C_{21}H_{25}ClN_4O$ (M=384.9 g/mol); ESI-MS: 385 [M+H]$^+$
$R_t$ (HPLC): 1.19 min (method L)

Example XIV.7

(S)-3-(1-{4-[1-(6-Chloro-pyrimidin-4-yl)-piperidin-4-yl]-phenyl}-ethyl)-1,1-dimethyl-urea

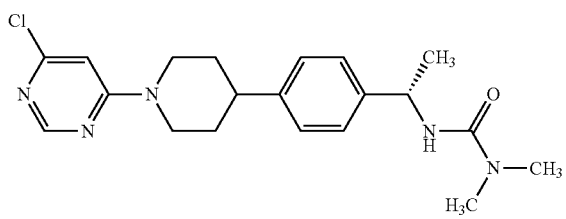 [SMILES: C[C@H](NC(=O)N(C)C)c1ccc(C2CCN(c3cc(Cl)ncn3)CC2)cc1]

Educts: V.3/4,6-dichloropyrimidine
$C_{20}H_{26}ClN_5O$ (M=387.9 g/mol); ESI-MS: 388 [M+H]$^+$
$R_t$ (HPLC): 1.17 min (method L)

Example XIV.8

(S)—N-(1-{4-[1-(4-Chloro-pyrimidin-2-yl)-piperidin-4-yl]-phenyl}-ethyl)-acetamide

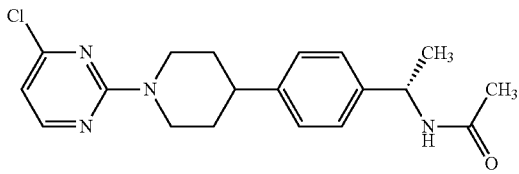 [SMILES: CC(=O)N[C@@H](C)c1ccc(C2CCN(c3nccc(Cl)n3)CC2)cc1]

Educts: V.1/4,6-dichloropyrimidine, solvent DMF; compound XIV.3 is obtained as a second product.
$C_{19}H_{23}ClN_4O$ (M=358.9 g/mol); ESI-MS: 359 [M+H]$^+$
$R_t$ (HPLC): 1.34 min (method L)

Example XV

Example XV.1

5-Chloro-2-phenyloxazolo[5,4-d]pyrimidine

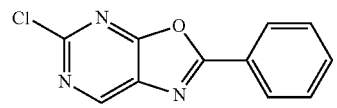 [SMILES: Clc1ncc2nc(-c3ccccc3)oc2n1]

7.82 g (64.0 mmol) Benzoic acid and 20 mL POCl$_3$ are stirred together at 100° C. for 30 min. Within 45 min 7.00 g (42.7 mmol) 2,6-dichloro-5-aminopyrimidine are added in several portions. The reaction mixture is stirred for additional 2 h at the same temperature. After that time, the mixture is carefully added to an ice cold aq. NaOH solution. The resulting precipitate is filtered off, washed with water and dried.

$C_{11}H_6ClN_3O$ (M=231.6 g/mol); ESI-MS: 232 [M+H]$^+$
$R_t$ (HPLC): 2.22 (method I)

The following compounds are prepared analogously to example XV.1:

| Ex. | Starting material | Product structure | Mass spec result | $R_t$ (HPLC) [min] (method) |
|---|---|---|---|---|
| XV.1 | benzoic acid | 5-chloro-2-phenyl-oxazolo[5,4-d]pyrimidine | 232 [M + H]$^+$ | 2.22 (I) |
| XV.2 | thiophene-3-carboxylic acid | 5-chloro-2-(thiophen-3-yl)-oxazolo[5,4-d]pyrimidine | 238 [M + H]$^+$ | 1.43 (I) |
| XV.3 | 5-methylthiophene-2-carboxylic acid | 5-chloro-2-(5-methylthiophen-2-yl)-oxazolo[5,4-d]pyrimidine | 252 [M + H]$^+$ | n.d. |
| XV.4 | thiophene-2-carboxylic acid | 5-chloro-2-(thiophen-2-yl)-oxazolo[5,4-d]pyrimidine | 238 [M + H]$^+$ | n.d. |

Example XV.5

5-Chloro-2-pyridin-4-yl-oxazolo[5,4-d]pyrimidine

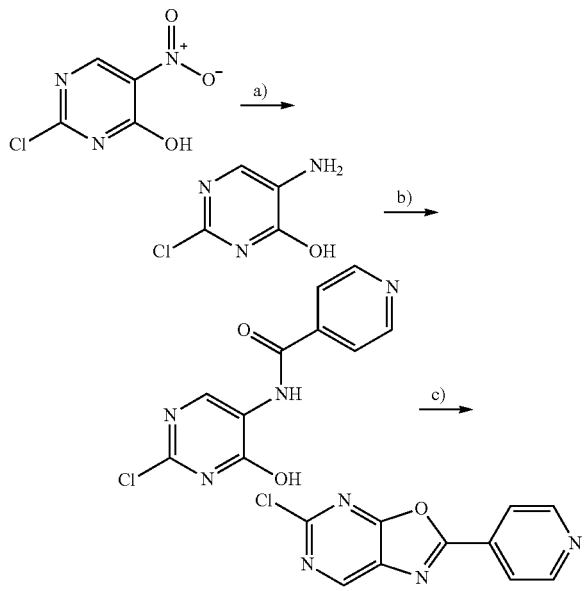

a)

25 g (126 mmol) 2-chloro-5-nitro-pyrimidin-4-ol, 2.0 g PtO$_2$ and 2.5 L MeOH are hydrogenated (50 psi) for 1 h. The mixture is filtered and concentrated and dried to yield 5-amino-2-chloro-pyrimidin-4-ol.

b)

5.88 g (47.7 mmol) isonicotinic acid and 7.74 g (47.7 mmol) 1,1'-carbonyldiimidazole in 30 mL DMF are stirred for 30 min at 45° C. prior to addition of 8.0 g (47.7 mmol) of 5-amino-2-chloro-pyrimidin-4-ol. The mixture is stirred for 12 h at rt, concentrated and purified by HPLC (reversed phase, water (+0.1% TFA)/MeOH) to yield N-(2-chloro-4-hydroxy-pyrimidin-5-yl)-isonicotinamide.

c)

12.0 g (35.9 mmol) polymer bound triphenylphosphine and 5.03 mL (35.9 mmol) triethylamine are added to 4.77 g (20.0 mmol) hexachloroethane in 40 mL 1,2-dichloroethane. The mixture is stirred for 5 min at rt. 1.00 g (4.0 mmol) N-(2-chloro-4-hydroxy-pyrimidin-5-yl)-isonicotinamide in 20 mL 1,2-dichloroethane are added and the mixture is stirred for 12 h at rt. Subsequently the mixture is concentrated in vacuo, treated with diethyl ether, filtered, and concentrated again. The residue is purified by HPLC (reversed phase; water (+0.1% TFA)/MeOH) to yield the desired product.

C$_{10}$H$_5$ClN$_4$O (M=232.6 g/mol); ESI-MS: 233 [M+H]$^+$

Example XVI

Example XVI.1

1-Bromo-4-(2-bromoethoxy)benzene

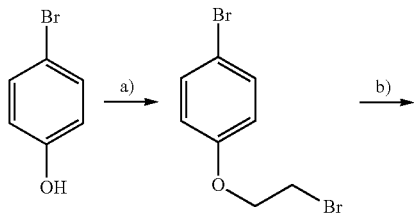

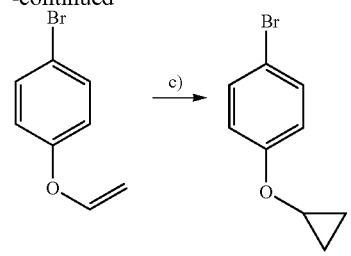

a)

55.0 g (318 mmol) 4-bromophenol and 14.1 g (352 mmol) NaOH are added to 110 mL water. 41.1 mL (477 mmol) dibromoethane are added slowly and the reaction mixture is stirred for 16 h under reflux. Afterwards the reaction mixture is extracted with dichloromethane and the solvent is removed in vacuo. The crude product is purified by column chromatography (silica gel, cyclohexane/EtOAc 4/1).

b)

52.0 g (186 mmol) 1-bromo-4-(2-bromoethoxy)benzene are added to 300 mL THF and cooled to 0° C. Within 30 min 25.0 g (223 mmol) KOtBu are added to this mixture in several portions. Cooling is removed and the reaction mixture is stirred at rt over night. The reaction is quenched by the addition of water. The resulting mixture is extracted with EtOAc (2×). The organic phases are combined, washed with brine, dried over MgSO$_4$ and the solvent is removed in vacuo. The resulting product is used without further purification.

c)

39.0 g (176 mmol) 1-bromo-4-vinyloxybenzene and 32.4 mL (441 mmol) chloroiodomethane are added to 500 mL dichloroethane and cooled to 0° C. During 1 h 200 mL (200 mmol) diethylzinc solution (c=1 mol/l in hexane) are added and stirring is continued for 2 h at 0° C. The reaction is quenched by the addition of 200 mL of a sat. aq. NH$_4$Cl solution and extracted with TBME (2×). The organic phases are combined, washed with brine, dried over MgSO$_4$ and the solvent is removed in vacuo. The crude product is purified by column chromatography (silica gel, PE)

C$_9$H$_9$BrO (M=213.1 g/mol)

EI-MS: 212/214 [M]$^+$

R$_f$(TLC): 0.4 (silica gel, PE)

The following compounds are prepared analogously to example XVI.1.

For the examples XVI.2/XVI.3 the phenolate in step a) is preformed by reacting the appropriate phenol with NaOH in a MeOH/water (1/1) mixture at rt for 1 h. Then the solvent is removed in vacuo and the resulting sodium salt is reacted with dibromoethane (5 eq.) at 100° C. for 24 h. The reaction mixture is quenched by the addition of water and extracted with DCM.

For example XVI.4 step a: To the diphenol and dibromoethane (8 eq.) in acetone is added Cs$_2$CO$_3$ (5 eq.) and the reaction mixture is stirred at 90° C. for 45 h. The reaction mixture is quenched by the addition of water and extracted with EtOAc.

| Example | Starting material | Product structure | Mass spec result | $R_t$ (HPLC) [min] (method) |
|---|---|---|---|---|
| XVI.1 | HO-C6H4-Br | cyclopropyl-O-C6H4-Br | 212/214 [M]+ | n.d. |
| XVI.2 | HO-C6H3(CH3)-Br | cyclopropyl-O-C6H3(CH3)-Br | n.d. | 5.89 (AF) |
| XVI.3 | HO-C6H3(OCH3)-Br | cyclopropyl-O-C6H3(OCH3)-Br | n.d. | 5.30 (J) |
| XVI.4 | HO-C6H3(OH)-Br | cyclopropyl-O-C6H3(O-cyclopropyl)-Br | n.d. | 8.50 (K) |
| XVI.5 | HO-C6H3(F)-Br | cyclopropyl-O-C6H3(F)-Br | 230/232 [M]+ | n.d. |

Example XVII

Example XVII.1

(S)-2-{4-[4-(1-Acetylamino-ethyl)-phenyl]-piperidin-1-yl}-pyrimidine-5-carboxylic acid

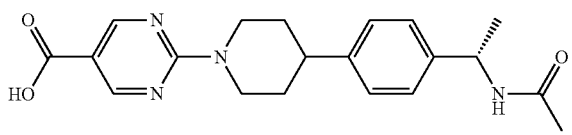 [SMILES: CC(=O)N[C@@H](C)c1ccc(C2CCN(c3ncc(C(=O)O)cn3)CC2)cc1]

To 1.52 g (8.5 mmol) 2-chloropyrimidine-5-carboxylic acid methyl ester in 80 mL NMP are added 2.1 g (8.5 mmol) (S)—N-[1-(4-piperidin-4-yl-phenyl)-ethyl]-acetamide (V.1) and 2.9 mL (17.1 mmol) DIPEA and the mixture is stirred for 4 h at 100° C. The solvent is removed in vacuo. The residue is treated with 100 mL MeOH and 10 mL 4N sodium hydroxide solution is added. The mixture is stirred for 1 h at 60° C. After cooling to rt 4N HCl solution is added until the pH is acidic. The precipitate is collected and dried to yield the desired product.

$C_{20}H_{24}N_4O_3$ (M=368.4 g/mol); ESI-MS: 369 [M+H]+

$R_t$ (HPLC): 2.04 min (method P)

Example XVIII

Example XVIII.1

(S)-Cyclopropanecarboxylic acid (1-{4-[1-(5-iodo-pyrimidin-2-yl)-piperidin-4-yl]-phenyl}-ethyl)-amide

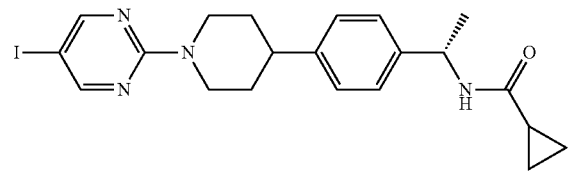 [SMILES: C[C@H](NC(=O)C1CC1)c1ccc(C2CCN(c3ncc(I)cn3)CC2)cc1]

633 mg (2.5 mmol) 2-Chloro-5-iodopyrimidine, 757 mg (2.5 mmol) (S)-cyclopropanecarboxylic acid [1-(4-piperidin-4-yl-phenyl)ethyl]-amide (V.4) and 0.855 mL (5.0 mmol) DIPEA in 10 mL NMP are stirred for 2 h at 130° C. After cooling to rt the mixture is treated with water and the precipitate is collected by filtration and triturated with ether to yield the desired compound.

$C_{21}H_{25}IN_4O$ (M=476.4 g/mol); ESI-MS: 477 [M+H]+

$R_t$ (HPLC): 2.25 min (method P)

The following compound is prepared analogously to Example XVII1.1:

Example XVIII.2

(S)-3-(1-{4-[1-(5-Iodo-pyrimidin-2-yl)-piperidin-4-yl]-phenyl}-ethyl)-1,1-dimethyl-urea

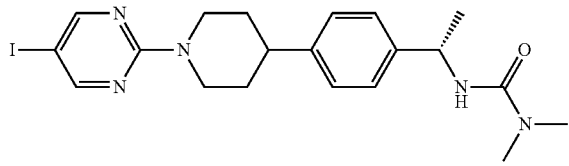 [SMILES: C[C@H](NC(=O)N(C)C)c1ccc(C2CCN(c3ncc(I)cn3)CC2)cc1]

Educts: V.3/2-chloro-5-iodopyrimidine
$C_{20}H_{26}IN_5O$ (M=479.4 g/mol); ESI-MS: 480 [M+H]$^+$
$R_t$ (HPLC): 2.22 min (method P)

Example XIX

Example XIX.1

(S)—N-{1-[4-(2'-Fluoro-3,4,5,6-tetrahydro-2H-[1,4']bipyridinyl-4-yl)-phenyl]-ethyl}-acetamide

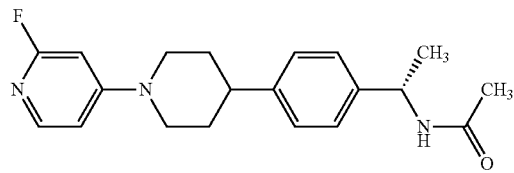 [SMILES: CC(=O)N[C@@H](C)c1ccc(C2CCN(c3ccnc(F)c3)CC2)cc1]

To 1.41 g (5.74 mmol) (S)-N-[1-(piperidin-4-yl-phenyl)-ethyl]-acetamide (V.1) in 10 mL THF and 10 mL DMF is added 0.80 mL (5.74 mmol) triethylamine and 0.60 g (5.21 mmol) 2,4-difluoropyridine. The mixture is stirred for 12 h at 0° C. Subsequently the mixture is concentrated in vacuo and the residue is purified by HPLC (C18 RP Sunfire; water (+0.1% TFA)/MeOH) to yield the desired product.
$C_{20}H_{24}FN_3O$ (M=341.4 g/mol); ESI-MS: 342 [M+H]$^+$
$R_t$ (HPLC): 1.59 min (method T)

Example XX

Example XX.1

(S)—N-(1-{4-[1-(4-Hydroxy-3-methyl-phenyl)-piperidin-4-yl]-phenyl}-ethyl)-acetamide

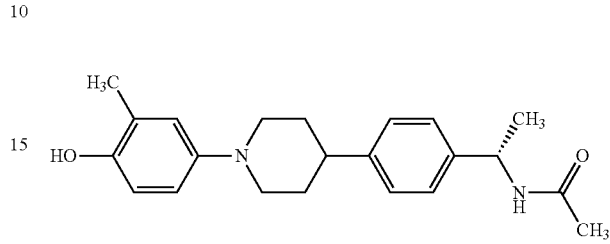

To a mixture of 760 mg (4.06 mmol) 4-bromo-2-methylphenol, 1.7 g (16.24 mmol) sodium-tert-butyl at and 484 mg (1.62 mmol) 2-(di-tert-butylphosphino)biphenyl in 40 mL dioxane is added 1.0 g (4.06 mmol) (S)—N-[1-(piperidin-4-yl-phenyl)-ethyl]-acetamide (V.1). Subsequently 371.7 mg (0.41 mmol) tris-(dibenzylidenaceton)-palladium(0) is added under an argon atmosphere and the mixture is stirred for 12 h at 45° C. The mixture is then poured on water, acidified using 1N HCl solution and extracted with dichloromethane. The DCM solution is subsequently extracted twice with 1N HCl solution and the combined aq. layers are brought to neutral pH using solid $Na_2HPO_4$. The precipitate is then treated with DCM/MeOH and the solvents are removed in vacuo. The residue is purified by HPLC (column: C18 RP Sunfire; eluent A: water+0.1% TFA, eluent B: MeOH) to yield the desired product.

$C_{20}H_{28}N_2O_2$ (M=352.5 g/mol); ESI-MS: 353 [M+H]$^+$
$R_t$ (HPLC): 1.14 min (method P)

The following compounds are prepared analogously to example XX.1, the educts used being shown in the column headed "E 1" and "E 2".

For the example XX.6 at the end of the reaction the solvent is removed in vacuo and to the residue is added 2N HCl. The aq. layer is extracted with EtOAc, filtered and then basified with 4N NaOH. The resulting precipitate is filtered and dried in vacuo.

| Ex. | Product | E 1 | E 2 | ESI-MS [m/z] | $R_t$ (HPLC) [min] (method) |
|---|---|---|---|---|---|
| XX.1 | ![structure] | | V.1 | 353 [M + H]$^+$ | 1.14 (P) |

-continued

| Ex. | Product | E 1 | E 2 | ESI-MS [m/z] | R$_t$ (HPLC) [min] (method) |
|---|---|---|---|---|---|
| XX.2 | (structure: 3-cyano-4-hydroxyphenyl-piperidinyl-phenyl-(S)-ethyl-NHAc) | (2-hydroxy-5-bromo-benzonitrile) | V.1 | 364 [M + H]$^+$ | 1.20 (P) |
| XX.3 | (structure: 3-fluoro-4-hydroxyphenyl-piperidinyl-phenyl-(S)-ethyl-NHAc) | (4-bromo-2-fluorophenol) | V.1 | 357 [M + H]$^+$ | 1.12 (P) |
| XX.4 | (structure: 3-chloro-4-hydroxyphenyl-piperidinyl-phenyl-(S)-ethyl-NHAc) | (4-bromo-2-chlorophenol) | V.1 | 373 [M + H]$^+$ | 1.21 (P) |
| XX.5 | (structure: 3-methoxy-4-hydroxyphenyl-piperidinyl-phenyl-(S)-ethyl-NHAc) | (4-bromo-2-methoxyphenol) | V.1 | 369 [M + H]$^+$ | 1.09 (P) |
| XX.6 | (structure: 4-aminophenyl-piperidinyl-phenyl-(S)-ethyl-NHAc) | (4-bromo-NHBoc-aniline) | V.1 | 338 [M + H]$^+$ | 0.81 (N) |

Example XXI

Example XXI.1

(S)-1-Benzyl-4-[4-(1-propionylamino-ethyl)phenyl]-pyridinium bromide

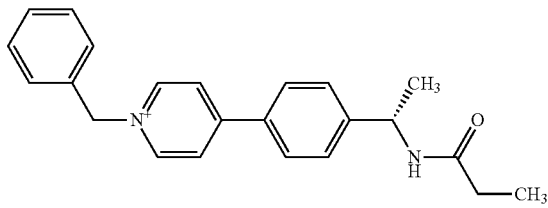 [SMILES: CCC(=O)N[C@@H](C)c1ccc(-c2cc[n+](Cc3ccccc3)cc2)cc1]

To 9.60 g (37.7 mmol) (S)—N-[1-(4-pyridin-4-yl-phenyl)-ethyl]-propionamide (IV.6) in 120 mL acetone are added 4.91 mL (41.5 mmol) benzyl bromide. The mixture is refluxed for 12 h. After that time, the precipitate is filtered off, washed with acetone and dried at 50° C. to yield the desired product.

$C_{23}H_{25}N_2O \cdot Br$ (M=425.4 g/mol), EI-MS: 345 [M]$^+$ $R_t$ (HPLC): 1.03 min (method O)

The following compounds are prepared analogously to Example XXI.1

Example XXI.2

1-Benzyl-4-[4-(1-acetylamino-propyl)-phenyl]-pyridinium bromide

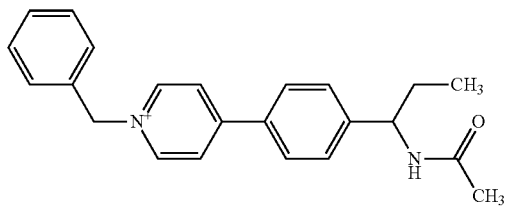

$C_{23}H_{25}N_2O \cdot Br$ (M=425.4 g/mol), EI-MS: 345 [M]$^+$ $R_t$ (HPLC): 0.93 min (method N)

Example XXII

Example XXII.1

(S)—N-{1-[4-(1-Benzyl-1,2,3,6-tetrahydro-pyridin-4-yl)-phenyl]-ethyl}-propionamide

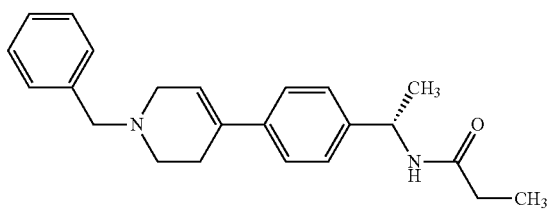

To 13.60 g (32.0 mmol) (S)-1-benzyl-4-[4-(1-propionylamino-ethyl)phenyl]-pyridinium bromide (XXI.1) in 270 mL ethanol are slowly added 2.42 g (64.1 mmol) sodium borohydride at 0° C. The mixture is stirred for 48 h at rt. After that time, the solvent is removed in vacuo and ethyl acetate is added. The mixture is extracted with 1N HCl. The aq. phase is neutralized with 4N NaOH, the precipitate is filtered off and dried at 45° C. to yield the desired product.

$C_{23}H_{28}N_2O$ (M=348.5 g/mol), ESI-MS: 349 [M+H]$^+$ $R_t$ (HPLC): 0.91 min (method N)

The following compounds are prepared analogously to Example XXII.1

Example XXII.2

(N-{1-[4-(1-Benzyl-1,2,3,6-tetrahydro-pyridin-4-yl)-phenyl]-propyl}-acetamide

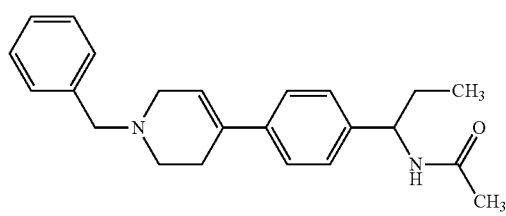 [SMILES: CCC(NC(C)=O)c1ccc(C2=CCN(Cc3ccccc3)CC2)cc1]

$C_{23}H_{28}N_2O$ (M=348.5 g/mol), ESI-MS: 349 [M+H]$^+$ $R_t$ (HPLC): 0.93 min (method N)

Example XXIII

Example XXIII.1

(S)—N-[1-(4-Piperidin-4-yl-phenyl)-ethyl]-propionamide

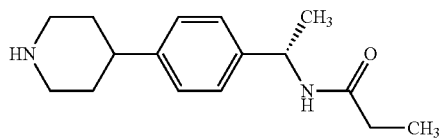

9.58 g (27.5 mmol) ((S)—N-{1-[4-(1-Benzyl-1,2,3,6-tetrahydro-pyridin-4-yl)-phenyl]-ethyl}-propionamide (XXII.1) in 130 mL ethanol are hydrogenated (3 bar) for 7 h at 50° C. using 0.80 g Pd/C (10%). After that time, the catalyst is filtered off and the solvent is evaporated. The residue is purified by HPLC (column: Gemini Phenomenex, 10 μM; eluent A: water+0.30% NH$_4$OH, eluent B: acetone) to yield the desired product.

$C_{16}H_{24}N_2O$ (M=260.4 g/mol), ESI-MS: 261 [M+H]$^+$ $R_t$ (HPLC): 0.69 min (method N)

The following compounds are prepared analogously to Example XXIII.1

Example XXIII.2

N-[1-(4-Piperidin-4-yl-phenyl)-propyl]-acetamide

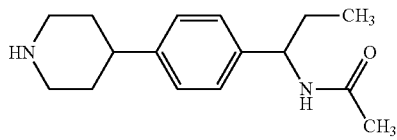 [SMILES: CCC(NC(C)=O)c1ccc(C2CCNCC2)cc1]

$C_{16}H_{24}N_2O$ (M=260.4 g/mol), ESI-MS: 261 [M+H]$^+$
$R_t$ (HPLC): 0.72 min (method N)

Example XXIV

Example XXIV.1

2-Chloro-5-(1-methanesulfonyl-cyclopropyl)-pyridine

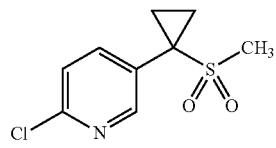

9 mL NaOH solution (50% in water) and 9 mL dichloromethane are mixed at rt and 137 mg (0.42 mmol) tetrabutylammonium bromide and 0.87 g (4.25 mmol) 2-chloro-5-[(methylsulfonyl)methyl]pyridine are added followed by 1.83 mL (21.2 mmol) dibromomethane. The mixture is stirred for 12 h at 35° C. The mixture is subsequently extracted with dichloromethane and the combined organic phases are washed with water and brine. The solvent is removed in vacuo and the residue is purified by HPLC (silica gel, cyclohexane/ethylacetate) to yield the desired product.
$C_9H_{10}ClNO_2S$ (M=231.7 g/mol), ESI-MS: 232 [M+H]$^+$ Example XXV Example XXV.1

2-Chloro-thiazole-4-carboxylic acid methylamide

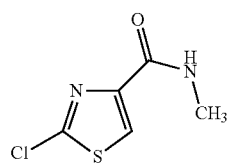

To 445 mg (2.44 mmol) 2-chloro-thiazole-4-carbonyl chloride in 8.0 mL dichloromethane is added a mixture of 0.38 mL (2.69 mmol) triethylamine and 1.35 mL (2.69 mmol) 2 molars solution of methylamine in THF. The mixture is stirred over night, concentrated and the residue is treated with water and NaHCO$_3$ solution. After extraction with ethylacetate the organic phases are combined, dried (Na$_2$SO$_4$) and concentrated to yield the desired product
$C_5H_5ClN_2OS$ (M=176.6 g/mol), ESI-MS: 177 [M+H]$^+$
$R_f$ (cyclohexane/ethylacetate=1:1)=0.3

Example XXVI

Example XXVI.1

6-Bromo-2,4-dimethyl-benzooxazole

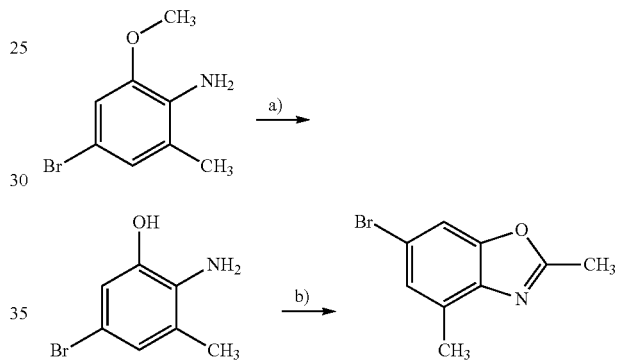

a)

0.50 g (2.31 mmol) 4-Bromo-2-methoxy-6-methyl-phenylamine in 5 mL dichloromethane is cooled with ice/ethanol and 0.24 mL (2.49 mmol) boron tribromide in 5 mL dichloromethane is added slowly. Stirring is continued for 30 under cooling and 2 h at rt. The mixture is poured onto ice, allowed to stand for 30 min and the aq. layer is extracted with dichloromethane. The aq. phase is treated with NaHCO$_3$ until the mixture shows basic pH, followed by extraction with dichloromethane. The combined organic phases are dried and concentrated to yield the desired product which is used without further purification.

b)

To 1.5 g (7.42 mmol) 2-amino-5-bromo-3-methyl-phenol in 30 mL xylene is added 1.15 mL (8.19 mmol) triethylamine, 0.68 g (2.70 mmol pyridinium p-toluenesulfonate and 0.55 mL (7.74 mmol) acetyl chloride. The mixture is refluxed for 3 d. Subsequently the solvent is removed in vacuo, and the residue is treated with 50 mL ethylacetate. The mixture is extracted twice with water. The combined aq. layers are extracted with ethylacetate. The combines organic layers are dried and concentrated to yield the desired product.
$C_9H_8BrNO$ (M=226.1 g/mol), ESI-MS: 226 [M+H]$^+$
$R_t$ (HPLC): 1.55 min (method Q)

Example XXVII

Example XXVII.1

(S)—N-{1-[4-(1-Cyano-piperidin-4-yl)-phenyl]-ethyl}-acetamide

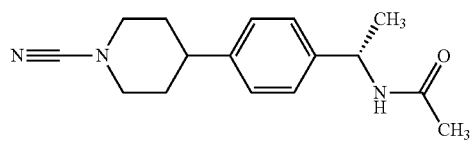 [SMILES: CC(=O)N[C@@H](C)c1ccc(C2CCN(C#N)CC2)cc1]

1.37 g (13.0 mmol) Cyanogen bromide are added to a mixture of 2.0 g (8.12 mmol) (S)—N-[1-(4-piperidin-4-yl-phenyl)-ethyl]-acetamide (V.1) and 4.86 mL (28.4 mmol) DIPEA in 15 mL THF and 15 mL dichloromethane. The mixture is stirred for 4 h at rt. After that time, the solvents are removed in vacuo. The residue is taken up in ethylacetate, the mixture is washed with water and the organic layer is concentrated. After addition of diethyl ether the precipitate is collected by filtration, followed by washing with diethylether to yield the desired product.

$C_{16}H_{21}N_3O$ (M=271.4 g/mol); ESI-MS: 272 [M+H]$^+$ $R_t$ (HPLC): 2.10 min (method R)

Example XXVII.2

(S)—N-(1-{4-[1-(N-Hydroxycarbamimidoyl)-piperidin-4-yl]-phenyl}-ethyl)-acetamide

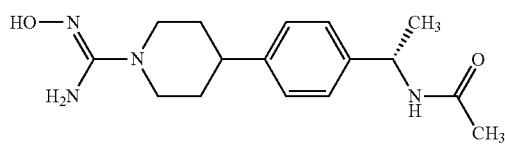 [SMILES: CC(=O)N[C@@H](C)c1ccc(C2CCN(/C(N)=N/O)CC2)cc1]

256.4 mg (3.69 mmol) Hydroxylamine hydrochloride are added to a mixture of 1.0 g (3.69 mmol) (S)-N-{1-[4-(1-cyano-piperidin-4-yl)-phenyl]ethyl}-acetamide (XXVII.1) and 0.63 mL (3.69 mmol) DIPEA in 20 mL ethanol. The mixture is refluxed for 4 h, an additional amount of 50 mg hydroxylamine hydrochloride is added and refluxing is continued for 2 h. The solvent is removed in vacuo and water is added. The mixture is then purified by HPLC (RP C18 Xbridge, water (+0.1% ammonia)/MeOH) to yield the desired product.

$C_{16}H_{24}N_4O_2$ (M=304.4 g/mol); ESI-MS: 305 [M+H]$^+$ $R_t$ (HPLC): 1.89 min (method S)

Example XXVIII

Example XXVIII

17-Bromo-8-fluoro-3,4-dihydro-2H-benzo-[1,4]-dioxepine

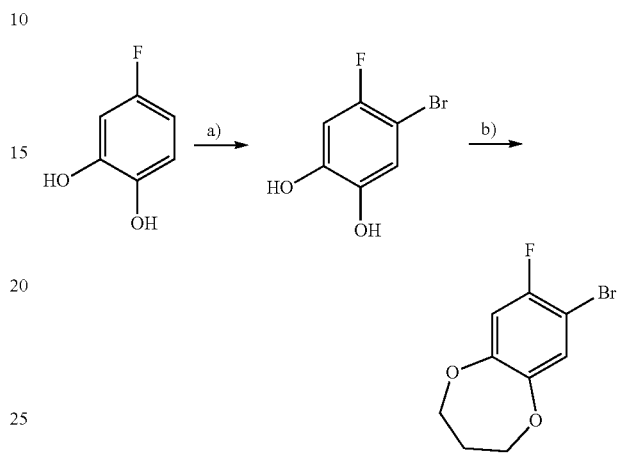

a) To 1.00 g (7.57 mmol) 4-fluorocatechol in 50 mL DCM are added 0.58 mL (11.4 mmol) bromine in 10 mL DCM. The reaction mixture is stirred at rt for 3 h. Then the solvent is removed in vacuo and the crude product is purified by column chromatography (silica gel, DCM/MeOH 9/1).

b) To 1.50 g (7.25 mmol) of 4-bromo-5-fluorobenzene-1,2-diol in 25 mL DMF are added 5.90 g (18.1 mmol) $Cs_2CO_3$ and 0.89 mL (8.70 mmol) 1,3-dibromopropane. The reaction mixture is stirred at 120° C. over night. The solvent is removed in vacuo and to the residue is added water. After extracting several times with EtOAc the org. phases are combined, washed with sat. aq. NaCl solution and dried with $MgSO_4$. The solvent is removed in vacuo and the resulting residue is purified by column chromatography (silica gel, PE/EtOAc 9/1→7/3).

$C_9H_8BrFO_2$ (M=247.1 g/mol), EI-MS: 246/248 [M]$^+$ $R_f$ (TLC): 0.50 (silica gel, PE/EtOAc 4/1)

The following compounds are prepared analogously to Example XXVIII.1:

Example XXVIII.2

6-Bromo-5-fluoro-2,3-dihydro-benzo[1,4]dioxine

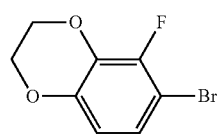

Educt: 3-fluorocatechol(step a)/dibromoethane (step b), in step b $K_2CO_3$ was used as base and ACN as solvent $C_8H_6BrFO_2$ (M=233.0 g/mol), EI-MS: 232 [M]$^+$

Example XXIX

Example XXIX.1

(S)—N-{1-[4-(1-(2-Bromoacetyl)piperidin-4-yl)-phenyl]-ethyl}-acetamide

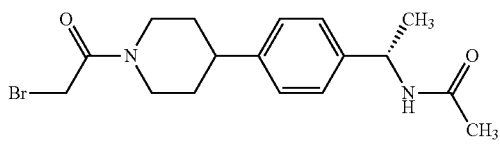

530 µl (6.09 mmol) Bromoacetylbromide are added dropwise to an ice cold mixture of 1.50 g (6.09 mmol) (S)—N-[1-(4-piperidin-4-yl-phenyl)-ethyl]-acetamide (V.1) and 1.03 mL (7.31 mmol) TEA in 20 mL dichloromethane. Then the cooling is removed and the mixture is allowed to warm to rt and then quenched by the addition of water. The mixture is extracted with DCM, the org. layers are combined, washed with water and dried with MgSO$_4$. The solvent is removed in vacuo and the crude product is used without further purification.

$C_{17}H_{23}BrN_2O_2$ (M=367.3 g/mol); ESI-MS: 367 [M+H]$^+$

R$_t$ (HPLC): 0.83 min (method G)

Example XXX (E)-5-Bromopent-2-ene

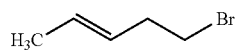

To 1.00 g (11.6 mmol) 1-cyclopropylethanol at 0° C. are carefully added 364 µL (3.83 mmol) PBr$_3$ and the mixture is allowed to warm to rt. Then 1 drop of water is added and the mixture is filtered through basic aluminum oxide.

$C_5H_9Br$ (M=149.0 g/mol); EI-MS: 148 [M]$^+$

Example XXXI

2-Methoxy-4-propoxyaniline

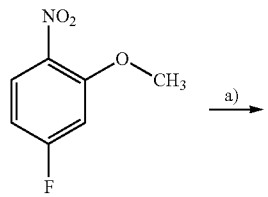

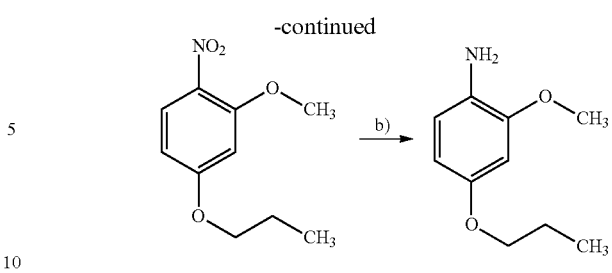

a)

To 1.80 g (10.5 mmol) 4-fluoro-2-methoxy-1-nitro-benzene and 0.87 mL (11.6 mmol) 1-propanol in 23 mL DMF at 0° C. are added 278 mg (11.6 mmol) NaH. The reaction mixture is stirred for 30 min at 0° C. and then allowed to warm to rt. The reaction is quenched by the addition of water. The resulting mixture is extracted with EtOAc. The org. layer is washed with water (2×) and dried with MgSO$_4$. The solvent is removed in vacuo and the residue is purified by HPLC (RP C18 Xbridge, water (+0.3% ammonia)/MeOH).

b)

1.40 g (6.63 mmol) 2-Methoxy-1-nitro-4-propoxybenzene in 20 mL EtOAc is charged with 100 mg Pd/C (5%) and hydrogenated at rt with a hydrogen pressure of 50 psi. The mixture is filtered and the solvent is removed in vacuo. The crude product is used without further purification.

$C_{10}H_{15}NO_2$ (M=181.2 g/mol), EI-MS: 182 [M]$^+$

R$_t$ (HPLC): 1.50 (method F)

Example XXXII

Example XXXII.1

1-(2-Methoxy-4-propoxyphenyl)piperidin-4-one

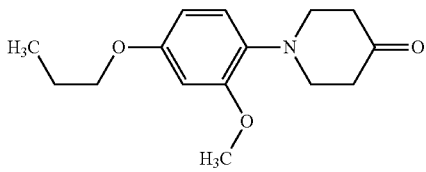

1.20 g (6.62 mmol) 2-methoxy-4-propoxyaniline (Example XXXI) in 8.5 mL EtOH and 1.8 mL water are stirred under reflux. During 30 min 2.19 g (6.62 mmol) N-methyl-N-benzyl-4-oxopiperidinium iodide (*Org. Lett.* 1999, 1, 1261-1262) are added by several portions. Stirring under reflux is continued for 1 h. Then the reaction mixture is cooled down to rt before water and DCM are added. The layers are separated and the org. layer is dried with MgSO$_4$, filtered and the solvent is removed in vacuo. The resulting residue is purified by column chromatography (silica gel, PE/EtOAc 8/2).

$C_{15}H_{21}NO_3$ (M=263.3 g/mol), ESI-MS: 264 [M+H]$^+$

R$_t$ (HPLC): 1.80 (method F)

The following compounds are prepared analogously to example XXXII.1.

| Example | Starting material | Product structure | Mass spec result | $R_t$ (HPLC) [min] (method) |
|---|---|---|---|---|
| XXXII.1 | | | 264 [M + H]⁺ | 1.80 (F) |
| XXXII.2 | | | 220 [M + H]⁺ | 1.63 (A) |

Example XXXIII

Example XXXIII.1

1-(2-Methoxy-4-propoxyphenyl)-1,2,3,6-tetrahydro-pyridin-4-yl trifluoromethanesulfonate

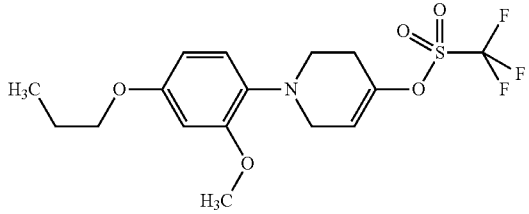 [SMILES: CCCOc1ccc(N2CC=C(OS(=O)(=O)C(F)(F)F)CC2)c(OC)c1]

To 0.60 g (2.28 mmol) of Example XXXII.1 and 0.85 g (2.39 mmol) N,N-bis(trifluoromethanesulfonyl)-aniline in 6 mL THF at −70° C. are added 2.51 mL (2.51 mmol) sodium bis(trimethylsilyl)amide (c=1.0 mol/l) over a period of 1 h. Cooling is removed and the mixture is allowed to warm to rt. An aq. half-saturated NaHCO₃ solution is added and the resulting mixture is extracted with DCM (2×). The org. layers are combined, dried with MgSO₄ and the solvent is removed in vacuo. The resulting residue is purified by column chromatography (silica gel, PE/EtOAc 8/2).

$C_{16}H_{20}F_3NO_5S$ (M=395.4 g/mol), ESI-MS: 396 [M+H]⁺

$R_t$ (HPLC): 1.68 (method F)

The following compounds are prepared analogously to example XXXIII.1.

| Example | Starting material | Product structure | Mass spec result | $R_t$ (HPLC) [min] (method) |
|---|---|---|---|---|
| XXXIII.1 | XXXII.1 | | 396 [M + H]⁺ | 1.68 (F) |
| XXXIII.2 | XXXII.2 | | 352 [M + H]⁺ | 2.20 (A) |

Example XXXIV (S)-2,2,2-Trifluoro-N-{1-[4-(4,4,5,5-tetramethyl-1,3,2-dioxaborolan-2-yl)phenyl]-ethyl}-acetamide

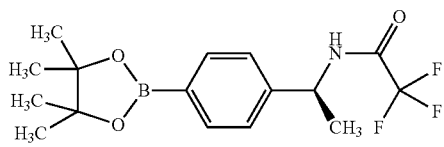 [SMILES: C[C@H](NC(=O)C(F)(F)F)c1ccc(B2OC(C)(C)C(C)(C)O2)cc1]

13.0 g (43.9 mmol) of (S)-N-(1-(4-bromophenyl)ethyl)-2,2,2-trifluoroacetamide and 14.5 g (148 mmol) KOAc are added to 130 mL DMSO. After degassing the mixture 13.7 g (52.9 mmol) bis(pinakolato)diboron and 1.10 mg (1.35 mmol) PdCl$_2$(dppf)*CH$_2$Cl$_2$ are added and the mixture is stirred at 90° C. for 3 h. 350 mL EtOAc and 100 mL water are added and the resulting mixture is filtered over celite. The org. layer is separated, washed with water (2×) and sat aq. NaCl solution (2×). The org. phase is dried with MgSO$_4$ and the solvent is removed in vacuo. The crude product is purified by column chromatography (silica gel, CyH/EtOAc 95/5→1/1).

C$_{16}$H$_{21}$BF$_3$NO$_3$ (M=343.2 g/mol), ESI-MS: 361 [M+NH$_4$]$^+$

Example XXXV

Example XXXV.1

(S)-2,2,2-Trifluoro-N-{1-[4-(1-(2-methoxy-4-propoxyphenyl)-1,2,3,6-tetrahydropyridin-4-yl)phenyl]-ethyl}-acetamide

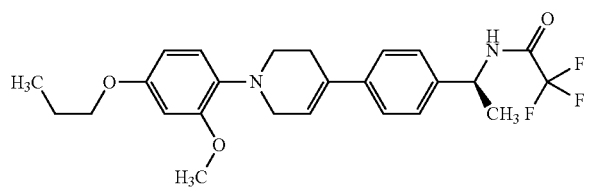 [SMILES: CCCOc1ccc(N2CC=C(c3ccc([C@H](C)NC(=O)C(F)(F)F)cc3)CC2)c(OC)c1]

To 0.30 g (0.76 mmol) of Example XXXIII.1 and 260 mg (0.76 mmol) of Example XXXIV in 6 mL dioxane and 6 mL MeOH are added 0.76 mL (1.52 mmol) of an aq. Na$_2$CO$_3$ solution (c=2 mol/L) and 21.3 mg (0.03 mmol) Pd(PPh$_3$)Cl$_2$. The reaction mixture is stirred at 95° C. for 3 h. Water and DCM are added and the layers are separated. The org. layer is dried with MgSO$_4$ ans the solvent is removed in vacuo. The resulting residue is purified by HPLC (RP C18 Xbridge, water(+0.3% ammonia)/MeOH).

C$_{25}$H$_{29}$F$_3$N$_2$O$_3$ (M=462.5 g/mol), ESI-MS: 463 [M+H]$^+$

R$_t$ (HPLC): 2.20 (method F)

The following compounds are prepared analogously to example XXXV.1.

| Example | Starting material | Product structure | Mass spec result | R$_t$ (HPLC) [min] (method) |
|---|---|---|---|---|
| XXXV.1 | XXXIII.1 | ![structure] | 463 [M + H]$^+$ | 2.20 (F) |
| XXXV.2 | XXXIII.2 | ![structure] | 419 [M + H]$^+$ | 2.16 (A) |

Example XXXVI

1-Bromo-4-(3,3,3-trifluoropropoxy)benzene

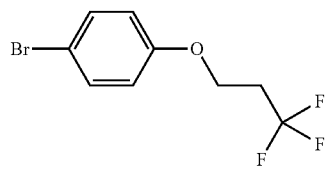

3.81 g (22.0 mmol) 4-bromophenol, 2.76 g (24.2 mmol) 3,3,3-trifluoro-1-propanol and 5.77 g (22.0 mmol) triphenylphosphine are added to 50 mL DCM and cooled down to 0° C. Then 4.55 mL (22.0 mmol) di-iso-propyl azodicarboxylate are added and the mixture is allowed to warm to rt ad stirring is continued over night. Then the reaction mixture is poured on water and extracted with DCM. The org. layers are combined, dried with Na$_2$SO$_4$, filtered and the solvent is removed in vacuo. The residue is purified using flash chromatography (silica gel, PE/EtOAc 8/2).

C$_9$H$_8$BrF$_3$O (M=269.1 g/mol), ESI-MS: 301 [M+MeOH+H]$^+$

R$_t$ (HPLC): 1.90 min (method A)

Example XXXVII

Example XXXVII.1

3-Bromo-6-ethoxy-pyridine-2-carbonitrile

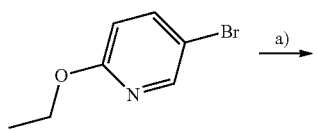

a)

To 4.50 g (22.3 mmol) of 3-bromo-6-ethoxy-pyridine in 100 mL DCM are added 20.5 g (89.1 mmol) mCPBA by several portions. The reaction mixture is stirred at rt over night, charged with MgSO$_4$ and filtered over 100 g of basic aluminum oxide. The solvent is removed in vacuo before DCM and an aq. NaHCO$_3$ solution are added and the layers are separated. The aq. layer is saturated with NaCl and extracted several times with DCM. The org. layers are combined and the solvent is removed in vacuo. The residue is filtered through a plug of silica gel.

b)

1.00 g (4.59 mmol) 5-bromo-2-ethoxy-pyridine-1-oxide, 2.46 mL (18.3 mmol) trimethylsilyl cyanide and 1.92 mL (13.8 mmol) TEA in 10 mL ACN are stirred together at 100° C. for 24 h. Then the volatile components are removed in vacuo and the residue is dissolved in DCM, washed with aq. NaHCO$_3$ solution, dried with MgSO$_4$ and filtered through a plug of silica gel. Then the solvent is removed in vacuo.

$C_8H_7BrN_2O$ (M=227.1 g/mol), ESI-MS: 227 [M+H]$^+$ $R_f$(TLC): 0.85 (silica gel, PE/EtOAc 7/3)

The following compounds are prepared analogously to example XXXVII.1. For the examples XXXVII.2 and XXXVII.3 the intermediates from step a are purified by HPLC after the filtration over basic alumnum oxide.

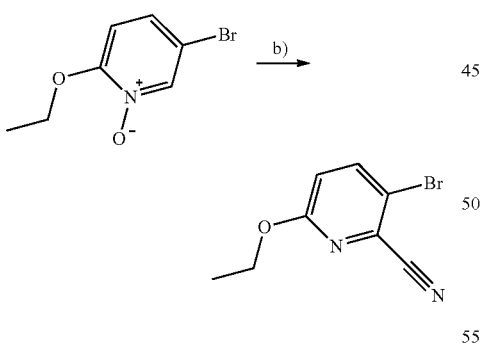

Example XXXVIII

3-Bromo-2,6-diethoxy-pyridine

To 59.1 μL (1.00 mmol) ethanol in 1 mL DMF are added 25.3 mg (1.00 mmol) NaH and afterwards 109 mg (0.50 mmol) 3-bromo-6-chloro-pyridine-2-carbonitrile. The resulting mixture is stirred at 50° C. for 1 h. Then the reaction mixture is poured onto water and extracted with TBME. The org. layers are combined, dried with MgSO$_4$, filtered and the solvent is removed in vacuo.

$C_9H_{12}BrNO_2$ (M=246.1 g/mol), ESI-MS: 246 [M+H]$^+$

Preparation of Final Compounds

Example 1

Example I.1

(S)—N-(1-{4-[1-(4-Ethoxy-phenyl)-piperidin-4-yl]-phenyl}-ethyl)-acetamide

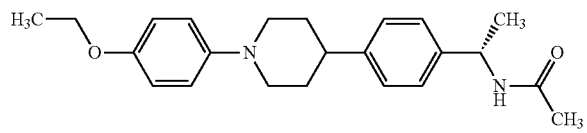 [SMILES: CCOc1ccc(N2CCC(c3ccc([C@H](C)NC(C)=O)cc3)CC2)cc1]

147 mg (0.60 mmol) (S)-N-[1-(Piperidin-4-yl-phenyl)-ethyl]-acetamide (V.1) are added to a mixture of 100 mg (0.50 mmol) 1-bromo-4-ethoxy-benzene, 197 mg (2.00 mmol) sodium tert-butyrat, 59 mg (0.20 mmol) 2-(di-tert-butylphosphino)biphenyl and 46 mg (0.05 mmol) tris-(dibenzylidenaceton)-dipalladium(0) in 2.0 mL 1,4-dioxane. The mixture is stirred for 4 h at 45° C. After that time, the mixture is filtered over celite. The solvent is removed in vacuo from the filtrate. The residue is purified by HPLC (column: Waters XBridge 5 µM; eluent A: water+0.3% NH$_4$OH, eluent B: MeOH) to yield the desired product.

$C_{23}H_{30}N_2O_2$ (M=366.5 g/mol)
ESI-MS: 367 [M+H]$^+$
$R_t$ (HPLC): 2.11 min (method A)

The following compounds of general formula (I-1) are prepared analogously to Example 1.1, the educts used being shown in the column headed "E 1" and "E 2" Alternatively reaction temperatures of up to 120° C. or heating in a microwave oven at up to 120° C. are used as reaction conditions in the examples below.

E.g., for the Example 1.177 the reaction temperature is 110° C.; for the examples 1.184 and 1.185 the reaction conditions are 45 min at 80° C. in a microwave oven.

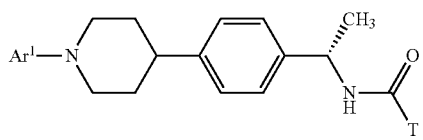

(1-1)

| Example | Ar$^1$ | T | E 1 | E 2 | ESI-MS [m/z] | R$_t$ (HPLC) [min] (method) |
|---|---|---|---|---|---|---|
| 1.1 | 4-ethoxyphenyl | *—CH$_3$ | 1-bromo-4-ethoxybenzene | V.1 | 367 [M + H]$^+$ | 2.11 (A) |
| 1.2 | 4-(cyclopentyloxy)phenyl | *—CH$_3$ | 1-bromo-4-(cyclopentyloxy)benzene | V.1 | 407 [M + H]$^+$ | 2.30 (A) |
| 1.3 | 4-propoxyphenyl | *—CH$_3$ | 1-bromo-4-propoxybenzene | V.1 | 395 [M + H]$^+$ | 2.30 (A) |
| 1.4 | 6-ethoxypyridin-3-yl | *—CH$_3$ | 5-bromo-2-ethoxypyridine | V.1 | 368 [M + H]$^+$ | 2.03 (A) |
| 1.5 | 4-ethoxyphenyl | *—O—CH$_3$ | 1-bromo-4-ethoxybenzene | V.2 | 383 [M + H]$^+$ | 2.18 (A) |

-continued

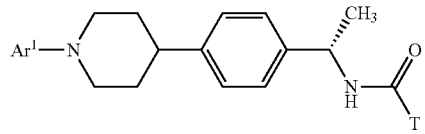
(1-1)

| Example | Ar¹ | T | E 1 | E 2 | ESI-MS [m/z] | R_t (HPLC) [min] (method) |
|---|---|---|---|---|---|---|
| 1.6 | H₃C—O—⟨C₆H₄⟩—* | *—N(CH₃)₂ | H₃C—O—⟨C₆H₄⟩—Br | V.3 | 396 [M + H]⁺ | 2.13 (A) |
| 1.7 | (H₃C)(CH₃)CH—O—⟨C₆H₄⟩—* | *—N(CH₃)₂ | (H₃C)(CH₃)CH—O—⟨C₆H₄⟩—Br | V.3 | 424 [M + H]⁺ | 2.26 (A) |
| 1.8 | H₃C—CH₂—CH₂—O—⟨C₆H₄⟩—* | *—N(CH₃)₂ | H₃C—CH₂—CH₂—O—⟨C₆H₄⟩—Br | V.3 | 410 [M + H]⁺ | 2.22 (A) |
| 1.9 | cyclobutyl-O—⟨C₆H₄⟩—* | *-cyclopropyl | cyclobutyl-O—⟨C₆H₄⟩—Br | V.4 | 419 [M + H]⁺ | 2.26 (A) |
| 1.10 | (H₃C)(CH₃)CH—O—⟨C₆H₄⟩—* | *-cyclopropyl | (H₃C)(CH₃)CH—O—⟨C₆H₄⟩—Br | V.4 | 421 [M + H]⁺ | 2.27 (A) |
| 1.11 | H₃C—CH₂—O—⟨pyridyl⟩—* | *—O—CH₃ | H₃C—CH₂—O—⟨pyridyl⟩—Br | V.2 | 384 [M + H]⁺ | 2.06 (A) |
| 1.12 | cyclobutyl-O—⟨C₆H₄⟩—* | *—O—CH₃ | cyclobutyl-O—⟨C₆H₄⟩—Br | V.2 | 409 [M + H]⁺ | 2.27 (A) |
| 1.13 | H₃C—CH₂—CH₂—O—⟨C₆H₄⟩—* | *—O—CH₃ | H₃C—CH₂—CH₂—O—⟨C₆H₄⟩—Br | V.2 | 397 [M + H]⁺ | 2.26 (A) |
| 1.14 | cyclopropyl-O—⟨C₆H₄⟩—* | *-cyclopropyl | cyclopropyl-O—⟨C₆H₄⟩—Br | V.4 | 405 [M + H]⁺ | 2.18 (A) |

-continued
(1-1)
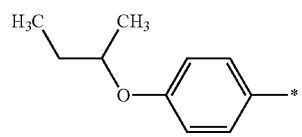 [SMILES: *c1ccc(OC(C)CC)cc1]
| Example | Ar¹ | T | E 1 | E 2 | ESI-MS [m/z] | R$_t$ (HPLC) [min] (method) |
|---|---|---|---|---|---|---|
| 1.15 |  | 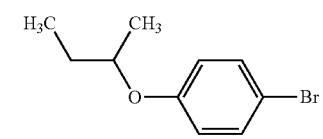 | 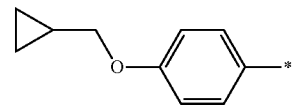 [SMILES: *c1ccc(OCC2CC2)cc1] | V.2 | 411 [M + H]⁺ | 2.29 (A) |
| 1.16 |  | 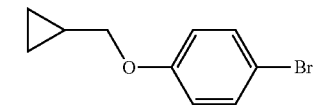 | 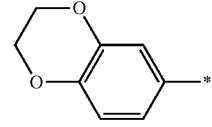 | V.4 | 419 [M + H]⁺ | 2.22 (A) |
| 1.17 |  | 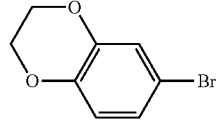 | 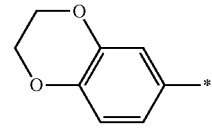 [SMILES: *c1ccc2c(c1)OCCO2] | V.2 | 397 [M + H]⁺ | 2.07 (A) |
| 1.18 |  | 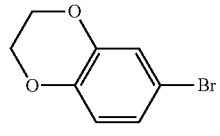 | 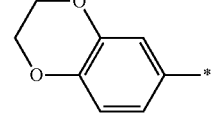 | V.3 | 410 [M + H]⁺ | 2.01 (A) |
| 1.19 |  | 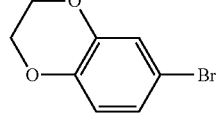 | 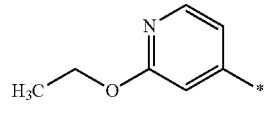 | V.4 | 407 [M + H]⁺ | 2.04 (A) |
| 1.20 |  | 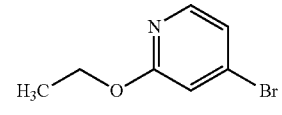 | 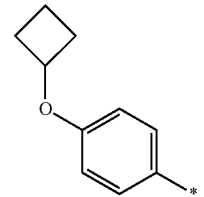 [SMILES: *c1ccc(OC2CCC2)cc1] | V.4 | 394 [M + H]⁺ | 2.04 (A) |
| 1.21 | 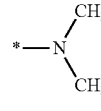 | 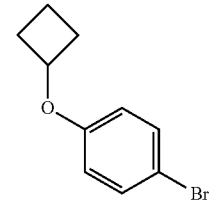 | 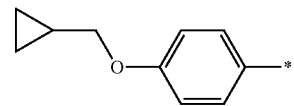 [SMILES: *c1ccc(OCC2CC2)cc1] | V.3 | 422 [M + H]⁺ | 2.24 (A) |
| 1.22 |  | 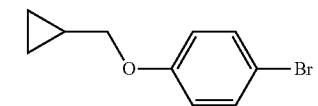 | 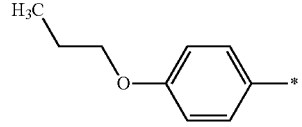 | V.2 | 409 [M + H]⁺ | 2.24 (A) |
| 1.23 |  | 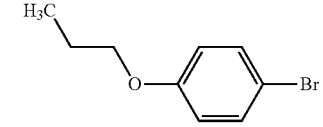 |  | V.4 | 407 [M + H]⁺ | 2.25 (A) |

(1-1)

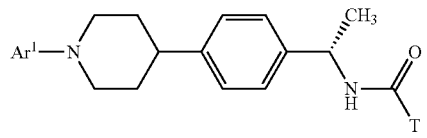

| Example | Ar¹ | T | E 1 | E 2 | ESI-MS [m/z] | $R_t$ (HPLC) [min] (method) |
|---|---|---|---|---|---|---|
| 1.24 | cyclopropylmethoxy-phenyl | *-N(CH₃)₂ | 4-bromo-(cyclopropylmethoxy)benzene | V.3 | 422 [M + H]⁺ | 2.20 (A) |
| 1.25 | 4-ethoxyphenyl | *-cyclopropyl | 4-bromo-1-ethoxybenzene | V.4 | 393 [M + H]⁺ | 2.16 (A) |
| 1.26 | cyclopropylmethoxy-phenyl | *—CH₃ | 4-bromo-(cyclopropylmethoxy)benzene | V.1 | 393 [M + H]⁺ | 2.16 (A) |
| 1.27 | 3-hydroxyphenyl | *—CH₃ | 3-bromophenol | V.1 | 339 [M + H]⁺ | 1.79 (A) |
| 1.28 | 4-cyclopropoxyphenyl | *—CH₃ | 4-bromo-1-cyclopropoxybenzene | V.1 | 379 [M + H]⁺ | 2.19 (A) |
| 1.29 | 4-(sec-butoxy)phenyl | *—CH₃ | 4-bromo-1-(sec-butoxy)benzene | V.1 | 395 [M + H]⁺ | 2.25 (A) |
| 1.30 | 4-methoxyphenyl | *—CH₃ | 4-bromo-1-methoxybenzene | V.1 | 353 [M + H]⁺ | 2.03 (A) |
| 1.31 | 2-methoxy-4-propoxyphenyl | *—CH₃ | 1-bromo-2-methoxy-4-propoxybenzene | V.1 | 411 [M + H]⁺ | 2.21 (A) |
| 1.32 | 2-methyl-4-propoxyphenyl | *—CH₃ | 1-bromo-2-methyl-4-propoxybenzene | V.1 | 395 [M + H]⁺ | 2.46 (A) |
| 1.33 | 2-chloro-4-propoxyphenyl | *—CH₃ | 1-bromo-2-chloro-4-propoxybenzene | V.1 | 415 [M + H]⁺ | 2.39 (A) |

-continued

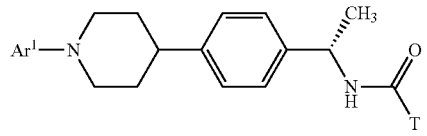
(1-1)

| Example | Ar¹ | T | E 1 | E 2 | ESI-MS [m/z] | R_t (HPLC) [min] (method) |
|---|---|---|---|---|---|---|
| 1.34 | 3-methoxy-6-* benzonitrile | *—CH₃ | 2-Br-5-methoxy benzonitrile | V.1 | 378 [M + H]⁺ | 2.10 (A) |
| 1.35 | 2-methoxy-4-isopropoxy-*-phenyl | *—CH₃ | 2-methoxy-4-isopropoxy-Br-phenyl | V.1 | 411 [M + H]⁺ | 2.20 (A) |
| 1.36 | 2-methoxy-4-(cyclopropylmethoxy)-*-phenyl | *—CH₃ | 2-methoxy-4-(cyclopropylmethoxy)-Br-phenyl | V.1 | 423 [M + H]⁺ | 2.22 (A) |
| 1.37 | 2-methoxy-4-cyclobutoxy-*-phenyl | *—CH₃ | 2-methoxy-4-cyclobutoxy-Br-phenyl | V.1 | 423 [M + H]⁺ | 2.26 (A) |
| 1.38 | 2-methoxy-4-ethoxy-*-phenyl | *—CH₃ | 2-methoxy-4-ethoxy-Br-phenyl | V.1 | 397 [M + H]⁺ | 2.15 (A) |
| 1.39 | 2-methoxy-4-(sec-butoxy)-*-phenyl | *—CH₃ | 2-methoxy-4-(sec-butoxy)-Br-phenyl | V.1 | 425 [M + H]⁺ | 2.28 (A) |
| 1.40 | 2,3-dihydrobenzo[1,4]dioxin-6-yl | *—CH₃ | 6-Br-2,3-dihydrobenzo[1,4]dioxine | V.1 | 381 [M + H]⁺ | 1.99 (A) |
| 1.41 | 2,4-dimethoxy-*-phenyl | *—CH₃ | 2,4-dimethoxy-Br-phenyl | V.1 | 383 [M + H]⁺ | 2.06 (A) |

-continued (1-1)

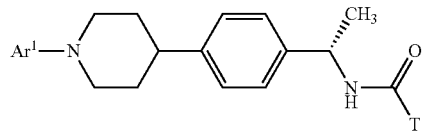

| Example | Ar¹ | T | E 1 | E 2 | ESI-MS [m/z] | R_t (HPLC) [min] (method) |
|---|---|---|---|---|---|---|
| 1.42 | 2,4-diethoxyphenyl | *—CH₃ | 2-bromo-4,5-diethoxyphenyl-like | V.1 | 411 [M + H]⁺ | 2.23 (A) |
| 1.43 | 2,3-dimethoxyphenyl | *—CH₃ | 4-bromo-2,3-dimethoxyphenyl | V.1 | 383 [M + H]⁺ | 1.85 (A) |
| 1.44 | 3,4-dihydro-2H-1,5-benzodioxepin-7-yl | *—CH₃ | 7-bromo-3,4-dihydro-2H-1,5-benzodioxepine | V.1 | 395 [M + H]⁺ | 2.00 (A) |
| 1.45 | phenyl | *—CH₃ | bromobenzene | V.1 | 323 [M + H]⁺ | 2.08 (A) |
| 1.46 | 4-chlorophenyl | *—CH₃ | 4-bromo-chlorobenzene | V.1 | 357 [M + H]⁺ | 2.21 (A) |
| 1.47 | 2,3-diethoxyphenyl | *—CH₃ | 4-bromo-2,3-diethoxyphenyl | V.1 | 411 [M + H]⁺ | 2.14 (A) |
| 1.48 | 4-hydroxyphenyl | *—CH₃ | 4-bromophenol | V.1 | 339 [M + H]⁺ | 1.70 (A) |
| 1.49 | 5-hydroxypyrazin-2-yl | *—CH₃ | 5-bromo-pyrazin-2-ol | V.1 | 341 [M + H]⁺ | 1.15 (A) |
| 1.50 | 2-cyano-4-isopropoxyphenyl | *—CH₃ | 2-bromo-5-isopropoxybenzonitrile | V.1 | 406 [M + H]⁺ | 2.18 (A) |

-continued

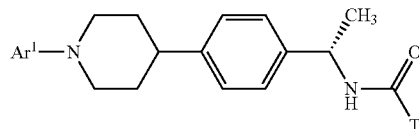
(1-1)

| Example | Ar¹ | T | E 1 | E 2 | ESI-MS [m/z] | R_t (HPLC) [min] (method) |
|---|---|---|---|---|---|---|
| 1.51 | 5-(cyclobutoxy)-2-cyanophenyl | *—CH₃ | 5-(cyclobutoxy)-2-bromo-3-cyanophenyl | V.1 | 418 [M + H]⁺ | 2.25 (A) |
| 1.52 | 4-isopropylphenyl | *—CH₃ | 4-isopropyl-bromophenyl | V.1 | 365 [M + H]⁺ | 2.32 (A) |
| 1.53 | 6-methoxypyridin-3-yl | *—CH₃ | 6-methoxy-5-bromopyridin-3-yl | V.1 | 354 [M + H]⁺ | 1.90 (A) |
| 1.54 | 6-benzyloxypyridin-3-yl | *—CH₃ | 6-benzyloxy-5-bromopyridin-3-yl | V.1 | 430 [M + H]⁺ | 2.21 (A) |
| 1.55 | 6-propoxypyridin-3-yl | *—CH₃ | 6-propoxy-5-bromopyridin-3-yl | V.1 | 382 [M + H]⁺ | 2.11 (A) |
| 1.56 | 6-methoxy-4-methylpyridin-3-yl | *—CH₃ | 6-methoxy-4-methyl-5-bromopyridin-3-yl | V.1 | 368 [M + H]⁺ | 2.09 (A) |
| 1.57 | 4-cyclopropoxy-2-methylphenyl | *—N(CH₃)₂ | 4-cyclopropoxy-2-methyl-bromophenyl | V.3 | 422 [M + H]⁺ | 2.30 (A) |
| 1.58 | 3,3-dimethyl-3,4-dihydro-2H-benzo[b][1,4]dioxepin-7-yl | *—N(CH₃)₂ | 3,3-dimethyl-7-bromo-3,4-dihydro-2H-benzo[b][1,4]dioxepine | V.3 | 452 [M + H]⁺ | 2.21 (A) |
| 1.59 | 6-(cyclopropylmethoxy)pyridin-3-yl | *—CH₃ | 6-(cyclopropylmethoxy)-5-bromopyridin-3-yl | V.1 | 394 [M + H]⁺ | 2.08 (A) |
| 1.60 | 6-isopropoxypyridin-3-yl | *—CH₃ | 6-isopropoxy-5-bromopyridin-3-yl | V.1 | 382 [M + H]⁺ | 2.06 (A) |

-continued

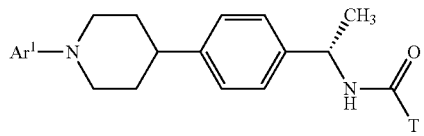
(1-1)

| Example | Ar¹ | T | E 1 | E 2 | ESI-MS [m/z] | R_t (HPLC) [min] (method) |
|---|---|---|---|---|---|---|
| 1.61 | 3,3-dimethyl-benzodioxepine | *—CH₃ | 7-bromo-3,3-dimethyl-benzodioxepine | V.1 | 423 [M + H]⁺ | 2.19 (A) |
| 1.62 | 2-cyclobutoxy-pyridin-5-yl | *—CH₃ | 5-bromo-2-cyclobutoxy-pyridine | V.1 | 394 [M + H]⁺ | 2.03 (F) |
| 1.63 | 3-fluoro-4-(tetrahydrofuran-3-yloxy)phenyl | *—CH₃ | 1-bromo-2-fluoro-4-(tetrahydrofuran-3-yloxy)benzene | V.1 | 427 [M + H]⁺ | 1.90 (F) |
| 1.64 | 3-fluoro-4-propoxyphenyl | *—CH₃ | 1-bromo-2-fluoro-4-propoxybenzene | V.1 | 399 [M + H]⁺ | 2.18 (F) |
| 1.65 | 3-fluoro-4-hydroxyphenyl | *—CH₃ | 4-bromo-3-fluorophenol | V.1 | 357 [M + H]⁺ | 1.02 (F) |
| 1.66 | 2-methyl-benzothiazol-6-yl | *—CH₃ | 6-bromo-2-methyl-benzothiazole | V.1 | 394 [M + H]⁺ | 1.93 (F) |
| 1.67 | benzo[1,3]dioxol-5-yl | *—CH₃ | 5-bromo-benzo[1,3]dioxole | V.1 | 367 [M + H]⁺ | 1.90 (F) |
| 1.68 | 2-oxo-2,3-dihydro-benzoxazol-5-yl | *—CH₃ | 5-bromo-2-oxo-2,3-dihydro-benzoxazole | V.1 | 380 [M + H]⁺ | 1.37 (F) |
| 1.69 | benzo[b]thiophen-5-yl | *—CH₃ | 5-bromo-benzo[b]thiophene | V.1 | 379 [M + H]⁺ | 2.08 (F) |

-continued

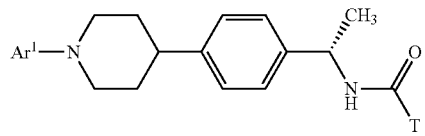
(1-1)

| Example | Ar¹ | T | E 1 | E 2 | ESI-MS [m/z] | R$_t$ (HPLC) [min] (method) |
|---|---|---|---|---|---|---|
| 1.70 | 1,2-dimethyl-benzimidazol-5-yl | *—CH₃ | 1,2-dimethyl-5-bromo-benzimidazole | V.1 | 391 [M + H]⁺ | 1.70 (F) |
| 1.71 | 2-phenyl-benzoxazol-5-yl | *—CH₃ | 2-phenyl-5-bromo-benzoxazole | V.1 | 440 [M + H]⁺ | 2.21 (F) |
| 1.72 | 1-methyl-benzimidazol-5-yl | *—CH₃ | 1-methyl-5-bromo-benzimidazole | V.1 | 377 [M + H]⁺ | 1.65 (F) |
| 1.73 | 6-cyano-benzo[1,3]dioxol-5-yl | *—CH₃ | 6-cyano-5-bromo-benzo[1,3]dioxole | V.1 | 392 [M + H]⁺ | 1.88 (F) |
| 1.74 | 4-isopropoxy-3-fluoro-phenyl | *—CH₃ | 4-isopropoxy-3-fluoro-bromobenzene | V.1 | 399 | 2.14 |
| 1.75 | 3-methyl-indol-5-yl | *—CH₃ | 3-methyl-5-bromo-indole | V.1 | 376 [M + H]⁺ | 1.23 (G) |
| 1.76 | 2-methyl-indol-5-yl | *—CH₃ | 2-methyl-5-bromo-indole | V.1 | 376 [M + H]⁺ | 1.23 (G) |
| 1.77 | 3-(cyclopropylmethoxy)-phenyl | *-cyclopropyl | 3-(cyclopropylmethoxy)-bromobenzene | V.4 | 419 [M + H]⁺ | 1.28 (G) |

-continued

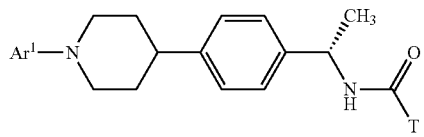
(1-1)

| Example | Ar¹ | T | E 1 | E 2 | ESI-MS [m/z] | R_t (HPLC) [min] (method) |
|---|---|---|---|---|---|---|
| 1.78 | 3-isopropoxyphenyl | cyclopropyl | 3-bromo-5-isopropoxyphenyl | V.4 | 407 [M + H]⁺ | 1.26 (G) |
| 1.79 | 2-fluoro-4-(cyclopropylmethoxy)phenyl | cyclopropyl | 4-bromo-2-fluoro-5-(cyclopropylmethoxy)phenyl | V.4 | 437 [M + H]⁺ | 1.30 (G) |
| 1.80 | 3-(cyclopropylmethoxy)phenyl | N(CH₃)₂ | 3-bromo-5-(cyclopropylmethoxy)phenyl | V.3 | 422 [M + H]⁺ | 1.27 (G) |
| 1.81 | 3-isopropoxyphenyl | N(CH₃)₂ | 3-bromo-5-isopropoxyphenyl | V.3 | 410 [M + H]⁺ | 1.26 (G) |
| 1.82 | 2-fluoro-4-ethoxyphenyl | cyclopropyl | 4-bromo-2-fluoro-5-ethoxyphenyl | V.4 | 411 [M + H]⁺ | 1.25 (G) |
| 1.83 | 2-fluoro-4-propoxyphenyl | cyclopropyl | 4-bromo-2-fluoro-5-propoxyphenyl | V.4 | 425 [M + H]⁺ | 1.31 (G) |
| 1.84 | 2-fluoro-4-(cyclopropylmethoxy)phenyl | N(CH₃)₂ | 4-bromo-2-fluoro-5-(cyclopropylmethoxy)phenyl | V.3 | 440 [M + H]⁺ | 1.28 (G) |
| 1.85 | 2-fluoro-4-ethoxyphenyl | N(CH₃)₂ | 4-bromo-2-fluoro-5-ethoxyphenyl | V.3 | 414 [M + H]⁺ | 1.24 (G) |

-continued
(1-1)
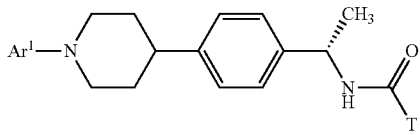
| Example | Ar¹ | T | E 1 | E 2 | ESI-MS [m/z] | R$_t$ (HPLC) [min] (method) |
|---|---|---|---|---|---|---|
| 1.86 | 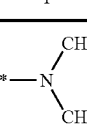 | 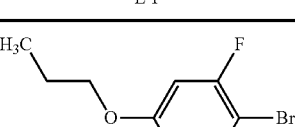 | 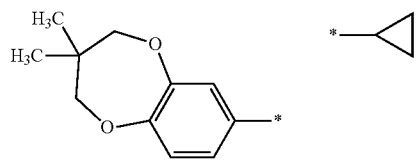 | V.3 | 428 [M + H]⁺ | 1.33 (G) |
| 1.87 |  | 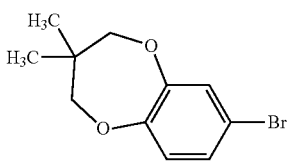 | 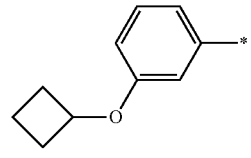 [SMILES: *c1cccc(OC2CCC2)c1] | V.4 | 449 [M + H]⁺ | 1.30 (G) |
| 1.88 | 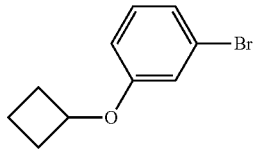 | *—CH₃ | 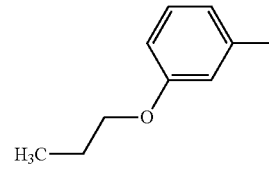 | V.1 | 393 [M + H]⁺ | 1.29 (G) |
| 1.89 | 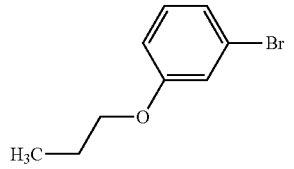 | *—CH₃ | 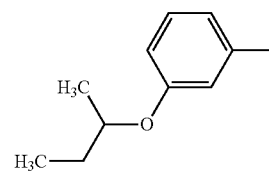 | V.1 | 381 [M + H]⁺ | 1.30 (G) |
| 1.90 | 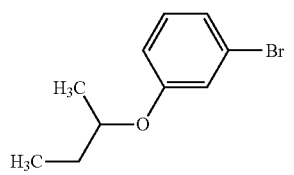 | *—CH₃ | 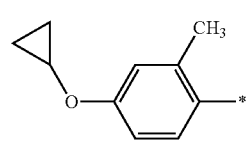 | V.1 | 395 [M + H]⁺ | 1.29 (G) |
| 1.91 | 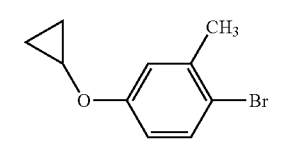 | 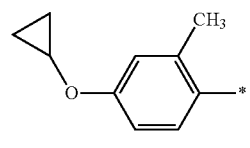 | 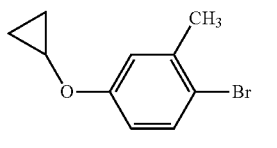 | V.4 | 419 [M + H]⁺ | 1.36 (G) |
| 1.92 | 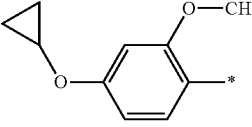 | *—CH₃ | 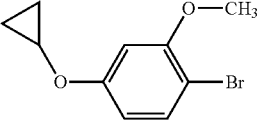 | V.1 | 393 [M + H]⁺ | 1.29 (G) |
| 1.93 |  |  |  | V.4 | 435 [M + H]⁺ | 1.26 (G) |

-continued

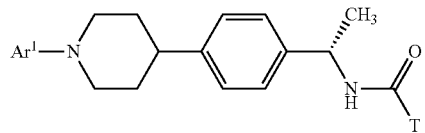
(1-1)

| Example | Ar¹ | T | E 1 | E 2 | ESI-MS [m/z] | R_f (HPLC) [min] (method) |
|---|---|---|---|---|---|---|
| 1.94 | 2,4-bis(cyclopropoxy)phenyl | *—CH₃ | 4-bromo-2,5-bis(cyclopropoxy)phenyl | V.1 | 435 [M + H]⁺ | 1.01 (G) |
| 1.95 | 2,4-dimethoxypyrimidin-5-yl | *—CH₃ | 5-bromo-2,4-dimethoxypyrimidine | V.1 | 385 [M + H]⁺ | 1.03 (G) |
| 1.96 | 2-fluoro-4-methoxyphenyl | *—CH₃ | 1-bromo-2-fluoro-4-methoxybenzene | V.1 | 371 [M + H]⁺ | 1.99 (A) |
| 1.97 | 2-fluoro-4-(2-methoxyethoxy)phenyl | *—CH₃ | 1-bromo-2-fluoro-4-(2-methoxyethoxy)benzene | V.1 | 415 [M + H]⁺ | 2.10 (F) |
| 1.98 | 2,3-dihydro-1,4-benzodioxin-5-yl | *—CH₃ | 5-bromo-2,3-dihydro-1,4-benzodioxine | V.1 | 381 [M + H]⁺ | 2.13 (F) |
| 1.99 | 2-fluoro-4-(3-methoxypropoxy)phenyl | *—CH₃ | 1-bromo-2-fluoro-4-(3-methoxypropoxy)benzene | V.1 | 429 [M + H]⁺ | 1.30 (L) |
| 1.100 | 5-ethoxy-3-fluoropyridin-2-yl | *—CH₃ | 2-chloro-5-ethoxy-3-fluoropyridine | V.1 | 386 [M + H]⁺ | 1.31 (L) |

-continued

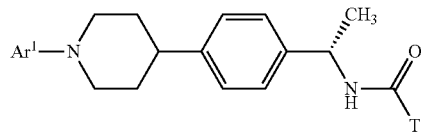

(1-1)

| Example | Ar¹ | T | E 1 | E 2 | ESI-MS [m/z] | R_f (HPLC) [min] (method) |
|---|---|---|---|---|---|---|
| 1.101 | cyclopropylethoxy-fluorophenyl* | *—CH₃ | cyclopropylethoxy-fluoro-Br-phenyl | V.1 | 425 [M + H]⁺ | 1.45 (L) |
| 1.102 | cyclopropoxy-methoxyphenyl* | *—CH₃ | cyclopropoxy-methoxy-Br-phenyl | V.1 | 409 [M + H]⁺ | 2.06 (F) |
| 1.103 | ethoxy-fluorophenyl* | *—CH₃ | ethoxy-fluoro-Br-phenyl | V.1 | 385 [M + H]⁺ | 2.17 (F) |
| 1.104 | cyclopropylmethoxy-fluoropyridyl* | *—CH₃ | cyclopropylmethoxy-fluoro-Cl-pyridyl | V.1 | 412 [M + H]⁺ | 1.36 (L) |
| 1.105 | propoxy-fluoropyridyl* | *—CH₃ | propoxy-fluoro-Cl-pyridyl | V.1 | 400 [M + H]⁺ | 1.37 (L) |
| 1.106 | cyclopropoxy-methoxyphenyl* | *—N(CH₃)₂ | cyclopropoxy-methoxy-Br-phenyl | V.3 | 438 [M + H]⁺ | 1.37 (L) |
| 1.107 | pyrimidinyloxy-pyridyl* | *—N(CH₃)₂ | pyrimidinyloxy-I-pyridyl | V.3 | 447 [M + H]⁺ | 1.18 (L) |
| 1.108 | pyrimidinyloxy-pyridyl* | *—cyclopropyl | pyrimidinyloxy-I-pyridyl | V.4 | 444 [M + H]⁺ | 1.19 (L) |

-continued

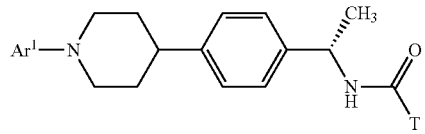
(1-1)

| Example | Ar¹ | T | E 1 | E 2 | ESI-MS [m/z] | R_t (HPLC) [min] (method) |
|---|---|---|---|---|---|---|
| 1.109 | imidazole-CH₂CH₂-O-C₆H₄-* | *—CH₃ | imidazole-CH₂CH₂-O-C₆H₄-Br | V.1 | 433 [M + H]⁺ | 1.17 (L) |
| 1.110 | pyrimidine-O-pyridine-* | *—CH₃ | pyrimidine-O-pyridine-Br | V.1 | 418 [M + H]⁺ | 1.16 (L) |
| 1.111 | ethoxy-pyridine-* | *—N(CH₃)₂ | ethoxy-pyridine-Br | V.3 | 397 [M + H]⁺ | 1.99 (A) |
| 1.112 | cyclopropyl-O-C₆H₄-* | *—N(CH₃)₂ | cyclopropyl-O-C₆H₄-Br | V.3 | 408 [M + H]⁺ | 2.14 (A) |
| 1.113 | cyclopropyl-O-C₆H₄-* | *—OCH₃ | cyclopropyl-O-C₆H₄-Br | V.2 | 395 [M + H]⁺ | 2.20 (A) |
| 1.114 | isobutoxy-C₆H₄-* | *-cyclopropyl | isobutoxy-C₆H₄-I | V.4 | 421 [M + H]⁺ | 2.30 (L) |
| 1.115 | propoxy-cyanophenyl-* | *-cyclopropyl | propoxy-cyanophenyl-Br | V.4 | 432 [M + H]⁺ | 2.15 (F) |

-continued

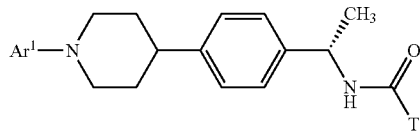
(1-1)

| Example | Ar¹ | T | E 1 | E 2 | ESI-MS [m/z] | R_t (HPLC) [min] (method) |
|---|---|---|---|---|---|---|
| 1.116 | H₃C—propoxy, H₃C—O methoxy phenyl * | * cyclopropyl | H₃C—propoxy, H₃C—O methoxy, Br-phenyl | V.4 | 437 [M + H]⁺ | 2.17 (F) |
| 1.117 | cyclopentyloxy phenyl * | * cyclopropyl | cyclopentyloxy, Br-phenyl | V.4 | 433 [M + H]⁺ | 1.33 (G) |
| 1.118 | isobutoxy pyridine * | * cyclopropyl | isobutoxy, Br-pyridine | V.4 | 422 [M + H]⁺ | 2.22 (A) |
| 1.119 | isopropoxy phenyl * | * cyclopropyl | isopropoxy, Br-phenyl | V.4 | 407 [M + H]⁺ | 2.18 (A) |
| 1.120 | pyridyl-O-isopropyl * | * cyclopropyl | pyridyl-Br-O-isopropyl | V.4 | 408 [M + H]⁺ | 2.09 (A) |
| 1.121 | H₃C—CH₂—O, H₃C—CH₂—O phenyl * | * cyclopropyl | H₃C—CH₂—O, H₃C—CH₂—O, Br-phenyl | V.4 | 437 [M + H]⁺ | 2.12 (A) |
| 1.122 | isobutoxy phenyl * | *—N(CH₃)₂ | isobutoxy, I-phenyl | V.3 | 424 [M + H]⁺ | 2.28 (A) |

-continued

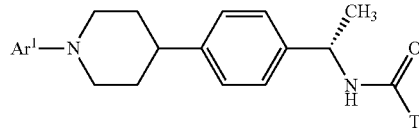
(1-1)

| Example | Ar¹ | T | E 1 | E 2 | ESI-MS [m/z] | R_t (HPLC) [min] (method) |
|---|---|---|---|---|---|---|
| 1.123 | 3-cyano-4-propoxyphenyl | *-N(CH₃)₂ | 2-bromo-4-propoxy-5-cyanophenyl | V.3 | 435 [M + H]⁺ | 2.15 (A) |
| 1.124 | 2-methoxy-4-propoxyphenyl | *-N(CH₃)₂ | 2-bromo-5-propoxy-3-methoxyphenyl | V.3 | 440 [M + H]⁺ | 2.15 (F) |
| 1.125 | 4-cyclopentyloxyphenyl | *-N(CH₃)₂ | 4-bromo-cyclopentyloxyphenyl | V.3 | 436 [M + H]⁺ | 1.82 (G) |
| 1.126 | 5-isobutoxypyridin-2-yl | *-N(CH₃)₂ | 6-bromo-3-isobutoxypyridin-... | V.3 | 425 [M + H]⁺ | 2.20 (A) |
| 1.127 | 4-isopropoxyphenyl | *-N(CH₃)₂ | 4-bromo-isopropoxyphenyl | V.3 | 410 [M + H]⁺ | 2.15 (A) |
| 1.128 | 2-isopropoxypyridin-4-yl | *-N(CH₃)₂ | 4-bromo-2-isopropoxypyridin | V.3 | 411 [M + H]⁺ | 2.06 (A) |
| 1.129 | 2,4-diethoxyphenyl | *-N(CH₃)₂ | 2-bromo-4,5-diethoxyphenyl | V.3 | 440 [M + H]⁺ | 2.09 (A) |

-continued

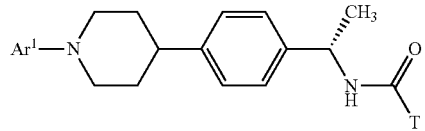
(1-1)

| Example | Ar¹ | T | E 1 | E 2 | ESI-MS [m/z] | $R_t$ (HPLC) [min] (method) |
|---|---|---|---|---|---|---|
| 1.130 | 4-(sec-butoxy)phenyl | *—OCH₃ | 4-(sec-butoxy)-1-bromophenyl | V.2 | 411 [M + H]⁺ | 2.31 (A) |
| 1.131 | 2-cyano-4-propoxyphenyl | *—OCH₃ | 2-bromo-5-propoxybenzonitrile | V.2 | 422 [M + H]⁺ | 2.16 (F) |
| 1.132 | 2-methoxy-4-propoxyphenyl | *—OCH₃ | 1-bromo-2-methoxy-4-propoxyphenyl | V.2 | 427 [M + H]⁺ | 2.22 (F) |
| 1.133 | 4-(cyclopentyloxy)phenyl | *—OCH₃ | 1-bromo-4-(cyclopentyloxy)phenyl | V.2 | 423 [M + H]⁺ | 2.31 (A) |
| 1.134 | 5-(isobutoxy)pyridin-2-yl | *—OCH₃ | 2-bromo-5-(isobutoxy)pyridine | V.2 | 412 [M + H]⁺ | 2.23 (A) |
| 1.135 | 4-(isopropoxy)phenyl | *—OCH₃ | 1-bromo-4-(isopropoxy)phenyl | V.2 | 397 [M + H]⁺ | 2.19 (A) |
| 1.136 | 2-(isopropoxy)pyridin-4-yl | *—OCH₃ | 4-bromo-2-(isopropoxy)pyridine | V.2 | 398 [M + H]⁺ | 2.11 (A) |

-continued

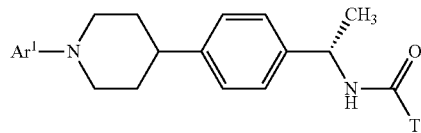
(1-1)

| Example | Ar¹ | T | E 1 | E 2 | ESI-MS [m/z] | R$_t$ (HPLC) [min] (method) |
|---|---|---|---|---|---|---|
| 1.137 | 2,4-bis(ethoxy)phenyl | *—O—CH₃ | 2,4-bis(ethoxy)-bromophenyl | V.2 | 427 [M + H]⁺ | 2.07 (F) |
| 1.138 | 2-phenoxypyridin-4-yl | *—N(CH₃)₂ | 2-phenoxy-4-iodopyridine | V.3 | 445 [M + H]⁺ | 1.30 (G) |
| 1.139 | 4-((2,2-difluorocyclopropyl)methoxy)phenyl | *-cyclopropyl | 4-((2,2-difluorocyclopropyl)methoxy)bromobenzene | V.4 | 455 [M + H]⁺ | 1.23 (G) |
| 1.140 | 4-((2,2-difluorocyclopropyl)methoxy)phenyl | *—N(CH₃)₂ | 4-((2,2-difluorocyclopropyl)methoxy)bromobenzene | V.3 | 458 [M + H]⁺ | 1.21 (G) |
| 1.141 | 4-(cyclobutylmethoxy)phenyl | *-cyclopropyl | 4-(cyclobutylmethoxy)bromobenzene | V.4 | 433 [M + H]⁺ | 1.35 (G) |
| 1.142 | 4-(cyclobutylmethoxy)phenyl | *—N(CH₃)₂ | 4-(cyclobutylmethoxy)bromobenzene | V.3 | 436 [M + H]⁺ | 1.34 (G) |
| 1.143 | 4-(2-cyclopropylethoxy)phenyl | *-cyclopropyl | 4-(2-cyclopropylethoxy)bromobenzene | V.4 | 433 [M + H]⁺ | 1.34 (G) |

-continued

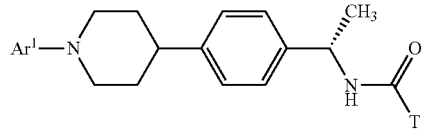

(1-1)

| Example | Ar¹ | T | E 1 | E 2 | ESI-MS [m/z] | R_t (HPLC) [min] (method) |
|---|---|---|---|---|---|---|
| 1.144 | cyclopropylmethyl-CH₂-O-(4-phenyl)-* | *-N(CH₃)₂ | cyclopropylmethyl-CH₂-O-(4-Br-phenyl) | V.3 | 436 [M + H]⁺ | 1.32 (G) |
| 1.145 | H₃C-CH₂CH₂-O-(4-phenyl)-* | *-CH₂CH₃ | H₃C-CH₂CH₂-O-(4-Br-phenyl) | XXIII.1 | 395 [M + H]⁺ | 1.18 (N) |
| 1.146 | 2,3-dihydrobenzo[1,4]dioxin-6-yl-* | *-CH₂CH₃ | 7-Br-2,3-dihydrobenzo[1,4]dioxine | XXIII.1 | 395 [M + H]⁺ | 1.04 (N) |
| 1.147 | H₃C-CH₂CH₂-O-(3-OMe-4-phenyl)-* | *-CH₂CH₃ | H₃C-CH₂CH₂-O-(3-OMe-4-Br-phenyl) | XXIII.1 | 425 [M + H]⁺ | 1.19 (N) |
| 1.148 | cyclopropyl-CH₂-O-(3-F-4-phenyl)-* | *-CH₂CH₃ | cyclopropyl-CH₂-O-(3-F-4-Br-phenyl) | XXIII.1 | 425 [M + H]⁺ | 1.40 (O) |
| 1.149 | isobutyl-O-(4-phenyl)-* | *-CH₂CH₃ | isobutyl-O-(4-Br-phenyl) | XXIII.1 | 409 [M + H]⁺ | 1.29 (N) |
| 1.150 | cyclopropyl-CH₂-O-(4-phenyl)-* | *-CH₂CH₃ | cyclopropyl-CH₂-O-(4-Br-phenyl) | XXIII.1 | 407 [M + H]⁺ | 1.16 (N) |
| 1.151 | cyclopropyl-O-(4-phenyl)-* | *-CH₂CH₃ | cyclopropyl-O-(4-Br-phenyl) | XXIII.1 | 393 [M + H]⁺ | 1.12 (N) |

-continued

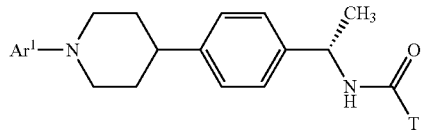
(1-1)

| Example | Ar¹ | T | E 1 | E 2 | ESI-MS [m/z] | R_t (HPLC) [min] (method) |
|---|---|---|---|---|---|---|
| 1.152 | (1,1-difluorocyclopropyl)methoxy-phenyl | *—CH₃ | (1,1-difluorocyclopropyl)methoxy-4-bromophenyl | XXIII.1 | 443 [M + H]⁺ | 1.16 (N) |
| 1.153 | 2-phenoxypyridin-4-yl | *—CH₃ | 2-phenoxy-4-bromopyridinyl | XXIII.1 | 430 [M + H]⁺ | 1.18 (N) |
| 1.154 | 5-ethoxy-2-cyanophenyl | *—CH₃ | 5-ethoxy-2-bromo-cyanophenyl | XXIII.1 | 406 [M + H]⁺ | 1.64 (N) |
| 1.155 | 4-fluoro-3-methylphenyl | *—CH₃ | 4-fluoro-3-methyl-bromophenyl | V.1 | 355 [M + H]⁺ | 1.43 (AA) |
| 1.156 | 4-chloro-3-methylphenyl | *—CH₃ | 4-chloro-3-methyl-bromophenyl | V.1 | 371 [M + H]⁺ | 1.51 (AA) |
| 1.157 | 4-methoxy-3-fluorophenyl | *—CH₃ | 4-methoxy-3-fluoro-bromophenyl | V.1 | 371 [M + H]⁺ | 1.31 (AA) |
| 1.158 | 4-methoxy-3-trifluoromethylphenyl | *—CH₃ | 4-methoxy-3-trifluoromethyl-bromophenyl | V.1 | 841 [2M + H]⁺ | 1.41 (AA) |
| 1.159 | 2-fluoro-5-cyanophenyl | *—CH₃ | 2-fluoro-5-bromo-cyanophenyl | V.1 | 366 [M + H]⁺ | 1.31 (AA) |
| 1.160 | 6-methoxy-5-methylpyridin-3-yl | *—CH₃ | 6-methoxy-5-methyl-5-bromopyridinyl | V.1 | 367 [M + H]⁺ | 1.36 (AA) |

-continued

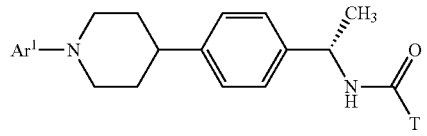
(1-1)

| Example | Ar¹ | T | E 1 | E 2 | ESI-MS [m/z] | R_t (HPLC) [min] (method) |
|---|---|---|---|---|---|---|
| 1.161 | 4-Cl-3-F-phenyl | *—CH₃ | 4-Cl-3-F-bromophenyl | V.1 | 375 [M + H]⁺ | 1.45 (AA) |
| 1.162 | 4-Cl-3-methoxy-phenyl | *—CH₃ | 4-Cl-3-methoxy-bromophenyl | V.1 | 387 [M + H]⁺ | 1.39 (AA) |
| 1.163 | 3,4-diF-phenyl | *—CH₃ | 3,4-diF-bromophenyl | V.1 | 359 [M + H]⁺ | 1.38 (AA) |
| 1.164 | 4-(2,2-difluoroethoxy)phenyl | *—CH₃ | 4-(2,2-difluoroethoxy)bromophenyl | V.1 | 403 [M + H]⁺ | 1.33 (AA) |
| 1.165 | 4-(3,3,3-trifluoropropoxy)phenyl | *—CH₃ | 4-(3,3,3-trifluoropropoxy)bromophenyl | V.1 | 435 [M + H]⁺ | 1.40 (AA) |
| 1.166 | 4-methoxy-3-cyclopropyl-phenyl | *—CH₃ | 4-methoxy-3-cyclopropyl-bromophenyl | V.1 | 393 [M + H]⁺ | 1.13 (N) |
| 1.167 | 4-(tetrahydrofuran-2-ylmethoxy)phenyl | *—CH₃ | 4-(tetrahydrofuran-2-ylmethoxy)bromophenyl | V.1 | 423 [M + H]⁺ | 1.05 (N) |
| 1.168 | 4-ethoxy-3-F-phenyl | *—CH₂CH₃ | 4-ethoxy-3-F-bromophenyl | XXIII.1 | 399 [M + H]⁺ | 1.32 (N) |

-continued

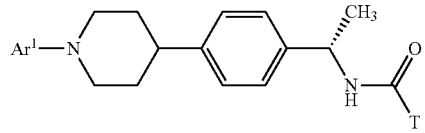
(1-1)

| Example | Ar¹ | T | E 1 | E 2 | ESI-MS [m/z] | R$_t$ (HPLC) [min] (method) |
|---|---|---|---|---|---|---|
| 1.169 | pyrimidine-O-pyridine-* | *-CH₂CH₃ | pyrimidine-O-pyridine-I | XXIII.1 | 432 [M + H]⁺ | 1.10 (N) |
| 1.170 | CH₃CH₂O-phenyl(F)-* | *-O-CH₃ | CH₃CH₂O-phenyl(F)-Br | V.2 | 401 [M + H]⁺ | 1.36 (N) |
| 1.171 | Cl-phenyl(CN)-* | *-CH₃ | Cl-phenyl(CN)-Br | V.1 | 382 [M + H]⁺ | 1.20 (G) |
| 1.172 | cyclohexyl-O-pyridine-* | *-CH₃ | cyclohexyl-O-pyridine-I | V.1 | 422 [M + H]⁺ | 1.35 (G) |
| 1.173 | cyclopropyl-pyrazine-* | *-CH₃ | cyclopropyl-pyrazine-Br | V.1 | 365 [M + H]⁺ | 1.51 (N) |
| 1.174 | cyclopropyl-pyridazine-* | *-CH₃ | cyclopropyl-pyridazine-Br | V.1 | 365 [M + H]⁺ | 0.99 (N) |
| 1.175 | cyclopropyl-pyridine-* | *-CH₃ | cyclopropyl-pyridine-Br | V.1 | 364 [M + H]⁺ | 1.06 (N) |
| 1.176 | cyclobutyl-O-phenyl-* | *-CH₃ | cyclobutyl-O-phenyl-I | V.1 | 393 [M + H]⁺ | 1.65 (D) |
| 1.177 | cyclopropyl-CH₂-O-phenyl(F)-* | *-CH₃ | cyclopropyl-CH₂-O-phenyl(F)-Br | V.1 | 411 [M + H]⁺ | 1.28 (G) |

-continued

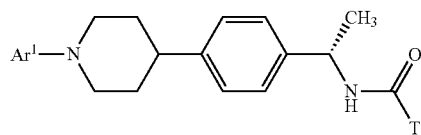
(1-1)

| Example | Ar¹ | T | E 1 | E 2 | ESI-MS [m/z] | R_t (HPLC) [min] (method) |
|---|---|---|---|---|---|---|
| 1.178 | 5-(2-methoxyethoxy)pyridin-2-yl | N(CH₃)₂ | 6-bromo-5-(2-methoxyethoxy)pyridin-3-yl (E1 variant) | V.3 | 411 [M + H]⁺ | 1.19 (G) |
| 1.179 | 5-ethoxypyridin-2-yl | N(CH₃)₂ | 6-bromo-5-ethoxypyridin-3-yl | V.3 | 397 [M + H]⁺ | 1.12 (G) |
| 1.180 | 2,6-diethoxypyridin-3-yl | *—CH₃ | 5-bromo-2,6-diethoxypyridin-3-yl | V.1 | 412 [M + H]⁺ | 1.25 (G) |
| 1.181 | 2-cyano-6-propoxypyridin-3-yl | *—CH₃ | 5-bromo-2-cyano-6-propoxypyridin-3-yl | V.1 | 407 [M + H]⁺ | 1.24 (G) |
| 1.182 | 2-cyano-6-ethoxypyridin-3-yl | *—CH₃ | 5-bromo-2-cyano-6-ethoxypyridin-3-yl | V.1 | 393 [M + H]⁺ | 1.16 (G) |
| 1.183 | 2-cyano-6-(cyclopropylmethoxy)pyridin-3-yl | *—CH₃ | 5-bromo-2-cyano-6-(cyclopropylmethoxy)pyridin-3-yl | V.1 | 419 [M + H]⁺ | 1.21 (G) |
| 1.184 | 8-fluoro-3,4-dihydro-2H-benzo[b][1,4]dioxepin-7-yl | *—CH₃ | 7-bromo-8-fluoro-3,4-dihydro-2H-benzo[b][1,4]dioxepin | V.1 | 413 [M + H]⁺ | 1.15 (G) |

-continued (1-1)

| Example | Ar¹ | T | E 1 | E 2 | ESI-MS [m/z] | R_t (HPLC) [min] (method) |
|---|---|---|---|---|---|---|
| 1.185 | 7-fluoro-3,4-dihydro-2H-benzo[b][1,4]dioxepin-6-yl | *-cyclopropyl | 8-bromo-7-fluoro-3,4-dihydro-2H-benzo[b][1,4]dioxepin-6-yl | V.4 | 439 [M + H]⁺ | 1.19 (G) |
| 1.186 | 4-(furan-3-ylmethoxy)phenyl | *—CH₃ | 4-bromo-2-(furan-3-ylmethoxy)phenyl | V.1 | 419 [M + H]⁺ | 1.40 (AE) |
| 1.187 | 4-((2,2-difluorocyclopropyl)methoxy)-2-fluorophenyl | *—CH₃ | 4-bromo-((2,2-difluorocyclopropyl)methoxy)-3-fluorophenyl | V.1 | 447 [M + H]⁺ | 1.43 (L) |
| 1.188 | 3-(trifluoromethyl)phenyl | *—CH₃ | 3-bromo-5-(trifluoromethyl)phenyl | V.1 | 391 [M + H]⁺ | 1.39 (L) |
| 1.189 | 4-cyclopropoxy-2-fluorophenyl | *—CH₃ | 4-bromo-2-cyclopropoxy-3-fluorophenyl | V.1 | 397 [M + H]⁺ | 1.37 (L) |
| 1.190 | 2-ethoxy-5-fluoropyridin-4-yl | *—CH₃ | 4-bromo-2-ethoxy-5-fluoropyridin-4-yl | V.1 | 386 [M + H]⁺ | 1.32 (L) |
| 1.191 | 2-ethoxypyridin-4-yl | *—CH₃ | 4-bromo-2-ethoxypyridin-4-yl | V.1 | 368 [M + H]⁺ | 1.05 (N) |
| 1.192 | 5-fluoro-2,3-dihydrobenzo[b][1,4]dioxin-6-yl | *—CH₃ | 6-bromo-5-fluoro-2,3-dihydrobenzo[b][1,4]dioxin-7-yl | V.1 | 399 [M + H]⁺ | 1.10 (G) |

The following compounds of general formula (1-2) are prepared analogously to Example 1.1, the educts used being shown in the column headed "Educts":

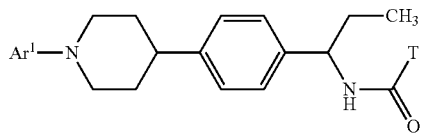

(1-2)

| Example | Ar¹ | T | Educt 1 | Educt 2 | ESI-MS [m/z] | $R_t$ (HPLC) [min] (method) |
|---|---|---|---|---|---|---|
| 1.200 | (4-ethoxyphenoxy, ethyl ether) | *—CH₃ | (4-bromophenyl ethoxy) | XXIII.2 | 395 [M + H]⁺ | 1.19 (N) |
| 1.201 | (2,3-dihydrobenzodioxin-6-yl) | *—CH₃ | (6-bromo-2,3-dihydrobenzodioxin) | XXIII.2 | 395 [M + H]⁺ | 0.94 (N) |
| 1.202 | (3-fluoro-4-(cyclopropylmethoxy)phenyl) | *—CH₃ | (4-bromo-2-fluoro-(cyclopropylmethoxy)benzene) | XXIII.2 | 425 [M + H]⁺ | 1.46 (N) |
| 1.203 | (4-(cyclopropylmethoxy)phenyl) | *—CH₃ | (4-bromo-(cyclopropylmethoxy)benzene) | XXIII.2 | 407 [M + H]⁺ | 1.18 (N) |
| 1.204 | (4-(cyclopropyloxy)phenyl) | *—CH₃ | (4-bromo-(cyclopropyloxy)benzene) | XXIII.2 | 393 [M + H]⁺ | 1.14 (N) |
| 1.205 | (4-((2,2-difluorocyclopropyl)methoxy)phenyl) | *—CH₃ | (4-bromo-((2,2-difluorocyclopropyl)methoxy)benzene) | XXIII.2 | 443 [M + H]⁺ | 1.18 (N) |
| 1.206 | (4-ethoxyphenyl) | *—CH₃ | (4-bromoethoxybenzene) | XXIII.2 | 381 [M + H]⁺ | 1.11 (N) |
| 1.207 | (3-fluoro-4-ethoxyphenyl) | *—CH₃ | (4-bromo-2-fluoroethoxybenzene) | XXIII.2 | 399 [M + H]⁺ | 1.34 (N) |

The following compound of general formula (1-3) is prepared analogously to Example 1.1, the educts used being shown in the column headed "E 1" and "E 2":

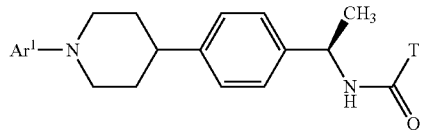
(1-3)

| Example | Ar¹ | T | E 1 | E 2 | ESI-MS [m/z] | $R_t$ (HPLC) [min] (method) |
|---|---|---|---|---|---|---|
| 1.300 | H₃C—O—⟨⟩(F)—* | *—CH₃ | H₃C—O—⟨⟩(F)—* | V.6 | 385 [M + H]⁺ | 1.21 (G) |
|  |  |  |  |  |  |  |
|  |  |  | (with F substituent) | (with F, Br) |  |  |

Example 2

Example 2.1

N-(2-{4-[1-(4-Ethoxy-phenyl)-piperidin-4-yl]-phenyl}-1-methyl-ethyl)-acetamide

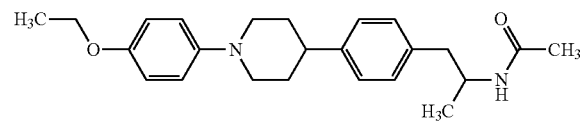

3.0 mL Toluene/tert-butanol (5:1) are added to a mixture of 130 mg (0.50 mmol) N-[1-methyl-2-(4-piperidin-4-yl-phenyl)-ethyl]-acetamide (VIII.1), 100 mg (0.50 mmol) 1-bromo-4-ethoxy-benzene, 80 mg (0.83 mmol) sodium tert-butyrat, 20 mg (0.040 mmol) X-Phos and 10 mg (0.040 mmol) palladium(II) acetate. The mixture is stirred for 10 min at 150° C. under microwave irradiation in a sealed tube. After that time, the mixture is poured into 1 mL 0.1 N HCl. 1 mL conc. ammonia is added and the mixture is extracted with ethyl acetate (3×). The combined organic layers are dried over sodium sulphate and the solvent is removed in vacuo. The residue is purified by column chromatography (silica gel; DCM/MeOH 19:1) to yield the desired product.

$C_{24}H_{32}N_2O_2$ (M=380.5 g/mol), ESI-MS: 381 [M+H]⁺
$R_t$ (HPLC): 2.15 min (method C)

The following compounds of general formula (2-1) are prepared analogously to Example 2.1, the educts used being shown in the column headed "Educts" For the examples 2.3-2.12 the piperidine building block is added to a mixture of the appropriate aryl bromide (1 eq), sodium tert-butyrat (4 eq), 2-(di-tert-butylphosphino)biphenyl (0.4 eq) and tris-(dibenzylidenaceton)-dipalladium(0) (0.1 eq) in 1,4-dioxane. The reaction mixture is stirred at 45° C. over night and afterwards purified by HPLC.

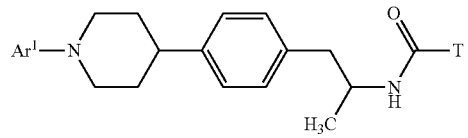
(2-1)

| Example | Ar¹ | T | Educt 1 | Educt 2 | ESI-MS [m/z] | $R_t$ (HPLC) [min] (method) |
|---|---|---|---|---|---|---|
| 2.1 | H₃C—O—⟨⟩—* | *—CH₃ | H₃C—O—⟨⟩—Br | VIII.1 | 381 [M + H]⁺ | 2.15 (C) |
| 2.3 | H₃C—CH₂—O—⟨⟩—* | *—CH₃ | H₃C—CH₂—O—⟨⟩—Br | VIII.1 | 395 [M + H]⁺ | 1.28 (G) |

-continued

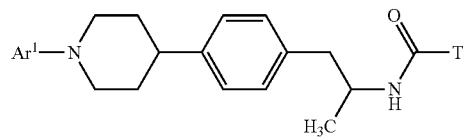

(2-1)

| Example | Ar¹ | T | Educt 1 | Educt 2 | ESI-MS [m/z] | R_t (HPLC) [min] (method) |
|---|---|---|---|---|---|---|
| 2.4 | benzodioxane | *—CH₃ | 6-bromo-benzodioxane | VIII.1 | 395 [M + H]⁺ | 1.16 (G) |
| 2.5 | 3-methoxy-4-propoxyphenyl | *—CH₃ | 1-bromo-2-methoxy-4-propoxybenzene | VIII.1 | 425 [M + H]⁺ | 1.31 (G) |
| 2.6 | 3-fluoro-4-(cyclopropylmethoxy)phenyl | *—CH₃ | 1-bromo-2-fluoro-4-(cyclopropylmethoxy)benzene | VIII.1 | 425 [M + H]⁺ | 1.30 (G) |
| 2.7 | 4-isobutoxyphenyl | *—CH₃ | 1-bromo-4-isobutoxybenzene | VIII.1 | 409 [M + H]⁺ | 1.34 (G) |
| 2.8 | 4-(cyclopropylmethoxy)phenyl | *—CH₃ | 1-bromo-4-(cyclopropylmethoxy)benzene | VIII.1 | 407 [M + H]⁺ | 1.27 (G) |
| 2.9 | 4-cyclopropoxyphenyl | *—CH₃ | 1-bromo-4-cyclopropoxybenzene | VIII.1 | 393 [M + H]⁺ | 1.03 (N) |
| 2.10 | 2-phenoxypyridin-4-yl | *—CH₃ | 4-bromo-2-phenoxypyridine | VIII.1 | 393 [M + H]⁺ | 1.03 (N) |

(2-1)

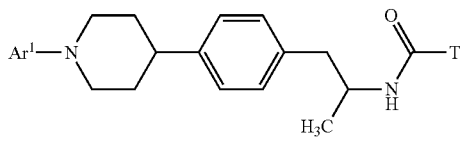

| Example | Ar¹ | T | Educt 1 | Educt 2 | ESI-MS [m/z] | R_t (HPLC) [min] (method) |
|---|---|---|---|---|---|---|
| 2.11 | 3-ethoxy-6-cyano-pyridinyl | *—CH₃ | 3-ethoxy-6-cyano-bromopyridine | VIII.1 | 406 [M + H]⁺ | 1.64 (N) |
| 2.12 | 2-fluoro-4-ethoxymethyl-phenyl | *—CH₃ | 2-fluoro-4-ethoxymethyl-bromobenzene | VIII.1 | 399 [M + H]⁺ | 1.33 (N) |

The following compound of general formula (2-2) is prepared analogously to Example 2.1, the educts used being shown in the column headed "Educts":

(2-2)

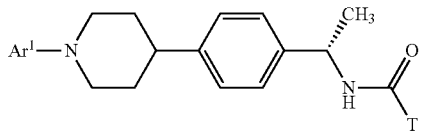

| Example | Ar¹ | T | Educt 1 | Educt 2 | ESI-MS [m/z] | R_t (HPLC) [min] (method) |
|---|---|---|---|---|---|---|
| 2.13 | 1-benzyl-pyrazol-4-yl | *—CH₃ | 1-benzyl-4-bromo-pyrazole | V.1 | 403 [M + H]⁺ | 1.91 (A) |

Under inert gas atmosphere 123 mg (0.50 mmol) (S)—N-[1-(piperidin-4-yl-phenyl)ethyl]-acetamide (V.1) is added to a mixture of 149 mg (0.50 mmol) 5-iodo-2-phenoxy-pyridine (J. Organomet. Chem. 2003, 677, 57), 212 mg (1.00 mmol) K₃PO₄, 62 mg (1.00 mmol) ethylenglycol and 5 mg (0.025 mmol) copper(I) iodide in 5.0 mL 2-propanol. The mixture is stirred for 12 h at 80° C. in a sealed tube. After cooling, the precipitate is filtered off and washed with acetonitrile. The precipitate is purified by HPLC (column: Agilent Zorbax Stablebond C18, 8 µM; eluent A: water+0.3% NH₄OH, eluent B: MeOH) to yield the desired product.

$C_{26}H_{29}N_3O_2$ (M=415.5 g/mol), ESI-MS: 416 [M+H]⁺

R_t (HPLC): 2.08 min (method A)

The following compounds of general formula (3-1) are prepared analogously to Example 3.1, the educts used being shown in the column headed "E 1" and "E 2":

Example 3

Example 3.1

(S)—N-{1-[4-(6'-Phenoxy-3,4,5,6-tetrahydro-2H-1,3']bipyridinyl-4-yl)-phenyl'-ethyl}-acetamide

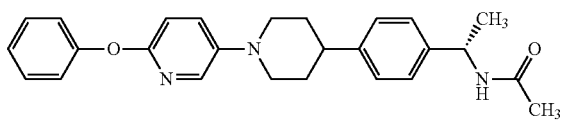

(3-1)

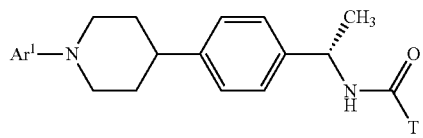

| Ex. | Ar¹ | T | E 1 | E 2 | ESI-MS [m/z] | R$_t$ (HPLC) [min] (method) |
|---|---|---|---|---|---|---|
| 3.1 | 5-phenoxypyridin-2-yl (phenoxy-pyridine attached at 5-position) | *—CH₃ | 5-iodo-2-phenoxypyridine | V.1 | 416 [M + H]⁺ | 2.08 (A) |
| 3.2 | 2-methoxypyridin-4-yl | *—CH₃ | 4-iodo-2-methoxypyridine | V.1 | 354 [M + H]⁺ | 1.90 (A) |
| 3.3 | 2-isopropoxypyridin-4-yl | *—CH₃ | 4-iodo-2-isopropoxypyridine | V.1 | 382 [M + H]⁺ | 2.06 (A) |
| 3.4 | 2-butoxypyridin-4-yl | *—CH₃ | 2-butoxy-4-iodopyridine | V.1 | 396 [M + H]⁺ | 2.18 (A) |
| 3.5 | 2-(pyrimidin-5-yloxy)pyridin-4-yl | *—CH₃ | 4-iodo-2-(pyrimidin-5-yloxy)pyridine | V.1 | 418 [M + H]⁺ | 1.82 (A) |
| 3.6 | 4-isopropoxyphenyl | *—CH₃ | 4-iodo-1-isopropoxybenzene | V.1 | 381 [M + H]⁺ | 2.15 (A) |
| 3.7 | 4-isobutoxyphenyl | *—CH₃ | 1-iodo-4-isobutoxybenzene | V.1 | 395 [M + H]⁺ | 2.29 (A) |
| 3.8 | 4-propoxyphenyl | *—CH₃ | 1-iodo-4-propoxybenzene | V.1 | 381 [M + H]⁺ | 2.21 (A) |
| 3.9 | 1-propyl-2-oxo-1,2-dihydropyridin-4-yl | *—CH₃ | 4-iodo-1-propylpyridin-2(1H)-one | V.1 | 382 [M + H]⁺ | 1.74 (A) |

(3-1)

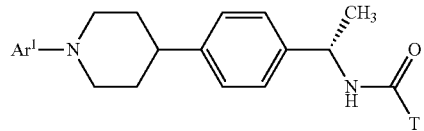

| Ex. | Ar¹ | T | E 1 | E 2 | ESI-MS [m/z] | R$_t$ (HPLC) [min] (method) |
|---|---|---|---|---|---|---|
| 3.10 | phenoxy-pyridazinyl | *—CH₃ | phenoxy-iodopyridazinyl | V.1 | 417 [M + H]⁺ | 1.91 (A) |
| 3.11 | H₃C-CH₂-O-pyridazinyl | *—CH₃ | H₃C-CH₂-O-iodopyridazinyl | V.1 | 369 [M + H]⁺ | 1.88 (A) |
| 3.12 | phenoxy-pyridinyl | *—CH₃ | phenoxy-iodopyridinyl | V.1 | 416 [M + H]⁺ | 2.06 (A) |
| 3.13 | H₃C-(CH₂)₃-O-pyridazinyl | *—CH₃ | H₃C-(CH₂)₃-O-iodopyridazinyl | V.1 | 397 [M + H]⁺ | 2.09 (A) |
| 3.14 | phenoxy-pyridinyl | *—cyclopropyl | phenoxy-iodopyridinyl | V.1 | 442 [M + H]⁺ | 1.32 (G) |

The following compound of general formula (3-2) is prepared analogously to Example 3.1, the educts used being shown in the column headed "E 1" and "E 2":

(3-2)

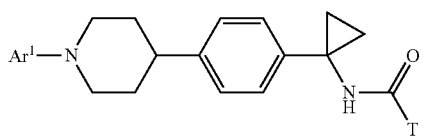

| Ex. | Ar¹ | T | E 1 | E 2 | ESI-MS [m/z] | R$_t$ (HPLC) [min] (method) |
|---|---|---|---|---|---|---|
| 3.20 | ethoxy-phenyl | *—CH₃ | ethoxy-iodophenyl | V.7 | 379 [M + H]⁺ | 2.01 (F) |

Example 4

Example 4.1

(S)—N-(1-{4-[1-(3-Cyanopyridin-2-yl)piperidin-4-yl]phenyl}ethyl)acetamide

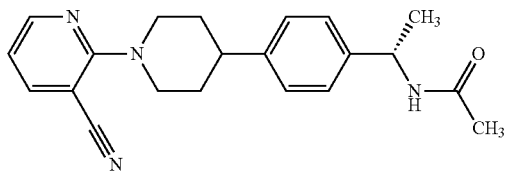 [SMILES: CC(=O)N[C@@H](C)c1ccc(C2CCN(c3ncccc3C#N)CC2)cc1]

50 μL (0.29 mmol) DIPEA are added to a mixture of 14 mg (0.10 mmol) 2-chloronicotinnitrile and 29 mg (0.11 mmol) (S)-N-[1-(4-piperidin-4-yl-phenyl)-ethyl]-acetamide (V.1) in 1.45 mL NMP. The mixture is stirred at 130° C. overnight. Subsequently the solvent is removed in vacuo, the residue is taken up in DMF and the mixture is purified using reversed phase HPLC (water/MeOH, 0.1% TFA) to yield the desired product.

$C_{10}H_{11}NO$ (M=348.4 g/mol), ESI-MS: 349 $[M+H]^+$ $R_t$ (HPLC): 1.89 min (method B)

The following compounds of general formula (4-1) are prepared analogously to Example 4.1, the educts used being shown in the column headed "E 1" and "E 2". For the examples 4.52 and 4.53 the reaction mixture is stirred at 130° C. for 2 h in a microwave oven.

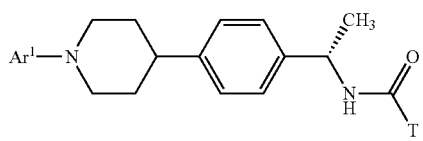

(4-1)

| Example | Ar¹ | T | E 1 | E 2 | ESI-MS [m/z] | $R_t$ (HPLC) [min] (method) |
|---|---|---|---|---|---|---|
| 4.1 | pyridin-2-yl with 3-CN | *—CH₃ | 2-chloro-3-cyanopyridine | V.1 | 349 [M + H]⁺ | 1.89 (B) |
| 4.2 | benzothiazol-2-yl | *—CH₃ | 2-chlorobenzothiazole | V.1 | 380 [M + H]⁺ | 1.78 (B) |
| 4.3 | quinolin-2-yl | *—CH₃ | 2-chloroquinoline | V.1 | 374 [M + H]⁺ | 1.24 (B) |
| 4.4 | 4-methylquinolin-2-yl | *—CH₃ | 2-chloro-4-methylquinoline | V.1 | 388 [M + H]⁺ | 1.32 (B) |
| 4.5 | 5-cyanopyridin-2-yl | *—CH₃ | 2-chloro-5-cyanopyridine | V.1 | 349 [M + H]⁺ | 1.86 (B) |

-continued

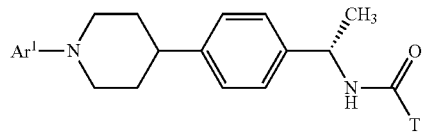
(4-1)

| Example | Ar¹ | T | E 1 | E 2 | ESI-MS [m/z] | R_t (HPLC) [min] (method) |
|---|---|---|---|---|---|---|
| 4.6 | 4-CF₃-pyrimidin-6-yl | *—CH₃ | 4-CF₃-6-chloropyrimidine | V.1 | 393 [M + H]⁺ | 1.93 (B) |
| 4.7 | quinazolin-4-yl | *—CH₃ | 4-chloroquinazoline | V.1 | 375 [M + H]⁺ | 1.20 (B) |
| 4.8 | 3-chloroisoquinolin-1-yl | *—CH₃ | 1,3-dichloroisoquinoline | V.1 | 408 [M + H]⁺ | 2.29 (B) |
| 4.9 | benzoxazol-2-yl | *—CH₃ | 2-chlorobenzoxazole | V.1 | 364 [M + H]⁺ | 1.91 (B) |
| 4.10 | 6-chloroquinolin-2-yl | *—CH₃ | 2,6-dichloroquinoline | V.1 | 408 [M + H]⁺ | 1.39 (B) |
| 4.11 | 4-CF₃-pyrimidin-2-yl | *—CH₃ | 2-chloro-4-CF₃-pyrimidine | V.1 | 393 [M + H]⁺ | 2.17 (B) |
| 4.12 | 1-methylbenzimidazol-2-yl | *—CH₃ | 2-chloro-1-methylbenzimidazole | V.1 | 377 [M + H]⁺ | 1.22 (B) |
| 4.13 | 5-isopropylpyridin-2-yl | *—CH₃ | 2-chloro-5-isopropylpyridine | V.1 | 366 [M + H]⁺ | 1.37 (B) |

-continued

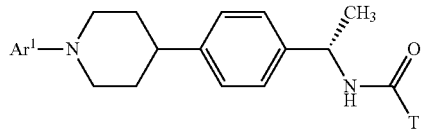
(4-1)

| Example | Ar¹ | T | E 1 | E 2 | ESI-MS [m/z] | R_t (HPLC) [min] (method) |
|---|---|---|---|---|---|---|
| 4.14 | 1-methyl-1H-[1,2,3]triazolo[4,5-b]pyridin-5-yl | *—CH₃ | 6-chloro-1-methyl-1H-[1,2,3]triazolo[4,5-b]pyridine | V.1 | 379 [M + H]⁺ | 1.86 (B) |
| 4.15 | 5-phenylpyridin-2-yl | *—CH₃ | 2-chloro-5-phenylpyridine | V.1 | 400 [M + H]⁺ | 1.43 (B) |
| 4.16 | 4-methoxypyridin-2-yl | *—CH₃ | 2-chloro-4-methoxypyridine | V.1 | 354 [M + H]⁺ | 1.16 (B) |
| 4.17 | 5-(trifluoromethyl)pyridin-2-yl | *—CH₃ | 2-fluoro-5-(trifluoromethyl)pyridine | V.1 | 392 [M + H]⁺ | 2.07 (B) |
| 4.18 | 4-(trifluoromethyl)pyridin-2-yl | *—CH₃ | 2-chloro-4-(trifluoromethyl)pyridine | V.1 | 392 [M + H]⁺ | 2.03 (B) |
| 4.19 | 6-(trifluoromethyl)pyridin-2-yl | *—CH₃ | 2-chloro-6-(trifluoromethyl)pyridine | V.1 | 392 [M + H]⁺ | 2.15 (B) |
| 4.20 | 3-methyl-1H-pyrazolo[3,4-d]pyrimidin-6-yl | *—CH₃ | 6-chloro-3-methyl-1H-pyrazolo[3,4-d]pyrimidine·HCl | V.1 | 379 [M + H]⁺ | 1.72 (B) |
| 4.21 | 4-phenylpyrimidin-2-yl | *—CH₃ | 2-chloro-4-phenylpyrimidine | V.1 | 401 [M + H]⁺ | 2.04 (B) |

-continued (4-1)

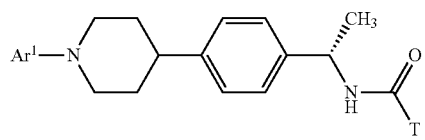

| Example | Ar¹ | T | E 1 | E 2 | ESI-MS [m/z] | R_t (HPLC) [min] (method) |
|---|---|---|---|---|---|---|
| 4.22 | 4-phenylpyrimidin-6-yl | *—CH₃ | 6-chloro-4-phenylpyrimidine | V.1 | 401 [M + H]⁺ | 1.33 (B) |
| 4.23 | 4-methylquinazolin-2-yl | *—CH₃ | 2-chloro-4-methylquinazoline | V.1 | 389 [M + H]⁺ | 1.39 (B) |
| 4.24 | thieno[3,2-d]pyrimidin-4-yl | *—CH₃ | 4-chlorothieno[3,2-d]pyrimidine | V.1 | 381 [M + H]⁺ | 1.22 (B) |
| 4.25 | 2-isopropylpyrimidin-4-yl | *—CH₃ | 4-chloro-2-isopropylpyrimidine | V.1 | 367 [M + H]⁺ | 1.36 (B) |
| 4.26 | 2-(trifluoromethyl)pyrimidin-4-yl | *—CH₃ | 4-chloro-2-(trifluoromethyl)pyrimidine | V.1 | 393 [M + H]⁺ | 1.95 (B) |
| 4.27 | 6-ethoxypyridin-2-yl | *—CH₃ | 6-chloro-2-ethoxypyridine | V.1 | 368 [M + H]⁺ | 2.04 (B) |

-continued (4-1)

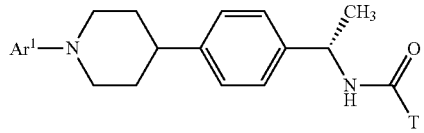

| Example | Ar¹ | T | E 1 | E 2 | ESI-MS [m/z] | R_f (HPLC) [min] (method) |
|---|---|---|---|---|---|---|
| 4.28 | 2-phenyl-oxazolo[5,4-d]pyrimidin-5-yl | *—CH₃ | 5-chloro-2-phenyl-oxazolo[5,4-d]pyrimidine | V.1 | 442 [M + H]⁺ | 2.28 (B) |
| 4.29 | 5-chloro-pyrimidin-2-yl | *—CH₃ | 2,5-dichloropyrimidine | V.1 | 359 [M + H]⁺ | 2.18 (B) |
| 4.30 | benzo[d]isoxazol-3-yl | *—CH₃ | 3-chloro-benzo[d]isoxazole | V.1 | 364 [M + H]⁺ | 1.83 (B) |
| 4.31 | 6,7-dimethoxy-isoquinolin-1-yl | *—CH₃ | 1-chloro-6,7-dimethoxyisoquinoline | V.1 | 434 [M + H]⁺ | 1.76 (B) |
| 4.32 | 3-methyl-quinoxalin-2-yl | *—CH₃ | 2-chloro-3-methyl-quinoxaline | V.1 | 389 [M + H]⁺ | 2.15 (B) |
| 4.33 | 5-methoxy-pyrimidin-2-yl | *—CH₃ | 2-chloro-5-methoxypyrimidine | V.1 | 355 [M + H]⁺ | 2.05 (B) |
| 4.34 | 5-acetamido-pyrimidin-2-yl | *—CH₃ | N-(2-chloropyrimidin-5-yl)acetamide | V.1 | 382 [M + H]⁺ | 1.67 (A) |
| 4.35 | 5-ethyl-pyrimidin-2-yl | *—CH₃ | 2-chloro-5-ethylpyrimidine | V.1 | 367 [M + H]⁺ | 2.15 (A) |

-continued (4-1)

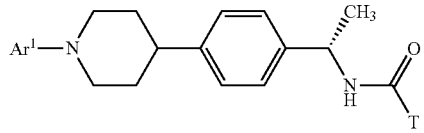

| Example | Ar¹ | T | E 1 | E 2 | ESI-MS [m/z] | R_t (HPLC) [min] (method) |
|---|---|---|---|---|---|---|
| 4.36 | methyl 2-pyrimidinyl-5-carboxylate | *—CH₃ | methyl 2-chloropyrimidine-5-carboxylate | V.1 | 383 [M + H]⁺ | 1.99 (A) |
| 4.37 | 5-(4-chlorophenyl)pyrimidin-2-yl | *—CH₃ | 5-(4-chlorophenyl)-2-chloropyrimidine | V.1 | 435 [M + H]⁺ | 2.32 (A) |
| 4.38 | 5-tert-butylpyrimidin-2-yl | *—CH₃ | 5-tert-butyl-2-chloropyrimidine | V.1 | 381 [M + H]⁺ | 2.20 (A) |
| 4.39 | 5-nitropyrimidin-2-yl | *—CH₃ | 2-chloro-5-nitropyrimidine | V.1 | 370 [M + H]⁺ | 1.98 (A) |
| 4.40 | 5-fluoropyrimidin-2-yl | *—CH₃ | 2-chloro-5-fluoropyrimidine | V.1 | 343 [M + H]⁺ | 2.01 (A) |
| 4.41 | 5-(4-methoxyphenyl)pyrimidin-2-yl | *—CH₃ | 2-chloro-5-(4-methoxyphenyl)pyrimidine | V.1 | 431 [M + H]⁺ | 2.20 (A) |
| 4.42 | 5-ethylpyrimidin-2-yl | *—CH₃ | 2-chloro-5-ethylpyrimidine | V.1 | 353 [M + H]⁺ | 2.05 (A) |
| 4.43 | 5-iodopyrimidin-2-yl | *—CH₃ | 2-chloro-5-iodopyrimidine | V.1 | 451 [M + H]⁺ | 2.21 (A) |
| 4.44 | 5-bromopyrimidin-2-yl | *—CH₃ | 5-bromo-2-chloropyrimidine | V.1 | 403 [M + H]⁺ | 2.19 (A) |
| 4.45 | pyrimidin-2-yl | *—CH₃ | 2-chloropyrimidine | V.1 | 325 [M + H]⁺ | 1.83 (A) |

-continued (4-1)

| Example | Ar¹ | T | E 1 | E 2 | ESI-MS [m/z] | R_f (HPLC) [min] (method) |
|---|---|---|---|---|---|---|
| 4.46 | 2-phenyl-oxazolo[5,4-d]pyrimidin-5-yl | *-cyclopropyl | 2-phenyl-5-chloro-oxazolo[5,4-d]pyrimidine | V.4 | 468 [M + H]⁺ | 2.31 (A) |
| 4.47 | 2-phenyl-oxazolo[5,4-d]pyrimidin-5-yl | *-N(CH₃)₂ | 2-phenyl-5-chloro-oxazolo[5,4-d]pyrimidine | V.3 | 471 [M + H]⁺ | 2.29 (A) |
| 4.48 | 2-phenyl-oxazolo[5,4-d]pyrimidin-5-yl | *-OCH₃ | 2-phenyl-5-chloro-oxazolo[5,4-d]pyrimidine | V.1 | 458 [M + H]⁺ | 2.32 (A) |
| 4.49 | 5-propoxy-pyrimidin-2-yl | *-CH₃ | 5-propoxy-2-chloropyrimidine | V.1 | 383 [M + H]⁺ | 2.04 (F) |
| 4.50 | 5-ethoxy-pyrimidin-2-yl | *-CH₃ | 5-ethoxy-2-chloropyrimidine | V.1 | 369 [M + H]⁺ | 1.92 (F) |
| 4.51 | 5-isopropoxy-pyrimidin-2-yl | *-CH₃ | 5-isopropoxy-2-chloropyrimidine | V.1 | 383 [M + H]⁺ | 1.99 (F) |

-continued (4-1)

| Example | Ar¹ | T | E 1 | E 2 | ESI-MS [m/z] | R_f (HPLC) [min] (method) |
|---|---|---|---|---|---|---|
| 4.52 | cyclopropylmethoxy-pyrimidine | *—CH₃ | cyclopropylmethoxy-pyrimidine | V.1 | 395 [M + H]⁺ | 1.56 (N) |
| 4.53 | (2,2-difluorocyclopropyl)methoxy-pyrimidine | *—CH₃ | (2,2-difluorocyclopropyl)methoxy-pyrimidine-Cl | V.1 | 431 [M + H]⁺ | 1.53 (N) |
| 4.54 | 5-cyclopropylpyrimidine | *—CH₂CH₃ | 5-cyclopropyl-2-chloropyrimidine | XXIII.1 | 379 [M + H]⁺ | 1.46 (N) |

The following compounds of general formula (4-1) are prepared analogously to Example 4.1 using refluxing ethanol as a solvent, the educts used being shown in the column headed "E 1" and "E 2":

(4-1)

| Ex. | Ar¹ | T | E 1 | E 2 | ESI-MS | R_f (HPLC) [min] (method) |
|---|---|---|---|---|---|---|
| 4.101 | methyl thiazole-5-carboxylate | *—CH₃ | methyl 2-bromothiazole-5-carboxylate | V.1 | 388 [M + H]⁺ | 1.87 (A) |
| 4.102 | 5-tert-butylthiazole | *—CH₃ | 5-tert-butyl-2-bromothiazole | V.1 | 386 [M + H]⁺ | 2.02 (A) |

The following compounds of general formula (4-1) are prepared analogously to Example 4.1 using refluxing DMA under microwave irradiation as a solvent and potassium carbonate as base, the educts used being shown in the column headed "E 1" and "E 2":

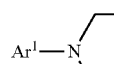

| Ex. | Ar¹ | T | E 1 | E 2 | ESI-MS [m/z] | R$_t$ (HPLC) [min] (method) |
|---|---|---|---|---|---|---|
| 4.201 | 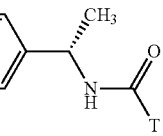 | *—CH$_3$ | 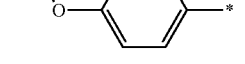 | V.1 | 420 [M + H]⁺ | 2.21 (F) |
| 4.202 | 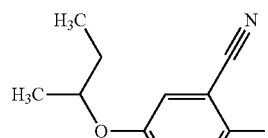 | *—CH$_3$ |  | V.1 | 420 [M + H]⁺ | 2.15 (F) |

The following compounds of general formula (4-1) are prepared analogously to Example 4.1 using refluxing DMSO as a solvent and N,N-diisopropylethylamine as base, the educts used being shown in the column headed "E 1" and "E 2":

| Ex. | Ar¹ | T | E 1 | E 2 | ESI-MS [m/z] | R$_t$ (HPLC) [min] (method) |
|---|---|---|---|---|---|---|
| 4.301 | | * | | V.4 | 474 [M + H]⁺ | 1.28 (G) |

(4-1)

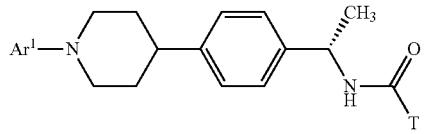

| Ex. | Ar¹ | T | E 1 | E 2 | ESI-MS [m/z] | $R_t$ (HPLC) [min] (method) |
|---|---|---|---|---|---|---|
| 4.302 | (thiophene-oxazolo-pyrimidine) | *—N(CH₃)CH₃ | (thiophene-oxazolo-pyrimidine-Cl) | V.3 | 477 [M + H]⁺ | 1.27 (G) |
| 4.303 | (5-cyclopropyl-pyrimidin-2-yl) | *-cyclopropyl | (5-cyclopropyl-2-Cl-pyrimidine) | V.4 | 391 [M + H]⁺ | 1.33 (G) |
| 4.304 | (5-cyclopropyl-pyrimidin-2-yl) | *—N(CH₃)CH₃ | (5-cyclopropyl-2-Cl-pyrimidine) | V.3 | 394 [M + H]⁺ | 1.31 (G) |
| 4.305 | (5-ethoxy-pyrimidin-2-yl, H₃C-CH₂-O-) | *-cyclopropyl | (5-ethoxy-2-Cl-pyrimidine) | V.4 | 409 [M + H]⁺ | 1.36 (G) |
| 4.306 | (5-ethoxy-pyrimidin-2-yl) | *—N(CH₃)CH₃ | (5-ethoxy-2-Cl-pyrimidine) | V.3 | 412 [M + H]⁺ | 1.34 (G) |

Example 5

Example 5.1

(S)—N-{1-[4-(5'-Ethoxy-3,4,5,6-tetrahydro-2H-[1,2']bipyridinyl-4-yl)-phenyl]-ethyl}-acetamide

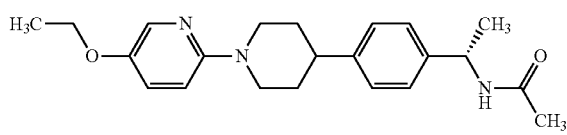 [SMILES: CCOc1ccc(N2CCC(c3ccc([C@H](C)NC(C)=O)cc3)CC2)nc1]

250 mg (1.24 mmol) 2-Bromo-5-ethoxy-pyridine are added to 250 mg (1.02 mmol) (S)-N-[1-(4-piperidin-4-yl-phenyl)-ethyl]-acetamide (V.1). The mixture is heated at 180° C. for 1 h. Subsequently the residue is taken up in DMF/methanol and the mixture is purified using reversed phase HPLC (column: Waters XBridge 5 μM; eluent A: water+0.3% NH₄OH, eluent B: MeOH+0.3% NH₄OH) to yield the desired product.

$C_{22}H_{29}N_3O_2$ (M=367.5 g/mol), ESI-MS: 368 [M+H]⁺
$R_t$ (HPLC): 2.20 min (method A)

The following compounds of general formula (5-1) are prepared analogously to Example 5.1, the educts used being shown in the column headed "E 1" and "E 2". For the preparation of compounds 5.5 to 5.35 and 5.38 to 5.56 DIPEA (3.0 equiv.) is added and NMP is used as solvent and the reaction mixture is stirred at 130° C. over night. For the preparation of compound 5.36 and 5.37 potassium cabonate (2.0 equiv.) is used as a base and acetone is used as solvent and the reaction mixture is stirred for 2 h at 0° C.

(5-1)

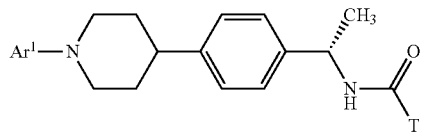

| Example | Ar¹ | T | E 1 | E 2 | ESI-MS [m/z] | $R_t$ (HPLC) [min] method |
|---|---|---|---|---|---|---|
| 5.1 | 5-ethoxypyridin-2-yl | *—CH₃ | 5-ethoxy-6-bromopyridin-3-yl | V.1 | 368 [M + H]⁺ | 2.20 (A) |
| 5.2 | 5-methoxypyridin-2-yl | *—CH₃ | 5-methoxy-6-bromopyridin-3-yl | V.1 | 354 [M + H]⁺ | 2.10 (A) |
| 5.3 | 5-propoxypyridin-2-yl | *—CH₃ | 5-propoxy-6-bromopyridin-3-yl | V.1 | 382 [M + H]⁺ | 2.30 (A) |
| 5.4 | 5-isobutoxypyridin-2-yl | *—CH₃ | 5-isobutoxy-6-bromopyridin-3-yl | V.1 | 396 [M + H]⁺ | 2.40 (A) |
| 5.5 | 2-(thiophen-3-yl)oxazolo[5,4-d]pyrimidin-5-yl | *—CH₃ | 5-chloro-2-(thiophen-3-yl)oxazolo[5,4-d]pyrimidine | V.1 | 448 [M + H]⁺ | 0.58 (V) |
| 5.6 | 2-(5-methylthiophen-2-yl)oxazolo[5,4-d]pyrimidin-5-yl | *—CH₃ | 5-chloro-2-(5-methylthiophen-2-yl)oxazolo[5,4-d]pyrimidine | V.1 | 462 [M + H]⁺ | 0.62 (V) |
| 5.7 | 2-(thiophen-2-yl)oxazolo[5,4-d]pyrimidin-5-yl | *—CH₃ | 5-chloro-2-(thiophen-2-yl)oxazolo[5,4-d]pyrimidine | V.1 | 448 [M + H]⁺ | 2.21 (W) |
| 5.8 | 6-(1-methanesulfonylcyclopropyl)pyridin-3-yl | *—CH₃ | 2-chloro-5-(1-methanesulfonylcyclopropyl)pyridine | V.1 | 442 [M + H]⁺ | 0.32 (V) |

(5-1)

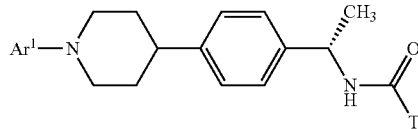

| Example | Ar¹ | T | E 1 | E 2 | ESI-MS [m/z] | R$_t$ (HPLC) [min] method |
|---|---|---|---|---|---|---|
| 5.9 | 2-methyl-thiazole-4-carboxylic acid methylamide | *—CH$_3$ | 2-chloro-thiazole-4-carboxylic acid methylamide | V.1 | 387 [M + H]$^+$ | 0.41 (V) |
| 5.10 | pyrimido-oxazole-pyridyl | *—CH$_3$ | 5-chloro-pyrimido-oxazole-pyridyl | V.1 | 443 [M + H]$^+$ | 1.95 (W) |
| 5.11 | 3-fluoro-4-trifluoromethyl-pyridyl | *—CH$_3$ | 2-chloro-3-fluoro-4-trifluoromethyl-pyridyl | V.1 | 410 [M + H]$^+$ | 0.61 (V) |
| 5.12 | 5-iodo-pyridyl | *—CH$_3$ | 2-chloro-5-iodo-pyridyl | V.1 | 450 [M + H]$^+$ | 0.4 (V) |
| 5.13 | 4-chloro-pyridyl | *—CH$_3$ | 2,4-dichloro-pyridyl | V.1 | 358 [M + H]$^+$ | 1.7 (W) |
| 5.14 | 4-cyano-pyrimidyl | *—CH$_3$ | 2-chloro-4-cyano-pyrimidyl | V.1 | 350 [M + H]$^+$ | 0.52 (V) |
| 5.15 | 5-cyano-2-trifluoromethyl-pyridyl-3-carboxylic acid ethyl ester | *—CH$_3$ | 6-chloro-5-cyano-2-trifluoromethyl-pyridyl-3-carboxylic acid ethyl ester | V.1 | 489 [M + H]$^+$ | 0.61 (V) |
| 5.16 | 3-chloro-5-trifluoromethyl-pyridyl | *—CH$_3$ | 2,3-dichloro-5-trifluoromethyl-pyridyl | V.1 | 426 [M + H]$^+$ | 2.14 (W) |

-continued

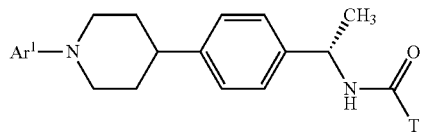
(5-1)

| Example | Ar¹ | T | E 1 | E 2 | ESI-MS [m/z] | R_t (HPLC) [min] method |
|---|---|---|---|---|---|---|
| 5.17 | 4-iodo-pyridin-2-yl | *—CH₃ | 4-iodo-6-chloro-pyridin-2-yl | V.1 | 450 [M + H]⁺ | 1.99 (W) |
| 5.18 | 4-bromo-pyridin-2-yl | *—CH₃ | 4-bromo-6-chloro-pyridin-2-yl | V.1 | 402 [M + H]⁺ | 0.36 (V) |
| 5.19 | 6-cyano-pyridin-2-yl | *—CH₃ | 6-cyano-2-chloro-pyridin-6-yl | V.1 | 349 [M + H]⁺ | 0.52 (V) |
| 5.20 | 4-phenyl-thiazol-2-yl | *—CH₃ | 4-phenyl-2-chloro-thiazol-5-yl | V.1 | 406 [M + H]⁺ | 1.88 (W) |
| 5.21 | 5-(cyclopropylcarbonyl)-pyridin-2-yl | *—CH₃ | 5-(cyclopropylcarbonyl)-6-chloro-pyridin-2-yl | V.1 | 392 [M + H]⁺ | 0.36 (V) |
| 5.22 | 4-methyl-thiazol-2-yl | *—CH₃ | 4-methyl-2-chloro-thiazol-5-yl | V.1 | 344 [M + H]⁺ | 0.32 (V) |
| 5.23 | 3-bromo-2-methyl-pyridin-6-yl | *—CH₃ | 3-bromo-2-methyl-6-chloro-pyridin | V.1 | 416 [M + H]⁺ | 0.42 (V) |
| 5.24 | 6-methoxy-quinolin-2-yl | *—CH₃ | 6-methoxy-2-chloro-quinolin | V.1 | 404 [M + H]⁺ | 0.37 (V) |
| 5.25 | 2-(benzimidazol-2-yl)-pyridin-6-yl | *—CH₃ | 2-(benzimidazol-2-yl)-6-chloro-pyridin | V.1 | 440 [M + H]⁺ | 0.37 (V) |

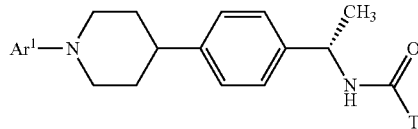

(5-1)

| Example | Ar¹ | T | E 1 | E 2 | ESI-MS [m/z] | R_t (HPLC) [min] method |
|---|---|---|---|---|---|---|
| 5.26 | 2-methylpyrimidin-4-yl | *—CH₃ | 4-chloro-2-methylpyrimidine | V.1 | 339 [M + H]⁺ | 1.67 (W) |
| 5.27 | 7-oxo-6,7-dihydro-5H-cyclopenta[b]pyridin-2-yl | *—CH₃ | 2-chloro-7-oxo-6,7-dihydro-5H-cyclopenta[b]pyridine | V.1 | 378 [M + H]⁺ | 1.6 (W) |
| 5.28 | 4-cyanopyridin-2-yl | *—CH₃ | 2-chloro-4-cyanopyridine | V.1 | 349 [M + H]⁺ | 0.41 (V) |
| 5.29 | ethyl 3-methylpyridine-4-carboxylate-2-yl | *—CH₃ | ethyl 2-chloro-3-methylpyridine-4-carboxylate | V.1 | 410 [M + H]⁺ | 1.93 (W) |
| 5.30 | 5-(phenylcarbamoyl)pyridin-2-yl | *—CH₃ | 6-chloro-N-phenylnicotinamide | V.1 | 443 [M + H]⁺ | 1.73 (W) |
| 5.31 | 7-chloroquinolin-2-yl | *—CH₃ | 2,7-dichloroquinoline | V.1 | 408 [M + H]⁺ | 2.07 (W) |
| 5.32 | 5-chloroquinolin-2-yl | *—CH₃ | 2,5-dichloroquinoline | V.1 | 408 [M + H]⁺ | 2.12 (W) |
| 5.33 | 5-phenyl-1,3,4-thiadiazol-2-yl | *—CH₃ | 2-chloro-5-phenyl-1,3,4-thiadiazole | V.1 | 407 [M + H]⁺ | 1.84 (W) |

-continued (5-1)

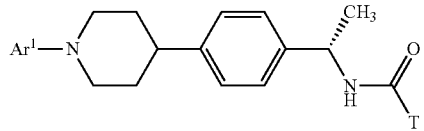

| Example | Ar¹ | T | E 1 | E 2 | ESI-MS [m/z] | R_t (HPLC) [min] method |
|---|---|---|---|---|---|---|
| 5.34 | 5-(1,1-difluoroethyl)pyridin-2-yl | *—CH₃ | 6-chloro-5-(1,1-difluoroethyl)pyridin-3-yl | V.1 | 388 [M + H]⁺ | 1.91 (W) |
| 5.35 | 1-(pyridin-3-yl)cyclopropanecarbonitrile | *—CH₃ | 1-(6-chloropyridin-3-yl)cyclopropanecarbonitrile | V.1 | 389 [M + H]⁺ | 0.33 (V) |
| 5.36 | 2-chloro-5-fluoropyrimidin-4-yl | *-cyclopropyl | 2,4-dichloro-5-fluoropyrimidine | V.4 | 403 [M + H]⁺ | 2.42 (S) |
| 5.37 | 6-chloro-5-fluoropyrimidin-4-yl | *-cyclopropyl | 4,6-dichloro-5-fluoropyrimidine | V.4 | 403 [M + H]⁺ | 2.65 (S) |
| 5.38 | 5-bromo-3-fluoropyridin-2-yl | *—CH₃ | 5-bromo-2-fluoro-3-fluoropyridine | V.1 | 420 [M + H]⁺ | 2.20 (B) |
| 5.39 | 4-iodo-3-methylpyridin-2-yl | *—CH₃ | 2-chloro-4-iodo-3-methylpyridine | V.1 | 464 [M + H]⁺ | 2.28 (R) |
| 5.40 | 2-chloro-3-methylpyridin-4-yl | *—CH₃ | 2-chloro-4-iodo-3-methylpyridine | V.1 | 372 [M + H]⁺ | 2.61 (R) |
| 5.41 | 4-methylpyridin-2-yl | *—CH₃ | 2-chloro-4-methylpyridine | V.1 | 338 [M + H]⁺ | 1.40 (P) |

-continued

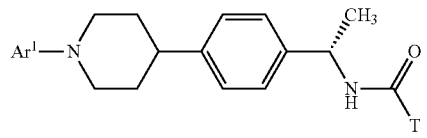

(5-1)

| Example | Ar¹ | T | E 1 | E 2 | ESI-MS [m/z] | R_t (HPLC) [min] method |
|---|---|---|---|---|---|---|
| 5.42 | 6-methylpyridin-2-yl | *—CH₃ | 6-methylpyridin-2-yl (with Cl) | V.1 | 338 [M + H]⁺ | 1.35 (P) |
| 5.43 | 6-methoxypyridin-2-yl | *—CH₃ | 6-methoxypyridin-2-yl (with Cl) | V.1 | 354 [M + H]⁺ | 2.10 (P) |
| 5.44 | 5-(4-chlorophenyl)-6-methylpyridin-2-yl | *—CH₃ | 5-(4-chlorophenyl)-6-chloropyridin-2-yl | V.1 | 434 [M + H]⁺ | 1.79 (P) |
| 5.45 | 5-((4-methylpiperidin-1-yl)methyl)pyridin-2-yl | *—CH₃ | 5-((4-methylpiperidin-1-yl)methyl)-6-chloropyridin-2-yl | V.1 | 435 [M + H]⁺ | 1.26 (P) |
| 5.46 | 5-methylpyridin-2-yl | *—CH₃ | 5-methyl-2-chloropyridin-2-yl | V.1 | 338 [M + H]⁺ | 1.39 (P) |
| 5.47 | 4-ethoxypyridin-2-yl | *—CH₃ | 4-ethoxy-2-chloropyridin-2-yl | V.1 | 368 [M + H]⁺ | 1.50 (P) |
| 5.48 | 4-propoxypyridin-2-yl | *—CH₃ | 4-propoxy-2-chloropyridin-2-yl | V.1 | 382 [M + H]⁺ | 1.60 (P) |
| 5.49 | 3-methylpyridin-2-yl | *—CH₃ | 3-methyl-2-chloropyridin-2-yl | V.1 | 338 [M + H]⁺ | 1.42 (P) |
| 5.50 | 4-chloro-5-phenylpyrimidin-2-yl | *—CH₃ | 4-chloro-5-phenyl-2-chloropyrimidin-2-yl | V.1 | 435 [M + H]⁺ | 2.49 (P) |

-continued

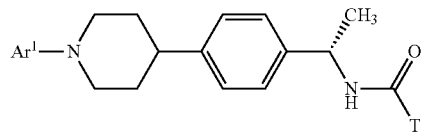
(5-1)

| Example | Ar¹ | T | E 1 | E 2 | ESI-MS [m/z] | R_t (HPLC) [min] method |
|---|---|---|---|---|---|---|
| 5.51 | 5-methyl-2-fluoropyridin-4-yl | *—CH₃ | 5-methyl-2-fluoro-4-iodopyridine | V.1 | 356 [M + H]⁺ | 2.53 (R) |
| 5.52 | 3-cyanopyrazin-2-yl | *—CH₃ | 3-cyano-2-chloropyrazine | V.1 | 325 [M + H]⁺ | 1.86 (U) |
| 5.53 | methyl 5-pyrazinecarboxylate | *—CH₃ | methyl 5-chloropyrazine-2-carboxylate | V.1 | 383 [M + H]⁺ | 1.84 (U) |
| 5.54 | methyl pyrazine-2-carboxylate | *—CH₃ | methyl 6-chloropyrazine-2-carboxylate | V.1 | 383 [M + H]⁺ | 1.83 (U) |
| 5.55 | ethyl pyridazinecarboxylate | *—CH₃ | ethyl 6-chloropyridazine-4-carboxylate | V.1 | 397 [M + H]⁺ | 1.51 (U) |
| 5.56 | 6-methylbenzothiazol-2-yl | *—CH₃ | 2-chloro-6-methylbenzothiazole | V.1 | 394 [M + H]⁺ | 1.76 (U) |
| 5.57 | 5-propoxypyridin-2-yl | *-cyclopropyl | 2-bromo-5-propoxypyridine | V.4 | 408 [M + H]⁺ | 1.21 (G) |
| 5.58 | 5-ethoxypyridin-2-yl | *-cyclopropyl | 2-bromo-5-ethoxypyridine | V.4 | 394 [M + H]⁺ | 1.14 (G) |

Example 5.200

(S)—N-(1-{4-[1-(6-Chloro-2-pyrrolidin-1-yl-pyrimidin-4-yl)-piperidin-4-yl]-phenyl}-ethyl)-acetamide

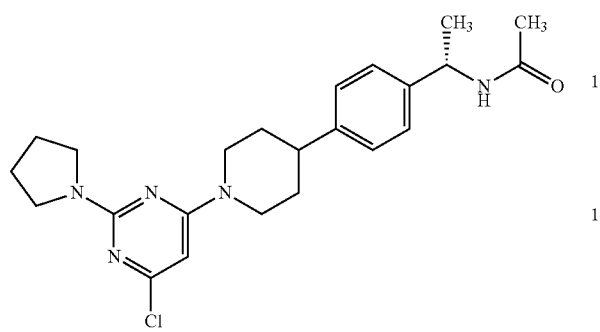

To 22 mg (0.1 mmol) 4,6-dichloro-2-pyrrolidin-1-yl-pyrimidine in 1 mL THF are added 17 μL (0.1 mol) DIPEA and 25 mg (0.1 mmol) (S)—N-[1-(4-piperidin-4-yl-phenyl)ethyl]-acetamide (V.1). The mixture is stirred at rt over night. The solvent is removed in vacuo and the residue is purified using reversed phase HPLC (eluent A: water+0.1% TFA, eluent B: MeOH) to yield the desired product.

$C_{23}H_{30}ClN_5O$ (M=427.97 g/mol), ESI-MS: 428 [M+H]$^+$
$R_t$ (HPLC): 1.91 min (method T)

The following compounds of general formula (5-2) are prepared analogously to Example 5.200, the educts used being shown in the column headed "E 1" and "E 2".

Example 6

Example 6.1

(S)-2-Cyano-N-(1-{4-[1-(4-ethoxy-phenyl)-piperidin-4-yl]-phenyl}-ethyl)-acetamide

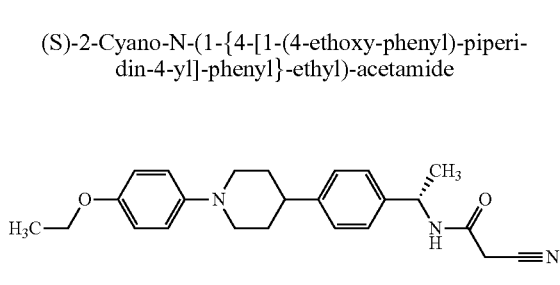

To 7.0 mg (0.08 mmol) cyanoacetic acid in 1 mL DMF 35 μL (0.20 mmol) DIPEA and 29 mg (0.08 mmol) TBTU are added and the mixture is stirred for 10 min at rt. Subsequently 29 mg (0.09 mmol) (S)-1-{4-[1-(4-ethoxy-phenyl)-piperidin-4-yl]-phenyl}-ethylamine (XIII.1) in 1 mL DMF are added and stirring is continued over night. The mixture is filtered through basic aluminum oxide, followed by washing with DMF/MeOH (9:1) and concentration in vacuo. The residue is purified using reversed phase column chromatography (water/MeOH, 0.1% TFA) and the corresponding fractions are concentrated to yield the desired product.

$C_{10}H_{11}NO$ (M=391.5 g/mol), ESI-MS: 392 [M+H]$^+$
$R_t$ (HPLC): 1.18 min (method B)

The following compounds of general formula (6-1) are prepared analogously to Example 6.1, the educts used being shown in the column headed "E 1" and "E 2":

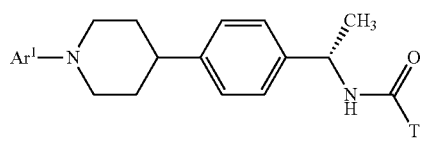

(5-2)

| Example | Ar$^1$ | T | E 1 | E 2 | ESI-MS [m/z] | R$_t$ (HPLC) [min] method |
|---|---|---|---|---|---|---|
| 5.200 | pyrrolidin-1-yl-pyrimidine with Cl | *—CH$_3$ | 4,6-dichloro-2-pyrrolidin-1-yl-pyrimidine | V.1 | 428 [M + H]$^+$ | 1.91 (T) |
| 5.201 | piperidin-1-yl-pyrimidine with CF$_3$ | *—CH$_3$ | 4-chloro-2-piperidin-1-yl-5-trifluoromethyl-pyrimidine | V.1 | 476 [M + H]$^+$ | 1.91 (T) |

(6-1)

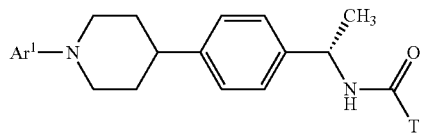

| Ex. | Ar¹ | T | E 1 | E 2 | ESI-MS [m/z] | $R_t$ (HPLC) [min] method |
|---|---|---|---|---|---|---|
| 6.1 | H₃C-O-C₆H₄-* | *-CH₂-CN | XIII.1 | HOOC-CH₂-CN | 392 [M + H]⁺ | 1.18 (B) |
| 6.2 | H₃C-O-C₆H₄-* | 4-pyrrolidin-2-one-yl | XIII.1 | 5-oxopyrrolidine-3-carboxylic acid | 354 [M + H]⁺ | 2.10 (B) |
| 6.3 | H₃C-O-C₆H₄-* | 4-tetrahydrofuran-2-one-yl | XIII.1 | tetrahydrofuran-3-carboxylic acid | 423 [M + H]⁺ | 1.23 (B) |
| 6.4 | H₃C-O-C₆H₄-* | furan-2-yl | XIII.1 | furan-2-carboxylic acid | 419 [M + H]⁺ | 1.28 (B) |
| 6.5 | H₃C-O-C₆H₄-* | *-CH(CH₃)₂ | XIII.1 | isobutyric acid | 495 [M + H]⁺ | 1.30 (B) |
| 6.6 | H₃C-O-C₆H₄-* | *-CH₂CH₂CH₃ | XIII.1 | butyric acid | 495 [M + H]⁺ | 1.30 (B) |
| 6.7 | H₃C-O-C₆H₄-* | *-cyclobutyl | XIII.1 | cyclobutanecarboxylic acid | 407 [M + H]⁺ | 1.33 (B) |
| 6.8 | H₃C-O-C₆H₄-* | *-CH₂CH₃ | XIII.1 | propionic acid | 381 [M + H]⁺ | 1.25 (B) |
| 6.9 | H₃C-O-C₆H₄-* | *-1-methylcyclopropyl | XIII.1 | 1-methylcyclopropanecarboxylic acid | 407 [M + H]⁺ | 1.33 (B) |

-continued (6-1)

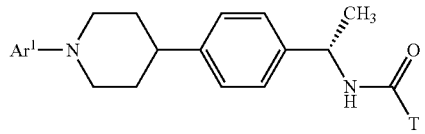

| Ex. | Ar¹ | T | E 1 | E 2 | ESI-MS [m/z] | R_t (HPLC) [min] method |
|---|---|---|---|---|---|---|
| 6.10 | H₃C-O-C₆H₄-* | 1H-pyrazol-4-yl | XIII.1 | 1H-pyrazole-4-carboxylic acid | 419 [M + H]⁺ | 1.20 (B) |
| 6.11 | H₃C-O-C₆H₄-* | thiazol-5-yl | XIII.1 | thiazole-5-carboxylic acid | 436 [M + H]⁺ | 1.27 (B) |
| 6.12 | H₃C-O-C₆H₄-* | isoxazol-5-yl | XIII.1 | isoxazole-5-carboxylic acid | 420 [M + H]⁺ | 0.39 (V) |
| 6.13 | H₃C-O-C₆H₄-* | cyclopropylmethyl | XIII.1 | cyclopropylacetic acid | 407 [M + H]⁺ | 0.58 (Y) |
| 6.14 | H₃C-O-C₆H₄-* | FCH₂-* | XIII.1 | fluoroacetic acid | 385 [M + H]⁺ | 0.55 (Y) |
| 6.15 | H₃C-O-C₆H₄-* | CH₃OCH₂-* | XIII.1 | methoxyacetic acid | 397 [M + H]⁺ | 0.55 (Y) |
| 6.16 | H₃C-O-C₆H₄-* | CH₂=CHCH₂-* | XIII.1 | but-3-enoic acid | 393 [M + H]⁺ | 0.57 (Y) |
| 6.17 | H₃C-O-C₆H₄-* | H₃CCH₂OCH₂-* | XIII.1 | ethoxyacetic acid | 411 [M + H]⁺ | 0.58 (Y) |
| 6.18 | H₃C-O-C₆H₄-* | 2-methylcyclopropyl | XIII.1 | 2-methylcyclopropanecarboxylic acid | 407 [M + H]⁺ | 0.59 (Y) |
| 6.19 | H₃C-O-C₆H₄-* | pyridazin-4-yl | XIII.1 | pyridazine-4-carboxylic acid | 431 [M + H]⁺ | 0.52 (Y) |

-continued

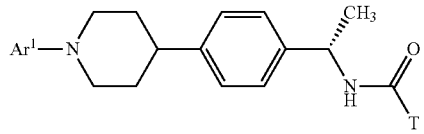
(6-1)

| Ex. | Ar¹ | T | E 1 | E 2 | ESI-MS [m/z] | R$_t$ (HPLC) [min] method |
|---|---|---|---|---|---|---|
| 6.20 | H₃C-O-C₆H₄-* (4-ethoxyphenyl) | 1-cyanocyclopropyl | XIII.1 | 1-cyanocyclopropane-1-carboxylic acid | 418 [M + H]⁺ | 0.59 (Y) |
| 6.21 | H₃C-O-C₆H₄-* | benzyl | XIII.1 | phenylacetic acid | 443 [M + H]⁺ | 0.6 (Y) |
| 6.22 | H₃C-O-C₆H₄-* | 1H-pyrrol-2-yl | XIII.1 | 1H-pyrrole-2-carboxylic acid | 418 [M + H]⁺ | 0.57 (Y) |
| 6.23 | H₃C-O-C₆H₄-* | 2,2-difluorocyclopropyl | XIII.1 | 2,2-difluorocyclopropane-1-carboxylic acid | 429 [M + H]⁺ | 0.58 (Y) |
| 6.24 | H₃C-O-C₆H₄-* | 1H-imidazol-5-yl | XIII.1 | 1H-imidazole-5-carboxylic acid | 419 [M + H]⁺ | 0.5 (Y) |
| 6.25 | H₃C-O-C₆H₄-* | oxazol-5-yl | XIII.1 | oxazole-5-carboxylic acid | 420 [M + H]⁺ | 0.53 (Y) |
| 6.26 | H₃C-O-C₆H₄-* | isothiazol-5-yl | XIII.1 | isothiazole-5-carboxylic acid | 436 [M + H]⁺ | 0.58 (Y) |
| 6.27 | H₃C-O-C₆H₄-* | 3-methyloxetan-3-yl | XIII.1 | 3-methyloxetane-3-carboxylic acid | 423 [M + H]⁺ | 0.54 (Y) |
| 6.28 | H₃C-O-C₆H₄-* | (1H-imidazol-1-yl)methyl | XIII.1 | 2-(1H-imidazol-1-yl)acetic acid | 433 [M + H]⁺ | 0.5 (Y) |

-continued (6-1)
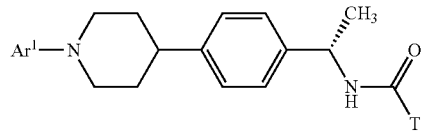

| Ex. | Ar¹ | T | E 1 | E 2 | ESI-MS [m/z] | R$_t$ (HPLC) [min] method |
|---|---|---|---|---|---|---|
| 6.29 | H₃C-O-C₆H₄-* | 1H-pyrazol-3-yl | XIII.1 | 1H-pyrazole-3-carboxylic acid | 419 [M + H]⁺ | 0.52 (Y) |
| 6.30 | H₃C-O-C₆H₄-* | CH₃OCH₂CH₂-* | XIII.1 | 3-methoxypropanoic acid | 411 [M + H]⁺ | 0.54 (Y) |
| 6.31 | H₃C-O-C₆H₄-* | pyridin-3-yl | XIII.1 | nicotinic acid | 430 [M + H]⁺ | 0.54 (Y) |
| 6.32 | H₃C-O-C₆H₄-* | pyridin-3-ylmethyl | XIII.1 | 2-(pyridin-3-yl)acetic acid | 444 [M + H]⁺ | 0.53 (Y) |
| 6.33 | H₃C-O-C₆H₄-* | thiazol-2-yl | XIII.1 | thiazole-2-carboxylic acid | 436 [M + H]⁺ | 0.61 (Y) |
| 6.34 | H₃C-O-C₆H₄-* | 1-(trifluoromethyl)cyclopropyl | XIII.1 | 1-(trifluoromethyl)cyclopropane-1-carboxylic acid | 461 [M + H]⁺ | 0.63 (Y) |
| 6.35 | H₃C-O-C₆H₄-* | 1H-imidazol-2-yl | XIII.1 | 1H-imidazole-2-carboxylic acid | 419 [M + H]⁺ | 0.54 (Y) |
| 6.36 | H₃C-O-C₆H₄-* | 1,2,5-oxadiazol-3-yl | XIII.1 | 1,2,5-oxadiazole-3-carboxylic acid | 421 [M + H]⁺ | 0.33 (Y) |
| 6.37 | H₃C-O-C₆H₄-* | 3-methoxycyclobutyl | XIII.1 | 3-methoxycyclobutane-1-carboxylic acid | 437 [M + H]⁺ | 0.56 (Y) |
| 6.38 | H₃C-O-C₆H₄-* | 3-fluorocyclobutyl | XIII.1 | 3-fluorocyclobutane-1-carboxylic acid | 425 [M + H]⁺ | 0.58 (Y) |

-continued

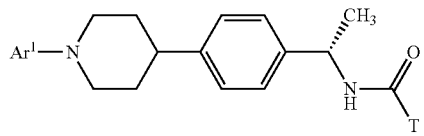

(6-1)

| Ex. | Ar¹ | T | E 1 | E 2 | ESI-MS [m/z] | $R_t$ (HPLC) [min] method |
|---|---|---|---|---|---|---|
| 6.39 | H₃C-O-C₆H₄-* | N≡C-CH₂-* | XIII.1 | HOOC-CH₂-CH(CN)- | 406 [M + H]⁺ | 0.53 (Y) |
| 6.40 | H₃C-O-C₆H₄-* | 4-pyridyl-* | XIII.1 | isonicotinic acid | 430 [M + H]⁺ | 0.54 (Y) |
| 6.41 | H₃C-O-C₆H₄-* | 1H-1,2,4-triazol-5-yl-* | XIII.1 | 1H-1,2,4-triazole-3-carboxylic acid | 420 [M + H]⁺ | 0.33 (Y) |
| 6.42 | H₃C-O-C₆H₄-* | pyrimidin-5-yl-* | XIII.1 | pyrimidine-5-carboxylic acid | 431 [M + H]⁺ | 0.53 (Y) |
| 6.43 | H₃C-O-C₆H₄-* | H₃C-O-N=CH-* | XIII.1 | H₃C-O-N=CH-COOH | 410 [M + H]⁺ | 0.58 (Y) |
| 6.44 | H₃C-O-C₆H₄-* | (H₃C)₂C(OCH₃)-* | XIII.1 | HOOC-C(CH₃)₂-OCH₃ | 425 [M + H]⁺ | 0.61 (Y) |
| 6.45 | H₃C-O-C₆H₄-* | 1-methylcyclobutyl-* | XIII.1 | 1-methylcyclobutane-1-carboxylic acid | 421 [M + H]⁺ | 0.61 (Y) |
| 6.46 | H₃C-O-C₆H₄-* | thiazol-4-yl-* | XIII.1 | thiazole-4-carboxylic acid | 436 [M + H]⁺ | 1.30 (B) |
| 6.47 | H₃C-O-C₆H₄-* | oxazol-4-yl-* | XIII.1 | oxazole-4-carboxylic acid | 420 [M + H]⁺ | 1.57 (P) |

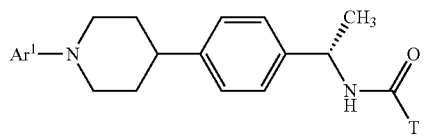

(6-1)

| Ex. | Ar¹ | T | E 1 | E 2 | ESI-MS [m/z] | $R_t$ (HPLC) [min] method |
|---|---|---|---|---|---|---|
| 6.48 |  |  | XIII.1 |  | 383 [M + H]⁺ | 1.15 (G) |
| 6.49 |  |  | XIII.1 |  | 482 [M + H]⁺ | 1.26 (G) |

Example 7

Example 7.1

(S)—N-[1-(4-{1-[4-(Tetrahydro-2H-pyran-4-yloxy)-phenyl]-piperidin-4-yl}-phenyl)-ethyl]-acetamide

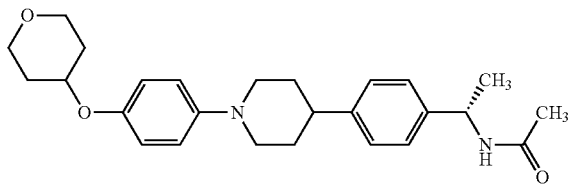 [SMILES: CC(=O)N[C@@H](C)c1ccc(C2CCN(c3ccc(OC4CCOCC4)cc3)CC2)cc1]

34 mg (0.10 mmol) (S)—N-{1-(4-[1-(4-Hydroxyphenyl)-piperidin-4-yl]-phenyl}-ethyl)-acetamide (compound 1.48), 15 mg (0.15 mmol) tetrahydro-4H-pyran-4-ol and 39 mg (0.15 mmol) triphenylphosphine on solid support are suspended in 2 mL anhydrous THF at 0° C. 35 mg (0.15 mmol) di-tert-Butyl azodicarboxylate are added and the mixture is allowed to warm to rt. Stirring is continued over night followed by addition of 0.5 equivalents of triphenylphosphine on solid support and 0.5 equivalents of di-tert-butyl azodicarboxylate. After stirring for 2 h at rt, the mixture is filtered over basic aluminum oxide and washed with DMF/MeOH (9:1). After evaporation the residue is purified using reversed phase HPLC (water/MeOH, 0.1% TFA) to yield the desired product.

$C_{26}H_{34}N_2O_3$ (M=422.5 g/mol), ESI-MS: 423 [M+H]⁺

$R_t$ (HPLC): 1.26 min (method B)

The following compounds of general formula (7-1) are prepared analogously to Example 7.1, the educts used being shown in the column headed "E 1" and "E 2":

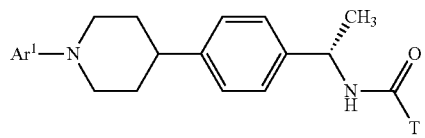

(7-1)

| Example | Ar¹ | T | E 1 | E 2 | ESI-MS [m/z] | $R_t$ (HPLC) [min] (method) |
|---|---|---|---|---|---|---|
| 7.1 |  | *—CH₃ | 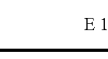 | 1.48 | 423 [M + H]⁺ | 1.26 (B) |

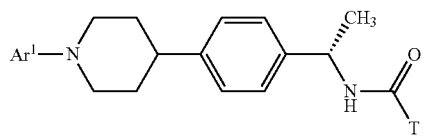

(7-1)

| Example | Ar¹ | T | E 1 | E 2 | ESI-MS [m/z] | $R_t$ (HPLC) [min] (method) |
|---|---|---|---|---|---|---|
| 7.2 | (tetrahydropyranyloxy-phenyl) | *—CH₃ | (tetrahydropyran) | 1.27 | 423 [M + H]⁺ | 1.56 (B) |

Example 8

Example 8.1

(S)—N-[1-(4-{1-[4-(Tetrahydro-2H-pyran-4-yloxy)-phenyl]-piperidin-4-yl}-phenyl)-ethyl]-acetamide

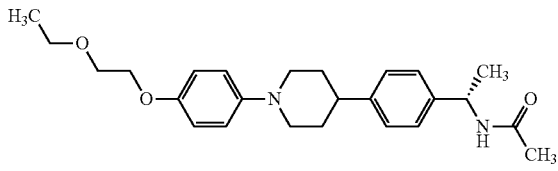

17 μL (0.15 mmol) 1-Bromo-2-ethoxy-ethane and 35 mg (0.25 mmol) K₂CO₃ are added to 34 mg (0.10 mmol) (S)-N-{1-(4-[1-(4-hydroxyphenyl)-piperidin-4-yl]-phenyl}-ethyl)-acetamide (compound 1.48) in 2 mL ACN. The mixture is stirred at 90° C. for 4 h followed by addition of 11 μL (0.10 mmol) 1-bromo-2-ethoxy-ethane. Stirring is continued at 90° C. over night. The solvent is removed in vacuo and the residue is purified using reversed phase HPLC (water/MeOH, 0.1% TFA) to yield the desired product.

$C_{10}H_{11}NO$ (M=410.5 g/mol), ESI-MS: 411 [M+H]⁺
$R_t$ (HPLC): 1.40 min (method B)

The following compounds of general formula (8-1) are prepared analogously to Example 8.1. For the examples 8.63-8.67 DMF is used as solvent and the reaction mixture is stirred at 60° C. over night. For example 8.67 the Boc protection group is afterwards removed by reaction with HCl (1.25 mol/L in MeOH). For Example 8.68 DMSO is used as solvent and the reaction mixture is stirred at 100° C. for 5 h. The educts used are shown in the column headed "E 1" and "E 2":

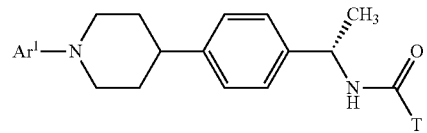

(8-1)

| Ex. | Ar¹ | T | E 1 | E 2 | ESI-MS [m/z] | $R_t$ (HPLC) [min] method |
|---|---|---|---|---|---|---|
| 8.1 | H₃C-O-CH₂CH₂-O-(phenyl)-* | *—CH₃ | H₃C-O-CH₂CH₂-Br | 1.48 | 411 [M + H]⁺ | 1.40 (B) |

-continued

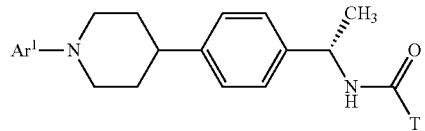
(8-1)

| Ex. | Ar¹ | T | E 1 | E 2 | ESI-MS [m/z] | R$_t$ (HPLC) [min] method |
|---|---|---|---|---|---|---|
| 8.2 | H₃C−O−CH₂CH₂−O−(3-phenyl)−* | *—CH₃ | H₃C−O−CH₂CH₂−Br | 1.27 | 411 [M + H]⁺ | 1.51 (B) |
| 8.3 | cyclopropyl-CH₂−O−(3-phenyl)−* | *—CH₃ | cyclopropyl-CH₂−Br | 1.27 | 393 [M + H]⁺ | 1.74 (B) |
| 8.4 | (CH₃)₂CHCH₂−O−(3-phenyl)−* | *—CH₃ | (CH₃)₂CHCH₂−I | 1.27 | 395 [M + H]⁺ | 1.81 (B) |
| 8.5 | cyclopentyl-O−(3-phenyl)−* | *—CH₃ | cyclopentyl-I | 1.27 | 407 [M + H]⁺ | 1.79 (B) |
| 8.6 | H₃C(CH₂)₃−O−(3-phenyl)−* | *—CH₃ | H₃C(CH₂)₃−Br | 1.27 | 395 [M + H]⁺ | 1.68 (B) |
| 8.7 | (CH₃)₂CH−O−(3-phenyl)−* | *—CH₃ | (CH₃)₂CH−Cl | 1.27 | 381 [M + H]⁺ | 2.30 (B) |
| 8.8 | H₃CCH₂CH₂−O−(pyrazin-2,5-diyl)−* | *—CH₃ | H₃CCH₂CH₂−Br | 1.49 | 383 [M + H]⁺ | 2.18 (A) |

-continued (8-1)

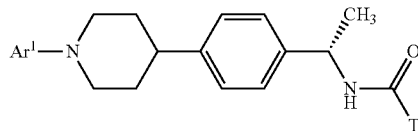

| Ex. | Ar¹ | T | E 1 | E 2 | ESI-MS [m/z] | R_t (HPLC) [min] method |
|---|---|---|---|---|---|---|
| 8.9 | oxetan-3-yloxy-phenyl- | *—CH₃ | oxetan-3-yl OTs | 1.49 | 395 [M + H]⁺ | 1.94 (A) |
| 8.10 | ethyl 1-(4-phenoxy)cyclobutanecarboxylate | *—CH₃ | ethyl 3-bromooxetane-3-carboxylate | 1.49 | 465 [M + H]⁺ | 2.20 (A) |
| 8.11 | 4-cyclobutoxy-3-methylphenyl- | *—CH₃ | cyclobutyl bromide | XX.1 | 407 [M + H]⁺ | 1.31 (B) |
| 8.12 | 4-cyclobutoxy-3-cyanophenyl- | *—CH₃ | cyclobutyl bromide | XX.2 | 418 [M + H]⁺ | 1.54 (B) |
| 8.13 | 4-cyclobutoxy-3-fluorophenyl- | *—CH₃ | cyclobutyl bromide | XX.3 | 411 [M + H]⁺ | 1.37 (B) |
| 8.14 | 4-cyclobutoxy-3-chlorophenyl- | *—CH₃ | cyclobutyl bromide | XX.4 | 427 [M + H]⁺ | 1.46 (B) |
| 8.15 | 4-ethoxy-3-methylphenyl- | *—CH₃ | H₃C—CH₂Br | XX.1 | 381 [M + H]⁺ | 1.2 (B) |

-continued (8-1)

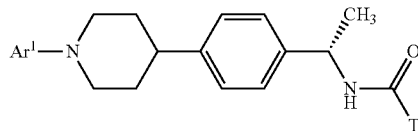

| Ex. | Ar¹ | T | E 1 | E 2 | ESI-MS [m/z] | R$_t$ (HPLC) [min] method |
|---|---|---|---|---|---|---|
| 8.16 | H₃C—O—(2-CN,5-*)-phenyl (ethoxy, CN) | *—CH₃ | H₃C—CH₂—Br | XX.2 | 392 [M + H]⁺ | 1.35 (B) |
| 8.17 | H₃C—O—(2-F,4-*)-phenyl (ethoxy, F) | *—CH₃ | H₃C—CH₂—Br | XX.3 | 385 [M + H]⁺ | 1.21 (B) |
| 8.18 | H₃C—O—(2-OMe,4-*)-phenyl | *—CH₃ | H₃C—CH₂—Br | XX.5 | 397 [M + H]⁺ | 1.06 (B) |
| 8.19 | H₃C—O—CH₂CH₂—O—(2-Me,4-*)-phenyl | *—CH₃ | Cl—CH₂CH₂—O—CH₃ | XX.1 | 411 [M + H]⁺ | 1.1 (B) |
| 8.20 | H₃C—O—CH₂CH₂—O—(2-CN,5-*)-phenyl | *—CH₃ | Cl—CH₂CH₂—O—CH₃ | XX.2 | 422 [M + H]⁺ | 1.26 (B) |
| 8.21 | H₃C—O—CH₂CH₂—O—(2-F,4-*)-phenyl | *—CH₃ | Cl—CH₂CH₂—O—CH₃ | XX.3 | 415 [M + H]⁺ | 1.11 (B) |
| 8.22 | H₃C—O—CH₂CH₂—O—(2-OMe,4-*)-phenyl | *—CH₃ | Cl—CH₂CH₂—O—CH₃ | XX.5 | 427 [M + H]⁺ | 1.01 (B) |
| 8.23 | (CH₃)₂CH—O—(2-Me,4-*)-phenyl | *—CH₃ | Cl—CH(CH₃)₂ | XX.1 | 395 [M + H]⁺ | 1.26 (B) |

-continued

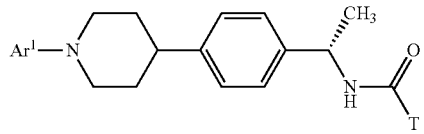

(8-1)

| Ex. | Ar¹ | T | E 1 | E 2 | ESI-MS [m/z] | R$_t$ (HPLC) [min] method |
|---|---|---|---|---|---|---|
| 8.24 | 3-cyano-4-isopropoxyphenyl | *—CH₃ | 2-chloropropane (isopropyl chloride) | XX.2 | 406 [M + H]⁺ | 1.44 (B) |
| 8.25 | 3-chloro-4-isopropoxyphenyl | *—CH₃ | 2-chloropropane (isopropyl chloride) | XX.4 | 415 [M + H]⁺ | 2.07 (W) |
| 8.26 | 4-isobutoxy-3-methylphenyl | *—CH₃ | 1-bromo-2-methylpropane | XX.1 | 409 [M + H]⁺ | 1.37 (B) |
| 8.27 | 3-cyano-4-isobutoxyphenyl | *—CH₃ | 1-bromo-2-methylpropane | XX.2 | 420 [M + H]⁺ | 1.61 (B) |
| 8.28 | 3-fluoro-4-isobutoxyphenyl | *—CH₃ | (S)-1-bromo-2-methylpropane | XX.3 | 413 [M + H]⁺ | 1.46 (B) |
| 8.29 | 4-isobutoxy-3-methoxyphenyl | *—CH₃ | 1-bromo-2-methylpropane | XX.5 | 425 [M + H]⁺ | 1.27 (B) |
| 8.30 | 3-chloro-4-isobutoxyphenyl | *—CH₃ | 1-bromo-2-methylpropane | XX.4 | 429 [M + H]⁺ | 1.55 (B) |

-continued (8-1)

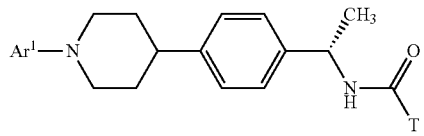

| Ex. | Ar¹ | T | E 1 | E 2 | ESI-MS [m/z] | R$_t$ (HPLC) [min] method |
|---|---|---|---|---|---|---|
| 8.31 | H₃C–O–(2-methyl-4-*)phenyl, propoxy | *–CH₃ | Cl–CH₂CH₂–CH₃ | XX.1 | 395 [M + H]⁺ | 1.29 (B) |
| 8.32 | H₃C–O–(2-cyano-4-*)phenyl, propoxy | *–CH₃ | Cl–CH₂CH₂–CH₃ | XX.2 | 406 [M + H]⁺ | 1.48 (B) |
| 8.33 | H₃C–O–(3-methoxy-4-*)phenyl, propoxy | *–CH₃ | Cl–CH₂CH₂–CH₃ | XX.5 | 411 [M + H]⁺ | 1.17 (B) |
| 8.34 | H₃C–O–(2-chloro-4-*)phenyl, propoxy | *–CH₃ | Cl–CH₂CH₂–CH₃ | XX.4 | 415 [M + H]⁺ | 1.44 (B) |
| 8.35 | cyclopentyl-O–(2-methyl-4-*)phenyl | *–CH₃ | cyclopentyl–Cl | XX.1 | 421 [M + H]⁺ | 1.38 (B) |
| 8.36 | cyclopentyl-O–(2-cyano-4-*)phenyl | *–CH₃ | cyclopentyl–Cl | XX.2 | 432 [M + H]⁺ | 1.6 (B) |
| 8.37 | cyclopentyl-O–(2-fluoro-4-*)phenyl | *–CH₃ | cyclopentyl–Cl | XX.3 | 425 [M + H]⁺ | 1.46 (B) |

-continued

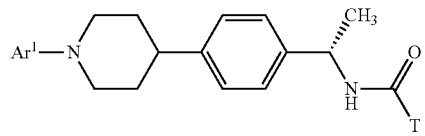
(8-1)

| Ex. | Ar¹ | T | E 1 | E 2 | ESI-MS [m/z] | R$_t$ (HPLC) [min] method |
|---|---|---|---|---|---|---|
| 8.38 | cyclopentyloxy, methoxyphenyl | *—CH₃ | chlorocyclopentane | XX.5 | 437 [M + H]⁺ | 1.26 (B) |
| 8.39 | cyclopentyloxy, chlorophenyl | *—CH₃ | chlorocyclopentane | XX.4 | 441 [M + H]⁺ | 1.55 (B) |
| 8.40 | propoxy, methylphenyl | *—CH₃ | 1-chlorobutane | XX.1 | 409 [M + H]⁺ | 1.38 (B) |
| 8.41 | propoxy, cyanophenyl | *—CH₃ | 1-chlorobutane | XX.2 | 420 [M + H]⁺ | 1.61 (B) |
| 8.42 | propoxy, fluorophenyl | *—CH₃ | 1-chlorobutane | XX.3 | 413 [M + H]⁺ | 1.46 (B) |
| 8.43 | propoxy, methoxyphenyl | *—CH₃ | 1-chlorobutane | XX.5 | 425 [M + H]⁺ | 1.27 (B) |
| 8.44 | propoxy, chlorophenyl | *—CH₃ | 1-chlorobutane | XX.4 | 429 [M + H]⁺ | 1.55 (B) |
| 8.45 | methoxy, cyanophenyl | *—CH₃ | CH₃I | XX.2 | 378 [M + H]⁺ | 1.23 (B) |

-continued (8-1)

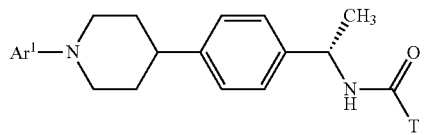

| Ex. | Ar¹ | T | E 1 | E 2 | ESI-MS [m/z] | R_t (HPLC) [min] method |
|---|---|---|---|---|---|---|
| 8.46 | 3-chloro-4-methoxyphenyl | *—CH₃ | H₃C—I | XX.4 | 387 [M + H]⁺ | 1.19 (B) |
| 8.47 | 3-methyl-4-(oxetan-2-ylmethoxy)phenyl | *—CH₃ | oxetan-2-ylmethyl bromide | XX.1 | 423 [M + H]⁺ | 1.08 (B) |
| 8.48 | 3-fluoro-4-(oxetan-2-ylmethoxy)phenyl | *—CH₃ | oxetan-2-ylmethyl bromide | XX.3 | 427 [M + H]⁺ | 1.11 (B) |
| 8.49 | 3-methoxy-4-(oxetan-2-ylmethoxy)phenyl | *—CH₃ | oxetan-2-ylmethyl bromide | XX.5 | 439 [M + H]⁺ | 1.01 (B) |
| 8.50 | 3-chloro-4-(oxetan-2-ylmethoxy)phenyl | *—CH₃ | oxetan-2-ylmethyl bromide | XX.4 | 443 [M + H]⁺ | 1.2 (B) |
| 8.51 | 4-(sec-butoxy)-3-methylphenyl | *—CH₃ | 2-bromobutane | XX.1 | 409 [M + H]⁺ | 1.34 (B) |
| 8.52 | 4-(sec-butoxy)-3-cyanophenyl | *—CH₃ | 2-bromobutane | XX.2 | 420 [M + H]⁺ | 1.55 (B) |

-continued

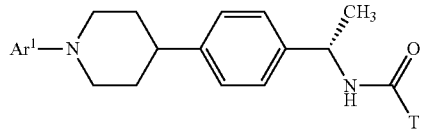
(8-1)

| Ex. | Ar¹ | T | E 1 | E 2 | ESI-MS [m/z] | R$_t$ (HPLC) [min] method |
|---|---|---|---|---|---|---|
| 8.53 | 4-(sec-butoxy)-3-fluorophenyl | *—CH₃ | 2-bromobutane | XX.3 | 413 [M + H]⁺ | 1.44 (B) |
| 8.54 | 4-(sec-butoxy)-3-methoxyphenyl | *—CH₃ | 2-bromobutane | XX.5 | 425 [M + H]⁺ | 1.23 (B) |
| 8.55 | 4-(sec-butoxy)-3-chlorophenyl | *—CH₃ | 2-bromobutane | XX.4 | 429 [M + H]⁺ | 1.51 (W) |
| 8.56 | 4-(pentan-2-yloxy)-3-methylphenyl | *—CH₃ | 2-bromopentane | XX.1 | 423 [M + H]⁺ | 1.42 (B) |
| 8.57 | 3-cyano-4-(pentan-2-yloxy)phenyl | *—CH₃ | 2-bromopentane | XX.2 | 434 [M + H]⁺ | 1.67 (B) |
| 8.58 | 3-fluoro-4-(pentan-2-yloxy)phenyl | *—CH₃ | 2-bromopentane | XX.3 | 427 [M + H]⁺ | 1.55 (B) |
| 8.59 | 3-methoxy-4-(pentan-2-yloxy)phenyl | *—CH₃ | 2-bromopentane | XX.5 | 439 [M + H]⁺ | 1.32 (B) |

-continued (8-1)

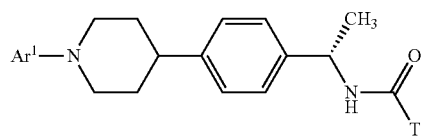

| Ex. | Ar¹ | T | E 1 | E 2 | ESI-MS [m/z] | R$_t$ (HPLC) [min] method |
|---|---|---|---|---|---|---|
| 8.60 | 2-chloro-4-[(pentan-2-yl)oxy]phenyl | *—CH₃ | 2-bromopentane | XX.4 | 443 [M + H]⁺ | 1.61 (B) |
| 8.61 | 2-chloro-4-ethoxyphenyl | *—CH₃ | ethyl bromide | XX.4 | 401 [M + H]⁺ | 1.31 (B) |
| 8.62 | 3-fluoro-4-propoxyphenyl | *—CH₃ | propyl chloride | XX.3 | 399 [M + H]⁺ | 1.59 (B) |
| 8.63 | 4-(2-cyclopropylethoxy)phenyl | *—CH₃ | (2-bromoethyl)cyclopropane | 1.48 | 407 [M + H]⁺ | 1.62 (A) |
| 8.64 | 4-((E)-pent-3-en-1-yloxy)phenyl | *—CH₃ | (E)-5-bromopent-2-ene | 1.48 | 407 [M + H]⁺ | 2.23 (A) |
| 8.65 | 4-((E)-4-cyclopropylbut-3-en-1-yloxy)phenyl | *—CH₃ | bromodicyclopropylmethane | 1.48 | 433 [M + H]⁺ | 1.58 (A) |
| 8.66 | 4-[(2,2-difluorocyclopropyl)methoxy]phenyl | *—CH₃ | (2,2-difluorocyclopropyl)methyl bromide | 1.48 | 429 [M + H]⁺ | 2.02 (A) |
| 8.67 | 4-[(trans-3-aminocyclobutyl)oxy]phenyl | *—CH₃ | trans-3-(Boc-amino)cyclobutyl tosylate | 1.48 | 445 [M + H]⁺ | 1.79 (A) |

Example 9

Example 9.1

(S)—N-[1-(4-{1-[3-(Isopentyloxy)-phenyl]-piperidin-4-yl}-phenyl)-ethyl]-acetamide

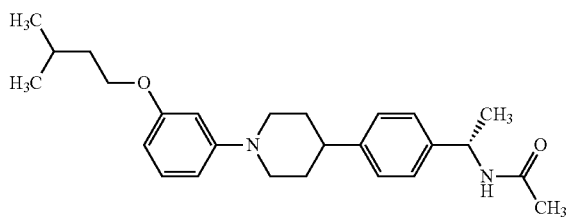

8 mg (0.2 mmol) NaH (60% in mineral oil) are added to a mixture of 34 mg (0.10 mmol) (S)—N-{1-(4-[1-(3-hydroxyphenyl)-piperidin-4-yl]-phenyl}-ethyl)-acetamide (compound 1.27) and 23 mg (0.15 mmol) 1-bromo-3-methylbutane in 2 mL DMF at 0° C. The mixture is stirred at 70° C. for 3 d. The reaction mixture is quenched with water, filtered and the solvent is evaporated. The residue is purified using reversed phase HPLC (water/MeOH, 0.1% TFA) to yield the desired product.

$C_{10}H_{11}NO$ (M=408.6 g/mol), ESI-MS: 409 $[M+H]^+$ $R_t$ (HPLC): 1.60 min (method B)

The following compounds of general formula (9-1) are prepared analogously to Example 9.1, the educts used being shown in the column headed "E 1" and "E 2":

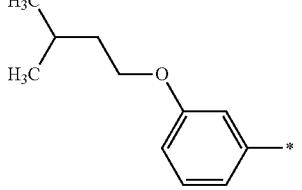

(9-1)

| Ex. | Ar¹ | T | E1 | E2 | ESI-MS [m/z] | $R_t$ (HPLC) [min] method |
|---|---|---|---|---|---|---|
| 9.1 |  | *—CH₃ | 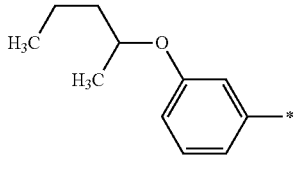 | 1.27 | 409 [M + H]⁺ | 1.60 (B) |
| 9.2 | 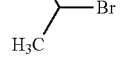 | *—CH₃ | 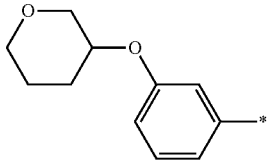 [SMILES: *c1cccc(OC2CCCOC2)c1] | 1.27 | 409 [M + H]⁺ | 1.55 (B) |
| 9.3 | 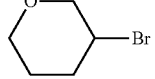 | *—CH₃ | 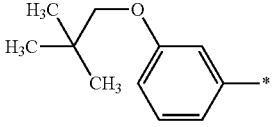 [SMILES: *c1cccc(OCC(C)(C)C)c1] | 1.27 | 423 [M + H]⁺ | 1.37 (E) |
| 9.4 | 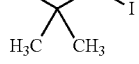 | *—CH₃ | 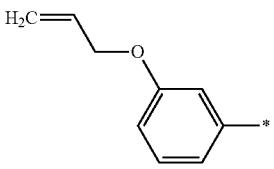 [SMILES: *c1cccc(OCC=C)c1] | 1.27 | 409 [M + H]⁺ | 1.60 (B) |
| 9.5 | 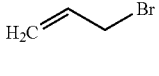 | *—CH₃ | H₂C=CH-CH₂-Br | 1.27 | 379 [M + H]⁺ | 1.32 (B) |

-continued (9-1)

| Ex. | Ar¹ | T | E1 | E2 | ESI-MS [m/z] | R$_t$ (HPLC) [min] method |
|---|---|---|---|---|---|---|
| 9.6 | cyclohexyl-O-phenyl-* | *—CH$_3$ | cyclohexyl-Br | 1.27 | 421 [M + H]$^+$ | 1.57 (B) |
| 9.7 | H$_3$C-O-CH$_2$CH$_2$-O-phenyl-* | *—CH$_3$ | H$_3$C-O-CH$_2$CH$_2$-Br | 1.27 | 397 [M + H]$^+$ | 1.13 (B) |
| 9.8 | H$_3$C-C≡C-CH$_2$-O-phenyl-* | *—CH$_3$ | H$_3$C-C≡C-CH$_2$-Br | 1.27 | 391 [M + H]$^+$ | 1.33 (B) |
| 9.9 | H$_3$C-O-CH$_2$CH$_2$CH$_2$-O-phenyl-* | *—CH$_3$ | H$_3$C-O-CH$_2$CH$_2$CH$_2$-Br | 1.27 | 411 [M + H]$^+$ | 1.26 (B) |
| 9.10 | H$_2$C=CH-CH$_2$CH$_2$-O-phenyl-* | *—CH$_3$ | H$_2$C=CH-CH$_2$CH$_2$-Br | 1.27 | 393 [M + H]$^+$ | 1.51 (E) |
| 9.11 | (5-methylisoxazol-3-yl)-CH$_2$-O-phenyl-* | *—CH$_3$ | (5-methylisoxazol-3-yl)-CH$_2$-Br | 1.27 | 434 [M + H]$^+$ | 1.29 (B) |
| 9.12 | cyclobutyl-CH$_2$-O-phenyl-* | *—CH$_3$ | cyclobutyl-CH$_2$-Br | 1.27 | 407 [M + H]$^+$ | 1.54 (B) |
| 9.13 | (tetrahydropyran-4-yl)-CH$_2$-O-phenyl-* | *—CH$_3$ | (tetrahydropyran-4-yl)-CH$_2$-I | 1.27 | 437 [M + H]$^+$ | 1.32 (B) |

-continued (9-1)

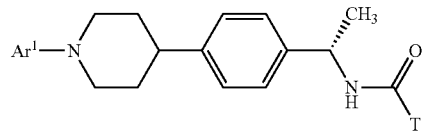

| Ex. | Ar¹ | T | E1 | E2 | ESI-MS [m/z] | R$_t$ (HPLC) [min] method |
|---|---|---|---|---|---|---|
| 9.14 | (3-(2-cyclopropyloxyethoxy)phenyl) | *—CH₃ | (2-chloroethoxy cyclopropane) | 1.27 | 423 [M + H]⁺ | 1.30 (B) |
| 9.15 | (3-((tetrahydropyran-2-yl)methoxy)phenyl) | *—CH₃ | (2-(bromomethyl)tetrahydropyran) | 1.27 | 437 [M + H]⁺ | 1.35 (B) |
| 9.16 | (3-(pentan-3-yloxy)phenyl) | *—CH₃ | (3-bromopentane) | 1.27 | 409 [M + H]⁺ | 1.54 (B) |
| 9.17 | (3-benzyloxyphenyl) | *—CH₃ | (benzyl bromide) | 1.27 | 429 [M + H]⁺ | 1.49 (B) |
| 9.18 | (3-(1-phenylethoxy)phenyl) | *—CH₃ | (1-bromoethylbenzene) | 1.27 | 443 [M + H]⁺ | 1.89 (B) |
| 9.19 | (4-(pentan-2-yloxy)phenyl) | *—CH₃ | (2-bromopentane) | 1.48 | 409 [M + H]⁺ | 1.40 (B) |
| 9.20 | (4-(3-methylbutoxy)phenyl) | *—CH₃ | (1-bromo-3-methylbutane) | 1.48 | 409 [M + H]⁺ | 1.43 (B) |
| 9.21 | (4-(neopentyloxy)phenyl) | *—CH₃ | (1-iodo-2,2-dimethylpropane) | 1.48 | 409 [M + H]⁺ | 1.44 (B) |

-continued

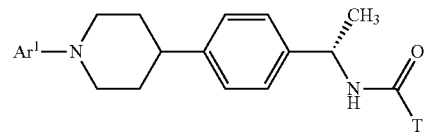
(9-1)

| Ex. | Ar¹ | T | E1 | E2 | ESI-MS [m/z] | R$_t$ (HPLC) [min] method |
|---|---|---|---|---|---|---|
| 9.22 | H₂C=CH-CH₂-O-C₆H₄-* | *—CH₃ | H₂C=CH-CH₂-Br | 1.48 | 379 [M + H]⁺ | 1.19 (B) |
| 9.23 | cyclohexyl-O-C₆H₄-* | *—CH₃ | cyclohexyl-Br | 1.48 | 421 [M + H]⁺ | 1.54 (E) |
| 9.24 | H₃C-O-CH₂CH₂-O-C₆H₄-* | *—CH₃ | H₃C-O-CH₂CH₂-Br | 1.48 | 397 [M + H]⁺ | 1.05 (B) |
| 9.25 | H₃C-C≡C-CH₂-O-C₆H₄-* | *—CH₃ | H₃C-C≡C-CH₂-Br | 1.48 | 391 [M + H]⁺ | 1.18 (B) |
| 9.26 | H₃C-O-CH₂CH₂CH₂-O-C₆H₄-* | *—CH₃ | H₃C-O-CH₂CH₂CH₂-Br | 1.48 | 411 [M + H]⁺ | 1.16 (B) |
| 9.27 | H₂C=CH-CH₂CH₂-O-C₆H₄-* | *—CH₃ | H₂C=CH-CH₂CH₂-Br | 1.48 | 393 [M + H]⁺ | 1.28 (B) |
| 9.28 | 5-methylisoxazol-3-yl-CH₂-O-C₆H₄-* | *—CH₃ | 5-methylisoxazol-3-yl-CH₂-Br | 1.48 | 434 [M + H]⁺ | 1.15 (B) |
| 9.29 | cyclobutyl-CH₂-O-C₆H₄-* | *—CH₃ | cyclobutyl-CH₂-Br | 1.48 | 407 [M + H]⁺ | 1.38 (B) |
| 9.30 | tetrahydropyran-4-yl-CH₂-O-C₆H₄-* | *—CH₃ | tetrahydropyran-4-yl-CH₂-I | 1.48 | 437 [M + H]⁺ | 1.19 (B) |
| 9.31 | cyclopropyl-O-CH₂CH₂-O-C₆H₄-* | *—CH₃ | cyclopropyl-O-CH₂CH₂-Cl | 1.48 | 423 [M + H]⁺ | 1.18 (B) |

(9-1)

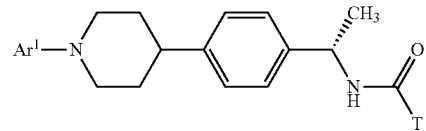

| Ex. | Ar¹ | T | E1 | E2 | ESI-MS [m/z] | R_t (HPLC) [min] method |
|---|---|---|---|---|---|---|
| 9.32 | (tetrahydropyran-2-ylmethoxy)phenyl | *—CH₃ | 2-(bromomethyl)tetrahydropyran | 1.48 | 437 [M + H]⁺ | 1.23 (B) |
| 9.33 | 4-(pentan-3-yloxy)phenyl | *—CH₃ | 3-bromopentane | 1.48 | 409 [M + H]⁺ | 1.39 (B) |
| 9.34 | 4-(benzyloxy)phenyl | *—CH₃ | benzyl bromide | 1.48 | 429 [M + H]⁺ | 1.34 (B) |
| 9.35 | 4-(1-phenylethoxy)phenyl | *—CH₃ | (1-bromoethyl)benzene | 1.48 | 443 [M + H]⁺ | 1.38 (B) |
| 9.36 | 2-(cyclobutylmethoxy)-5-cyanophenyl | *—CH₃ | (bromomethyl)cyclobutane | XX.2 | 432 [M + H]⁺ | 1.43 (AB) |
| 9.37 | 4-(cyclobutylmethoxy)-3-methylphenyl | *—CH₃ | (bromomethyl)cyclobutane | XX.1 | 421 [M + H]⁺ | 1.63 (P) |
| 9.38 | 4-(cyclopropylmethoxy)-3-methylphenyl | *—CH₃ | (chloromethyl)cyclopropane | XX.1 | 407 [M + H]⁺ | 1.52 (P) |
| 9.40 | 2-(cyclopropylmethoxy)-5-cyanophenyl | *—CH₃ | (chloromethyl)cyclopropane | XX.2 | 418 [M + H]⁺ | 1.74 (P) |
| 9.41 | 4-(cyclopropylmethoxy)-3-fluorophenyl | *—CH₃ | (chloromethyl)cyclopropane | XX.3 | 411 [M + H]⁺ | 1.58 (P) |

-continued (9-1)

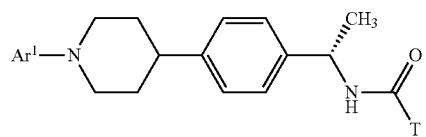

| Ex. | Ar¹ | T | E1 | E2 | ESI-MS [m/z] | $R_t$ (HPLC) [min] method |
|---|---|---|---|---|---|---|
| 9.42 | (4-(cyclobutylmethoxy)-3-fluorophenyl) | *—CH₃ | (cyclobutylmethyl-Br) | XX.3 | 425 [M + H]⁺ | 1.78 (P) |
| 9.43 | (4-(cyclobutylmethoxy)-3-methoxyphenyl) | *—CH₃ | (cyclobutylmethyl-Br) | XX.5 | 437 [M + H]⁺ | 1.52 (P) |
| 9.44 | (4-(cyclopropylmethoxy)-3-methoxyphenyl) | *—CH₃ | (cyclopropylmethyl-Cl) | XX.5 | 423 [M + H]⁺ | 1.38 (P) |
| 9.45 | (4-(cyclobutylmethoxy)-3-chlorophenyl) | *—CH₃ | (cyclobutylmethyl-Br) | XX.4 | 441 [M + H]⁺ | 1.87 (P) |
| 9.46 | (4-(cyclopropylmethoxy)-3-chlorophenyl) | *—CH₃ | (cyclopropylmethyl-Cl) | XX.4 | 427 [M + H]⁺ | 1.69 (P) |

Example 10

Example 10.1

(S)—N-[1-(4-{1-[5-(4-Cyano-3-fluorophenyl)-pyrimidin-2-yl]-piperidin-4-yl}-phenyl)ethyl]-acetamide

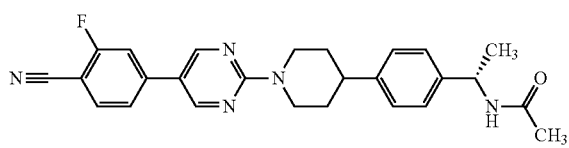 [SMILES: CC(=O)N[C@@H](C)c1ccc(C2CCN(c3ncc(-c4ccc(C#N)c(F)c4)cn3)CC2)cc1]

Under argon atmosphere 0.1 mL sat. Na₂CO₃-solution and 3 mg (0.004 mmol) bis(triphenylphosphine)-palladium(II) chloride are added to a mixture of 16 mg (0.10 mmol) 4-cyano-3-fluorophenylboronic acid and 45 mg (0.10 mmol) (S)—N-(1-{4-[1-(5-iodopyrimidin-2-yl)-piperidin-4-yl]-phenyl}-ethyl)-acetamide (compound 4.43) in 2 mL dioxane/1 mL MeOH. The mixture was stirred at 70° C. for 6 h. After that time, the mixture was diluted with DMF and filtered. The filtrate was purified using reversed phase HPLC (water/MeOH, 0.1% TFA) to yield the desired product.

$C_{10}H_{11}NO$ (M=443.5 g/mol), ESI-MS: 444 [M+H]⁺
$R_t$ (HPLC): 2.28 min (method B)

The following compounds of general formula (10-1) are prepared analogously to Example 10.1, the educts used being shown in the column headed "E 1" and "E 2". In case that Boc-protected amino boronic acids are used, the Boc group is finally removed using TFA/CH₂Cl₂=1:1 (5% H₂O):

(10-1)

| Ex. | R^A | T | E1 | E2 | ESI-MS [m/z] | R_t (HPLC) [min] method |
|---|---|---|---|---|---|---|
| 10.1 | 4-cyano-3-fluorophenyl | *—CH_3 | 4-cyano-3-fluorophenylboronic acid | 4.43 | 432 [M + H]^+ | 2.28 (B) |
| 10.2 | 6-methoxypyridin-3-yl | *—CH_3 | 6-methoxypyridin-3-ylboronic acid | 4.43 | 432 [M + H]^+ | 2.28 (B) |
| 10.3 | 3-methoxyphenyl | *—CH_3 | 3-methoxyphenylboronic acid | 4.43 | 431 [M + H]^+ | 2.35 (B) |
| 10.4 | 2-methoxyphenyl | *—CH_3 | 2-methoxyphenylboronic acid | 4.43 | 431 [M + H]^+ | 2.29 (B) |
| 10.5 | 4-ethoxyphenyl | *—CH_3 | 4-ethoxyphenylboronic acid | 4.43 | 445 [M + H]^+ | 2.28 (B) |
| 10.6 | 4-ethylphenyl | *—CH_3 | 4-ethylphenylboronic acid | 4.43 | 429 [M + H]^+ | 2.17 (B) |
| 10.7 | 3-methylphenyl | *—CH_3 | 3-methylphenylboronic acid | 4.43 | 415 [M + H]^+ | 2.12 (B) |
| 10.8 | 2-methylphenyl | *—CH_3 | 2-methylphenylboronic acid | 4.43 | 415 [M + H]^+ | 2.09 (B) |
| 10.9 | 4-fluorophenyl | *—CH_3 | 4-fluorophenylboronic acid | 4.43 | 419 [M + H]^+ | 2.05 (B) |
| 10.10 | 4-cyanophenyl | *—CH_3 | 4-cyanophenylboronic acid | 4.43 | 426 [M + H]^+ | 1.92 (B) |

-continued

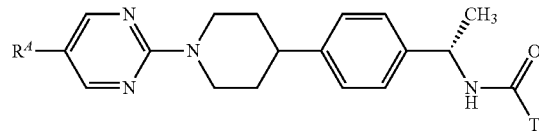
(10-1)

| Ex. | R^A | T | E1 | E2 | ESI-MS [m/z] | R_t (HPLC) [min] method |
|---|---|---|---|---|---|---|
| 10.11 | 4-isopropylphenyl | *—CH$_3$ | 4-isopropylphenylboronic acid | 4.43 | 443 [M + H]$^+$ | 2.21 (B) |
| 10.12 | pyridin-3-yl | *—CH$_3$ | pyridin-3-ylboronic acid | 4.43 | 402 [M + H]$^+$ | 1.34 (B) |
| 10.13 | 2-fluorophenyl | *—CH$_3$ | 2-fluorophenylboronic acid | 4.43 | 419 [M + H]$^+$ | 2.07 (B) |
| 10.14 | benzofuran-2-yl | *—CH$_3$ | benzofuran-2-ylboronic acid | 4.43 | 441 [M + H]$^+$ | 2.20 (B) |
| 10.15 | 4-(trifluoromethoxy)phenyl | *—CH$_3$ | 4-(trifluoromethoxy)phenylboronic acid | 4.43 | 485 [M + H]$^+$ | 2.13 (B) |
| 10.16 | pyridin-4-yl | *—CH$_3$ | pyridin-4-ylboronic acid | 4.43 | 402 [M + H]$^+$ | 1.24 (B) |
| 10.17 | furan-3-yl | *—CH$_3$ | furan-3-ylboronic acid | 4.43 | 390 [M + H]$^+$ | 1.90 (B) |
| 10.18 | 4-(cyanomethyl)phenyl | *—CH$_3$ | 4-(cyanomethyl)phenylboronic acid | 4.43 | 440 [M + H]$^+$ | 1.84 (B) |
| 10.19 | 4-(methylsulfonyl)phenyl | *—CH$_3$ | 4-(methylsulfonyl)phenylboronic acid | 4.43 | 479 [M + H]$^+$ | 1.74 (B) |
| 10.20 | 3,5-dimethylisoxazol-4-yl | *—CH$_3$ | 3,5-dimethylisoxazol-4-ylboronic acid | 4.43 | 420 [M + H]$^+$ | 1.84 (B) |

-continued (10-1)

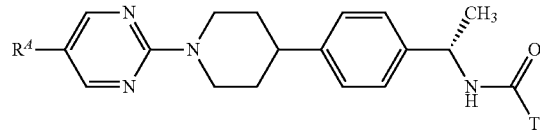

| Ex. | R^A | T | E1 | E2 | ESI-MS [m/z] | R_t (HPLC) [min] method |
|---|---|---|---|---|---|---|
| 10.21 | quinolin-3-yl | *—CH$_3$ | quinolin-3-yl boronic acid | 4.43 | 452 [M + H]$^+$ | 1.77 (B) |
| 10.22 | 2-methoxypyrimidin-5-yl | *—CH$_3$ | 2-methoxypyrimidin-5-yl boronic acid | 4.43 | 433 [M + H]$^+$ | 1.81 (B) |
| 10.23 | 2,3-dihydrobenzo[1,4]dioxin-6-yl | *—CH$_3$ | 2,3-dihydrobenzo[1,4]dioxin-6-yl boronic acid | 4.43 | 459 [M + H]$^+$ | 2.01 (B) |
| 10.24 | 2,3-dihydrobenzofuran-5-yl | *—CH$_3$ | 2,3-dihydrobenzofuran-5-yl boronic acid | 4.43 | 443 [M + H]$^+$ | 2.01 (B) |
| 10.25 | 1-methylindol-5-yl | *—CH$_3$ | 1-methylindol-5-yl boronic acid | 4.43 | 454 [M + H]$^+$ | 2.01 (B) |
| 10.26 | 3,4-dihydro-2H-benzo[b][1,4]dioxepin-7-yl | *—CH$_3$ | 3,4-dihydro-2H-benzo[b][1,4]dioxepin-7-yl boronic acid | 4.43 | 473 [M + H]$^+$ | 2.03 (B) |
| 10.27 | 4-isopropoxyphenyl | *—CH$_3$ | 4-isopropoxyphenyl boronic acid | 4.43 | 459 [M + H]$^+$ | 2.10 (B) |
| 10.28 | 4-morpholinophenyl | *—CH$_3$ | 4-morpholinophenyl boronic acid | 4.43 | 486 [M + H]$^+$ | 1.92 (B) |
| 10.29 | 2-methoxypyridin-4-yl | *—CH$_3$ | 2-methoxypyridin-4-yl boronic acid | 4.43 | 432 [M + H]$^+$ | 1.91 (B) |

-continued

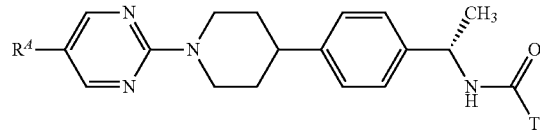
(10-1)

| Ex. | R^A | T | E1 | E2 | ESI-MS [m/z] | R_t (HPLC) [min] method |
|---|---|---|---|---|---|---|
| 10.30 | 3-methyl-4-methoxyphenyl | *—CH$_3$ | 3-methyl-4-methoxyphenylboronic acid | 4.43 | 445 [M + H]$^+$ | 2.10 (B) |
| 10.31 | 4-(methylthio)phenyl | *—CH$_3$ | 4-(methylthio)phenylboronic acid | 4.43 | 447 [M + H]$^+$ | 2.12 (B) |
| 10.32 | 4-(methoxymethyl)phenyl | *—CH$_3$ | 4-(methoxymethyl)phenylboronic acid | 4.43 | 445 [M + H]$^+$ | 1.99 (B) |
| 10.33 | 6-methylpyridin-3-yl | *—CH$_3$ | 4-methylphenylboronic acid | 4.43 | 416 [M + H]$^+$ | 1.28 (B) |
| 10.34 | 3,5-dimethoxyphenyl | *—CH$_3$ | 3,5-dimethoxyphenylboronic acid | 4.43 | 461 [M + H]$^+$ | 2.06 (B) |
| 10.35 | 3,4-dimethoxyphenyl | *—CH$_3$ | 3,4-dimethoxyphenylboronic acid | 4.43 | 461 [M + H]$^+$ | 1.90 (B) |
| 10.36 | 2-trifluoromethyl-4-methoxyphenyl | *—CH$_3$ | 2-trifluoromethyl-4-methoxyphenylboronic acid | 4.43 | 499 [M + H]$^+$ | 2.08 (B) |
| 10.37 | 2-fluoro-4-methoxyphenyl | *—CH$_3$ | 2-fluoro-4-methoxyphenylboronic acid | 4.43 | 449 [M + H]$^+$ | 2.07 (B) |
| 10.38 | 6-ethoxypyridin-3-yl | *—CH$_3$ | 6-ethoxypyridin-3-ylboronic acid | 4.43 | 446 [M + H]$^+$ | 2.02 (B) |
| 10.39 | 4-(N-methylsulfamoyl)phenyl | *—CH$_3$ | 4-(N-methylsulfamoyl)phenylboronic acid | 4.43 | 494 [M + H]$^+$ | 1.75 (B) |

-continued

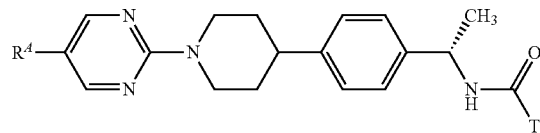
(10-1)

| Ex. | R<sup>A</sup> | T | E1 | E2 | ESI-MS [m/z] | R<sub>t</sub> (HPLC) [min] method |
|---|---|---|---|---|---|---|
| 10.40 | H₃CO-naphthyl-* | *—CH₃ | H₃CO-naphthyl-B(OH)₂ | 4.43 | 481 [M + H]⁺ | 2.16 (B) |
| 10.41 | cyclopropyl-C₆H₄-* | *—CH₃ | cyclopropyl-C₆H₄-B(OH)₂ | 4.43 | 441 [M + H]⁺ | 2.17 (B) |
| 10.42 | H₃C-CH₂-CH₂-O-C₆H₄-* | *—CH₃ | H₃C-CH₂-CH₂-O-C₆H₄-B(OH)₂ | 4.43 | 459 [M + H]⁺ | 2.14 (B) |
| 10.43 | C₆H₅-* | *—CH₃ | C₆H₅-B(OH)₂ | 4.43 | 401 [M + H]⁺ | 2.05 (B) |
| 10.44 | H₃C-C₆H₄-* | *—CH₃ | H₃C-C₆H₄-B(OH)₂ | 4.43 | 415 [M + H]⁺ | 2.12 (B) |
| 10.45 | F₃C-C₆H₄-* | *—CH₃ | F₃C-C₆H₄-B(OH)₂ | 4.43 | 469 [M + H]⁺ | 2.13 (B) |
| 10.46 | *-indol-5-yl | *—CH₃ | (HO)₂N-indol-5-yl | 4.43 | 440 [M + H]⁺ | 1.96 (W) |
| 10.47 | 3,4-dimethylphenyl-* | *—CH₃ | 3,4-dimethylphenyl-B(OH)₂ | 4.43 | 429 [M + H]⁺ | 2.28 (W) |
| 10.48 | 2,4-dimethylphenyl-* | *—CH₃ | 2,4-dimethylphenyl-B(OH)₂ | 4.43 | 429 [M + H]⁺ | 2.25 (W) |

-continued (10-1)

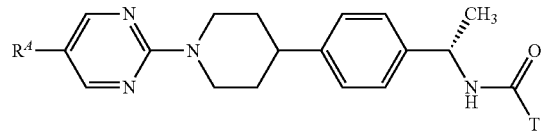

| Ex. | R$^A$ | T | E1 | E2 | ESI-MS [m/z] | R$_t$ (HPLC) [min] method |
|---|---|---|---|---|---|---|
| 10.49 | 4-F, 3-Me-phenyl | *—CH$_3$ | 4-F, 3-Me-phenyl boronic acid | 4.43 | 433 [M + H]$^+$ | 2.21 (W) |
| 10.50 | 2-F, 3-CN-phenyl | *—CH$_3$ | 4-F, 3-CN-phenyl boronic acid | 4.43 | 444 [M + H]$^+$ | 1.97 (W) |
| 10.51 | 2-(cyclopropylmethoxy)pyridin-5-yl | *—CH$_3$ | 2-(cyclopropylmethoxy)pyridin-5-yl pinacol boronate | 4.43 | 472 [M + H]$^+$ | 2.16 (W) |
| 10.52 | 3,4-difluorophenyl | *—CH$_3$ | 3,4-difluorophenyl boronic acid | 4.43 | 437 [M + H]$^+$ | 2.12 (W) |
| 10.53 | 2,4-difluorophenyl | *—CH$_3$ | 2,4-difluorophenyl boronic acid | 4.43 | 437 [M + H]$^+$ | 2.13 (W) |
| 10.54 | 2,5-dimethylphenyl | *—CH$_3$ | 2,5-dimethylphenyl boronic acid | 4.43 | 429 [M + H]$^+$ | 2.25 (W) |
| 10.55 | 2-cyanophenyl | *—CH$_3$ | 2-cyanophenyl boronic acid | 4.43 | 426 [M + H]$^+$ | 1.92 (W) |

-continued

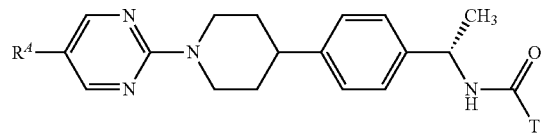
(10-1)

| Ex. | R^A | T | E1 | E2 | ESI-MS [m/z] | R_t (HPLC) [min] method |
|---|---|---|---|---|---|---|
| 10.56 | 4-methyl-thiophen-3-yl | *—CH_3 | (4-methylthiophen-3-yl)boronic acid | 4.43 | 421 [M + H]+ | 2.13 (W) |
| 10.57 | 3-chloro-4-methoxyphenyl | *—CH_3 | (3-chloro-4-methoxyphenyl)boronic acid | 4.43 | 465 [M + H]+ | 2.15 (W) |
| 10.58 | 2-methoxypyridin-3-yl | *—CH_3 | (2-methoxypyridin-3-yl)boronic acid | 4.43 | 432 [M + H]+ | 2.01 (W) |
| 10.59 | 4-methoxypyridin-3-yl | *—CH_3 | (4-methoxypyridin-3-yl)boronic acid | 4.43 | 432 [M + H]+ | 2.01 (W) |
| 10.60 | 4-fluoro-2-methylphenyl | *—CH_3 | (4-fluoro-2-methylphenyl)boronic acid | 4.43 | 433 [M + H]+ | 2.16 (W) |
| 10.61 | 4-cyano-2-methylphenyl | *—CH_3 | (4-cyano-2-methylphenyl)boronic acid | 4.43 | 440 [M + H]+ | 2.01 (W) |
| 10.62 | thiophen-3-yl | *—CH_3 | (4-methylthiophen-3-yl)boronic acid | 4.43 | 407 [M + H]+ | 2.07 (W) |

-continued

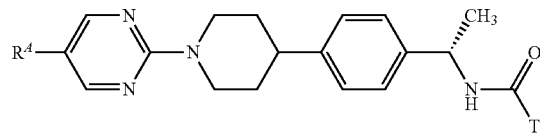

(10-1)

| Ex. | R<sup>A</sup> | T | E1 | E2 | ESI-MS [m/z] | R<sub>t</sub> (HPLC) [min] method |
|---|---|---|---|---|---|---|
| 10.63 | thiophene-2-CN, attached at 5 | *—CH$_3$ | 5-cyanothiophene-2-boronic acid | 4.43 | 432 [M + H]$^+$ | 2.01 (W) |
| 10.64 | 4-(ethylthio)phenyl | *—CH$_3$ | 4-(ethylthio)phenylboronic acid | 4.43 | 461 [M + H]$^+$ | 2.25 (W) |
| 10.65 | 3-methoxy-4-methylphenyl | *—CH$_3$ | 3-methoxy-4-methylphenylboronic acid | 4.43 | 445 [M + H]$^+$ | 2.22 (W) |
| 10.66 | 2-chloro-4-methylphenyl | *—CH$_3$ | 2-chloro-4-methylphenylboronic acid | 4.43 | 449 [M + H]$^+$ | 2.26 (W) |
| 10.67 | 3-chloro-4-methylphenyl | *—CH$_3$ | 3-chloro-4-methylphenylboronic acid | 4.43 | 449 [M + H]$^+$ | 2.35 (W) |
| 10.68 | 5-methoxypyridin-3-yl | *—CH$_3$ | 5-methoxypyridine-3-boronic acid | 4.43 | 432 [M + H]$^+$ | 1.88 (W) |
| 10.69 | 5-fluoropyridin-3-yl | *—CH$_3$ | 5-fluoropyridine-3-boronic acid | 4.43 | 420 [M + H]$^+$ | 1.9 (W) |
| 10.70 | quinolin-6-yl | *—CH$_3$ | quinoline-6-boronic acid | 4.43 | 452 [M + H]$^+$ | 1.99 (W) |

-continued

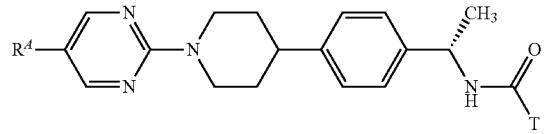
(10-1)

| Ex. | R^A | T | E1 | E2 | ESI-MS [m/z] | R_t (HPLC) [min] method |
|---|---|---|---|---|---|---|
| 10.71 | cyclohexenyl | *—CH_3 | cyclohexenyl boronic acid | 4.43 | 405 [M + H]+ | 2.26 (W) |
| 10.72 | N-methylpyrrolyl | *—CH_3 | N-methylpyrrole pinacol boronate | 4.43 | 404 [M + H]+ | 1.99 (W) |
| 10.73 | quinoxalinyl | *—CH_3 | quinoxaline boronic acid | 4.43 | 453 [M + H]+ | 1.95 (W) |
| 10.74 | 2-bromo-1-methylimidazolyl | *—CH_3 | 2-bromo-1-methylimidazole pinacol boronate | 4.43 | 483 [M + H]+ | 1.82 (W) |
| 10.75 | benzothiophenyl | *—CH_3 | benzothiophene boronic acid | 4.43 | 457 [M + H]+ | 2.22 (W) |
| 10.76 | 4-chloro-3-methylphenyl | *—CH_3 | 4-chloro-3-methylphenylboronic acid | 4.43 | 449 [M + H]+ | 2.31 (W) |
| 10.77 | 4-methylthio-2-trifluoromethylphenyl | *—CH_3 | 4-methylthio-2-trifluoromethylphenylboronic acid | 4.43 | 515 [M + H]+ | 2.21 (W) |
| 10.78 | 3-chloro-4-hydroxyphenyl | *—CH_3 | 3-chloro-4-hydroxyphenylboronic acid | 4.43 | 451 [M + H]+ | 1.5 (W) |

-continued (10-1)

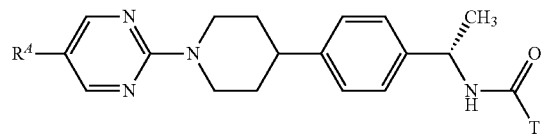

| Ex. | R^A | T | E1 | E2 | ESI-MS [m/z] | R_t (HPLC) [min] method |
|---|---|---|---|---|---|---|
| 10.79 | 5-cyanopyridin-3-yl | *—CH_3 | 5-cyanopyridin-3-ylboronic acid | 4.43 | 427 [M + H]^+ | 1.8 (W) |
| 10.80 | 3-cyanophenyl | *—CH_3 | 3-cyanophenylboronic acid | 4.43 | 426 [M + H]^+ | 1.94 (W) |
| 10.81 | 6-(dimethylamino)pyridin-3-yl | *—CH_3 | 6-(dimethylamino)pyridin-3-ylboronic acid | 4.43 | 445 [M + H]^+ | 2 (W) |
| 10.82 | 6-cyanopyridin-3-yl | *—CH_3 | 6-cyanopyridin-3-yl pinacol boronate | 4.43 | 427 [M + H]^+ | 1.79 (W) |
| 10.83 | 2-cyanopyrimidin-5-yl | *—CH_3 | 2-cyanopyrimidin-5-yl pinacol boronate | 4.43 | 428 [M + H]^+ | 0.51 (V) |
| 10.84 | 3,6-dihydro-2H-pyran-4-yl | *—CH_3 | 3,6-dihydro-2H-pyran-4-yl pinacol boronate | 4.43 | 407 [M + H]^+ | 1.88 (W) |
| 10.85 | 6-(trifluoromethyl)pyridin-3-yl | *—CH_3 | 6-(trifluoromethyl)pyridin-3-ylboronic acid | 4.43 | 470 [M + H]^+ | 1.98 (W) |
| 10.86 | 1H-indazol-5-yl | *—CH_3 | 1H-indazol-5-ylboronic acid | 4.43 | 441 [M + H]^+ | 1.88 (W) |

-continued

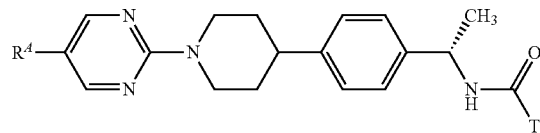
(10-1)

| Ex. | R^A | T | E1 | E2 | ESI-MS [m/z] | R_t (HPLC) [min] method |
|---|---|---|---|---|---|---|
| 10.87 | benzo[1,3]dioxol-5-yl | *—CH₃ | benzo[1,3]dioxol-5-yl boronic acid | 4.43 | 445 [M + H]⁺ | 2.09 (W) |
| 10.88 | benzofuran-5-yl | *—CH₃ | benzofuran-5-yl pinacol boronate | 4.43 | 441 [M + H]⁺ | 2.14 (W) |
| 10.89 | 2-methylfuran-3-yl | *—CH₃ | 2-methylfuran-3-yl pinacol boronate | 4.43 | 405 [M + H]⁺ | 2.08 (W) |
| 10.90 | chroman-6-yl | *—CH₃ | chroman-6-yl pinacol boronate | 4.43 | 457 [M + H]⁺ | 2.14 (B) |
| 10.91 | benzofuran-3-yl | *—CH₃ | benzofuran-3-yl pinacol boronate | 4.43 | 441 [M + H]⁺ | 2.21 (W) |
| 10.92 | 2,3-dihydrobenzofuran-7-yl | *—CH₃ | 2,3-dihydrobenzofuran-7-yl boronic acid | 4.43 | 443 [M + H]⁺ | 2.15 (W) |
| 10.93 | 1,4-dioxaspiro[4.5]dec-7-en-8-yl | *—CH₃ | 1,4-dioxaspiro[4.5]dec-7-en-8-yl pinacol boronate | 4.43 | 463 [M + H]⁺ | 1.96 (W) |

-continued (10-1)

| Ex. | R^A | T | E1 | E2 | ESI-MS [m/z] | R_t (HPLC) [min] method |
|---|---|---|---|---|---|---|
| 10.94 | 2-methylpyridin-3-yl | *—CH$_3$ | 2-methylpyridin-3-yl boronic acid | 4.43 | 416 [M + H]$^+$ | 1.87 (W) |
| 10.95 | 4-methylpyridin-3-yl | *—CH$_3$ | 4-methylpyridin-3-yl boronic acid | 4.43 | 416 [M + H]$^+$ | 1.87 (W) |
| 10.96 | furan-2-yl | *—CH$_3$ | furan-2-yl boronic acid | 4.43 | 391 [M + H]$^+$ | 0.54 (V) |
| 10.97 | 2-(cyanomethyl)phenyl | *—CH$_3$ | 2-(cyanomethyl)phenyl boronic acid pinacol ester | 4.43 | 440 [M + H]$^+$ | 1.9 (W) |
| 10.98 | 2,3-dihydrobenzofuran-5-yl | cyclopropyl | 2,3-dihydrobenzofuran-5-yl boronic acid | XVIII.1 | 469 [M + H]$^+$ | 2.13 (Z) |
| 10.99 | 2,3-dihydrobenzofuran-5-yl | *—N(CH$_3$)$_2$ | 2,3-dihydrobenzofuran-5-yl boronic acid | XVIII.2 | 472 [M + H]$^+$ | 2.08 (Z) |
| 10.100 | 3-methylphenyl | cyclopropyl | 3-methylphenyl boronic acid | XVIII.1 | 441 [M + H]$^+$ | 2.20 (Z) |
| 10.101 | 4-fluorophenyl | cyclopropyl | 4-fluorophenyl boronic acid | XVIII.1 | 445 [M + H]$^+$ | 2.14 (Z) |

-continued

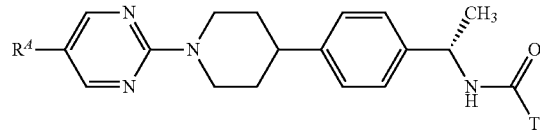
(10-1)

| Ex. | R^A | T | E1 | E2 | ESI-MS [m/z] | R_t (HPLC) [min] method |
|---|---|---|---|---|---|---|
| 10.102 | 4-NC-C6H4-* | cyclopropyl-* | 4-NC-C6H4-B(OH)2 | XVIII.1 | 452 [M+H]+ | 2.05 (Z) |
| 10.103 | 2-F-C6H4-* | cyclopropyl-* | 2-F-C6H4-B(OH)2 | XVIII.1 | 445 [M+H]+ | 2.19 (Z) |
| 10.104 | 3-furyl-* | cyclopropyl-* | 3-furyl-B(OH)2 | XVIII.1 | 417 [M+H]+ | 2.02 (Z) |
| 10.105 | C6H5-* | cyclopropyl-* | C6H5-B(OH)2 | XVIII.1 | 427 [M+H]+ | 2.17 (Z) |
| 10.106 | 4-Me-C6H4-* | cyclopropyl-* | 4-Me-C6H4-B(OH)2 | XVIII.1 | 441 [M+H]+ | 2.21 (Z) |
| 10.107 | 3-Me-C6H4-* | *-N(Me)2 | 3-Me-C6H4-B(OH)2 | XVIII.2 | 444 [M+H]+ | 2.21 (Z) |
| 10.108 | 4-F-C6H4-* | *-N(Me)2 | 4-F-C6H4-B(OH)2 | XVIII.1 | 448 [M+H]+ | 2.14 (Z) |
| 10.109 | 4-NC-C6H4-* | *-N(Me)2 | 4-NC-C6H4-B(OH)2 | XVIII.2 | 455 [M+H]+ | 2.01 (Z) |
| 10.110 | 2-F-C6H4-* | *-N(Me)2 | 2-F-C6H4-B(OH)2 | XVIII.2 | 448 [M+H]+ | 2.14 (Z) |
| 10.111 | C6H5-* | *-N(Me)2 | C6H5-B(OH)2 | XVIII.2 | 430 [M+H]+ | 2.15 (Z) |
| 10.112 | 4-Me-C6H4-* | *-N(Me)2 | 4-Me-C6H4-B(OH)2 | XVIII.1 | 444 [M+H]+ | 2.27 (Z) |

-continued
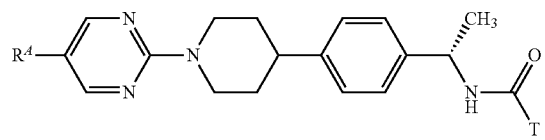
(10-1)
| Ex. | $R^A$ | T | E1 | E2 | ESI-MS [m/z] | $R_t$ (HPLC) [min] method |
|---|---|---|---|---|---|---|
| 10.113 | 3-furyl | *N(CH3)2 | 3-furylboronic acid (HO)2B | XVIII.2 | 420 [M + H]+ | 1.98 (Z) |
| 10.114 | 6-indolyl | *—CH3 | 6-indolyl-B(OH)2 | 4.43 | 440 [M + H]+ | 2.69 (R) |
| 10.115 | 5-methoxy-2-indolyl | *—CH3 | 5-methoxy-N-Boc-indol-2-yl-B(OH)2 | 4.43 | 470 [M + H]+ | 2.70 (R) |
| 10.116 | 6-methyl-2-indolyl | *—CH3 | 6-methyl-N-Boc-indol-2-yl-B(OH)2 | 4.43 | 454 [M + H]+ | 2.81 (R) |
| 10.117 | 5-cyano-2-indolyl | *—CH3 | 5-cyano-N-Boc-indol-2-yl-B(OH)2 | 4.43 | 465 [M + H]+ | 2.66 (R) |
| 10.118 | 7-indolyl | *—CH3 | 7-indolyl-Bpin | 4.43 | 440 [M + H]+ | 2.74 (R) |

-continued (10-1)

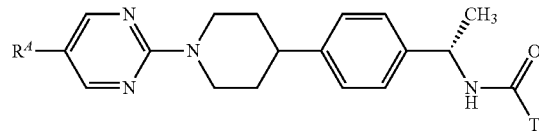

| Ex. | R^A | T | E1 | E2 | ESI-MS [m/z] | R_t (HPLC) [min] method |
|---|---|---|---|---|---|---|
| 10.119 | 2-indolyl (NH) | *—CH$_3$ | 1-Boc-indol-2-yl boronic acid | 4.43 | 440 [M+H]$^+$ | 2.75 (R) |
| 10.120 | indol-4-yl | *—CH$_3$ | indol-4-yl boronic acid | 4.43 | 440 [M+H]$^+$ | 2.64 (R) |
| 10.121 | 5-methylpyridin-2-yl | *—CH$_3$ | 5-methylpyridin-2-yl N-phenyldiethanolamine boronate | 4.43 | 416 [M+H]$^+$ | 2.64 (R) |
| 10.122 | 4-methylpyridin-2-yl | *—CH$_3$ | 4-methylpyridin-2-yl N-phenyldiethanolamine boronate | 4.43 | 416 [M+H]$^+$ | 2.64 (R) |
| 10.123 | 3-(cyanomethyl)phenyl | *—CH$_3$ | 3-(cyanomethyl)phenyl pinacol boronate | 4.43 | 440 [M+H]$^+$ | 2.17 (P) |
| 10.124 | 3-fluoro-4-methylphenyl | *—CH$_3$ | 3-fluoro-4-methylphenyl boronic acid | 4.43 | 443 [M+H]$^+$ | 2.46 (P) |
| 10.125 | 4-ethoxy-3-methylphenyl | *—CH$_3$ | 4-ethoxy-3-methylphenyl boronic acid | 4.43 | 459 [M+H]$^+$ | 2.47 (P) |

(10-1)

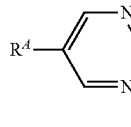

| Ex. | $R^A$ | T | E1 | E2 | ESI-MS [m/z] | $R_t$ (HPLC) [min] method |
|---|---|---|---|---|---|---|
| 10.126 | 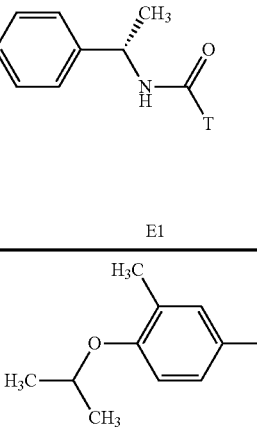 | *—CH$_3$ | 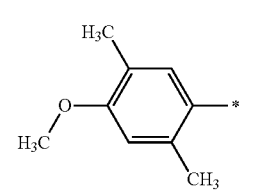 | 4.43 | 473 [M + H]$^+$ | 2.49 (P) |
| 10.127 | 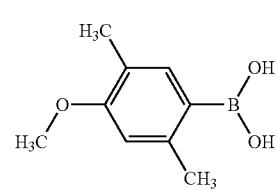 | *—CH$_3$ | 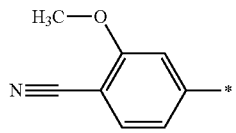 | 4.43 | 459 [M + H]$^+$ | 2.43 (P) |
| 10.128 | 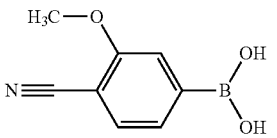 | *—CH$_3$ | 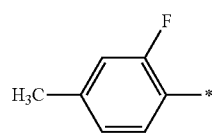 | 4.43 | 456 [M + H]$^+$ | 2.24 (P) |
| 10.129 | 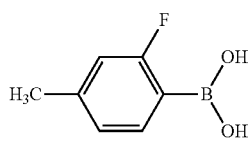 | *—CH$_3$ | 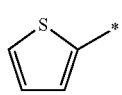 | 4.43 | 433 [M + H]$^+$ | 2.45 (P) |
| 10.130 | 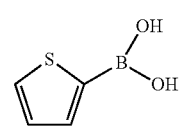 | *—CH$_3$ | 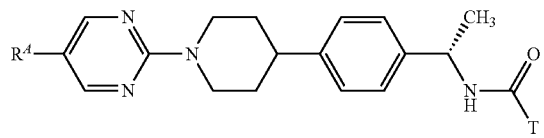 | 4.43 | 407 [M + H]$^+$ | 2.39 (P) |

The following compounds of general formula (10-2) are prepared analogously to Example 10.1 using palladium(II) acetate/tricyclohexylphosphine/tripotassium phosphate hydrate in toluene/water instead of bis(triphenylphosphine)-palladium(II) chloride/Na$_2$CO$_3$. The educts used are shown in the column headed "E 1" and "E 2":

(10-2)

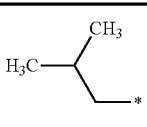

| Ex. | $R^A$ | T | E1 | E2 | ESI-MS [m/z] | $R_t$ (HPLC) [min] method |
|---|---|---|---|---|---|---|
| 10.201 | 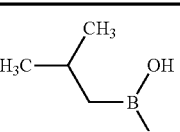 | *—CH$_3$ | 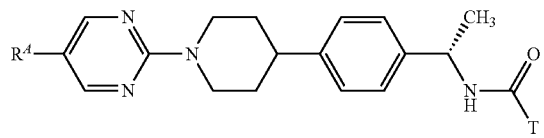 | 4.43 | 381 [M + H]$^+$ | 2.19 (B) |

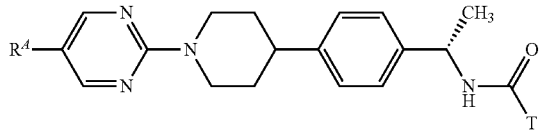

(10-2)

| Ex. | $R^A$ | T | E1 | E2 | ESI-MS [m/z] | $R_t$ (HPLC) [min] method |
|---|---|---|---|---|---|---|
| 10.202 | cyclopropyl | *—CH₃ | cyclopropylboronic acid | 4.43 | 365 [M + H]⁺ | 2.09 (A) |
| 10.203 | 2-pyridyl | *—CH₃ | 2-pyridylboronic acid | 4.43 | 402 [M + H]⁺ | 2.56 (R) |
| 10.204 | 3,5-dimethyl-4-methoxyphenyl | *—CH₃ | 2,6-dimethyl-4-methoxyphenylboronic acid | 4.43 | 459 [M + H]⁺ | 2.82 (R) |

The following compounds of general formula (10-3) are prepared analogously to Example 10.1, the educts used being shown in the column headed "E 1" and "E 2":

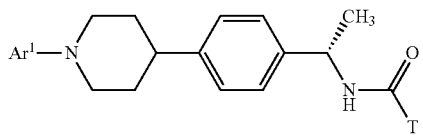

(10-3)

| Ex. | Ar¹ | T | E1 | E2 | ESI-MS [m/z] | $R_t$ (HPLC) [min] method |
|---|---|---|---|---|---|---|
| 10.301 | 5-(1H-indol-5-yl)pyridin-2-yl | *—CH₃ | 1H-indol-5-ylboronic acid | 5.12 | 439 [M + H]⁺ | 1.74 (W) |
| 10.302 | 5-(1H-indol-5-yl)-3-fluoropyridin-2-yl | *—CH₃ | 1H-indol-5-ylboronic acid | 5.38 | 457 [M + H]⁺ | 1.84 (W) |

-continued (10-3)

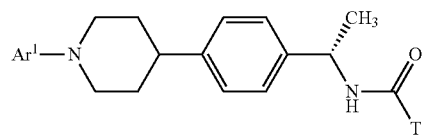

| Ex. | Ar¹ | T | E1 | E2 | ESI-MS [m/z] | R_t (HPLC) [min] method |
|---|---|---|---|---|---|---|
| 10.303 | 4-cyclopropyl-3-methylpyridin-2-yl | *—CH₃ | cyclopropylboronic acid | 5.39 | 378 [M + H]⁺ | 1.87 (W) |
| 10.304 | 5-cyclopropylpyridin-2-yl | *—CH₃ | cyclopropylboronic acid | 5.12 | 364 [M + H]⁺ | 1.1 (B) |
| 10.305 | 5-cyclopropyl-3-fluoropyridin-2-yl | *—CH₃ | cyclopropylboronic acid | 5.38 | 382 [M + H]⁺ | 1.89 (W) |
| 10.306 | 5-(3-ethoxyphenyl)pyridin-2-yl | *—CH₃ | 3-ethoxyphenylboronic acid | 5.12 | 444 [M + H]⁺ | 1.94 (W) |
| 10.307 | 5-(3-ethoxyphenyl)-3-fluoropyridin-2-yl | *—CH₃ | 3-ethoxyphenylboronic acid | 5.38 | 462 [M + H]⁺ | 2.04 (W) |
| 10.308 | 5-(5-cyanothiophen-2-yl)pyridin-2-yl | *—CH₃ | 5-cyanothiophen-2-ylboronic acid | 5.12 | 431 [M + H]⁺ | 1.78 (W) |
| 10.309 | 5-(5-cyanothiophen-2-yl)-3-fluoropyridin-2-yl | *—CH₃ | 5-cyanothiophen-2-ylboronic acid | 5.38 | 449 [M + H]⁺ | 1.88 (W) |
| 10.310 | 5-(4-fluorophenyl)pyridin-2-yl | *—CH₃ | 4-fluorophenylboronic acid | 5.12 | 418 [M + H]⁺ | 1.89 (W) |
| 10.311 | 5-(4-fluorophenyl)-3-fluoropyridin-2-yl | *—CH₃ | 4-fluorophenylboronic acid | 5.38 | 436 [M + H]⁺ | 1.98 (W) |

(10-3)

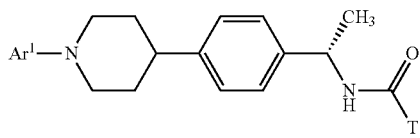

| Ex. | Ar¹ | T | E1 | E2 | ESI-MS [m/z] | $R_t$ (HPLC) [min] method |
|---|---|---|---|---|---|---|
| 10.312 | benzo[1,3]dioxol-5-yl-pyridin-2-yl | *—CH₃ | benzo[1,3]dioxol-5-yl boronic acid | 5.12 | 444 [M + H]⁺ | 1.87 (W) |
| 10.313 | 3-fluoro-5-(benzo[1,3]dioxol-5-yl)pyridin-2-yl | *—CH₃ | benzo[1,3]dioxol-5-yl boronic acid | 5.38 | 462 [M + H]⁺ | 1.97 (W) |
| 10.314 | 5-(4-methylphenyl)pyridin-2-yl | *—CH₃ | 4-methylphenyl boronic acid | 5.12 | 414 [M + H]⁺ | 1.98 (W) |
| 10.315 | 3-fluoro-5-(4-methylphenyl)pyridin-2-yl | *—CH₃ | 4-methylphenyl boronic acid | 5.38 | 432 [M + H]⁺ | 2.08 (W) |

Example 11

Example 11.1

(S)—N-(1-{4-[1-(6-Propoxy-pyrimidin-4-yl)-piperidin-4-yl]-phenyl}-ethyl)acetamide

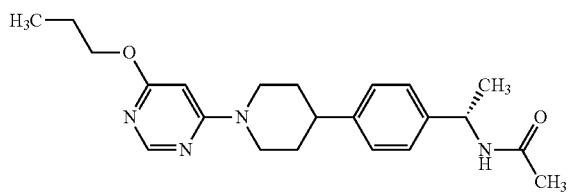 [SMILES: CCCOc1cc(N2CCC(c3ccc([C@H](C)NC(C)=O)cc3)CC2)ncn1]

1.33 mL (2.79 mmol) Sodium n-propoxide (20% in n-propanol) are added to 200 mg (0.56 mmol) (S)—N-(1-{4-[1-(6-chloro-pyrimidin-4-yl)-piperidin-4-yl]-phenyl}-ethyl)-acetamide (XIV.1) in 0.5 mL acetonitrile. The mixture is heated at 140° C. for 1 min under microwave irradiation. After that time, water is added and the mixture is extracted with dichloromethane. The solvent is evaporated and the residue is purified using reversed phase HPLC (column: Waters XBridge 5 µM; eluent A: water+0.3% NH₄OH, eluent B: MeOH) to yield the desired product.

$C_{22}H_{30}N_4O_2$ (M=382.5 g/mol), ESI-MS: 383 [M+H]⁺

$R_t$ (HPLC): 2.04 min (method A)

The following compounds of general formula (11-1) are prepared analogously to Example 11.1. In case the free alcohol is used the corresponding alcohol (5.0 equiv.) is dissolved in NMP, XIV.1 or XIV.3, respectively, and potassium tert-butoxide (2.5 equiv.) are added and the mixture is stirred over night at 130° C. In case an amine is used as a nucleophile the corresponding amine (5.0 equiv.) is dissolved in DMSO. DIPEA (5.0-10.0 equiv.) and XIV.1 or XIV.3, respectively, are added and the mixture is stirred over night at 130° C. Compound 11.116 is obtained as a second product. The educts used are shown in the column headed "E 1" and "E 2":

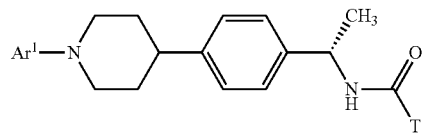

(11-1)

| Ex. | Ar¹ | T | E1 | E2 | ESI-MS [m/z] | $R_t$ (HPLC) [min] method |
|---|---|---|---|---|---|---|
| 11.1 | H₃C propoxy-pyrimidine | *—CH₃ | sodium n-propoxide | XIV.1 | 383 [M + H]⁺ | 2.04 (A) |
| 11.2 | H₃C isopropoxy-pyrimidine | *—CH₃ | sodium sec-propoxide | XIV.1 | 383 [M + H]⁺ | 2.01 (A) |
| 11.3 | cyclopropylethoxy-pyrimidine | *—CH₃ | HO-CH₂CH₂-cyclopropyl | XIV.1 | 409 [M + H]⁺ | 2.01 (W) |
| 11.4 | cyclopropylethoxy-pyrimidine | *—CH₃ | HO-CH₂CH₂-cyclopropyl | XIV.3 | 409 [M + H]⁺ | 1.98 (W) |
| 11.5 | 4-fluorophenoxy-pyrimidine | *—CH₃ | HO-C₆H₄-F | XIV.1 | 435 [M + H]⁺ | 1.9 (W) |
| 11.6 | 4-fluorophenoxy-pyrimidine | *—CH₃ | HO-C₆H₄-F | XIV.3 | 435 [M + H]⁺ | 1.88 (W) |
| 11.7 | cyclopentyloxy-pyrimidine | *—CH₃ | HO-cyclopentyl | XIV.1 | 409 [M + H]⁺ | 2.01 (W) |

-continued (11-1)

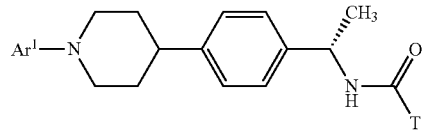

| Ex. | Ar¹ | T | E1 | E2 | ESI-MS [m/z] | R$_t$ (HPLC) [min] method |
|---|---|---|---|---|---|---|
| 11.8 | cyclopentyl-O-pyrimidin-2-yl | *—CH$_3$ | cyclopentanol | XIV.3 | 409 [M + H]$^+$ | 1.99 (W) |
| 11.9 | cyclopentylmethyl-O-pyrimidin-2-yl | *—CH$_3$ | cyclopentylmethanol | XIV.3 | 423 [M + H]$^+$ | 2.07 (W) |
| 11.10 | cyclopentylmethyl-O-pyrimidin-4-yl | *—CH$_3$ | cyclopentylmethanol | XIV.1 | 423 [M + H]$^+$ | 2.13 (W) |
| 11.11 | 3,3-dimethylbutyl-O-pyrimidin-2-yl | *—CH$_3$ | 3,3-dimethylbutan-1-ol | XIV.3 | 425 [M + H]$^+$ | 2.09 (W) |
| 11.12 | 3,3-dimethylbutyl-O-pyrimidin-4-yl | *—CH$_3$ | 3,3-dimethylbutan-1-ol | XIV.1 | 425 [M + H]$^+$ | 2.16 (W) |
| 11.13 | phenethyl-O-pyrimidin-2-yl | *—CH$_3$ | 2-phenylethanol | XIV.3 | 445 [M + H]$^+$ | 2.01 (W) |

-continued

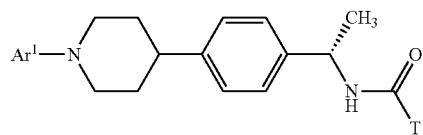

(11-1)

| Ex. | Ar¹ | T | E1 | E2 | ESI-MS [m/z] | R$_t$ (HPLC) [min] method |
|---|---|---|---|---|---|---|
| 11.14 | phenethyloxy-pyrimidine | *—CH₃ | 2-phenylethanol | XIV.1 | 445 [M + H]⁺ | 2.06 (W) |
| 11.15 | isobutoxy-pyrimidin-4-yl | *—CH₃ | isobutanol | XIV.1 | 397 [M + H]⁺ | 2.00 (W) |
| 11.16 | isobutoxy-pyrimidin-2-yl | *—CH₃ | isobutanol | XIV.3 | 397 [M + H]⁺ | 1.97 (W) |
| 11.17 | (tetrahydrofuran-3-yloxy)pyrimidin-4-yl | *—CH₃ | (S)-tetrahydrofuran-3-ol | XIV.1 | 411 [M + H]⁺ | 1.76 (W) |
| 11.18 | (tetrahydrofuran-3-yloxy)pyrimidin-2-yl | *—CH₃ | (S)-tetrahydrofuran-3-ol | XIV.3 | 411 [M + H]⁺ | 1.7 (W) |
| 11.19 | (but-2-ynyloxy)pyrimidin-4-yl | *—CH₃ | but-2-yn-1-ol | XIV.1 | 393 [M + H]⁺ | 1.86 (W) |

-continued
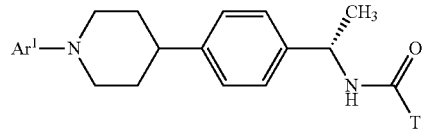
(11-1)
| Ex. | Ar¹ | T | E1 | E2 | ESI-MS [m/z] | $R_t$ (HPLC) [min] method |
|---|---|---|---|---|---|---|
| 11.20 | 2-(but-2-yn-1-yloxy)pyrimidin-4-yl | *—CH₃ | prop-2-yn-1-ol | XIV.3 | 393 [M + H]⁺ | 1.82 (W) |
| 11.21 | 2-(pentan-3-yloxy)pyrimidin-4-yl | *—CH₃ | pentan-3-ol | XIV.3 | 411 [M + H]⁺ | 2.01 (W) |
| 11.22 | 6-(pentan-3-yloxy)pyrimidin-4-yl | *—CH₃ | pentan-3-ol | XIV.1 | 411 [M + H]⁺ | 0.43 (V) |
| 11.23 | 2-(benzyloxy)pyrimidin-4-yl | *—CH₃ | benzyl alcohol | XIV.3 | 431 [M + H]⁺ | 1.95 (W) |
| 11.24 | 6-(benzyloxy)pyrimidin-4-yl | *—CH₃ | benzyl alcohol | XIV.1 | 431 [M + H]⁺ | 2.02 (W) |
| 11.25 | 6-(2-fluorophenoxy)pyrimidin-4-yl | *—CH₃ | 2-fluorophenol | XIV.1 | 435 [M + H]⁺ | 1.9 (W) |

(11-1)

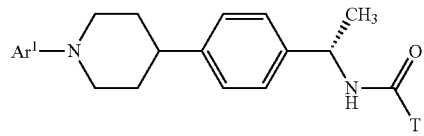

| Ex. | Ar¹ | T | E1 | E2 | ESI-MS [m/z] | R$_t$ (HPLC) [min] method |
|---|---|---|---|---|---|---|
| 11.26 | 2-fluorophenoxy pyrimidin-4-yl | *—CH₃ | 2-fluorophenol | XIV.3 | 435 [M + H]⁺ | 1.84 (W) |
| 11.27 | 3-fluorophenoxy pyrimidin-4-yl | *—CH₃ | 3-fluorophenol | XIV.1 | 435 [M + H]⁺ | 1.92 (W) |
| 11.28 | 3-fluorophenoxy pyrimidin-2-yl | *—CH₃ | 3-fluorophenol | XIV.3 | 435 [M + H]⁺ | 1.89 (W) |
| 11.29 | 2-methoxyethoxy pyrimidin-4-yl | *—CH₃ | 2-methoxyethanol | XIV.1 | 399 [M + H]⁺ | 1.74 (W) |
| 11.30 | 2-methoxyethoxy pyrimidin-2-yl | *—CH₃ | 2-methoxyethanol | XIV.3 | 399 [M + H]⁺ | 1.7 (W) |
| 11.31 | 3-methoxyphenoxy pyrimidin-4-yl | *—CH₃ | 3-methoxyphenol | XIV.1 | 447 [M + H]⁺ | 1.9 (W) |

-continued (11-1)

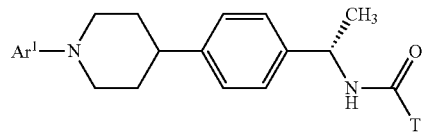

| Ex. | Ar¹ | T | E1 | E2 | ESI-MS [m/z] | R$_t$ (HPLC) [min] method |
|---|---|---|---|---|---|---|
| 11.32 | 3-methoxyphenoxy-phenyl-pyrimidine | *—CH₃ | 3-methoxyphenol | XIV.3 | 447 [M + H]⁺ | 1.87 (W) |
| 11.33 | pyridin-3-ylmethoxy-pyrimidine | *—CH₃ | pyridin-3-ylmethanol | XIV.1 | 432 [M + H]⁺ | 1.77 (W) |
| 11.34 | pyridin-3-ylmethoxy-pyrimidine | *—CH₃ | pyridin-3-ylmethanol | XIV.3 | 432 [M + H]⁺ | 1.7 (W) |
| 11.35 | cyanocyclopropyl-methoxy-pyrimidine | *—CH₃ | 1-(hydroxymethyl)cyclopropanecarbonitrile | XIV.1 | 420 [M + H]⁺ | 1.74 (W) |
| 11.36 | ethoxy-pyrimidine | *—CH₃ | ethanol | XIV.1 | 369 [M + H]⁺ | 1.83 (W) |
| 11.37 | ethoxy-pyrimidine | *—CH₃ | ethanol | XIV.3 | 369 [M + H]⁺ | 1.81 (W) |

-continued

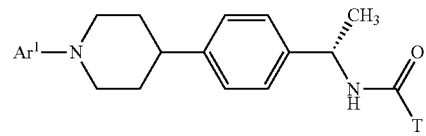
(11-1)

| Ex. | Ar¹ | T | E1 | E2 | ESI-MS [m/z] | R$_t$ (HPLC) [min] method |
|---|---|---|---|---|---|---|
| 11.38 | 2-isopropoxy-pyrimidin-4-yl | *—CH₃ | isopropanol | XIV.3 | 383 [M + H]⁺ | 1.88 (W) |
| 11.39 | 2-(1-phenylethylamino)pyrimidin-4-yl | *—CH₃ | 1-phenylethylamine | XIV.3 | 444 [M + H]⁺ | 1.92 (W) |
| 11.40 | 6-(1-phenylethylamino)pyrimidin-4-yl | *—CH₃ | 1-phenylethylamine | XIV.1 | 444 [M + H]⁺ | 1.8 (W) |
| 11.41 | 2-(propylamino)pyrimidin-4-yl | *—CH₃ | propylamine | XIV.3 | 382 [M + H]⁺ | 1.81 (W) |
| 11.42 | 6-(propylamino)pyrimidin-4-yl | *—CH₃ | propylamine | XIV.1 | 382 [M + H]⁺ | 1.68 (W) |
| 11.43 | 2-(isopropylamino)pyrimidin-4-yl | *—CH₃ | isopropylamine | XIV.3 | 382 [M + H]⁺ | 1.82 (W) |
| 11.44 | 6-(isopropylamino)pyrimidin-4-yl | *—CH₃ | isopropylamine | XIV.1 | 382 [M + H]⁺ | 1.68 (W) |

-continued (11-1)

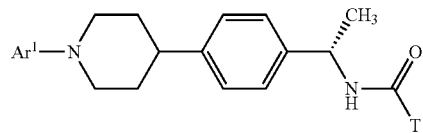

| Ex. | Ar¹ | T | E1 | E2 | ESI-MS [m/z] | R$_t$ (HPLC) [min] method |
|---|---|---|---|---|---|---|
| 11.45 | cyclobutyl-NH-pyrimidin-2-yl (4-*) | *—CH₃ | cyclobutyl-NH₂ | XIV.3 | 394 [M + H]⁺ | 1.85 (W) |
| 11.46 | cyclobutyl-NH-pyrimidin-4-yl (6-*) | *—CH₃ | cyclobutyl-NH₂ | XIV.1 | 394 [M + H]⁺ | 1.73 (W) |
| 11.47 | N-methyl-N-isopropyl-pyrimidin-2-yl (4-*) | *—CH₃ | N-methyl isopropylamine | XIV.3 | 396 [M + H]⁺ | 1.94 (W) |
| 11.48 | N-methyl-N-isopropyl-pyrimidin-4-yl (6-*) | *—CH₃ | N-methyl isopropylamine | XIV.1 | 396 [M + H]⁺ | 1.79 (W) |
| 11.49 | indolin-1-yl-pyrimidin-2-yl (4-*) | *—CH₃ | indoline | XIV.3 | 442 [M + H]⁺ | 2.07 (W) |
| 11.50 | ethyl-NH-pyrimidin-2-yl (4-*) | *—CH₃ | ethylamine | XIV.3 | 368 [M + H]⁺ | 1.73 (W) |
| 11.51 | ethyl-NH-pyrimidin-4-yl (6-*) | *—CH₃ | ethylamine | XIV.1 | 368 [M + H]⁺ | 1.6 (W) |

-continued
(11-1)
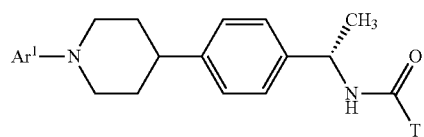
| Ex. | Ar¹ | T | E1 | E2 | ESI-MS [m/z] | R_t (HPLC) [min] method |
|---|---|---|---|---|---|---|
| 11.52 | (HN=pyridinylidene-N-pyrimidinyl) | *—CH₃ | 4-aminopyridine | XIV.1 | 417 [M + H]⁺ | 1.21 (B) |
| 11.53 | (4-methoxyphenyl-NH-pyrimidin-4-yl) | *—CH₃ | 4-methoxyaniline | XIV.1 | 446 [M + H]⁺ | 1.74 (W) |
| 11.54 | (4-methoxyphenyl-NH-pyrimidin-2-yl) | *—CH₃ | 4-methoxyaniline | XIV.3 | 446 [M + H]⁺ | 1.81 (W) |
| 11.55 | (benzyl-NH-pyrimidin-4-yl) | *—CH₃ | benzylamine | XIV.1 | 430 [M + H]⁺ | 1.75 (W) |
| 11.56 | (benzyl-NH-pyrimidin-2-yl) | *—CH₃ | benzylamine | XIV.3 | 430 [M + H]⁺ | 1.87 (W) |

-continued (11-1)

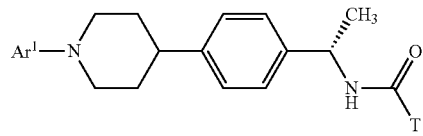

| Ex. | Ar¹ | T | E1 | E2 | ESI-MS [m/z] | R_t (HPLC) [min] method |
|---|---|---|---|---|---|---|
| 11.57 | piperidinyl-pyrimidine | *—CH₃ | piperidine (HN) | XIV.1 | 408 [M + H]⁺ | 1.83 (W) |
| 11.58 | piperidinyl-pyrimidine (2-position) | *—CH₃ | piperidine (HN) | XIV.3 | 408 [M + H]⁺ | 1.97 (W) |
| 11.59 | furfurylamino-pyrimidine | *—CH₃ | furfurylamine (H₂N-CH₂-furan) | XIV.1 | 420 [M + H]⁺ | 1.65 (W) |
| 11.60 | furfurylamino-pyrimidine (2-position) | *—CH₃ | furfurylamine (H₂N-CH₂-furan) | XIV.3 | 420 [M + H]⁺ | 1.77 (W) |
| 11.61 | cyclopentylamino-pyrimidine | *—CH₃ | cyclopentylamine (H₂N-cyclopentyl) | XIV.3 | 408 [M + H]⁺ | 1.92 (W) |
| 11.62 | butylamino-pyrimidine | *—CH₃ | H₂N-butyl | XIV.1 | 396 [M + H]⁺ | 1.78 (W) |

-continued

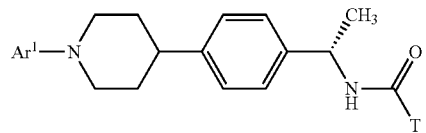

(11-1)

| Ex. | Ar¹ | T | E1 | E2 | ESI-MS [m/z] | R$_t$ (HPLC) [min] method |
|---|---|---|---|---|---|---|
| 11.63 | butyl-NH-pyrimidin-2-yl (4-position) | *—CH₃ | H₂N-propyl | XIV.3 | 396 [M + H]⁺ | 1.9 (W) |
| 11.64 | methoxyethyl-NH-pyrimidin-2-yl (4-position) | *—CH₃ | H₂N-CH₂CH₂-OCH₃ | XIV.3 | 398 [M + H]⁺ | 1.66 (W) |
| 11.65 | isobutyl-NH-pyrimidin-4-yl (6-position) | *—CH₃ | isobutyl-NH₂ | XIV.1 | 396 [M + H]⁺ | 1.76 (W) |
| 11.66 | isobutyl-NH-pyrimidin-2-yl (4-position) | *—CH₃ | isobutyl-NH₂ | XIV.3 | 396 [M + H]⁺ | 1.89 (W) |
| 11.67 | (pyridin-2-ylmethyl)-NH-pyrimidin-4-yl (6-position) | *—CH₃ | pyridin-2-yl-CH₂-NH₂ | XIV.1 | 431 [M + H]⁺ | 1.55 (W) |
| 11.68 | N-propyl-N-methyl-pyrimidin-4-yl (6-position) | *—CH₃ | propyl-NH-CH₃ | XIV.1 | 396 [M + H]⁺ | 1.8 (W) |

-continued
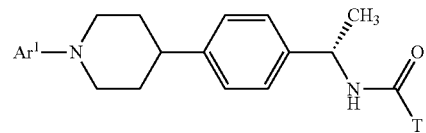
(11-1)
| Ex. | Ar¹ | T | E1 | E2 | ESI-MS [m/z] | R$_t$ (HPLC) [min] method |
|---|---|---|---|---|---|---|
| 11.69 | | *—CH₃ | | XIV.3 | 396 [M + H]⁺ | 1.95 (W) |
| 11.70 | | *—CH₃ | | XIV.1 | 410 [M + H]⁺ | 1.86 (W) |
| 11.71 | | *—CH₃ | | XIV.3 | 410 [M + H]⁺ | 1.97 (W) |
| 11.72 | | *—CH₃ | | XIV.1 | 444 [M + H]⁺ | 1.82 (W) |
| 11.73 | | *—CH₃ | | XIV.3 | 424 [M + H]⁺ | 1.68 (W) |
| 11.74 | | *—CH₃ | | XIV.1 | 424 [M + H]⁺ | 1.56 (W) |
| 11.75 | | *—CH₃ | | XIV.3 | 410 [M + H]⁺ | 1.96 (W) |

-continued
(11-1)
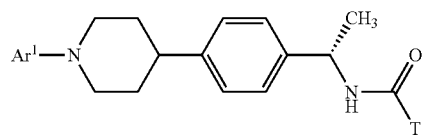
| Ex. | Ar¹ | T | E1 | E2 | ESI-MS [m/z] | R$_t$ (HPLC) [min] method |
|---|---|---|---|---|---|---|
| 11.76 | | *—CH₃ | | XIV.1 | 410 [M + H]⁺ | 1.82 (W) |
| 11.77 | | *—CH₃ | | XIV.1 | 434 [M + H]⁺ | 1.93 (W) |
| 11.78 | | *—CH₃ | | XIV.3 | 434 [M + H]⁺ | 2.07 (W) |
| 11.79 | | *—CH₃ | | XIV.1 | 410 [M + H]⁺ | 1.6 (W) |
| 11.80 | | *—CH₃ | | XIV.3 | 410 [M + H]⁺ | 1.7 (W) |

-continued

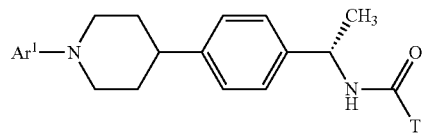

(11-1)

| Ex. | Ar¹ | T | E1 | E2 | ESI-MS [m/z] | R$_t$ (HPLC) [min] method |
|---|---|---|---|---|---|---|
| 11.81 | (4-methoxypiperidin-1-yl-pyrimidinyl) | *—CH₃ | (4-methoxypiperidine) | XIV.1 | 438 [M + H]⁺ | 1.69 (W) |
| 11.82 | (N-benzyl-N-methylamino-pyrimidinyl) | *—CH₃ | (N-methylbenzylamine) | XIV.1 | 444 [M + H]⁺ | 1.88 (W) |
| 11.83 | (N-benzyl-N-methylamino-pyrimidinyl) | *—CH₃ | (N-methylbenzylamine) | XIV.3 | 444 [M + H]⁺ | 2.00 (W) |
| 11.84 | (methylamino-pyrimidinyl) | *—CH₃ | H₂N— | XIV.3 | 354 [M + H]⁺ | 1.63 (W) |
| 11.85 | (methylamino-pyrimidinyl) | *—CH₃ | H₂N— | XIV.1 | 354 [M + H]⁺ | 1.51 (W) |
| 11.86 | (N-cyclopropyl-N-methylamino-pyrimidinyl) | *—CH₃ | (N-methylcyclopropylamine) | XIV.3 | 394 [M + H]⁺ | 1.90 (W) |

-continued

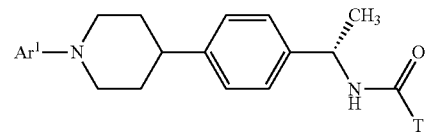
(11-1)

| Ex. | Ar¹ | T | E1 | E2 | ESI-MS [m/z] | R_t (HPLC) [min] method |
|---|---|---|---|---|---|---|
| 11.87 | (N-cyclopropyl-N-methyl-pyrimidin-4-yl) | *—CH₃ | N-methyl-cyclopropylamine | XIV.1 | 394 [M + H]⁺ | 1.75 (W) |
| 11.88 | (2-isoindolinyl-pyrimidin-2-yl) | *—CH₃ | isoindoline | XIV.3 | 442 [M + H]⁺ | 2.06 (W) |
| 11.89 | (2-isoindolinyl-pyrimidin-4-yl) | *—CH₃ | isoindoline | XIV.1 | 442 [M + H]⁺ | 1.91 (W) |
| 11.90 | (N-cyclopropylmethyl-N-methyl-pyrimidin-2-yl) | *—CH₃ | N-methyl-cyclopropylmethylamine | XIV.3 | 408 [M + H]⁺ | 1.96 (W) |
| 11.91 | (N-cyclopropylmethyl-N-methyl-pyrimidin-4-yl) | *—CH₃ | N-methyl-cyclopropylmethylamine | XIV.1 | 408 [M + H]⁺ | 1.82 (W) |
| 11.92 | (5-azaspiro[2.4]heptan-5-yl-pyrimidin-4-yl) | *—CH₃ | 5-azaspiro[2.4]heptane | XIV.1 | 420 [M + H]⁺ | 1.84 (W) |

-continued (11-1)

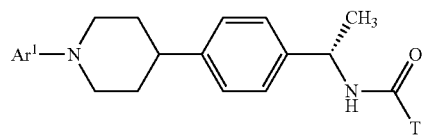

| Ex. | Ar¹ | T | E1 | E2 | ESI-MS [m/z] | $R_t$ (HPLC) [min] method |
|---|---|---|---|---|---|---|
| 11.93 | spiro[2.4]heptane-pyrrolidine-pyrimidine | *—CH₃ | spiro[2.4]heptane-pyrrolidine NH | XIV.3 | 420 [M + H]⁺ | 1.99 (W) |
| 11.94 | cyclobutylmethyl-NH-pyrimidine | *—CH₃ | cyclobutylmethyl-NH₂ | XIV.3 | 408 [M + H]⁺ | 1.93 (W) |
| 11.95 | cyclobutylmethyl-NH-pyrimidine | *—CH₃ | cyclobutylmethyl-NH₂ | XIV.1 | 408 [M + H]⁺ | 1.80 (W) |
| 11.96 | N-methyl-N-cyclopentyl-pyrimidine | *—CH₃ | N-methyl-cyclopentylamine | XIV.3 | 422 [M + H]⁺ | 2.05 (W) |
| 11.97 | N-methyl-N-cyclopentyl-pyrimidine | *—CH₃ | N-methyl-cyclopentylamine | XIV.1 | 422 [M + H]⁺ | 1.92 (W) |
| 11.98 | azetidinyl-pyrimidine | *—CH₃ | azetidine | XIV.3 | 380 [M + H]⁺ | 1.77 (W) |

-continued (11-1)

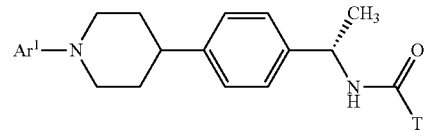

| Ex. | Ar¹ | T | E1 | E2 | ESI-MS [m/z] | $R_t$ (HPLC) [min] method |
|---|---|---|---|---|---|---|
| 11.99 | azetidinyl-pyrimidinyl | *—CH₃ | azetidine (NH) | XIV.1 | 380 [M + H]⁺ | 1.65 (W) |
| 11.100 | furfurylamino-pyrimidinyl | *—CH₃ | furan-3-CH₂NH₂ | XIV.3 | 420 [M + H]⁺ | 1.76 (W) |
| 11.101 | furfurylamino-pyrimidinyl | *—CH₃ | furan-3-CH₂NH₂ | XIV.1 | 420 [M + H]⁺ | 1.64 (W) |
| 11.102 | 2-fluoroethylamino-pyrimidinyl | *—CH₃ | H₂N-CH₂CH₂-F | XIV.3 | 386 [M + H]⁺ | 1.65 (W) |
| 11.103 | cyclopentylamino-pyrimidinyl | *—CH₃ | H₂N-cyclopentyl | XIV.1 | 408 [M + H]⁺ | 1.79 (W) |
| 11.104 | dimethylamino-pyrimidinyl | *—CH₃ | HN(CH₃)₂ | XIV.3 | 368 [M + H]⁺ | 1.80 (W) |
| 11.105 | dimethylamino-pyrimidinyl | *—CH₃ | HN(CH₃)₂ | XIV.1 | 368 [M + H]⁺ | 1.63 (W) |

-continued

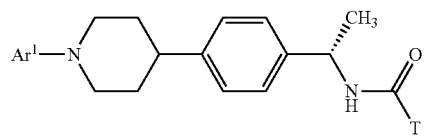
(11-1)

| Ex. | Ar¹ | T | E1 | E2 | ESI-MS [m/z] | R_t (HPLC) [min] method |
|---|---|---|---|---|---|---|
| 11.106 | cyclopropylethyl-NH-pyrimidin-2-yl | *—CH₃ | H₂N-CH₂-CH₂-cyclopropyl | XIV.3 | 408 [M + H]⁺ | 1.91 (W) |
| 11.107 | cyclopropylethyl-NH-pyrimidin-4-yl | *—CH₃ | H₂N-CH₂-CH₂-cyclopropyl | XIV.1 | 408 [M + H]⁺ | 1.78 (W) |
| 11.108 | cyclopropylmethoxy-pyrimidin-4-yl | *—CH₃ | HO-CH₂-cyclopropyl | XIV.1 | 395 [M + H]⁺ | 1.79 (P) |
| 11.109 | cyclobutoxy-pyrimidin-4-yl | *—CH₃ | HO-cyclobutyl | XIV.1 | 395 [M + H]⁺ | 1.81 (P) |
| 11.110 | cyclobutoxy-pyrimidin-2-yl | *—CH₃ | HO-cyclobutyl | XIV.3 | 395 [M + H]⁺ | 1.63 (P) |
| 11.111 | cyclopropylmethyl-NH-pyrimidin-2-yl | *—CH₃ | H₂N-CH₂-cyclopropyl | XIV.3 | 394 [M + H]⁺ | 1.40 (P) |
| 11.112 | cyclopropylmethyl-NH-pyrimidin-4-yl | *—CH₃ | H₂N-CH₂-cyclopropyl | XIV.1 | 394 [M + H]⁺ | 1.65 (P) |

-continued (11-1)

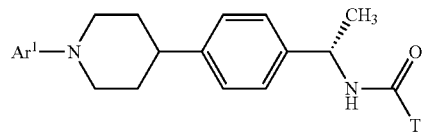

| Ex. | Ar¹ | T | E1 | E2 | ESI-MS [m/z] | R$_t$ (HPLC) [min] method |
|---|---|---|---|---|---|---|
| 11.113 | pyrrolidinyl-pyrimidin-4-yl | *—CH₃ | pyrrolidine NH | XIV.1 | 394 [M + H]⁺ | 1.54 (P) |
| 11.114 | pyrrolidinyl-pyrimidin-4-yl | *—CH₃ | pyrrolidine NH | XIV.3 | 394 [M + H]⁺ | 1.68 (P) |
| 11.115 | cyclopropylamino-pyrimidin-4-yl | *—CH₃ | cyclopropylamine NH₂ | XIV.3 | 380 [M + H]⁺ | 1.32 (P) |
| 11.116 | hydroxy-pyrimidin-4-yl | *—CH₃ | pyrrolidine NH | XIV.1 | 341 [M + H]⁺ | 1.40 (P) |
| 11.117 | pyrimidin-5-ylamino-pyrimidin-4-yl | *—CH₃ | 5-aminopyrimidine | XIV.3 | 418 [M + H]⁺ | 1.18 (P) |
| 11.118 | phenylamino-pyrimidin-4-yl | *—CH₃ | phenol OH | XIV.1 | 417 [M + H]⁺ | 2.09 (P) |
| 11.119 | phenoxy-pyrimidin-4-yl | *—CH₃ | phenol OH | XIV.3 | 417 [M + H]⁺ | 1.65 (P) |

-continued

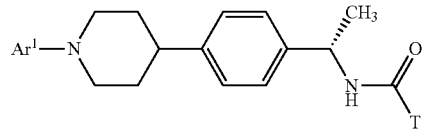

(11-1)

| Ex. | Ar¹ | T | E1 | E2 | ESI-MS [m/z] | R_t (HPLC) [min] method |
|---|---|---|---|---|---|---|
| 11.120 | 4-F-phenyl-O-(5-F-pyrimidin-2-yl) | cyclopropyl | 4-fluorophenol | 5.36 | 479 [M + H]⁺ | 1.11 (AC) |
| 11.121 | pyrrolidin-1-yl-(5-F-pyrimidin-2-yl) | cyclopropyl | pyrrolidine | 5.36 | 438 [M + H]⁺ | 1.11 (AC) |
| 11.122 | pyrrolidin-1-yl-(5-CN-pyrimidin-2-yl) | cyclopropyl | pyrrolidine | XIV.4 | 445 [M + H]⁺ | 1.23 (AC) |
| 11.123 | pyrrolidin-1-yl-(5-F-pyrimidin-4-yl) | cyclopropyl | pyrrolidine | 5.37 | 438 [M + H]⁺ | 1.15 (AC) |
| 11.124 | cyclobutyl-O-(5-F-pyrimidin-2-yl) | cyclopropyl | cyclobutanol | 5.36 | 439 [M + H]⁺ | 1.12 (AC) |

-continued

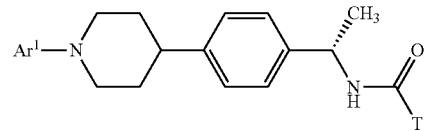
(11-1)

| Ex. | Ar¹ | T | E1 | E2 | ESI-MS [m/z] | $R_t$ (HPLC) [min] method |
|---|---|---|---|---|---|---|
| 11.125 | cyclopropylmethyl-N(Me)-pyrimidine-5-F | cyclopropyl* | cyclopropylmethyl-NH— | 5.36 | 452 [M + H]⁺ | 1.07 (AC) |
| 11.126 | cyclopropylmethyl-N(Me)-pyrimidine-5-CN | cyclopropyl* | cyclopropylmethyl-NH— | XIV.4 | 459 [M + H]⁺ | 1.16 (AC) |
| 11.127 | cyclopropylmethyl-N(Me)-5-CN-pyrimidine | cyclopropyl* | cyclopropylmethyl-NH— | XIV.5 | 459 [M + H]⁺ | 1.18 (AC) |
| 11.128 | pyrimidine-F-N(Me)-cyclopropylmethyl | cyclopropyl* | cyclopropylmethyl-NH— | 5.37 | 452 [M + H]⁺ | 1.08 (AC) |
| 11.129 | isopropoxy-pyrimidine-5-F | cyclopropyl* | isopropanol-OH | 5.36 | 427 [M + H]⁺ | 0.99 (AC) |

(11-1)

[Structure: Ar¹—N-piperidine-phenyl-CH(CH₃)-NH-C(=O)-T]

| Ex. | Ar¹ | T | E1 | E2 | ESI-MS [m/z] | R_t (HPLC) [min] method |
|---|---|---|---|---|---|---|
| 11.130 | [5-fluoro-6-isopropoxy-pyrimidin-4-yl] | *-cyclopropyl | *-CH(CH₃)₂-OH (isopropanol) | 5.37 | 427 [M+H]⁺ | 0.97 (AC) |
| 11.131 | [2-(cyclopropylmethoxy)-pyrimidin-4-yl] | *—CH₃ | HO-CH₂-cyclopropyl | XIV.3 | 395 [M+H]⁺ | 1.60 (P) |
| 11.132 | [6-(cyclopropylamino)-pyrimidin-4-yl] | *—CH₃ | cyclopropyl-NH₂ | XIV.! | 380 [M+H]⁺ | 1.54 (P) |

Example 12

Example 12.1

N-[2-(4-{1-[2-(Cyclopentyl-methyl-amino)-pyrimidin-4-yl]-piperidin-4-yl}-phenyl)-1-methyl-ethyl]-acetamide

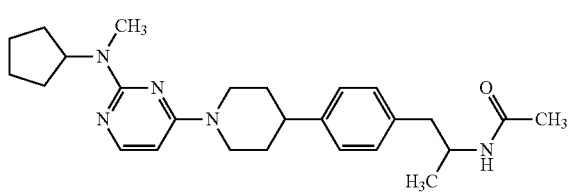 [SMILES: CC(=O)NC(C)Cc1ccc(C2CCN(c3ccnc(N(C)C4CCCC4)n3)CC2)cc1]

181 µL (1.61 mmol) N-Methyl-cyclopentylamine are added to 120 mg (0.32 mmol) N-(2-{4-[1-(2-chloro-pyrimidin-4-yl)-piperidin-4-yl]-phenyl}-1-methyl-ethyl)-acetamide (XIV.2) in 3 mL acetonitrile. The mixture is heated at 150° C. for 30 min under microwave irradiation. After that time, the solvent is evaporated and the residue is purified using reversed phase HPLC (eluent A: water+0.1% TFA, eluent B: acetonitrile+0.1% TFA) to yield the desired product.

$C_{26}H_{37}N_5O$ (M=435.6 g/mol), ESI-MS: 436 [M+H]⁺

Example 13

Example 13.1

(S)—N-(1-{4-[1-(2-Cyano-4-propoxy-phenyl)-piperidin-4-yl]-phenyl}-ethyl)-acetamide

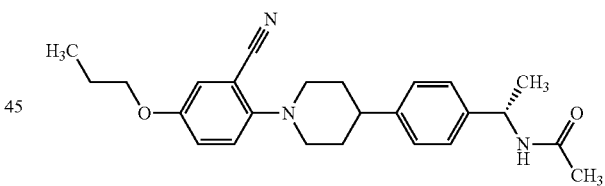

100 mg (0.41 mmol) (S)—N-[1-(Piperidin-4-yl-phenyl)-ethyl]-acetamide (V.1) in 2 mL DMSO are added to a mixture of 97 mg (0.41 mmol) 2-bromo-5-propoxy-benzonitrile, 112 mg (0.82 mmol) potassium carbonate, 7.7 mg (0.041 mmol) copper(I) iodide and 9 mg (0.08 mmol) (L)-proline under inert gas atmosphere. The mixture is stirred for 7 d at 90° C. After that time, water is added and the mixture is extracted with ethyl acetate. The organic layer is dried over sodium sulphate and the solvent is removed in vacuo. The residue is purified by HPLC (column: Waters XBridge 5 µM; eluent A: water+0.3% NH₄OH, eluent B: MeOH) to yield the desired product.

$C_{25}H_{31}N_3O_2$ (M=405.5 g/mol), ESI-MS: 406 [M+H]⁺

R_t (HPLC): 2.23 min (method A)

The following compounds of general formula (13-1) are prepared analogously to Example 13.1, the educts used being shown in the column headed "E 1" and "E 2":

(13-1)

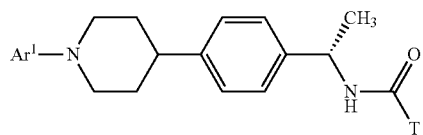

| Ex. | Ar¹ | T | E 1 | E 2 | ESI-MS [m/z] | $R_t$ (HPLC) [min] (method) |
|---|---|---|---|---|---|---|
| 13.1 | 3-cyano-4-*-phenyl, 5-propoxy | *—CH₃ | 3-cyano-5-propoxy-2-bromo-phenyl | V.1 | 406 [M + H]⁺ | 2.23 (A) |
| 13.2 | 3-cyano-4-*-phenyl, 5-(cyclopropylmethoxy) | *—CH₃ | 3-cyano-5-(cyclopropylmethoxy)-2-bromo-phenyl | V.1 | 418 [M + H]⁺ | 2.21 (A) |
| 13.3 | 3-cyano-4-*-phenyl, 5-ethoxymethoxy | *—CH₃ | 3-cyano-5-ethoxymethoxy-2-bromo-phenyl | V.1 | 392 [M + H]⁺ | 2.13 (A) |

Example 14

Example 14.1

(S)-1-(1-{4-[1-(4-Ethoxy-phenyl)-piperidin-4-yl]-phenyl}-ethyl)-3-methyl-urea

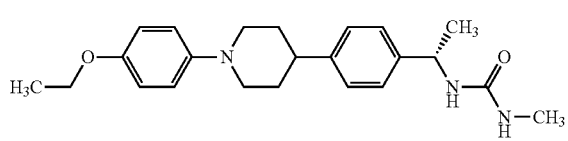

To 100 mg (0.31 mmol) (S)-1-{4-[1-(4-ethoxy-phenyl)-piperidin-4-yl]-phenyl}-ethylamine (XIII.1) in 2 mL DMF, 87 µL (0.62 mmol) TEA and 52 mg (0.32 mmol) CDI are added at 0° C. and the mixture is stirred for 30 min at 0° C. Subsequently 48 mg (1.54 mmol) methylamine are added and stirring is continued for 1 h at 50° C. The mixture is filtered through basic aluminum oxide and concentrated in vacuo. The residue is purified using reversed phase column chromatography (water+0.15% NH₄OH; acetone) and the corresponding fractions are concentrated to yield the desired product.

$C_{23}H_{31}N_{13}O_2$ (M=381.5 g/mol), ESI-MS: 382 [M+H]⁺

$R_t$ (HPLC): 2.10 min (method A)

The following compounds of general formula (14-1) are prepared analogously to Example 14.1. In case of Example 14.5 CDT is used instead of CDI. The educts used are shown in the column headed "E 1" and "E 2":

(14-1)

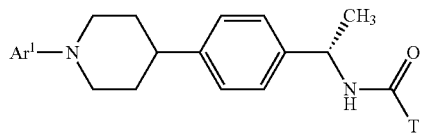

| Ex. | Ar¹ | T | E 1 | E 2 | ESI-MS [m/z] | $R_t$ (HPLC) [min] (method) |
|---|---|---|---|---|---|---|
| 14.1 | H₃C—O—⟨phenyl⟩—* | *—N(H)—CH₃ | XIII.1 | methylamine | 382 [M + H]⁺ | 2.10 (A) |
| 14.2 | H₃C—O—⟨phenyl⟩—* | *—N(H)—CH₂CH₃ | XIII.1 | ethylamine | 396 [M + H]⁺ | 2.14 (A) |
| 14.3 | H₃C—O—⟨phenyl⟩—* | *—N(H)—cyclopropyl | XIII.1 | cyclopropyl-amine | 408 [M + H]⁺ | 2.19 (A) |
| 14.4 | H₃C—O—⟨phenyl⟩—* | *—N(H)—phenyl | XIII.1 | aniline | 444 [M + H]⁺ | 1.94 (A) |
| 14.5 | CH₃CH₂—O—⟨phenyl⟩—* | *—NH₂ | XIII.1 | ammonia | 368 [M + H]⁺ | 1.13 (G) |

Example 14.50

(S)-1-Cyclopropyl-3-(1-{4-[1-(4-ethoxy-phenyl)-piperidin-4-yl]-phenyl}-ethyl)-1-methylurea

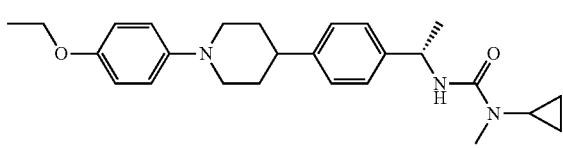 [SMILES: CCOc1ccc(N2CCC(c3ccc([C@H](C)NC(=O)N(C)C4CC4)cc3)CC2)cc1]

To 32.5 mg (0.10 mmol) (S)-1-{4-[1-(4-ethoxy-phenyl)-piperidin-4-yl]-phenyl}-ethylamine (XIII.1) in 1.5 mL dioxane, 30 μL (0.20 mmol) DBU and 33 mg (0.20 mmol) CDT are added at rt and the mixture is stirred for 5 min. Subsequently 8.5 mg (0.15 mmol cyclopropyl-methyl-amine are added and stirring is continued over night. The mixture is concentrated in vacuo. The residue is purified using reversed phase column chromatography (water+0.1% TFA:MeOH) and the corresponding fractions are concentrated to yield the desired product.

$C_{26}H_{35}N_3O_2$ (M=421.6 g/mol), ESI-MS: 422 [M+H]⁺

$R_t$ (HPLC): 1.24 min (method B)

The following compounds of general formula (14-1) are prepared analogously to Example 14.50. In case that aromatic amines are used as reagents the activation step was inverted and the aromatic amines are first treated with CDT prior to addition to XIII.1. The educts used are shown in the column headed "E 1" and "E 2":

(14-1)

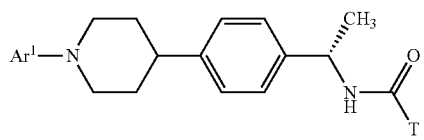

| Ex. | Ar¹ | T | E 1 | E 2 | ESI-MS [m/z] | R$_t$ (HPLC) [min] (method) |
|---|---|---|---|---|---|---|
| 14.50 | H₃C–O–C₆H₄–* | *N(CH₃)(cyclopropyl) | XIII.1 | HN(CH₃)(cyclopropyl) | 422 [M + H]⁺ | 2.13 (W) |
| 14.51 | H₃C–O–C₆H₄–* | H₃C-CH₂-N(CH₃)-* | XIII.1 | H₃C-CH₂-NH-CH₃ | 410 [M + H]⁺ | 2.06 (W) |
| 14.52 | H₃C–O–C₆H₄–* | cyclobutyl-NH-* | XIII.1 | cyclobutyl-NH₂ | 422 [M + H]⁺ | 2.1 (W) |
| 14.53 | H₃C–O–C₆H₄–* | *N(CH₃)CH(CH₃)₂ | XIII.1 | H₃C-NH-CH(CH₃)₂ | 424 [M + H]⁺ | 2.1 (W) |
| 14.54 | H₃C–O–C₆H₄–* | H₃C-CH₂-CH₂-N(CH₃)-* | XIII.1 | H₃C-CH₂-CH₂-NH-CH₃ | 424 [M + H]⁺ | 2.12 (W) |
| 14.55 | H₃C–O–C₆H₄–* | pyridin-3-yl-NH-* | XIII.1 | pyridin-3-yl-NH₂ | 445 [M + H]⁺ | 2.07 (W) |
| 14.56 | H₃C–O–C₆H₄–* | *NH-pyrimidin-2-yl | XIII.1 | H₂N-pyrimidin-2-yl | 446 [M + H]⁺ | 2.11 (W) |
| 14.57 | H₃C–O–C₆H₄–* | *NH-thiazol-2-yl | XIII.1 | NH₂-thiazol-2-yl | 451 [M + H]⁺ | 1.56 (U) |
| 14.58 | H₃C–O–C₆H₄–* | *NH-pyridazin-4-yl | XIII.1 | NH₂-pyridazin-4-yl | 446 [M + H]⁺ | 2.03 (W) |
| 14.59 | H₃C–O–C₆H₄–* | pyrimidin-5-yl-NH-* | XIII.1 | pyrimidin-5-yl-NH₂ | 446 [M + H]⁺ | 2.03 (W) |

(14-1)

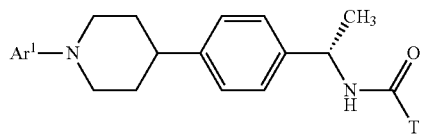

| Ex. | Ar¹ | T | E 1 | E 2 | ESI-MS [m/z] | $R_t$ (HPLC) [min] (method) |
|---|---|---|---|---|---|---|
| 14.60 | H₃C-O-C₆H₄-* | (pyrimidin-4-yl)methyl-NH-* | XIII.1 | (pyrimidin-4-yl)methyl-NH₂ | 460 [M + H]⁺ | 1.99 (W) |
| 14.61 | H₃C-O-C₆H₄-* | 2-(1H-pyrazol-4-yl)ethyl-N(CH₃)-* | XIII.1 | 2-(1H-pyrazol-4-yl)ethyl-NH(CH₃) | 476 [M + H]⁺ | 2.01 (W) |
| 14.62 | H₃C-O-C₆H₄-* | (pyrimidin-5-yl)methyl-NH-* | XIII.1 | (pyrimidin-5-yl)methyl-NH₂ | 460 [M + H]⁺ | 1.99 (W) |
| 14.63 | H₃C-O-C₆H₄-* | morpholin-4-yl-* | XIII.1 | morpholine | 438 [M + H]⁺ | 2.04 (W) |
| 14.64 | H₃C-O-C₆H₄-* | (1-methyl-1H-pyrazol-3-yl)methyl-N(CH₃)-* | XIII.1 | (1-methyl-1H-pyrazol-3-yl)methyl-NH(CH₃) | 476 [M + H]⁺ | 2.04 (W) |
| 14.65 | H₃C-O-C₆H₄-* | cyclopropylmethyl-N(CH₃)-* | XIII.1 | cyclopropylmethyl-NH(CH₃) | 436 [M + H]⁺ | 2.12 (W) |
| 14.66 | H₃C-O-C₆H₄-* | azetidin-1-yl-* | XIII.1 | azetidine | 408 [M + H]⁺ | 2.04 (W) |
| 14.67 | H₃C-O-C₆H₄-* | N,N-diethyl-* | XIII.1 | diethylamine | 424 [M + H]⁺ | 2.14 (W) |
| 14.68 | H₃C-O-C₆H₄-* | pyrrolidin-1-yl-* | XIII.1 | pyrrolidine | 422 [M + H]⁺ | 2.09 (W) |
| 14.69 | H₃C-O-C₆H₄-* | piperidin-1-yl-* | XIII.1 | piperidine | 436 [M + H]⁺ | 2.12 (W) |

(14-1)

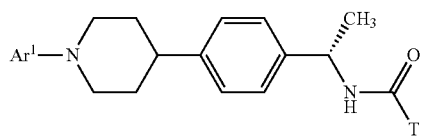

| Ex. | Ar¹ | T | E 1 | E 2 | ESI-MS [m/z] | $R_t$ (HPLC) [min] (method) |
|---|---|---|---|---|---|---|
| 14.70 | H₃C—O—(phenyl)—* | *—NH—(isoxazole) | XIII.1 | H₂N—(isoxazole) | 435 [M + H]⁺ | 1.01 (L) |

Example 15

Example 15.1

(S)-(4-{4-[4-(1-Acetylamino-ethyl)-phenyl]-piperidin-1-yl}-phenyl)-acetic acid methyl ester

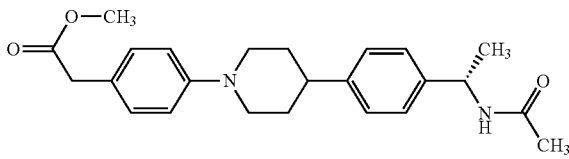 [SMILES: COC(=O)Cc1ccc(N2CCC(c3ccc([C@H](C)NC(C)=O)cc3)CC2)cc1]

1.2 mL Toluene/tert-butanol (5:1) are added to a mixture of 100 mg (0.41 mmol) (S)—N-[1-(piperidin-4-yl-phenyl)-ethyl]-acetamide (V.1), 93 mg (0.41 mmol) 4-bromo-phenyl-acetic acid methyl ester, 10 mg (0.020 mmol) X-Phos and 4.5 mg (0.020 mmol) palladium(II) acetate. Finally 132 mg (0.41 mmol) cesium carbonate are added under inert gas atmosphere. The mixture is stirred for 12 h at 90° C. in a sealed tube under inert gas atmosphere. After that time, the mixture is diluted with 1 mL methanol and the residue is purified by HPLC (column: Waters XBridge 5 μM; eluent A: water+ 0.10% NH₄OH, eluent B: MeOH) to yield the desired product.

$C_{24}H_{30}N_2O_3$ (M=394.5 g/mol), ESI-MS: 395 [M+H]⁺

$R_t$ (HPLC): 1.10 min (method F)

The following compounds of general formula (15-1) are prepared analogously to Example 15.1, the educts used being shown in the column headed "Educts":

(15-1)

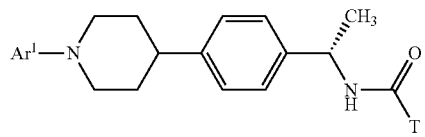

| Example | Ar¹ | T | Educt 1 | Educt 2 | ESI-MS [m/z] | $R_t$ (HPLC) [min] (method) |
|---|---|---|---|---|---|---|
| 15.1 | O=C(O—CH₃)—CH₂—(phenyl)—* | *—CH₃ | O=C(O—CH₃)—CH₂—(phenyl)—Br | V.1 | 395 [M + H]⁺ | 1.10 (G) |
| 15.2 | O=C(O—CH₃)—(phenyl)—* | *—CH₃ | O=C(O—CH₃)—(phenyl)—Br | V.1 | 381 [M + H]⁺ | 1.15 (G) |

-continued

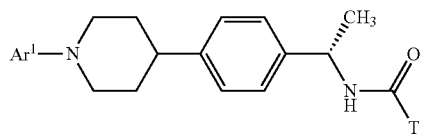
(15-1)

| Example | Ar¹ | T | Educt 1 | Educt 2 | ESI-MS [m/z] | R_t (HPLC) [min] (method) |
|---|---|---|---|---|---|---|
| 15.3 | 2-benzyloxy-pyridin-4-yl | *—CH₃ | 4-bromo-2-benzyloxy-pyridine | V.1 | 430 [M + H]⁺ | 1.12 (AB) |
| 15.4 | 2,4-dimethyl-benzoxazol-6-yl | *—CH₃ | 6-bromo-2,4-dimethyl-benzoxazole | V.1 | 392 [M + H]⁺ | 1.19 (B) |
| 15.5 | 6-methyl-pyridin-3-yl | *—CH₃ | 5-bromo-2-methyl-pyridine | V.1 | 338 [M + H]⁺ | 1.02 (B) |
| 15.6 | 2-isopropyl-benzoxazol-5-yl | *—CH₃ | 5-bromo-2-isopropyl-benzoxazole | V.1 | 406 [M + H]⁺ | 1.26 (B) |
| 15.7 | 2-(methoxymethyl)-benzoxazol-5-yl | *—CH₃ | 5-bromo-2-(methoxymethyl)-benzoxazole | V.1 | 408 [M + H]⁺ | 1.07 (B) |
| 15.8 | 6-(trifluoromethyl)-pyridin-3-yl | *—CH₃ | 5-bromo-2-(trifluoromethyl)-pyridine | V.1 | 392 [M + H]⁺ | 1.76 (B) |
| 15.9 | 5-methoxy-pyridin-3-yl | *—CH₃ | 3-bromo-5-methoxy-pyridine | V.1 | 354 [M + H]⁺ | 1.07 (B) |
| 15.10 | 4-methyl-pyridin-3-yl | *—CH₃ | 3-bromo-4-methyl-pyridine | V.1 | 338 [M + H]⁺ | 1.05 (B) |
| 15.11 | 6-(thiophen-2-yl)-pyridin-3-yl | *—CH₃ | 5-bromo-2-(thiophen-2-yl)-pyridine | V.1 | 406 [M + H]⁺ | 1.44 (B) |

-continued (15-1)

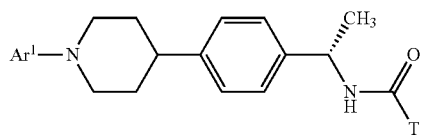

| Example | Ar¹ | T | Educt 1 | Educt 2 | ESI-MS [m/z] | R_t (HPLC) [min] (method) |
|---|---|---|---|---|---|---|
| 15.12 | 5-(2-tert-butyl)pyridin-2-yl | *—CH₃ | 5-bromo-2-tert-butylpyridine | V.1 | 380 [M + H]⁺ | 1.18 (B) |
| 15.13 | 2-methylbenzoxazol-5-yl | *—CH₃ | 5-bromo-2-methylbenzoxazole | V.1 | 378 [M + H]⁺ | 1.05 (B) |
| 15.14 | 2-cyclopropylbenzoxazol-5-yl | *—CH₃ | 5-bromo-2-cyclopropylbenzoxazole | V.1 | 404 [M + H]⁺ | 1.20 (B) |
| 15.15 | 2-methylbenzoxazol-6-yl | *—CH₃ | 6-bromo-2-methylbenzoxazole | V.1 | 378 [M + H]⁺ | 1.05 (B) |
| 15.16 | 2-methylpyridin-4-yl | *—CH₃ | 4-bromo-2-methylpyridine | V.1 | 338 [M + H]⁺ | 0.98 (B) |
| 15.17 | ethyl 5-benzofuran-2-carboxylate | *—CH₃ | ethyl 5-bromobenzofuran-2-carboxylate | V.1 | 435 [M + H]⁺ | 1.27 (B) |
| 15.18 | 5-ethoxy-2-cyanophenyl | *—OCH₃ | 2-bromo-5-ethoxybenzonitrile | V.2 | 408 [M + H]⁺ | 1.65 (N) |

The following compounds of general formula (15-2) are prepared analogously to Example 15.1, the educts used being shown in the column headed "Educts":

(15-2)

| Example | Ar¹ | T | Educt 1 | Educt 2 | ESI-MS [m/z] | $R_t$ (HPLC) [min] (method) |
|---|---|---|---|---|---|---|
| 15.19 | (2-phenoxypyridin-4-yl) | *—CH₃ | (4-bromo-2-phenoxypyridine) | XXIII.2 | 430 [M + H]⁺ | 1.20 (N) |
| 15.20 | (4-propoxy-2-methoxyphenyl) | *—CH₃ | (4-bromo-2-methoxy-5-propoxybenzene) | XXIII.2 | 425 [M + H]⁺ | 1.20 (N) |
| 15.21 | (4-(2-methylpropoxy)phenyl) | *—CH₃ | (4-bromo-(2-methylpropoxy)benzene) | XXIII.3 | 409 [M + H]⁺ | 1.26 (N) |

The following compounds of general formula (15-3) are prepared analogously to Example 15.1, the educts used being shown in the column headed "Educts":

(15-3)

| Example | Ar¹ | T | Educt 1 | Educt 2 | ESI-MS [m/z] | $R_t$ (HPLC) [min] (method) |
|---|---|---|---|---|---|---|
| 15.22 | (4-(cyclopropylmethoxy)phenyl) | *—CH₃ | (4-bromo-(cyclopropylmethoxy)benzene) | V.6 | 393 [M + H]⁺ | 2.10 (A) |
| 15.23 | | *—CH₃ | | V.6 | 411 [M + H]⁺ | 2.21 (A) |

Example 16

Example 16.1

(S)—N-(1-M{4-[1-(2-Ethoxy-pyrimidin-5-yl)-piperidin-4-yl]-phenyl}-ethyl)-acetamide

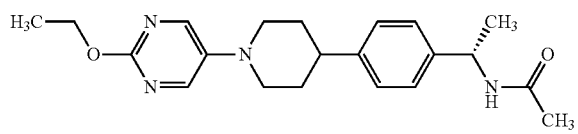

3.0 mL Toluene are added to a mixture of 100 mg (0.41 mmol) (S)—N-[1-(piperidin-4-yl-phenyl)-ethyl]-acetamide (V.1), 82 mg (0.41 mmol) 5-bromo-2-ethoxy-pyrimidine, 24 mg (0.082 mmol) BINAP and 9.1 mg (0.041 mmol) palladium(II) acetate. Finally 200 mg (0.61 mmol) cesium carbonate are added under inert gas atmosphere. The mixture is stirred for 12 h at 120° C. in a sealed tube under inert gas atmosphere. After that time, 1 mL water is added, the mixture is extracted with ethyl acetate and the organic layer is separated and washed with water. The organic layer is dried over sodium sulphate and the solvent is removed in vacuo. The residue is purified by HPLC (column: Waters XBridge 5 μM; eluent A: water+0.30% NH$_4$OH, eluent B: MeOH) to yield the desired product.

$C_{21}H_{28}N_4O_2$ (M=368.5 g/mol), ESI-MS: 369 [M+H]$^+$
$R_t$ (HPLC): 1.02 min (method G)

The following compounds of general formula (16-1) are prepared analogously to Example 16.1, the educts used being shown in the column headed "Educts":

(16-1)

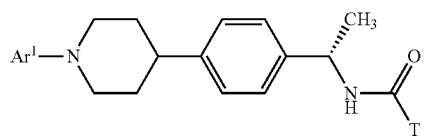

| Example | Ar$^1$ | T | Educt 1 | Educt 2 | ESI-MS [m/z] | R$_t$ (HPLC) [min] (method) |
|---|---|---|---|---|---|---|
| 16.1 | H$_3$C-O-pyrimidin-5-yl | *—CH$_3$ | H$_3$C-O-pyrimidin-Br | V.1 | 369 [M + H]$^+$ | 1.02 (G) |
| 16.2 | H$_3$C-O-pyrimidin-5-yl | *—CH$_3$ | H$_3$C-O-pyrimidin-Br | V.1 | 355 [M + H]$^+$ | 0.87 (H) |
| 16.3 | H$_3$C-NH-pyrimidin-5-yl | *—CH$_3$ | H$_3$C-NH-pyrimidin-Br | V.1 | 354 [M + H]$^+$ | 0.91 (G) |
| 16.4 | H$_3$C-NH-pyrimidin-5-yl | *—CH$_3$ | H$_3$C-NH-pyrimidin-Br | V.1 | 368 [M + H]$^+$ | 0.97 (G) |
| 16.5 | cyclopropyl-CH$_2$-O-pyrimidin-5-yl | *—CH$_3$ | cyclopropyl-CH$_2$-O-pyrimidin-Br | V.1 | 395 [M + H]$^+$ | 1.12 (H) |
| 16.6 | cyclopropyl-CH$_2$-O-pyrimidin-5-yl | *—N(CH$_3$)$_2$ | cyclopropyl-CH$_2$-O-pyrimidin-Br | V.3 | 424 [M + H]$^+$ | 1.13 (G) |
| 16.7 | H$_3$C-O-pyrimidin-5-yl | *—N(CH$_3$)$_2$ | H$_3$C-O-pyrimidin-Br | V.3 | 398 [M + H]$^+$ | 1.07 (G) |

-continued (16-1)

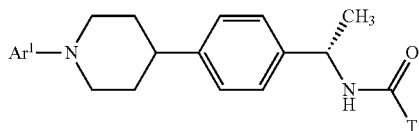

| Example | Ar¹ | T | Educt 1 | Educt 2 | ESI-MS [m/z] | R$_t$ (HPLC) [min] (method) |
|---|---|---|---|---|---|---|
| 16.8 | H₃C—O—[pyrimidine]—* | *—cyclopropyl | H₃C—O—[pyrimidine]—Br | V.4 | 395 [M + H]⁺ | 1.09 (G) |
| 16.9 | cyclopropyl-CH₂-NH-[pyrimidine]-* | *—cyclopropyl | cyclopropyl-CH₂-NH-[pyrimidine]-Br | V.4 | 420 [M + H]⁺ | 1.12 (G) |
| 16.10 | CH₃CH₂O-[pyrimidine(OCH₃)]-* | *—CH₃ | CH₃CH₂O-[pyrimidine(OCH₃)]-Br | V.1 | 399 [M + H]⁺ | 1.25 (L) |
| 16.11 | cyclopropyl-CH₂-O-[pyrimidine(OCH₃)]-* | *—CH₃ | cyclopropyl-CH₂-O-[pyrimidine(OCH₃)]-Br | V.1 | 425 [M + H]⁺ | 2.16 (F) |

Example 17

Example 17.1

(S)—N-(1-{4-[1-(4-Ethoxy-phenyl)-piperidin-4-yl]-phenyl}-ethyl)-methanesulfonamide

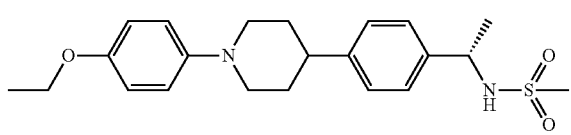 [SMILES: CCOc1ccc(N2CCC(c3ccc([C@H](C)NS(C)(=O)=O)cc3)CC2)cc1]

To 17 mg (0.15 mmol) methanesulfonyl chloride is added a solution of 32 mg (0.1 mmol) (S)-1-{4-[1-(4-ethoxy-phenyl)-piperidin-4-yl]-phenyl}-ethylamine (XIII.1) and 42 µL triethyl amine in 2 mL dichloromethane. The mixture is stirred for 2 d at rt. The solvent is removed under reduced pressure and the residue is purified using reversed phase column chromatography (water/MeOH, 0.1% TFA) and the corresponding fractions are concentrated to yield the desired product.

$C_{22}H_{30}N_2O_2O_3S$ (M=402.6 g/mol), ESI-MS: 403 [M+H]⁺
R$_t$ (HPLC): 0.37 min (method B)

The following compounds of general formula (17-1) are prepared analogously to Example 17.1, the educts used being shown in the column headed "Educts":

(17-1)

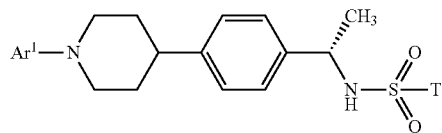

| Example | Ar¹ | T | Educt 1 | Educt 2 | ESI-MS [m/z] | $R_t$ (HPLC) [min] (method) |
|---|---|---|---|---|---|---|
| 17.1 | H₃C-O-C₆H₄-* | *—CH₃ | CH₃SO₂Cl | XIII.1 | 403 [M + H]⁺ | 0.37 (B) |
| 17.2 | H₃C-O-C₆H₄-* | H₃C-CH₂-* | EtSO₂Cl | XIII.1 | 417 [M + H]⁺ | 0.39 (B) |
| 17.3 | H₃C-O-C₆H₄-* | *-cyclobutyl | cyclobutyl-SO₂Cl | XIII.1 | 443 [M + H]⁺ | 0.42 (B) |
| 17.4 | H₃C-O-C₆H₄-* | *-CF₃ | CF₃SO₂Cl | XIII.1 | 457 [M + H]⁺ | 0.46 (B) |

Example 18

Example 18.1

(S)-2-{4-[4-(1-Acetylamino-ethyl)-phenyl]-piperidin-1-yl}-pyrimidine-5-carboxylic acid methyl-pyridin-4-ylmethyl-amide

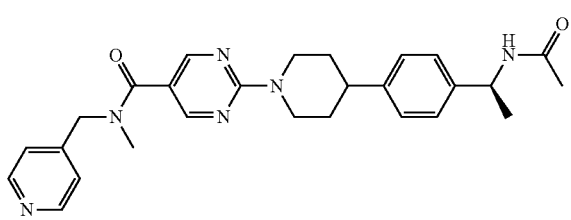 [SMILES: CC(=O)N[C@@H](C)c1ccc(C2CCN(c3ncc(C(=O)N(C)Cc4ccncc4)cn3)CC2)cc1]

To 36.8 mg (0.1 mmol) (S)-2-{4-[4-(1-acetylamino-ethyl)-phenyl]-piperidin-1-yl}-pyrimidine-5-carboxylic acid (XVII.1) and 51 μL (0.3 mmol) DIPEA in 2 mL DMF is added 38.0 mg (0.1 mmol) HATU and the mixture is stirred for 15 min at rt. Subsequent the mixture is added to 12.2 mg (0.1 mmol) methylpyridin-4-ylmethylamine and stirring is continued for 12 h. The solvent is removed in vacuo and the residue is purified using reversed phase column chromatography (water+0.1% NH₄OH/MeOH) and the corresponding fractions are concentrated to yield the desired product.

$C_{27}H_{32}N_6O_2$ (M=472.6 g/mol), ESI-MS: 473 [M+H]⁺

$R_t$ (HPLC): 1.56 (method W)

The following compounds 18.1-18.40 of general formula (18-1) are prepared analogously to Example 18.1, compounds 18.41-18.89 are prepared analogously to Example 18.1, but the batch size is reduced to 0.01 mmol acid XVII.1. These compounds are purified by filtration through basic aluminum oxide, followed by washing with DMF/MeOH (9:1) and concentration in vacuo to yield the desired product. In case that Boc-protected diamines are used, the Boc protecting group is finally removed using DCM/TFA=1/1 (5% H₂O). The educts used are shown in the column headed "Educts":

(18-1)

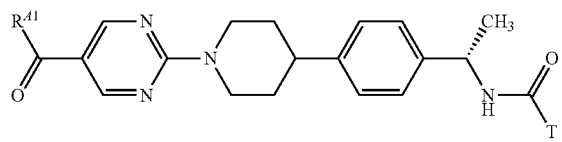

| Example | R41 | T | Educt 1 | Educt 2 | ESI-MS [m/z] | Rt (HPLC) [min] (method) |
|---|---|---|---|---|---|---|
| 18.1 | (N-methyl-N-(pyridin-4-ylmethyl)) | *—CH3 | (N-methyl-pyridin-4-ylmethylamine) | XVII.1 | 473 [M + H]+ | 1.56 (W) |
| 18.2 | (3-fluorophenyl-NH-) | *—CH3 | (3-fluoroaniline) | XVII.1 | 462 [M + H]+ | 1.82 (B) |
| 18.3 | (4-fluorophenyl-NH-) | *—CH3 | (4-fluoroaniline) | XVII.1 | 462 [M + H]+ | 1.81 (W) |
| 18.4 | (N-methyl-N-(4-methylphenyl)) | *—CH3 | (N-methyl-4-methylaniline) | XVII.1 | 472 [M + H]+ | 1.87 (W) |
| 18.5 | (cyclopropyl-NH-) | *—CH3 | (cyclopropylamine) | XVII.1 | 408 [M + H]+ | 1.57 (B) |
| 18.6 | (2-fluorophenyl-NH-) | *—CH3 | (2-fluoroaniline) | XVII.1 | 462 [M + H]+ | 1.72 (B) |
| 18.7 | (2-methylphenyl-NH-) | *—CH3 | (2-methylaniline) | XVII.1 | 458 [M + H]+ | 1.76 (W) |
| 18.8 | (3-methylphenyl-NH-) | *—CH3 | (3-methylaniline) | XVII.1 | 458 [M + H]+ | 1.86 (W) |
| 18.9 | (indolin-1-yl) | *—CH3 | (indoline) | XVII.1 | 470 [M + H]+ | 1.88 (W) |

-continued (18-1)

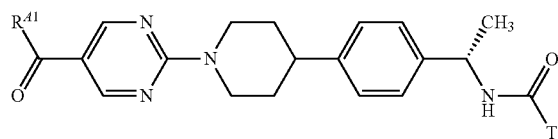

| Example | R^{A1} | T | Educt 1 | Educt 2 | ESI-MS [m/z] | R_t (HPLC) [min] (method) |
|---|---|---|---|---|---|---|
| 18.10 | (N-methyl-N-((1,3-dioxolan-2-yl)methyl)amino) | *—CH_3 | (1,3-dioxolan-2-yl)methyl-methylamine | XVII.1 | 468 [M + H]^+ | 1.60 (W) |
| 18.11 | piperidin-1-yl | *—CH_3 | piperidine | XVII.1 | 436 [M + H]^+ | 1.77 (W) |
| 18.12 | 3-methoxyphenylamino | *—CH_3 | 3-methoxyaniline | XVII.1 | 474 [M + H]^+ | 1.80 (W) |
| 18.13 | (pyridin-2-yl)methylamino | *—CH_3 | (pyridin-2-yl)methylamine | XVII.1 | 459 [M + H]^+ | 1.59 (W) |
| 18.14 | (2-methoxyphenyl)methylamino | *—CH_3 | (2-methoxyphenyl)methylamine | XVII.1 | 488 [M + H]^+ | 1.78 (W) |
| 18.15 | pyridin-2-ylamino | *—CH_3 | 2-aminopyridine | XVII.1 | 445 [M + H]^+ | 1.43 (B) |
| 18.16 | 2-methoxyphenylamino | *—CH_3 | 2-methoxyaniline | XVII.1 | 474 [M + H]^+ | 1.82 (W) |
| 18.17 | 4-methylphenylamino | *—CH_3 | 4-methylaniline | XVII.1 | 458 [M + H]^+ | 1.82 (B) |

(18-1)

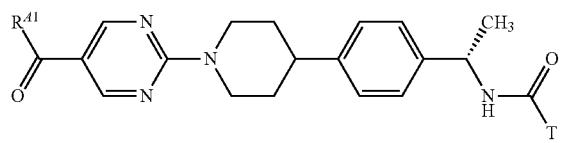

| Example | $R^{A1}$ | T | Educt 1 | Educt 2 | ESI-MS [m/z] | $R_t$ (HPLC) [min] (method) |
|---|---|---|---|---|---|---|
| 18.18 | benzo[d][1,3]dioxol-5-yl-NH-* | *—CH₃ | benzo[d][1,3]dioxol-5-amine | XVII.1 | 488 [M + H]⁺ | 1.76 (W) |
| 18.19 | (4-methoxybenzyl)amino-* | *—CH₃ | 4-methoxybenzylamine | XVII.1 | 488 [M + H]⁺ | 1.7 (W) |
| 18.20 | octahydrocyclopenta[c]pyrrol-2-yl | *—CH₃ | octahydrocyclopenta[c]pyrrole | XVII.1 | 462 [M + H]⁺ | 1.88 (W) |
| 18.21 | (1H-pyrazol-3-yl)methylamino-* | *—CH₃ | (1H-pyrazol-3-yl)methanamine | XVII.1 | 448 [M + H]⁺ | 1.52 (W) |
| 18.22 | (1-methyl-1H-pyrazol-3-yl)methylamino-* | *—CH₃ | (1-methyl-1H-pyrazol-3-yl)methanamine | XVII.1 | 462 [M + H]⁺ | 1.54 (W) |
| 18.23 | 3-methoxyazetidin-1-yl | *—CH₃ | 3-methoxyazetidine | XVII.1 | 438 [M + H]⁺ | 1.56 (B) |
| 18.24 | 4-methoxypiperidin-1-yl | *—CH₃ | 4-methoxypiperidine | XVII.1 | 466 [M + H]⁺ | 1.65 (W) |

-continued (18-1)

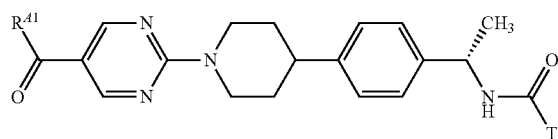

| Example | R^{A1} | T | Educt 1 | Educt 2 | ESI-MS [m/z] | R_t (HPLC) [min] (method) |
|---|---|---|---|---|---|---|
| 18.25 | (N,N-methyl, 2-methoxyethyl) | *—CH_3 | H_3C-NH-CH_2CH_2-O-CH_3 | XVII.1 | 440 [M + H]^+ | 1.60 (W) |
| 18.26 | (N-cyclopropyl, N-methyl) | *—CH_3 | HN(CH_3)-cyclopropyl | XVII.1 | 422 [M + H]^+ | 1.60 (B) |
| 18.27 | ((S)-2-(methoxymethyl)pyrrolidinyl) | *—CH_3 | (S)-2-(methoxymethyl)pyrrolidine | XVII.1 | 466 [M + H]^+ | 1.71 (W) |
| 18.28 | (1-methyl-1,4,5,6-tetrahydropyrrolo[3,4-c]pyrazol-5-yl) | *—CH_3 | 1-methyl-1,4,5,6-tetrahydropyrrolo[3,4-c]pyrazole | XVII.1 | 474 [M + H]^+ | 1.55 (B) |
| 18.29 | (oxazol-4-ylmethylamino) | *—CH_3 | oxazol-4-ylmethanamine | XVII.1 | 449 [M + H]^+ | 1.49 (B) |
| 18.30 | (2,2-difluorocyclopropylamino) | *—CH_3 | 2,2-difluorocyclopropylamine | XVII.1 | 444 [M + H]^+ | 1.46 (W) |
| 18.31 | (N-methyl, N-(pyridin-3-ylmethyl)) | *—CH_3 | N-methyl-1-(pyridin-3-yl)methanamine | XVII.1 | 473 [M + H]^+ | 1.58 (W) |
| 18.32 | (furan-3-ylmethylamino) | *—CH_3 | furan-3-ylmethanamine | XVII.1 | 448 [M + H]^+ | 1.66 (W) |

-continued (18-1)

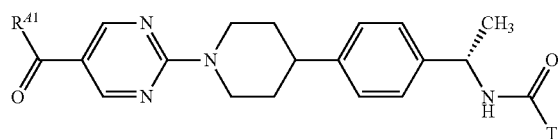

| Example | R<sup>A1</sup> | T | Educt 1 | Educt 2 | ESI-MS [m/z] | R<sub>t</sub> (HPLC) [min] (method) |
|---|---|---|---|---|---|---|
| 18.33 | benzo[d][1,3]dioxol-4-yl-NH- | *—CH₃ | 4-amino-benzo[d][1,3]dioxole | XVII.1 | 488 [M + H]⁺ | 1.72 (W) |
| 18.34 | (pyrimidin-2-yl)methyl-NH- | *—CH₃ | (pyrimidin-2-yl)methylamine | XVII.1 | 460 [M + H]⁺ | 1.49 (W) |
| 18.35 | (tetrahydrofuran-3-yl)-NH- | *—CH₃ | (tetrahydrofuran-3-yl)amine | XVII.1 | 438 [M + H]⁺ | 1.55 (W) |
| 18.36 | 3-hydroxy-8-azabicyclo[3.2.1]octan-8-yl | *—CH₃ | 3-hydroxy-8-azabicyclo[3.2.1]octane | XVII.1 | 478 [M + H]⁺ | 1.61 (W) |
| 18.37 | N-methyl-N-((pyridin-2-yl)methyl)- | *—CH₃ | N-methyl-((pyridin-2-yl)methyl)amine | XVII.1 | 473 [M + H]⁺ | 1.62 (W) |
| 18.38 | 6,7-dihydro-5H-pyrrolo[3,4-b]pyridin-6-yl | *—CH₃ | 6,7-dihydro-5H-pyrrolo[3,4-b]pyridine | XVII.1 | 471 [M + H]⁺ | 1.53 (B) |
| 18.39 | (oxetan-3-yl)-NH- | *—CH₃ | (oxetan-3-yl)amine | XVII.1 | 424 [M + H]⁺ | 1.49 (B) |
| 18.40 | 2,3-dihydro-1H-pyrrolo[3,2-c]pyridin-1-yl | *—CH₃ | 2,3-dihydro-1H-pyrrolo[3,2-c]pyridine | XVII.1 | 471 [M + H]⁺ | 1.2 (B) |

-continued (18-1)

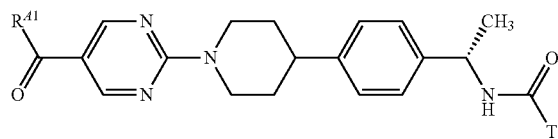

| Example | R^{A1} | T | Educt 1 | Educt 2 | ESI-MS [m/z] | R_t (HPLC) [min] (method) |
|---|---|---|---|---|---|---|
| 18.41 | (tetrahydropyran-2-yl)methyl-NH-* | *—CH$_3$ | (tetrahydropyran-2-yl)methyl-NH$_2$ | XVII.1 | 466 [M + H]$^+$ | 1.58 (B) |
| 18.42 | N≡C–CH$_2$–N(CH$_3$)–* | *—CH$_3$ | N≡C–CH$_2$–NH–CH$_3$ | XVII.1 | 421 [M + H]$^+$ | 1.46 (B) |
| 18.43 | (CH$_3$)$_2$N–CH$_2$CH$_2$–N(CH$_3$)–* | *—CH$_3$ | (CH$_3$)$_2$N–CH$_2$CH$_2$–NH–CH$_3$ | XVII.1 | 453 [M + H]$^+$ | 1.13 (B) |
| 18.44 | (1-ethyl-pyrrolidin-2-yl)methyl-NH-* | *—CH$_3$ | (1-ethyl-pyrrolidin-2-yl)methyl-NH$_2$ | XVII.1 | 479 [M + H]$^+$ | 1.2 (B) |
| 18.45 | H$_2$N–C(O)–CH$_2$–NH–* | *—CH$_3$ | H$_2$N–C(O)–CH$_2$–NH$_2$ | XVII.1 | 425 [M + H]$^+$ | 1.33 (B) |
| 18.46 | 2,3-dihydro-1H-pyrrolo[3,4-c]pyridin-2-yl | *—CH$_3$ | 2,3-dihydro-1H-pyrrolo[3,4-c]pyridine | XVII.1 | 471 [M + H]$^+$ | 1.17 (B) |
| 18.47 | HO–CH$_2$CH$_2$CH$_2$–NH–* | *—CH$_3$ | HO–CH$_2$CH$_2$CH$_2$–NH$_2$ | XVII.1 | 426 [M + H]$^+$ | 1.44 (B) |
| 18.48 | (CH$_3$)$_2$CH–NH–* | *—CH$_3$ | (CH$_3$)$_2$CH–NH$_2$ | XVII.1 | 410 [M + H]$^+$ | 1.61 (B) |
| 18.49 | cyclobutyl-NH–* | *—CH$_3$ | cyclobutyl-NH$_2$ | XVII.1 | 442 [M + H]$^+$ | 1.66 (B) |

-continued (18-1)

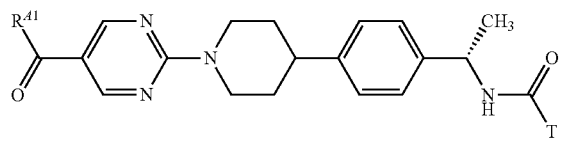

| Example | R<sup>A1</sup> | T | Educt 1 | Educt 2 | ESI-MS [m/z] | R$_t$ (HPLC) [min] (method) |
|---|---|---|---|---|---|---|
| 18.50 | HO, OH (S) with NH-* | *—CH$_3$ | HO, OH (S) with NH$_2$ | XVII.1 | 442 [M + H]$^+$ | 1.36 (B) |
| 18.51 | pyrrolidine-CH$_2$CH$_2$-NH-* | *—CH$_3$ | pyrrolidine-CH$_2$CH$_2$-NH$_2$ | XVII.1 | 465 [M + H]$^+$ | 1.17 (B) |
| 18.52 | 4-methylpiperazin-1-yl | *—CH$_3$ | 1-methylpiperazine | XVII.1 | 451 [M + H]$^+$ | 1.10 (B) |
| 18.53 | 4-acetylpiperazin-1-yl | *—CH$_3$ | 1-acetylpiperazine | XVII.1 | 479 [M + H]$^+$ | 1.42 (B) |
| 18.54 | pyrrolidin-1-yl | *—CH$_3$ | pyrrolidine | XVII.1 | 422 [M + H]$^+$ | 1.6 (B) |
| 18.55 | H$_3$C-O-CH$_2$CH$_2$-NH-* | *—CH$_3$ | H$_3$C-O-CH$_2$CH$_2$-NH$_2$ | XVII.1 | 426 [M + H]$^+$ | 1.51 (B) |
| 18.56 | (1-methylpyrrolidin-2-yl)CH$_2$CH$_2$-NH-* | *—CH$_3$ | (1-methylpyrrolidin-2-yl)CH$_2$CH$_2$-NH$_2$ | XVII.1 | 479 [M + H]$^+$ | 1.19 (B) |
| 18.57 | (tetrahydrofuran-2-yl)CH$_2$-NH-* | *—CH$_3$ | (tetrahydrofuran-2-yl)CH$_2$-NH$_2$ | XVII.1 | 452 [M + H]$^+$ | 1.57 (B) |

(18-1)

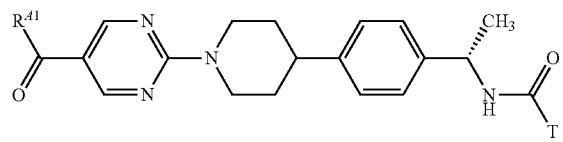

| Example | R[41] | T | Educt 1 | Educt 2 | ESI-MS [m/z] | R_t (HPLC) [min] (method) |
|---|---|---|---|---|---|---|
| 18.58 | H3C-NH-CH2CH2-NH-* | *—CH3 | H2N-CH2CH2-N(CH3)-C(O)-O-C(CH3)3 | XVII.1 | 425 [M + H]+ | 1.14 (B) |
| 18.59 | piperidine-N-CH2CH2-NH-* | *—CH3 | H2N-CH2CH2-N(piperidine) | XVII.1 | 479 [M + H]+ | 1.20 (B) |
| 18.60 | piperidin-4-yl-CH2-NH-* | *—CH3 | Boc-piperidin-4-yl-CH2-NH2 | XVII.1 | 465 [M + H]+ | 1.18 (B) |
| 18.61 | H2N-C(O)-piperidin-4-yl-N-* (N-methyl) | *—CH3 | H2N-C(O)-piperidin-4-yl-NH | XVII.1 | 479 [M + H]+ | 1.39 (B) |
| 18.62 | 1-benzylpyrrolidin-3-yl-CH2-NH-* | *—CH3 | 1-benzylpyrrolidin-3-yl-CH2-NH2 | XVII.1 | 541 [M + H]+ | 1.28 (B) |
| 18.63 | CF3-CH(OH)-CH2-NH-* | *—CH3 | CF3-CH(OH)-CH2-NH2 | XVII.1 | 480 [M + H]+ | 1.57 (B) |
| 18.64 | H3C-S(O)2-CH2CH2-NH-* | *—CH3 | H3C-S(O)2-CH2CH2-NH2 | XVII.1 | 474 [M + H]+ | 1.4 (B) |

-continued
(18-1)
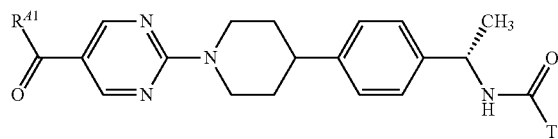
| Example | R^{A1} | T | Educt 1 | Educt 2 | ESI-MS [m/z] | $R_t$ (HPLC) [min] (method) |
|---|---|---|---|---|---|---|
| 18.65 | | *—CH₃ | | XVII.1 | 465 [M + H]⁺ | 1.19 (B) |
| 18.66 | | *—CH₃ | | XVII.1 | 467 [M + H]⁺ | 1.48 (B) |
| 18.67 | | *—CH₃ | | XVII.2 | 527 [M + H]⁺ | 1.82 (B) |
| 18.68 | | *—CH₃ | | XVII.1 | 466 [M + H]⁺ | 1.53 (B) |
| 18.69 | | *—CH₃ | | XVII.1 | 500 [M + H]⁺ | 1.40 (B) |
| 18.70 | | *—CH₃ | | XVII.1 | 433 [M + H]⁺ | 1.50 (B) |
| 18.71 | | *—CH₃ | | XVII.1 | 461 [M + H]⁺ | 1.50 (B) |
| 18.72 | | *—CH₃ | | XVII.1 | 439 [M + H]⁺ | 1.38 (B) |

(18-1)
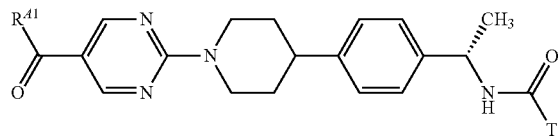
| Example | R^{A1} | T | Educt 1 | Educt 2 | ESI-MS [m/z] | R_t (HPLC) [min] (method) |
|---|---|---|---|---|---|---|
| 18.73 | | *—CH$_3$ | | XVII.1 | 462 [M + H]$^+$ | 1.15 (B) |
| 18.74 | | *—CH$_3$ | | XVII.1 | 437 [M + H]$^+$ | 1.17 (B) |
| 18.75 | | *—CH$_3$ | | XVII.1 | 440 [M + H]$^+$ | 1.50 (B) |
| 18.76 | | *—CH$_3$ | | XVII.1 | 408 [M + H]$^+$ | 1.55 (B) |
| 18.77 | | *—CH$_3$ | | XVII.1 | 422 [M + H]$^+$ | 1.64 (B) |
| 18.78 | | *—CH$_3$ | | XVII.1 | 449 [M + H]$^+$ | 1.66 (B) |
| 18.79 | | *—CH$_3$ | | XVII.1 | 451 [M + H]$^+$ | 1.17 (B) |
| 18.80 | | *—CH$_3$ | | XVII.1 | 421 [M + H]$^+$ | 1.45 (B) |
| 18.81 | | *—CH$_3$ | | XVII.1 | 451 [M + H]$^+$ | 1.16 (B) |
| 18.82 | | *—CH$_3$ | | XVII.1 | 439 [M + H]$^+$ | 1.38 (B) |

-continued (18-1)

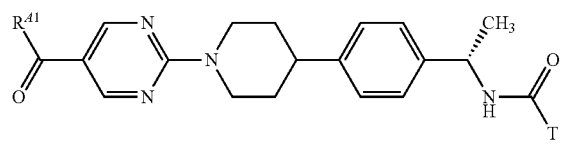

| Example | R<sup>A1</sup> | T | Educt 1 | Educt 2 | ESI-MS [m/z] | $R_t$ (HPLC) [min] (method) |
|---|---|---|---|---|---|---|
| 18.83 | (1,3-dioxolan-2-ylmethyl)(methyl)amino | *—CH$_3$ | (1,3-dioxolan-2-yl)methanamine | XVII.1 | 454 [M + H]$^+$ | 1.49 (B) |
| 18.84 | (1-methylpyrrolidin-3-yl)(methyl)amino | *—CH$_3$ | N-methyl-1-methylpyrrolidin-3-amine | XVII.1 | 465 [M + H]$^+$ | 1.13 (B) |
| 18.85 | octahydropyrrolo[3,4-c]pyridin-2-yl | *—CH$_3$ | tert-butyl octahydropyrrolo[3,4-c]pyridine-5-carboxylate | XVII.1 | 477 [M + H]$^+$ | 1.13 (B) |
| 18.86 | {4-[(dimethylamino)methyl]phenyl}(methyl)amino | *—CH$_3$ | 4-[(dimethylamino)methyl]aniline | XVII.1 | 501 [M + H]$^+$ | 1.27 (B) |
| 18.87 | (1-methylpiperidin-4-yl)(methyl)amino | *—CH$_3$ | 1-methylpiperidin-4-amine | XVII.1 | 465 [M + H]$^+$ | 1.17 (B) |
| 18.88 | {[(dimethylamino)methyl]pyrrolidin-1-yl} | *—CH$_3$ | N,N-dimethyl-1-(pyrrolidin-2-yl)methanamine | XVII.1 | 479 [M + H]$^+$ | 1.18 (B) |
| 18.89 | methyl(phenyl)amino | *—CH$_3$ | N-methylaniline | XVII.1 | 458 [M + H]$^+$ | 2.14 (P) |
| 18.90 | ethylamino | *—CH$_3$ | ethylamine · HCl | XVII.1 | 396 [M + H]$^+$ | 1.98 (P) |
| 18.91 | diethylamino | *—CH$_3$ | diethylamine | XVII.1 | 424 [M + H]$^+$ | 2.08 (P) |

(18-1)

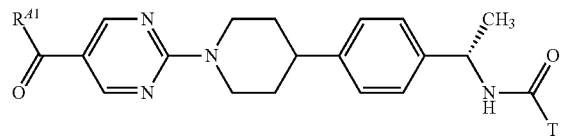

| Example | R$^{A1}$ | T | Educt 1 | Educt 2 | ESI-MS [m/z] | R$_t$ (HPLC) [min] (method) |
|---|---|---|---|---|---|---|
| 18.92 | benzyl-NH—* | *—CH$_3$ | benzyl-NH$_2$ | XVII.1 | 458 [M + H]$^+$ | 2.14 (P) |
| 18.93 | (H$_3$C)(benzyl)N—* | *—CH$_3$ | H$_3$C-NH-benzyl | XVII.1 | 472 [M + H]$^+$ | 2.19 (P) |
| 18.94 | morpholinyl—* | *—CH$_3$ | morpholine | XVII.1 | 438 [M + H]$^+$ | 1.90 (P) |
| 18.95 | N-methyl-N-phenyl—* | *—CH$_3$ | aniline | XVII.1 | 444 [M + H]$^+$ | 2.18 (P) |

Example 19

Example 19.1

(S)—N-{1-[4-(2'-Isobutoxy-3,4,5,6-tetrahydro-2H-[1,4']bipyridinyl-4-yl)-phenyl]-ethyl}-acetamide

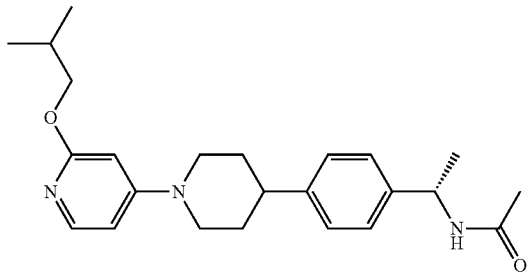 [SMILES: CC(=O)N[C@@H](C)c1ccc(C2CCN(c3ccnc(OCC(C)C)c3)CC2)cc1]

To a mixture of 34 mg (0.10 mmol) (S)—N-{1-[4-(2'-fluoro-3,4,5,6-tetrahydro-2H-[1,4']bipyridinyl-4-yl)-phenyl]-ethyl}-acetamide (XIX.1) and 74 mg (1.0 mmol) isobutyl alcohol in 2 mL dioxane is added 20 mg (0.50 mmol) NaH (60% in mineral oil). The mixture is stirred at 130° C. for 12 h. The solvent is removed in vacuo and the residue is purified by HPLC (RP X-Bridge; water (+0.1% TFA)/MeOH) to yield the desired product.

$C_{24}H_{33}N_3O_2$ (M=395.5 g/mol), ESI-MS: 396 [M+H]$^+$

R$_t$ (HPLC): 1.35 min (method L)

The following compounds of general formula (19-1) are prepared analogously to Example 19.1, the educts used being shown in the column headed "Educts":

(19-1)

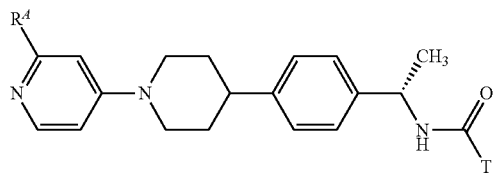

| Example | R$^A$ | T | Educt 1 | Educt 2 | ESI-MS [m/z] | R$_t$ (HPLC) [min] (method) |
|---|---|---|---|---|---|---|
| 19.1 | isobutyl-O-* | *—CH$_3$ | isobutanol | XIX.1 | 396 [M + H]$^+$ | 1.35 (L) |
| 19.2 | cyclobutyl-O-* | *—CH$_3$ | cyclobutanol | XIX.1 | 394 [M + H]$^+$ | 1.08 (AB) |
| 19.3 | *-O-CH$_2$CH$_2$-O-CH$_3$ | *—CH$_3$ | HO-CH$_2$CH$_2$-O-CH$_3$ | XIX.1 | 398 [M + H]$^+$ | 1.54 (X) |
| 19.4 | cyclopentyl-O-* | *—CH$_3$ | cyclopentanol | XIX.1 | 408 [M + H]$^+$ | 1.85 (X) |
| 19.5 | neopentyl-O-* | *—CH$_3$ | neopentanol | XIX.1 | 410 [M + H]$^+$ | 1.90 (X) |
| 19.6 | cyclohexyl-O-* | *—CH$_3$ | cyclohexanol | XIX.1 | 422 [M + H]$^+$ | 1.92 (X) |
| 19.7 | *-O-CH(CH$_3$)-Ph | *—CH$_3$ | HO-CH(CH$_3$)-Ph | XIX.1 | 444 [M + H]$^+$ | 1.84 (X) |
| 19.8 | *-O-CH$_2$-(3-OMe-C$_6$H$_4$) | *—CH$_3$ | HO-CH$_2$-(3-OMe-C$_6$H$_4$) | XIX.1 | 460 [M + H]$^+$ | 1.81 (X) |
| 19.9 | Ph-CH$_2$CH$_2$-O-* | *—CH$_3$ | Ph-CH$_2$CH$_2$-OH | XIX.1 | 444 [M + H]$^+$ | 1.87 (X) |
| 19.10 | *-O-CH$_2$-cyclopropyl | *—CH$_3$ | HO-CH$_2$-cyclopropyl | XIX.1 | 394 [M + H]$^+$ | 1.76 (X) |
| 19.11 | *-O-CH$_2$-cyclobutyl | *—CH$_3$ | HO-CH$_2$-cyclobutyl | XIX.1 | 408 [M + H]$^+$ | 1.87 (X) |
| 19.12 | *-O-CH$_2$CH$_2$-cyclopropyl | *—CH$_3$ | HO-CH$_2$CH$_2$-cyclopropyl | XIX.1 | 408 [M + H]$^+$ | 1.85 (X) |
| 19.13 | *-O-CH(CH$_3$)$_2$ | *—CH$_3$ | HO-CH(CH$_3$)$_2$ | XIX.1 | 396 [M + H]$^+$ | 1.82 (X) |

-continued (19-1)

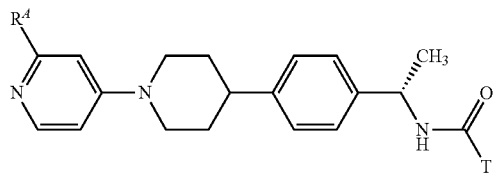

| Example | R⁴ | T | Educt 1 | Educt 2 | ESI-MS [m/z] | R_t (HPLC) [min] (method) |
|---|---|---|---|---|---|---|
| 19.14 | *—O—CH(CH₃)—CH₂—O—CH₃ | *—CH₃ | HO—CH(CH₃)—CH₂—O—CH₃ | XIX.1 | 412 [M + H]⁺ | 1.65 (X) |
| 19.15 | *—O—CH₂—C(CH₃)(cyclopropyl) | *—CH₃ | HO—CH₂—C(CH₃)(cyclopropyl) | XIX.1 | 408 [M + H]⁺ | 1.84 (X) |
| 19.16 | (S)-tetrahydrofuran-3-yloxy* | *—CH₃ | (S)-3-hydroxytetrahydrofuran | XIX.1 | 410 [M + H]⁺ | 1.58 (X) |
| 19.17 | tetrahydropyran-4-yloxy* | *—CH₃ | 4-hydroxytetrahydropyran | XIX.1 | 424 [M + H]⁺ | 1.64 (X) |
| 19.18 | (tetrahydrofuran-3-yl)methoxy* | *—CH₃ | (tetrahydrofuran-3-yl)methanol | XIX.1 | 424 [M + H]⁺ | 1.62 (X) |
| 19.19 | *—O—CH₂—CHF₂ | *—CH₃ | HO—CH₂—CHF₂ | XIX.1 | 404 [M + H]⁺ | 1.67 (X) |
| 19.20 | (R)-tetrahydrofuran-3-yloxy* | *—CH₃ | (R)-3-hydroxytetrahydrofuran | XIX.1 | 410 [M + H]⁺ | 1.58 (X) |
| 19.21 | (CH₃)₂CH—CH₂—CH₂—O* | *—CH₃ | (CH₃)₂CH—CH₂—CH₂—OH | XIX.1 | 410 [M + H]⁺ | 1.91 (X) |
| 19.22 | (1-methyl-1H-pyrazol-4-yl)methoxy* | *—CH₃ | (1-methyl-1H-pyrazol-4-yl)methanol | XIX.1 | 434 [M + H]⁺ | 1.53 (X) |
| 19.23 | *—O—CH₂—CH₂—CH₃ | *—CH₃ | HO—CH₂—CH₂—CH₃ | XIX.1 | 382 [M + H]⁺ | 1.77 (X) |
| 19.24 | (CH₃CH₂)₂CH—O* | *—CH₃ | (CH₃CH₂)₂CH—OH | XIX.1 | 410 [M + H]⁺ | 1.90 (X) |

-continued (19-1)

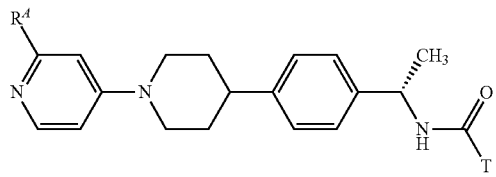

| Example | R^A | T | Educt 1 | Educt 2 | ESI-MS [m/z] | $R_t$ (HPLC) [min] (method) |
|---|---|---|---|---|---|---|
| 19.25 | cyclopent-2-enyl-O-* | *—CH$_3$ | cyclopent-2-enol | XIX.1 | 406 [M + H]$^+$ | 1.80 (X) |
| 19.26 | 2,2-difluorocyclopropyl-CH$_2$-O-* | *—CH$_3$ | 2,2-difluorocyclopropyl-CH$_2$OH | XIX.1 | 430 [M + H]$^+$ | 1.72 (X) |
| 19.27 | *—O—CH(CH$_3$)-cyclopropyl | *—CH$_3$ | HO-CH(CH$_3$)-cyclopropyl | XIX.1 | 408 [M + H]$^+$ | 1.81 (X) |
| 19.28 | 1-cyanocyclopropyl-CH$_2$-O-* | *—CH$_3$ | 1-cyanocyclopropyl-CH$_2$OH | XIX.1 | 419 [M + H]$^+$ | 1.57 (X) |
| 19.29 | isoxazol-3-yl-CH$_2$-O-* | *—CH$_3$ | isoxazol-3-yl-CH$_2$OH | XIX.1 | 421 [M + H]$^+$ | 1.49 (X) |
| 19.30 | indan-2-yl-O-* | *—CH$_3$ | indan-2-ol | XIX.1 | 456 [M + H]$^+$ | 1.91 (X) |
| 19.31 | 2-fluorobenzyl-O-* | *—CH$_3$ | 2-fluorobenzyl alcohol | XIX.1 | 448 [M + H]$^+$ | 1.84 (X) |
| 19.32 | 3-fluorobenzyl-O-* | *—CH$_3$ | 3-fluorobenzyl alcohol | XIX.1 | 448 [M + H]$^+$ | 1.85 (X) |
| 19.33 | 4-fluorobenzyl-O-* | *—CH$_3$ | 4-fluorobenzyl alcohol | XIX.1 | 448 [M + H]$^+$ | 1.84 (X) |
| 19.34 | pyridin-3-yl-CH$_2$-O-* | *—CH$_3$ | pyridin-3-yl-CH$_2$OH | XIX.1 | 431 [M + H]$^+$ | 1.60 (X) |

(19-1)

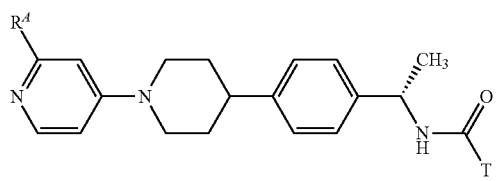

| Example | $R^A$ | T | Educt 1 | Educt 2 | ESI-MS [m/z] | $R_t$ (HPLC) [min] (method) |
|---|---|---|---|---|---|---|
| 19.35 | *—O—CH₂—C₆H₄—O—CH₃ | *—CH₃ | HO—CH₂—C₆H₄—O—CH₃ | XIX.1 | 460 [M + H]⁺ | 1.8 (X) |
| 19.36 | (H₃C)(H₃C)N—CH₂CH₂—O—* | *—CH₃ | (H₃C)(H₃C)N—CH₂CH₂—OH | XIX.1 | 411 [M + H]⁺ | 1.61 (X) |
| 19.37 | 2-pyridyl-CH₂—O—* | *—CH₃ | 2-pyridyl-CH₂—OH | XIX.1 | 431 [M + H]⁺ | 1.61 (X) |
| 19.38 | *—O—CH₂—4-pyridyl | *—CH₃ | HO—CH₂—4-pyridyl | XIX.1 | 431 [M + H]⁺ | 1.61 (X) |

Example 20

Example 20.1

(S)-Cyclopropanecarboxylic acid (1-{4-[1-(6-isopropoxy-pyrimidin-4-yl)-piperidin-4-yl]-phenyl}-ethyl)-amide

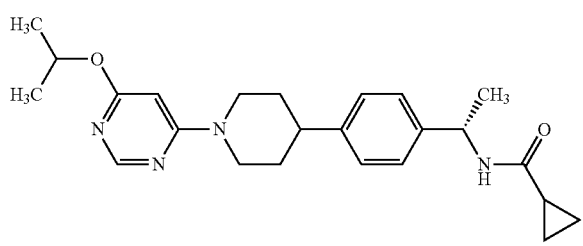 [SMILES: CC(C)Oc1cc(N2CCC(c3ccc([C@H](C)NC(=O)C4CC4)cc3)CC2)ncn1]

25 mg (1.04 mmol) Sodium hydride are added to 2 mL 2-propanol and heated at 80° C. for 10 min. After that time, 80 mg (0.21 mmol) (S)-cyclopropanecarboxylic acid (1-{4-[1-(6-chloro-pyrimidin-4-yl)-piperidin-4-yl]-phenyl}-ethyl)-amide (XIV.6) are added. The mixture is heated at 80° C. for 12 h. After that time, water is added and the mixture is extracted with dichloromethane. The solvent is evaporated and the residue is purified using reversed phase HPLC (column: Waters XBridge 5 µM; eluent A: water+0.3% NH₄OH, eluent B: MeOH) to yield the desired product.

$C_{22}H_{32}N_4O_2$ (M=408.5 g/mol), ESI-MS: 409 [M+H]⁺

$R_t$ (HPLC): 1.31 min (method L)

The following compounds of general formula (20-1) are prepared analogously to Example 20.1, the educts used being shown in the column headed "E 1" and "E 2":

(20-1)

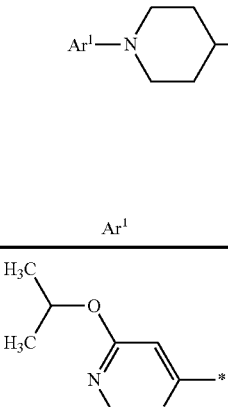

| Ex. | Ar¹ | T | E 1 | E 2 | ESI-MS [m/z] | R$_t$ (HPLC) [min] (method) |
|---|---|---|---|---|---|---|
| 20.1 |  | 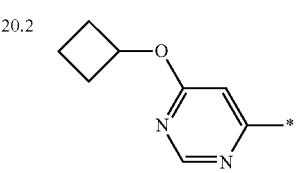 | 2-propanol | XIV.6 | 409 [M + H]⁺ | 1.31 (L) |
| 20.2 |  | 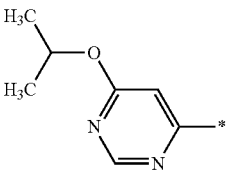 [SMILES: *c1cc(OC(C)C)ncn1] | cyclobutanol | XIV.6 | 421 [M + H]⁺ | 1.32 (L) |
| 20.3 | 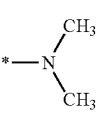 | 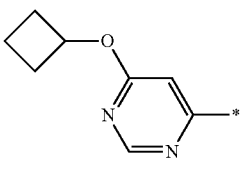 [SMILES: *c1cc(OC2CCC2)ncn1] | 2-propanol | XIV.7 | 412 [M + H]⁺ | 1.32 (L) |
| 20.4 | 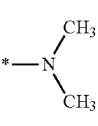 | 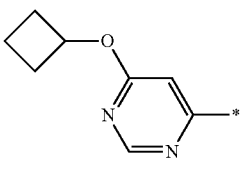 [SMILES: *c1cc(OC2CCC2)ncn1] | 2-propanol | XIV.7 | 424 [M + H]⁺ | 1.30 (L) |

Example 21

Example 21.1

(S)—N-(1-{4-[1-(4-Methoxy-5-phenyl-pyrimidin-2-yl)-piperidin-4-yl]-phenyl}-ethyl)-acetamide

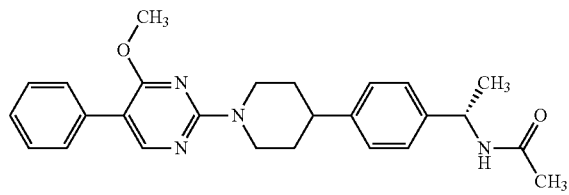 [SMILES: COc1nc(N2CCC(c3ccc([C@H](C)NC(C)=O)cc3)CC2)ncc1-c1ccccc1]

To 43.5 mg (0.10 mmol) (S)—N-(1-{4-[1-(4-chloro-5-phenyl-pyrimidin-2-yl)-piperidin-4-yl]-phenyl}-ethylyac-etamide (5.50 mmol) in 4 mL MeOH is added 0.074 mL (0.40 mmol) sodium methoxide and the mixture is stirred for 3 h at 80° C. After cooling the crude mixture is purified by HPLC (C18 RP Sunfire; water (+0.1% TFA)/MeOH) to yield the desired product.

C$_{26}$H$_{30}$N$_4$O$_2$ (M=430.5 g/mol), ESI-MS: 431 [M+H]⁺
R$_t$ (HPLC): 1.88 min (method P)

Example 21.2

(S)—N-(1-{4-[1-(4-Methyl-5-phenyl-pyrimidin-2-yl)-piperidin-4-yl]-phenyl}-ethyl)-acetamide

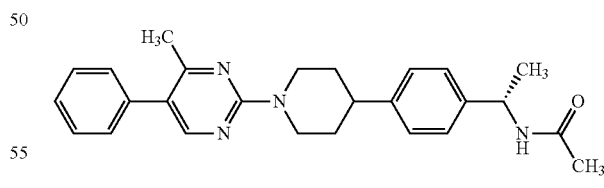

To 43.5 mg (0.10 mmol) (S)—N-(1-{4-[1-(4-chloro-5-phenyl-pyrimidin-2-yl)-piperidin-4-yl]-phenyl}-ethyl)-acetamide (5.50 mmol) in 1 mL MeOH and 2 mL dioxane is added under an argon atmosphere 0.042 mL (0.30 mmol) trimethylboroxine, 0.1 mL NaHCO$_3$ solution (2 mmol/mL) and 2.9 mg (0.0042 mmol) bis(triphenylphosphin)palladium (II)chloride and the mixture is stirred for 3 h at 80° C. After that time, another 100 µL (0.7 mmol) trimethylboroxine and 2.9 mg (0.0042 mmol) bis(triphenylphosphin)-palladium(II) chloride are added and stirring is continued for 12 h at 80° C. The mixture is diluted with DMF, filtered and purified by HPLC (C18 RP Sunfire; water (+0.1% TFA)/MeOH) to yield the desired product.

$C_{26}H_{30}N_4O$ (M=414.5 g/mol), ESI-MS: 415 [M+H]$^+$ $R_t$ (HPLC): 2.28 min (method P)

Example 21.3

(S)—N-(1-{4-[1-(4-Methylamino-5-phenyl-pyrimidin-2-yl)-piperidin-4-yl]-phenyl}-ethyl)-acetamide

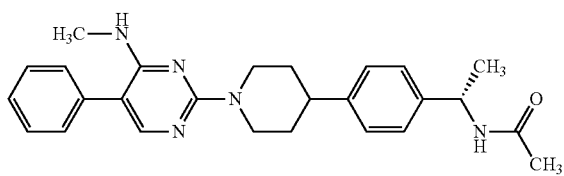 [SMILES: CNc1nc(N2CCC(c3ccc([C@H](C)NC(C)=O)cc3)CC2)ncc1-c1ccccc1]

To 34.0 mg (0.078 mmol) (S)—N-(1-{4-[1-(4-chloro-5-phenyl-pyrimidin-2-yl)-piperidin-4-yl]-phenyl}-ethylyacetamide (5.50 mmol) in 2 mL dimethylacetamide is added 0.027 mL (0.16 mmol) DIPEA and 1.15 mL (2.3 mmol) methylamine. The mixture is stirred for 16 h at 100° C. Subsequently the crude mixture is purified by HPLC (C18 RP Sunfire; water (+0.1% TFA)/MeOH) to yield the desired product.

$C_{26}H_{31}N_5O$ (M=429.6 g/mol), ESI-MS: 430 [M+H]$^+$ $R_t$ (HPLC): 1.66 min (method P)

Example 22

Example 22.1

(S)—N-(1-{4-[1-(2-Benzo[1,3]dioxol-5-yl-pyrimidin-4-yl)-piperidin-4-yl]-phenyl}-ethyl)-acetamide

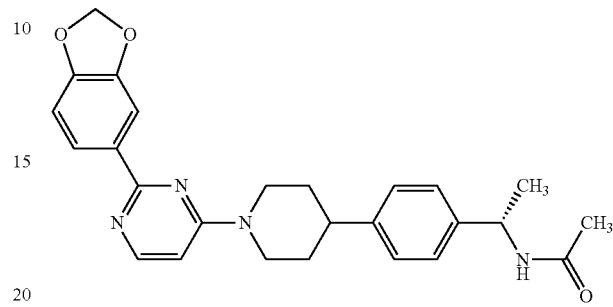

Under argon atmosphere 0.2 mL $Na_2CO_3$-solution (2 mol/L) and 3 mg (0.004 mmol) bis(triphenylphosphine)-palladium(II) chloride are added to a mixture of 50 mg (0.30 mmol) 3,4-(methylenedioxy)phenylboronic acid and 36 mg (0.10 mmol) (S)—N-(1-{4-[1-(2-chloro-pyrimidin-4-yl)-piperidin-4-yl]-phenyl}-ethyl)-acetamide (compound XIV.3) in 2 mL dioxane/1 mL MeOH. The mixture is stirred at 90° C. for 3 h. After that time, the mixture is diluted with DMF/water and is filtered. The filtrate is purified using reversed phase HPLC (water (+0.1% TFA)/MeOH) to yield the desired product.

$C_{26}H_{28}N_4O_3$ (M=444.5 g/mol), ESI-MS: 445 [M+H]$^+$ $R_t$ (HPLC): 1.38 min (method E)

The following compounds of general formula (22-1) are prepared analogously to Example 10.1, the educts used being shown in the column headed "E 1" and "E 2".

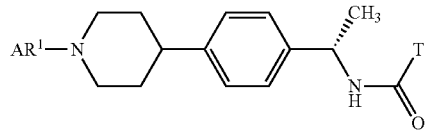

(22-1)

| Ex. | Ar$^1$ | T | E 1 | E 2 | ESI-MS [m/z] | Rt (HPLC) [min] method |
|---|---|---|---|---|---|---|
| 22.1 | benzo[1,3]dioxol-5-yl-pyrimidin-2-yl | *—CH$_3$ | 3,4-(methylenedioxy)phenylboronic acid | XIV.3 | 445 [M + H]$^+$ | 1.38 (E) |
| 22.2 | benzo[1,3]dioxol-5-yl-pyrimidin-4-yl | *—CH$_3$ | 3,4-(methylenedioxy)phenylboronic acid | XIV.1 | 445 [M + H]$^+$ | 1.39 (E) |
| 22.3 | benzo[1,3]dioxol-5-yl-pyrimidin-2-yl | *—CH$_3$ | 3,4-(methylenedioxy)phenylboronic acid | XIV.8 | 445 [M + H]$^+$ | 1.54 (E) |

-continued (22-1)

| Ex. | Ar¹ | T | E 1 | E 2 | ESI-MS [m/z] | Rt (HPLC) [min] method |
|---|---|---|---|---|---|---|
| 22.4 | 3-ethoxyphenyl-pyrimidin-2-yl | *—CH₃ | 3-ethoxyphenylboronic acid | XIV.3 | 445 [M + H]⁺ | 2.71 (S) |
| 22.5 | 5-cyanothiophen-2-yl-pyrimidin-2-yl | *—CH₃ | 5-cyanothiophene-2-boronic acid | XIV.3 | 432 [M + H]⁺ | 2.60 (S) |
| 22.6 | 4-ethoxyphenyl-pyrimidin-2-yl | *—CH₃ | 4-ethoxyphenylboronic acid | XIV.3 | 445 [M + H]⁺ | 2.72 (S) |
| 22.7 | 3-ethoxyphenyl-pyrimidin-4-yl | *—CH₃ | 3-ethoxyphenylboronic acid | XIV.1 | 445 [M + H]⁺ | 2.67 (S) |
| 22.8 | 5-cyanothiophen-2-yl-pyrimidin-4-yl | *—CH₃ | 5-cyanothiophene-2-boronic acid | XIV.1 | 432 [M + H]⁺ | 2.56 (S) |
| 22.9 | 4-ethoxyphenyl-pyrimidin-4-yl | *—CH₃ | 4-ethoxyphenylboronic acid | XIV.1 | 445 [M + H]⁺ | 2.65 (S) |
| 22.10 | 3-ethoxyphenyl-pyrimidin-4-yl | *—CH₃ | 3-ethoxyphenylboronic acid | XIV.8 | 445 [M + H]⁺ | 1.74 (E) |

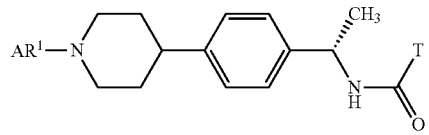

(22-1)

| Ex. | Ar¹ | T | E 1 | E 2 | ESI-MS [m/z] | Rt (HPLC) [min] method |
|---|---|---|---|---|---|---|
| 22.11 | (5-cyanothiophen-2-yl)pyrimidin-2-yl | *—CH₃ | 5-cyanothiophen-2-yl boronic acid | XIV.8 | 432 [M + H]⁺ | 1.94 (E) |
| 22.12 | 4-(4-ethoxyphenyl)pyrimidin-2-yl | *—CH₃ | 4-ethoxyphenyl boronic acid | XIV.8 | 445 [M + H]⁺ | 1.61 (E) |
| 22.13 | 4-(1H-indol-5-yl)pyrimidin-6-yl | *—CH₃ | 1H-indol-5-yl boronic acid | XIV.1 | 440 [M + H]⁺ | 1.39 (E) |

Example 23

Example 23.1

(S)—N-[1-(4-{1-[5-(1H-Benzoimidazol-2-yl)-pyrimidin-2-yl]-piperidin-4-yl}-phenyl)-ethyl]-acetamide

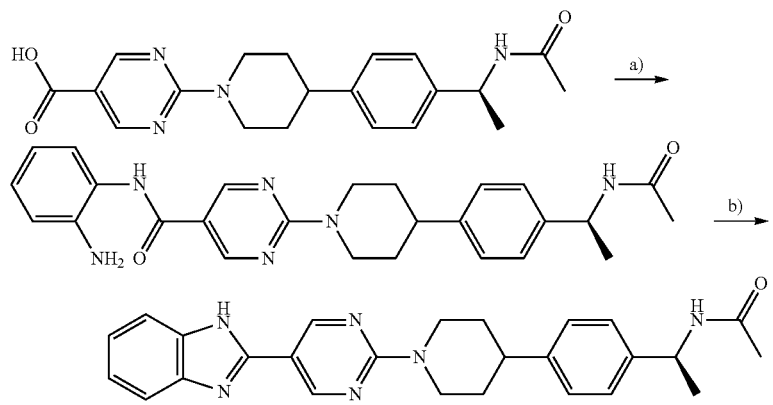

a)

To 74.0 mg (0.2 mmol) (S)-2-{4-[4-(1-acetylamino-ethyl)-phenyl]-piperidin-1-yl}-pyrimidine-5-carboxylic acid (XV11.1) and 42 μL (0.24 mmol) DIPEA in 4 mL DMF is added 77.0 mg (0.2 mmol) TBTU and the mixture is stirred for 10 min at rt. Subsequent 40.0 mg (0.37 mmol) o-phenylenediamine are added and stirring is continued for 5 h. The mixture is filtered through basic aluminum oxide and is washed with DMF/MeOH (9:1). The solvent is removed in vacuo the crude product is directly used for the next step.

$C_{26}H_{30}N_6O_2$ (M=458.6 g/mol), ESI-MS: 459 [M+H]⁺
$R_t$ (HPLC): 1.79 (method P)

b)

A mixture of 92 mg (S)-2-{4-[4-(1-acetylamino-ethyl)-phenyl]-piperidin-1-yl}-pyrimidine-5-carboxylic acid (2-amino-phenyl)-amide in 2 mL HOAc is refluxed for 12 h at 110° C. After concentration in vacuo water is added and the precipitate is collected by filtration to yield the desired product.

$C_{26}H_{28}N_6O$ (M=440.5 g/mol), ESI-MS: 441 [M+H]$^+$ $R_t$ (HPLC): 1.69 min (method P)

Example 24

Example 24.1

(S)—N-(1-{4-[1-(4-(Propylamino)phenyl)-piperidin-4-yl]-phenyl}-ethyl)-acetamide

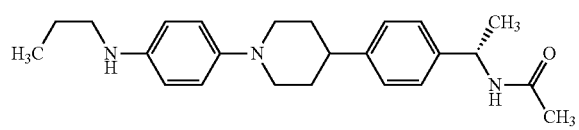

To 75.0 mg (0.22 mmol) of the aniline XX.6 in 1 mL DCM are added 16.2 µl (0.22 mmol) propionaldehyde and the resulting mixture is stirred at rt for 30 min. Then 51.8 mg (0.24 mmol) NaB(OAc)$_3$H are added and the mixture is stirred at rt over night. Afterwards the mixture is directly purified by HPLC (water/MeOH/TFA).

$C_{24}H_{33}N_3O$ (M=379.5 g/mol), ESI-MS: 380 [M+H]$^+$ $R_t$ (HPLC): 1.08 min (method N)

The following compounds of general formula (24-1) are prepared analogously to Example 24.1, the educts used being shown in the column headed "E 1" and "E 2".

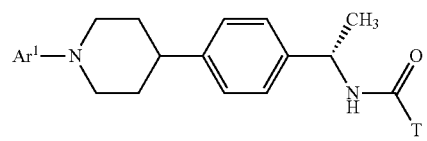

(24-1)

| Ex. | Ar$^1$ | T | E 1 | E 2 | ESI-MS [m/z] | R$_t$ (HPLC) [min] method |
|---|---|---|---|---|---|---|
| 24.1 | 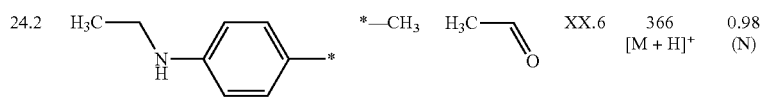 | *—CH$_3$ | | XX.6 | 380 [M + H]$^+$ | 1.08 (N) |
| 24.2 | | *—CH$_3$ | | XX.6 | 366 [M + H]$^+$ | 0.98 (N) |
| 24.3 | 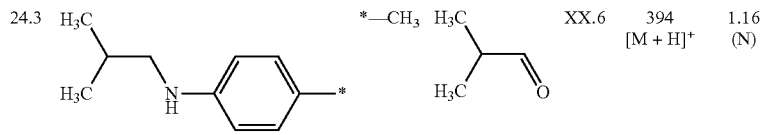 | *—CH$_3$ | | XX.6 | 394 [M + H]$^+$ | 1.16 (N) |
| 24.4 | 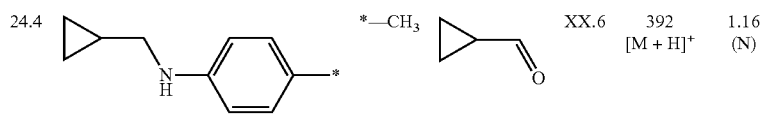 | *—CH$_3$ | | XX.6 | 392 [M + H]$^+$ | 1.16 (N) |

Example 25

Example 25.1

(S)—N-(1-{4-[1-(3-Isopropyl-[1,2,4]oxadiazol-5-yl)-piperidin-4-yl]-phenyl}-ethyl)-acetamide

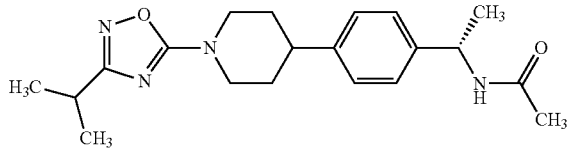

0.9 mL (0.45 mmol) Zinc(II)chloride (0.5 M solution in THF) is added dropwise to a mixture of 40.7 mg (0.15 mmol) (S)—N-{1-[4-(1-cyano-piperidin-4-yl)-phenyl]-ethyl}-acetamide (XXVII.1) and 30.6 mg (0.30 mmol N'-hydroxy-2-methylpropanimidamide in 12 mL ethylacetate. The mixture is stirred for 12 h at rt. After that the solvent is removed in vacuo and 15 mL ethanol and 2 mL conc. HCl solution are added. The mixture is refluxed for 3 h. Subsequently the mixture is concentrated, water is added and the precipitate is collected and washed with water to yield the desired product.

$C_{20}H_{28}N_4O_2$ (M=356.5 g/mol), ESI-MS: 357 [M+H]$^+$
$R_t$ (HPLC): 2.06 min (method S)

The following compounds of general formula (25-1) are prepared analogously to Example 25.1, the educts used being shown in the column headed "E 1" and "E 2".

Example 26

Example 26.1

(S)—N-(1-{4-[1-(5-Phenyl-[1,2,4]oxadiazol-3-yl)-piperidin-4-yl]-phenyl}-ethyl)-acetamide

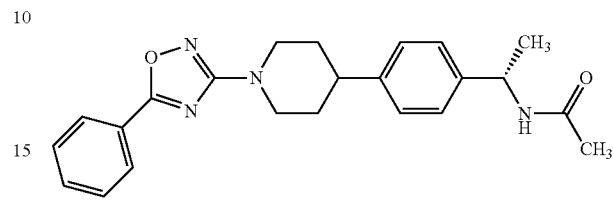

0.019 mL (0.16 mmol) Benzoyl chloride are added to a mixture of 45.7 mg (0.15 mmol) (S)—N-(1-{4-[1-(N-hydroxycarbamimidoyl)-piperidin-4-yl]-phenyl}-ethyl)-acetamide (XXVII.2) and 0.063 mL (0.45 mmol) triethylamine in 4 mL THF. The mixture is stirred for 12 h at 80° C. and is subsequently purified by HPLC (RP C18 Sunfire; water (+0.1% TFA)/MeOH) to yield the desired product.

$C_{23}H_{26}N_4O_2$ (M=390.5 g/mol), ESI-MS: 391 [M+H]$^+$
$R_t$ (HPLC): 2.12 min (method T)

The following compounds of general formula (26-1) are prepared analogously to Example 26.1, the educts used being shown in the column headed "E 1" and "E 2".

(25-1)

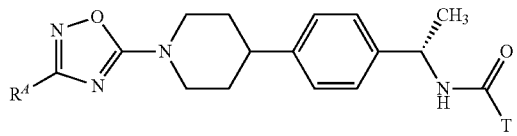

| Ex. | R$^A$ | T | E 1 | E 2 | ESI-MS [m/z] | R$_t$ (HPLC) [min] method |
|---|---|---|---|---|---|---|
| 25.1 | H₃C–CH(CH₃)–* | *—CH₃ | H₃C–CH(CH₃)–C(=N–OH)–NH₂ | XXVII.1 | 357 [M+H]$^+$ | 2.06 (S) |
| 25.2 | H₃C–CH₂–* | *—CH₃ | H₃C–CH₂–C(=N–OH)–NH₂ | XXVII.1 | 343 [M+H]$^+$ | 2.39 (S) |
| 25.3 | Ph–* | *—CH₃ | Ph–C(=N–OH)–NH₂ | XXVII.1 | 391 [M+H]$^+$ | 2.63 (S) |

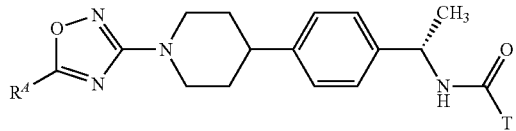

(26-1)

| Ex. | R<sup>A</sup> | T | E 1 | E 2 | ESI-MS [m/z] | R<sub>t</sub> (HPLC) [min] method |
|---|---|---|---|---|---|---|
| 26.1 | phenyl* | *—CH$_3$ | benzoyl chloride | XXVII.2 | 391 [M+H]$^+$ | 2.12 (T) |
| 26.2 | H$_3$C—CH$_2$—* | *—CH$_3$ | propionyl chloride | XXVII.2 | 343 [M+H]$^+$ | 2.50 (S) |
| 26.3 | (H$_3$C)$_2$CH—* | *—CH$_3$ | isobutyryl chloride | XXVII.2 | 357 [M+H]$^+$ | 2.58 (S) |
| 26.4 | CH$_3$-O-CH$_2$-* | *—CH$_3$ | methoxyacetyl chloride | XXVII.2 | 359 [M+H]$^+$ | 2.34 (S) |

Example 27

Example 27.1

N-((1S)-1-(4-(1-(4-((2-methylcyclopropyl)methoxy)phenyl)-piperidin-4-yl)phenyl)-ethyl)acetamide

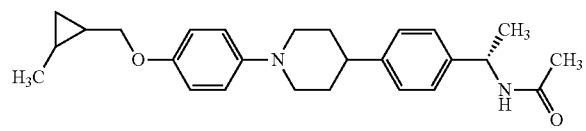 [SMILES: CC(=O)N[C@@H](C)c1ccc(C2CCN(c3ccc(OCC4CC4C)cc3)CC2)cc1]

50 mg (0.15 mmol) (S)—N-{1-(4-[1-(4-Hydroxyphenyl)-piperidin-4-yl]-phenyl}-ethyl)-acetamide (compound 1.48), 14 mg (0.16 mmol) 2-methylcyclopropanemethanol and 38.8 mg (0.15 mmol) triphenylphosphine are added to 2 mL 2-methyl-tetrahydrofurane at 0° C. 30.5 μl (0.15 mmol) di-isopropyl azodicarboxylate are added and the mixture is allowed to warm to rt. Stirring is continued over night followed by addition of 0.5 equivalents of triphenylphosphine and 0.5 equivalents of di-iso-propyl azodicarboxylate. Stirring is continued for one day and again additional triphenylphosphine and di-iso-propyl azodicarboxylate are added and stirring is continued for 16 h at 50° C. Then the mixture is filtered and purified using reversed phase HPLC (water/MeOH, 0.1% FA) to yield the desired product.

C$_{26}$H$_{34}$N$_2$O$_2$ (M=406.6 g/mol), ESI-MS: 407 [M+H]$^+$
R$_t$ (HPLC): 1.58 min (method A)

The following compounds of general formula (27-1) are prepared analogously to Example 27.1, the educts used being shown in the column headed "E 1" and "E 2":

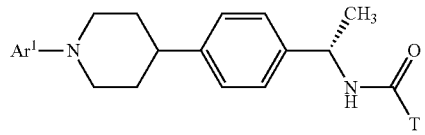

(27-1)

| Example | Ar$^1$ | T | E 1 | E 2 | ESI-MS [m/z] | R$_t$(HPLC) [min] (method) |
|---|---|---|---|---|---|---|
| 27.1 | (2-methylcyclopropyl)methoxy-phenyl | *—CH$_3$ | (2-methylcyclopropyl)methanol | 1.48 | 407 [M+H]$^+$ | 1.58 (A) |

-continued

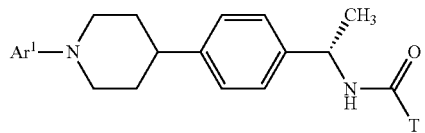
(27-1)

| Example | Ar¹ | T | E 1 | E 2 | ESI-MS [m/z] | $R_t$(HPLC) [min] (method) |
|---|---|---|---|---|---|---|
| 27.2 | (4-((1-cyanocyclopropyl)methoxy)phenyl) | *—CH₃ | (1-(hydroxymethyl)cyclopropyl)nitrile | 1.48 | 417 [M + H]⁺ | 2.04 (A) |
| 27.3 | (4-((1-(cyanomethyl)cyclopropyl)methoxy)phenyl) | *—CH₃ | 2-(1-(hydroxymethyl)cyclopropyl)acetonitrile | 1.48 | 432 [M + H]⁺ | 2.11 (A) |

Example 28

Example 28.1

(S)-3-(4-(4-(1-Acetamidoethyl)phenyl)piperidin-1-yl)benzoic acid

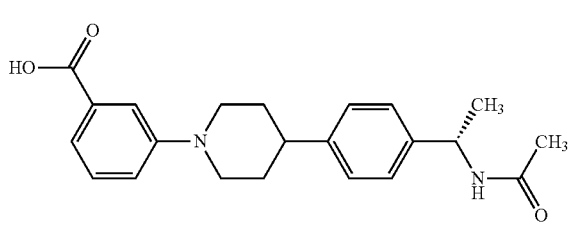 [SMILES: CC(=O)N[C@@H](C)c1ccc(C2CCN(c3cccc(C(=O)O)c3)CC2)cc1]

2.90 g (7.62 mmol) of the ester 15.02 are added to 50 mL MeOH and 8 mL of an 1 N aq. NaOH solution. The reaction mixture is stirred at 70° C. for 1 h. After cooling down to rt the solution acidified with diluted aq. HCl solution and the resulting precipitate is filtered, washed with water and dried in vacuo at 50° C.

$C_{22}H_{26}N_2O_3$ (M=366.5 g/mol), ESI-MS: 367 [M+H]⁺

$R_t$ (HPLC): 1.11 min (method H)

Example 29

Example 29.1

(S)—N-(1-(4-(1-(3-(1,2,3,4-Tetrahydroisoquinoline-2-carbonyl)phenyl)piperidin-4-yl)phenyl)ethyl)acetamide

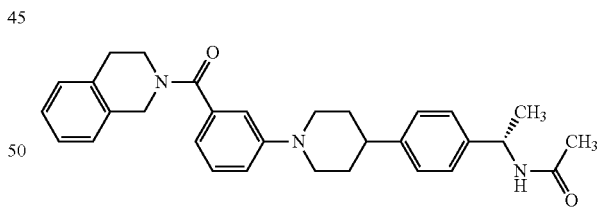

To 73.3 mg (0.20 mmol) of Example 28.1 in 2 mL DMF are added 64.2 mg (0.20 mmol) TBTU and 41.8 µL (0.20 mmol) TEA and the mixture is stirred at rt for 15 min. Then 26.6 mg (0.20 mmol) 1,2,3,4-tetrahydroisoquinoline are added and stirring is continued for 1 h. The reaction mixture is purified directly by HPLC (water+0.1% NH₄OH/MeOH).

$C_{31}H_{35}N_3O_2$ (M=481.6 g/mol), ESI-MS: 482 [M+H]⁺

$R_t$ (HPLC): 1.39 min (method O)

The following compounds are prepared analogously to Example 29.1. The educts used are shown in the column headed "Educts":

(29-1)

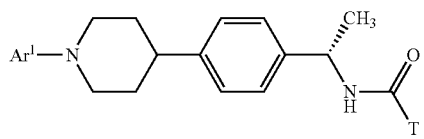

| Example | Ar¹ | T | Educt 1 | Educt 2 | ESI-MS [m/z] | $R_f$ (HPLC) [min] (method) |
|---|---|---|---|---|---|---|
| 29.1 | (1,2,3,4-tetrahydroisoquinolin-2-yl carbonyl phenyl) | *—CH₃ | 28.1 | (1,2,3,4-tetrahydroisoquinoline) | 482 [M + H]⁺ | 1.39 (O) |
| 29.2 | (isoindolin-2-yl carbonyl phenyl) | *—CH₃ | 28.1 | (isoindoline) | 468 [M + H]⁺ | 1.35 (O) |
| 29.3 | (3-(ethylcarbamoyl)phenyl) | *—CH₃ | 28.1 | ethylamine | 394 [M + H]⁺ | 1.02 (W) |
| 29.4 | (3-(dimethylcarbamoyl)phenyl) | *—CH₃ | 28.1 | dimethylamine | 394 [M + H]⁺ | 1.00 (W) |

Example 30

Example 30.1

(S)—N-1-(4-(1-(4-Ethoxyphenyl)piperidin-4-yl)phenyl)ethyl)-3-oxobutanamide

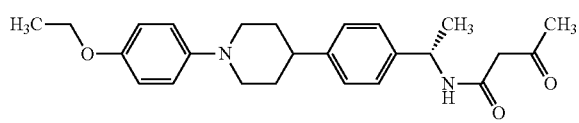

150 mg (0.46 mmol) of the amine XIII.1 are added to 1.5 mL THF and 5.65 mg (0.05 mmol) DMAP and cooled down to 0° C. Then 42.8 mg (0.51 mmol) diketene are added and the resulting mixture is stirred at 0° C. for 1 h. The solvent is removed in vacuo and the residue is purified by column chromatography (silica gel; PE/ethyl acetate, gradient 80:20-50:50).

$C_{25}H_{32}N_2O_3$ (M=408.5 g/mol), ESI-MS: 409 [M+H]⁺

$R_f$ (HPLC): 0.88 min (method AD)

Example 31

Example 31.1

(S)-Methyl 3-(1-(4-(1-(4-Ethoxyphenyl)piperidin-4-yl)phenyl)ethylamino)-3-oxopropanoate

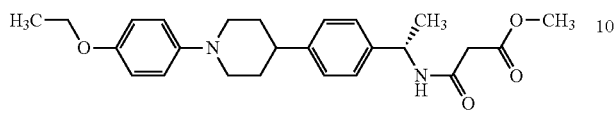

324 mg (1.00 mmol) of the amine XIII.1 are added to 10 mL THF and 154 µL (1.10 mmol) TEA. While cooling the mixture 108 µL (1.00 mmol) methyl malonyl chloride are added dropwise. The resulting mixture is stirred at rt over night. The mixture is filtered, the solvent is removed in vacuo and the residue is purified by HPLC (water+0.15% FA/acetone).

$C_{25}H_{32}N_2O_4$ (M=424.5 g/mol), ESI-MS: 425 [M+H]$^+$
$R_t$ (HPLC): 0.73 min (method AD)

Example 32

Example 32.1

(S)-3-(1-(4-(1-(4-Ethoxyphenyl)piperidin-4-yl)phenyl)ethylamino)-3-oxopropanoic Acid

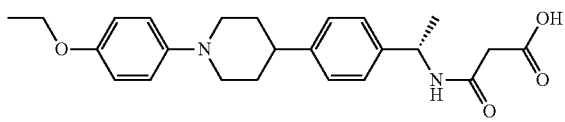 [SMILES: CCOc1ccc(N2CCC(c3ccc([C@H](C)NC(=O)CC(=O)O)cc3)CC2)cc1]

250 mg (0.59 mmol) of the ester 31.1 are added to 5 mL EtOH and 0.6 mL of an 1N aq. NaOH solution and stirred at rt. The solvent is removed in vacuo and the residue is partioned between DCM and an aq. pH7-buffer solution. The org. layer is separated, washed with water, dried with MgSO$_4$ and the solvent is removed in vacuo.

$C_{24}H_{30}N_2O_4$ (M=410.5 g/mol), ESI-MS: 411 [M+H]$^+$
$R_t$ (HPLC): 0.90 min (method G)

Example 33

Example 33.1

(S)—N-(1-{4-[1-(4-Ethoxyphenyl)piperidin-4-yl]phenyl}ethyl)malonamide

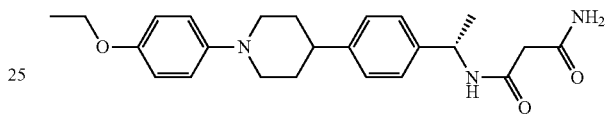

To 50.0 mg (0.12 mmol) of the carboxylic acid 32.1 in 1 mL DMF are added 25.3 µL (0.18 mmol) TEA, 41.1 mg (0.13 mmol) TBTU and 200 µL of an aq. ammonia solution (32%). Then the mixture is filtered purified by HPLC (water/MeOH, 0.15% NH$_4$OH).

$C_{24}H_{31}N_3O_3$ (M=409.5 g/mol), ESI-MS: 410 [M+H]$^+$
$R_t$ (HPLC): 1.10 min (method G)

The following compounds of general formula (33-1) are prepared analogously to Example 33.1, the educts used being shown in the column headed "E 1" and "E 2":

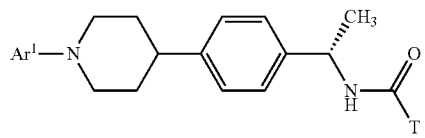

(33-1)

| Ex. | Ar$^1$ | T | E 1 | E 2 | ESI-MS [m/z] | R$_t$ (HPLC) [min] method |
|---|---|---|---|---|---|---|
| 33.1 | H$_3$C—O—C$_6$H$_4$—* | *—CH$_2$—C(O)—NH$_2$ | 32.1 | ammonia | 410 [M + H]$^+$ | 1.10 (G) |
| 33.2 | H$_3$C—O—C$_6$H$_4$—* | *—CH$_2$—C(O)—NH—CH$_3$ | 32.1 | methylamine | 424 [M + H]$^+$ | 1.15 (G) |

Example 34

Example 34.1

(S)—N-(1-(4-(1-(2-(Pyridin-2-yl)thiazol-5-yl)piperidin-4-yl)phenyl)ethyl)acetamide

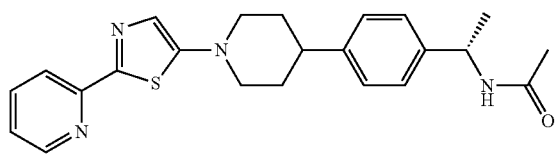 [SMILES: CC(=O)N[C@@H](C)c1ccc(C2CCN(c3cnc(-c4ccccn4)s3)CC2)cc1]

90.0 mg (0.25 mmol) of the acetylbromide XXIX.1 and 33.9 mg (0.25 mmol) pyridine-2-carbothioic acid amide are added to 2 mL ethanol and stirred at 80° C. for 4 h. Then the reaction mixture is purified directly by HPLC (water+0.3% NH₄OH/MeOH).

$C_{23}H_{26}N_4OS$ (M=406.5 g/mol), ESI-MS: 407 [M+H]⁺
$R_t$ (HPLC): 1.16 min (method G)

The following compounds are prepared analogously to Example 34.1. The educts used are shown in the column headed "Educts":

resulting precipitate is collected, dissolved in DCM, washed with water and dried with MgSO₄. The solvent is removed in vacuo.

$C_{24}H_{33}N_3O_2$ (M=395.5 g/mol), ESI-MS: 396 [M+H]⁺
$R_t$ (HPLC): 1.16 min (method G)

Example 36

Example 36.1

(S)-2-(Dimethylamino)-N-(1-{4-[1-(4-ethoxyphenyl)piperidin-4-yl]phenyl}ethyl)acetamide

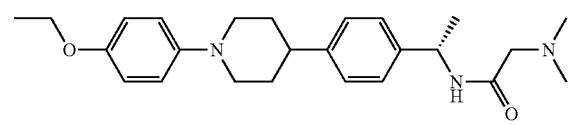 [SMILES: CCOc1ccc(N2CCC(c3ccc([C@H](C)NC(=O)CN(C)C)cc3)CC2)cc1]

To 59.3 mg (0.15 mmol) of Example 35.1 in 5 mL THF are added 36.5 µL (0.45 mmol) formalin, 1 mL of an aq. pH-5 buffer solution and 95.4 mg sodium triacetoxyborohydride. The resulting mixture is stirred at rt for 2 h and purified directly by HPLC (water+0.15% NH₄OH/MeOH).

(34-1)

| Example | Ar¹ | T | Educt 1 | Educt 2 | ESI-MS [m/z] | $R_t$ (HPLC) [min] (method) |
|---|---|---|---|---|---|---|
| 34.1 | 2-pyridyl-thiazole | *—CH₃ | XXIX.1 | pyridine-2-carbothioamide | 407 [M + H]⁺ | 1.16 (G) |
| 34.2 | 5-(trifluoromethyl)pyridyl-thiazole | *—CH₃ | XXIX.1 | 5-(trifluoromethyl)pyridine-2-carbothioamide | 475 [M + H]⁺ | 1.32 (G) |

Example 35

Example 35.1

(S)-2-Amino-N-(1-{4-[1-(4-ethoxyphenyl)piperidin-4-yl]phenyl}ethyl)acetamide

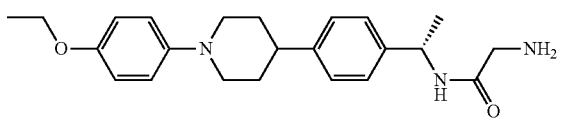

250 mg (0.50 mmol) of Example 6.49 in dichloromethane are charged with 2.02 mL methanolic HCl solution (c=1.25 mol/l). The mixture is refluxed over night, the solvent is removed in vacuo and to the residue is added water. Then the mixture is basified with a diluted aq. NaOH solution and the $C_{26}H_{37}N_3O_2$ (M=423.6 g/mol), ESI-MS: 424 [M+H]⁺
$R_t$ (HPLC): 1.22 min (method G)

Example 37

Example 37.1

(S)-2-(4-(4-(1-Acetamidoethyl)phenyl)piperidin-1-yl)-5-ethoxybenzamide

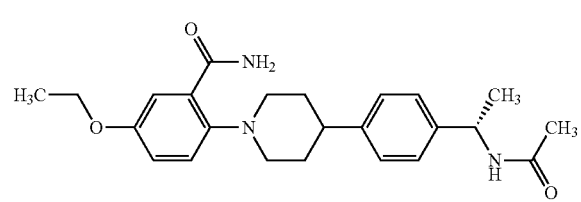 [SMILES: CCOc1ccc(N2CCC(c3ccc([C@H](C)NC(C)=O)cc3)CC2)c(C(N)=O)c1]

50.0 mg (0.13 mmol) of Example 13.3 in 2 mL DMSO are cooled down to 0° C. and charged with 19.5 mg (0.14 mmol) K$_2$CO$_3$. Then 113 µL H$_2$O$_2$ (30% in water) are added and the mixture is allowed to warm to rt and stirred over night. Additional 113 µL H$_2$O$_2$ (30% in water) are added and stirring is continued for 2 h at 45° C. The reaction mixture is filtered and directly purified by HPLC (water+0.15% FA/MeOH).

C$_{23}$H$_{29}$N$_3$O$_3$ (M=409.5 g/mol), ESI-MS: 410 [M+H]$^+$
R$_t$ (HPLC): 1.09 min (method G)

Example 38

Example 38.1

(S)-N-(1-(4-(1-(4-Ethoxyphenyl)piperidin-4-yl)phenyl)ethyl)ethanethioamide

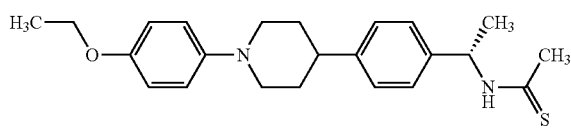 [SMILES: CCOc1ccc(N2CCC(c3ccc([C@H](C)NC(C)=S)cc3)CC2)cc1]

50.0 mg (0.14 mmol) of Example 1.1 and 55.1 mg (0.14 mmol) of Lawesson's reagent in 3 mL toluene are refluxed for 2 h. Then the solvent is removed in vacuo and the residue is purified by HPLC (water+0.3% NH$_4$OH/MeOH).

C$_{23}$H$_{30}$N$_2$OS (M=382.6 g/mol), ESI-MS:383 [M+H]$^+$
R$_t$ (HPLC): 1.22 min (method G)

The following compounds are prepared analogously to Example 38.1. The educt used is shown in the column headed "Educt":

Example 39

Example 39.1

(S)—N-(1-(4-(1-(4-Cyclopropylmethoxyphenyl)piperidin-4-yl)phenyl)ethyl)-N-methylacetamide

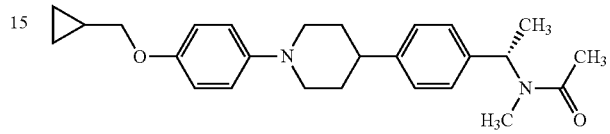

To 32.2 mg (1.27 mmol) NaH in 2.5 mL THF at 0° C. are added 50.0 mg (0.13 mmol) of Example I.26. The mixture is stirred for 10 min at 0° C. before 15.9 µL (0.26 mmol) methyl iodide are added and the mixture is stirred at rt for 2 h. The reaction is quenched by the addition of water and a sat. aq. NH$_4$Cl solution. The resulting mixture is extracted with DCM, the org. layers are combined and dried with MgSO$_4$. The solvent is removed in vacuo and the residue is resolved in ACN and some water and freeze-dried.

C$_{26}$H$_{34}$N$_2$O$_2$ (M=406.6 g/mol), ESI-MS: 407 [M+H]$^+$
R$_t$ (HPLC): 2.36 min (method F)

The following compounds are prepared analogously to Example 39.1. The educt used is shown in the column headed "Educt":

(38-1)

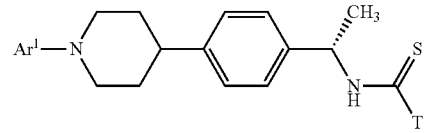

| Example | Ar$^1$ | T | Educt | ESI-MS [m/z] | R$_t$ (HPLC) [min] (method) |
|---|---|---|---|---|---|
| 38.1 | H$_3$C—O—⟨phenyl⟩—* | *—CH$_3$ | 1.1 | 383 [M + H]$^+$ | 1.22 (G) |
| 38.2 | H$_3$C—O—⟨phenyl-F⟩—* | *—CH$_3$ | 1.103 | 401 [M + H]$^+$ | 1.26 (G) |

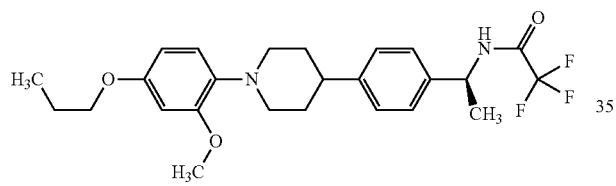

| Example | Ar$^1$ | R$^N$ | Educt | ESI-MS [m/z] | R$_t$ (HPLC) [min] (method) |
|---|---|---|---|---|---|
| 39.1 | cyclopropylmethoxy-phenyl | *—CH$_3$ | 1.26 | 407 [M + H]$^+$ | 2.36 (F) |
| 39.2 | cyclopropylmethoxy-phenyl | *—CH$_2$CH$_3$ | 1.26 | 421 [M + H]$^+$ | 2.41 (F) |

Example 40

Example 40.1

(S)-2,2,2-Trifluoro-N-{1-[4-(1-(2-methoxy-4-propoxyphenyl)piperidin-4-yl)phenyl]-ethyl}acetamide 100 mg (0.22 mmol) of Example XXXV.1 in 5 mL MeOH are charged with 10 mg Pd/C and stirred in an atmosphere of hydrogen (50 psi) at rt over night. Then the reaction mixture is filtered, the solvent is removed in vacuo and the resulting residue is purified by HPLC (RP C18 Xbridge, water(+0.3% ammonia)/MeOH).

C$_{25}$H$_{31}$F$_3$N$_2$O$_3$ (M=464.5 g/mol), EI-MS: 465 [M+H]$^+$
R$_t$ (HPLC): 2.40 min (method F)

The following compounds are prepared analogously to example XXXIII.1.

Examples of Formulations

The following examples of formulations, which may be obtained analogously to methods known in the art, serve to illustrate the present invention more fully without restricting it to the contents of these examples. The term "active substance" denotes one or more compounds according to the invention, including the salts thereof.

Example 1

Tablet Containing 50 mg of Active Substance
Composition:

| | |
|---|---|
| (1) Active substance | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Preparation:

(1), (2) and (3) are mixed together and granulated with an aq. solution of (4). (5) is added to the dried granulated material. From this mixture tablets are pressed, biplanar, faceted on both sides and with a dividing notch on one side.

| Example | Starting material | Product structure | Mass spec result | R$_t$ (HPLC) [min] (method) |
|---|---|---|---|---|
| 40.1 | XXXV.1 | (structure) | 465 [M + H]$^+$ | 2.40 (F) |
| 40.2 | XXXV.2 | (structure) | 421 [M + H]$^+$ | 2.11 (F) |

Example 2

Tablet Containing 350 mg of Active Substance
Preparation:

| | |
|---|---|
| (1) Active substance | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

(1), (2) and (3) are mixed together and granulated with an aq. solution of (4). (5) is added to the dried granulated material. From this mixture tablets are pressed, biplanar, faceted on both sides and with a dividing notch on one side.

Diameter of the tablets: 12 mm.

Example 3

Capsules Containing 50 mg of Active Substance
Composition:

| | |
|---|---|
| (1) Active substance | 50.0 mg |
| (2) Dried maize starch | 58.0 mg |
| (3) Powdered lactose | 50.0 mg |
| (4) Magnesium stearate | 2.0 mg |
| | 160.0 mg |

Preparation:
(1) is triturated with (3). This trituration is added to the mixture of (2) and (4) with vigorous mixing. This powder mixture is packed into size 3 hard gelatin capsules in a capsule filling machine.

Example 4

Capsules Containing 350 mg of Active Substance
Composition:

| | |
|---|---|
| (1) Active substance | 350.0 mg |
| (2) Dried maize starch | 46.0 mg |
| (3) Powdered lactose | 30.0 mg |
| (4) Magnesium stearate | 4.0 mg |
| | 430.0 mg |

Preparation:
(1) is triturated with (3). This trituration is added to the mixture of (2) and (4) with vigorous mixing. This powder mixture is packed into size 0 hard gelatin capsules in a capsule filling machine.

Example 5

Dry Ampoule Containing 35 mg of Active Substance Per 2 mL Composition:

| | |
|---|---|
| Active substance | 35.0 mg |
| Mannitol | 100.0 mg |
| water for injections | ad 2.0 mL |

Preparation:
The active substance and mannitol are dissolved in water. After packaging, the solution is freeze-dried. To produce the solution ready for use, the product is dissolved in water for injections.

The invention claimed is:
1. A compound of formula (I)

$$Ar^1-N\underset{}{\bigcirc}-Ar^2-X-N\underset{R^N}{\overset{Y}{\diamond}}T$$

wherein
$Ar^1$ is selected from the group consisting of:

[structures of aryl/heteroaryl groups]

wherein the asterisk to the right side of the cyclic group indicates the bond which is connected to the piperidine ring of the core structure of the formula (I), and the asterisk to the left side of the cyclic group indicates the bond which is connected to a substituent $R^A$ or H, and in addition the before mentioned cyclic group is optionally substituted with one or two substituents $R^A$;

$R^A$ is selected from the group consisting of F, Cl, Br, I, CN, $C_{1-5}$-alkyl, $C_{3-6}$-cycloalkyl, $C_{1-5}$-alkyl-O—, $C_{3-5}$-alkenyl-O—, $C_{3-5}$-alkynyl-O—, $C_{3-6}$-cycloalkyl-O—, $C_{3-6}$-cycloalkyl-$C_{1-3}$-alkyl-O—, $R^{N1}R^{N2}N$—, phenyl, phenyl-O—, phenyl-$C_{1-3}$-alkyl-O—, heteroaryl, heteroaryl-O— and heteroaryl-$C_{1-3}$-alkyl-O—; and wherein each cycloalkyl may be optionally substituted with one or more $C_{1-3}$-alkyl, which may be substituted as defined hereinafter; and wherein each alkyl and cycloalkyl may be optionally substituted with one or more substituents selected from F; and wherein in each cycloalkyl group a CH$_2$-group may optionally be replaced by —O—; and wherein each alkyl and cycloalkyl may be optionally substituted with one or two substituents R$^C$, wherein R$^C$ is selected from the group consisting of Cl, Br, CN, OH, C$_{1-3}$-alkyl-O—, C$_{3-6}$-cycloalkyl-O—, HO—C$_{1-3}$-alkyl-O—, H$_2$N—, (C$_{1-3}$-alkyl)NH—, (C$_{1-3}$-alkyl)$_2$N—, HO—C(=O)— and C$_{1-3}$-alkyl-O—C(=O)—; and wherein each R$^{N1}$ is selected from the group consisting of H, C$_{1-6}$-alkyl, C$_{3-6}$-cycloalkyl, C$_{3-6}$-cycloalkyl-CH$_2$—, wherein each cycloalkyl may be optionally substituted with one or more C$_{1-4}$-alkyl, and wherein each alkyl and cycloalkyl may be optionally substituted with one or more substituents selected from F, and wherein each alkyl and cycloalkyl may be optionally substituted with a substituent selected from OH, C$_{1-3}$-alkyl-O— and H$_2$N—; and wherein each R$^{N2}$ is H or C$_{1-4}$-alkyl; and wherein heteroaryl is selected from the group consisting of pyrrolyl, pyridyl, pyrimidinyl, pyridazinyl, pyrazinyl, furanyl, oxazolyl, isoxazolyl, pyrazolyl, thiazolyl, benzofuranyl, indolyl and quinolinyl; and wherein each phenyl and heteroaryl group may be optionally substituted with one or more substituents L;

Ar$^2$ is selected from the group consisting of

wherein the before mentioned group may be optionally substituted with one or more substituents L; and L is selected from the group consisting of:
F, Cl, Br, CN, OH, C$_{1-3}$-alkyl-, C$_{1-3}$-alkyl-O—, C$_{1-3}$-alkyl-S—, H$_2$N—, (C$_{1-3}$-alkyl)NH—, (C$_{1-3}$-alkyl)$_2$N— and heterocyclyl;

wherein each alkyl of L may be optionally substituted with one or more F-atoms and/or a substituent selected from OH, C$_{1-3}$-alkyl-O— and CN; and wherein heterocyclyl denotes a C$_{3-6}$-cycloalkyl ring wherein one or two —CH$_2$-groups are replaced by a group selected from —O—, —NH—, —N(C$_{1-3}$-alkyl)-; and wherein two substituents L attached to an aryl or heteroaryl group may be linked to each other and form a C$_{2-5}$-alkylene bridging group in which 1 or 2 —CH$_2$-groups may be replaced by a group independently of each other selected from O, NH and N(C$_{1-4}$-alkyl)-, wherein the C$_{2-5}$-alkylene bridging group is optionally be substituted by 1 or 2 C$_{1-3}$-alkyl groups;

X is selected from the group consisting of:

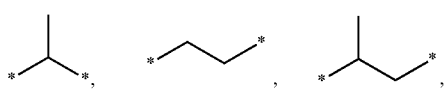

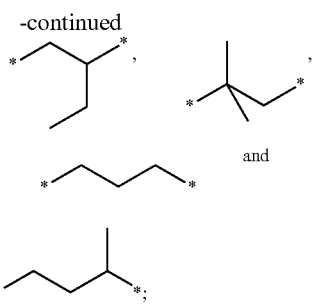

Y is —C(=O)—;

R$^N$ is H; and

T is selected from the group consisting of C$_{1-3}$-alkyl, C$_{3-5}$-cycloalkyl, C$_{1-3}$-alkyl-O— and R$^{T1}$R$^{T2}$—N—;

wherein each cycloalkyl may be optionally substituted with one or more C$_{1-3}$-alkyl; and wherein R$^{T1}$ and R$^{T2}$ are independently of each other selected from H and C$_{1-3}$-alkyl;

or a tautomer or salt thereof.

2. A compound according to claim 1, wherein R$^A$ is selected from the group consisting of F, Cl, Br, CN, F$_3$C—,

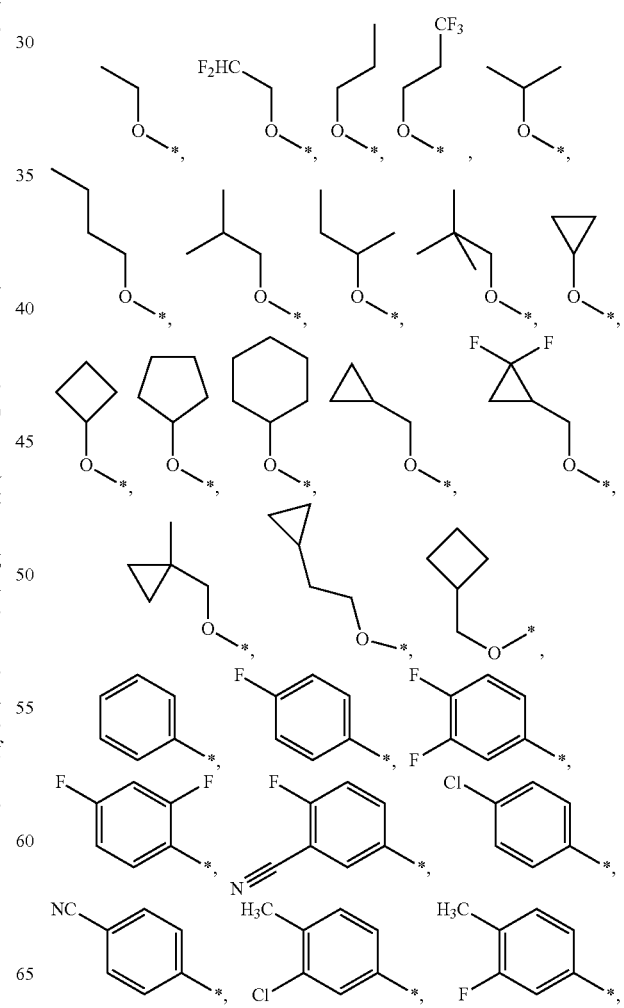

-continued

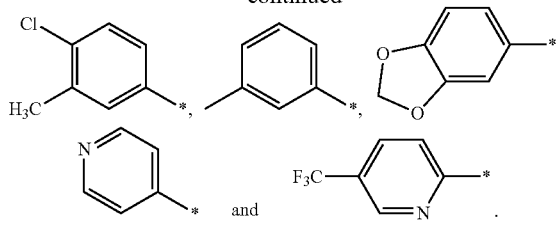

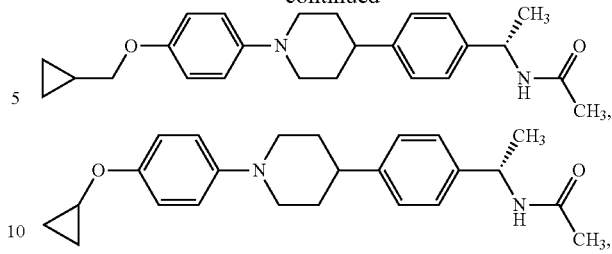

3. A compound according to claim 1, wherein X is

4. A compound according to claim 1, wherein L is selected from the group consisting of F, Cl, CN, OH, $C_{1-3}$-alkyl-, $C_{1-3}$-alkyl-O—, $C_{1-3}$-alkyl-S—, $H_2N$—, $(C_{1-3}$-alkyl)NH—, $(C_{1-3}$-alkyl)$_2$N— and heterocyclyl;
   wherein each alkyl may be optionally substituted with one or more F-atoms and/or a substituent selected from OH, $CH_3$—O— and CN; and
   wherein heterocyclyl denotes a $C_{3-6}$-cycloalkyl ring wherein one or two —$CH_2$-groups are replaced by a group selected from —O—, —NH—, —N($C_{1-3}$-alkyl)-; and
   wherein two substituents L attached to adjacent C-atoms of an aryl or heteroaryl group may be linked to each other and form a —$CH_2$—$CH_2$—O—, —O—$CH_2$—$CH_2$—O— or —O—$CH_2$—O— bridging group which is optionally substituted by 1 or 2 $CH_3$— groups.

5. A compound selected from the group consisting of:

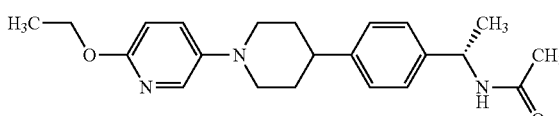

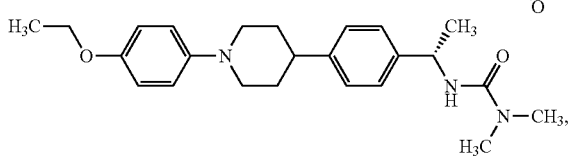

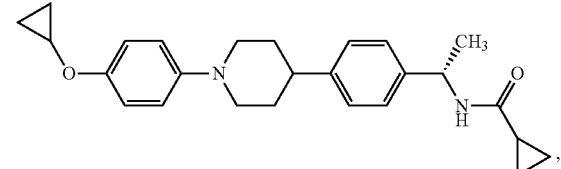

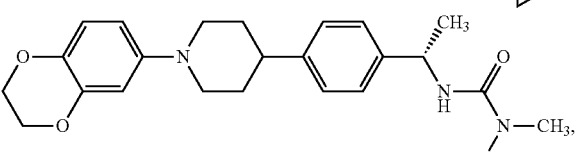

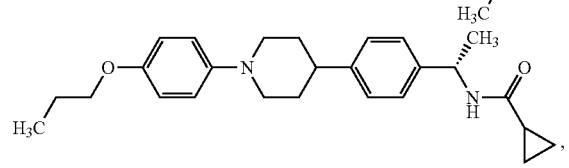

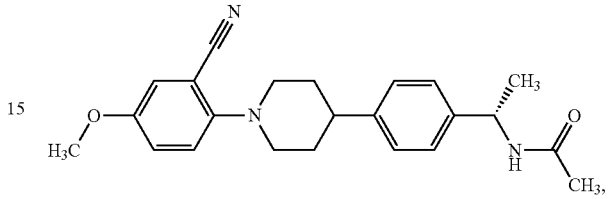

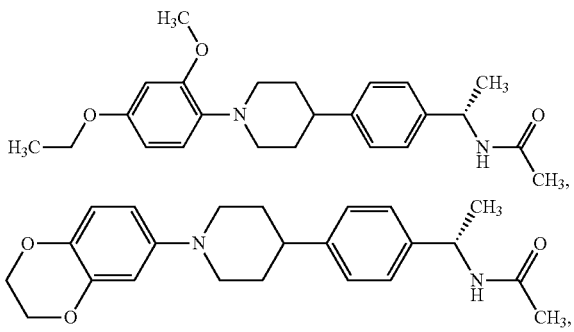

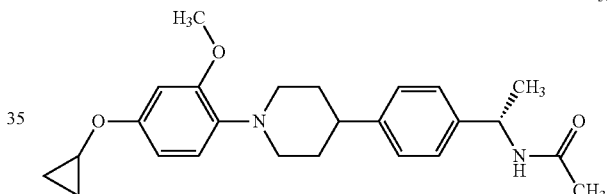

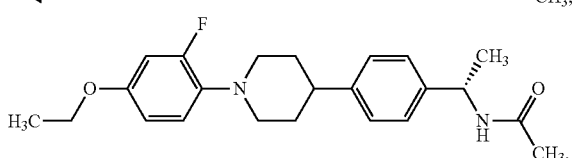

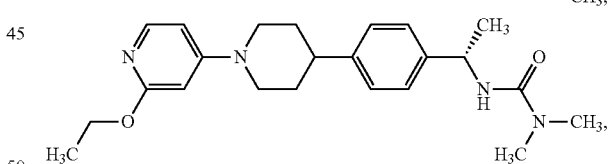

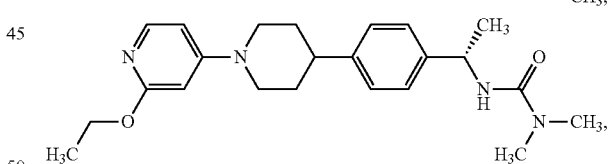

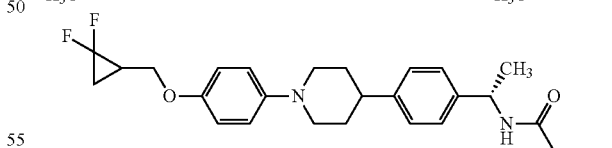

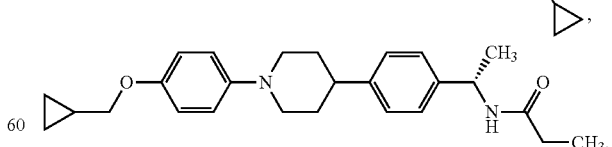

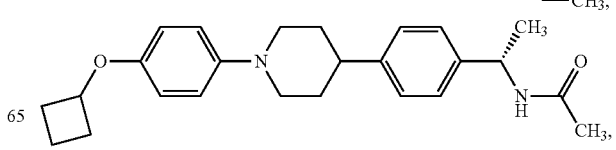

-continued

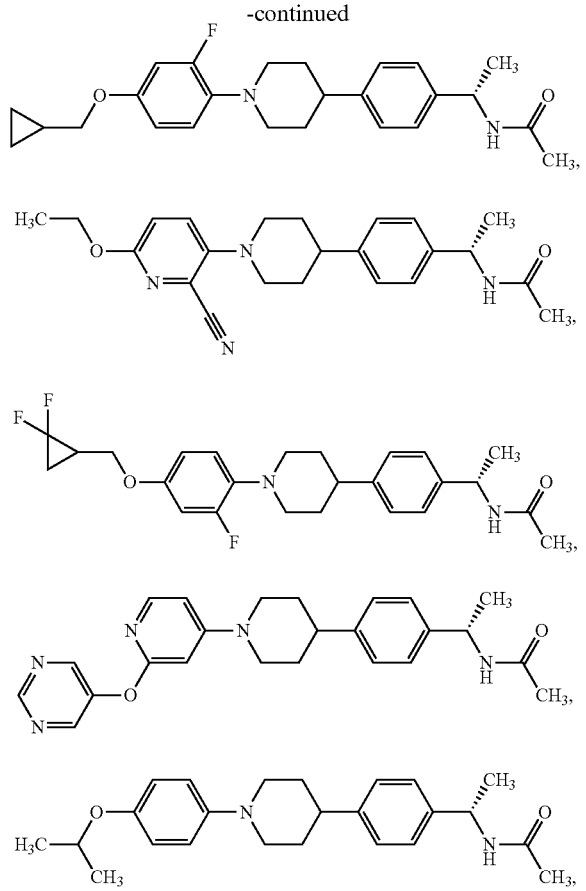

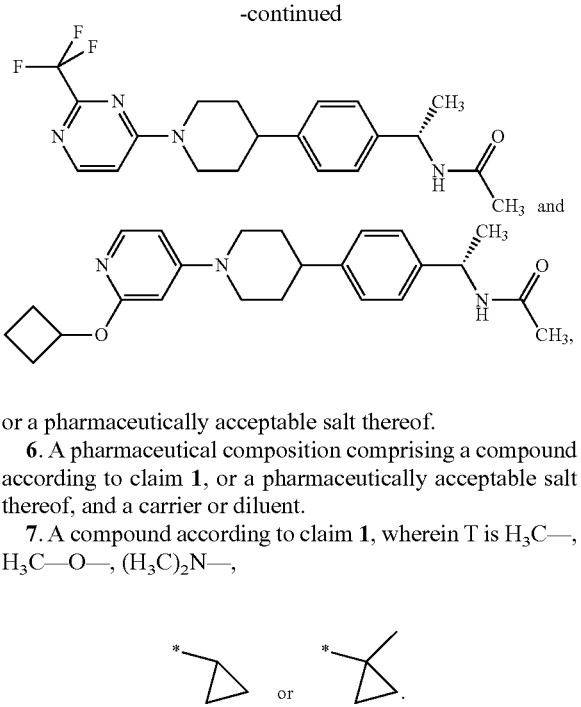

or a pharmaceutically acceptable salt thereof.

6. A pharmaceutical composition comprising a compound according to claim 1, or a pharmaceutically acceptable salt thereof, and a carrier or diluent.

7. A compound according to claim 1, wherein T is H$_3$C—, H$_3$C—O—, (H$_3$C)$_2$N—,

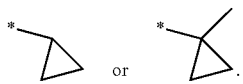

or

8. A compound according to claim 1, wherein T is H$_3$C—, (H$_3$C)$_2$N— or cyclopropyl.

9. A method for treating obesity and/or diabetes in a patient suffering from the same, wherein a therapeutically effective amount of a compound according to claim 1, or a pharmaceutically acceptable salt thereof, is administered to the patient.

* * * * *